(12) United States Patent
Cowart et al.

(10) Patent No.: US 7,576,110 B2
(45) Date of Patent: Aug. 18, 2009

(54) BENZOTHIAZOLE CYCLOBUTYL AMINE DERIVATIVES

(75) Inventors: Marlon D. Cowart, Round Lake Beach, IL (US); Minghua Sun, Libertyville, IL (US); Chen Zhao, Libertyville, IL (US); Guo Zhu Zheng, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 507 days.

(21) Appl. No.: 11/518,132

(22) Filed: Sep. 8, 2006

(65) Prior Publication Data

US 2007/0066588 A1 Mar. 22, 2007

Related U.S. Application Data

(60) Provisional application No. 60/719,516, filed on Sep. 22, 2005.

(51) Int. Cl.
*A61K 31/428* (2006.01)
*C07D 277/62* (2006.01)

(52) U.S. Cl. .................. 514/367; 548/146; 548/152; 546/139; 546/152; 546/184; 544/111; 544/135; 544/242; 544/359; 514/231.5; 514/252.12; 514/311; 514/336

(58) Field of Classification Search .................. 548/146; 548/152; 546/139, 152, 184; 544/111, 135, 544/359; 514/231.5, 252.12, 256, 311, 336, 514/365, 367
See application file for complete search history.

(56) References Cited

U.S. PATENT DOCUMENTS

| 2004/0224952 A1 | 11/2004 | Cowart et al. |
| 2005/0171181 A1 | 8/2005 | Wager et al. |
| 2007/0078133 A1 | 4/2007 | Liu et al. |

FOREIGN PATENT DOCUMENTS

| DE | 491224 | 1/1930 |
| EP | 0 259 977 | 3/1988 |
| RU | 2 174 505 | 2/2000 |
| WO | 94/15928 | 7/1994 |
| WO | 00/44728 | 8/2000 |

OTHER PUBLICATIONS

A.C.S. Symposium Series, V14, Table of Contents, (1987).
Aranyos, A., et al., "Novel Electron-Rich Bulky Phosphine Ligands Facilitate the Palladium-Catalyzed Preparation of Diaryl Ethers", *J. Am. Chem. Soc.*, 121:4369-4378 (1999).
Arrang, J.-M., et al., "Auto-inhibition of brain histamine release mediated by a novel class ($H_3$) of histamine receptor", *Nature*, 302:832-837 (1983).
Arrang, J.-M., et al., "Highly potent and selective ligands for histamine $H_3$-receptors", *Nature*, 327:117-123 (1987).

Arrang, J.-M., et al., "Histamine $H_3$ receptor binding sites in rat brain membranes: modulations by guanine nucleotides and divalent cations", *Eur. J. of Pharmacology*, 188:219-227 (1990).
Gil-Av, E. & Shabtai, J., "Synthesis and Reactions of 3-Methylcyclobutene", *J. of Org. Chem.*, 29(2):257-262 (1964).
Barbier, A.J., et al., "Acute wake-promoting actions of JNJ-5207852, a novel, diamine-based $H_3$ antagonist", *Brit. J. of Pharmacology*, 143:649-661 (2004).
Baston, E. & Hartmann, R.W., "A New Route to 6-Arly-Substituted 3,4-Dihydronaphthalene Derivatives Via Pd (O)-Catalyzed Cross-Coupling Reaction of Aryl Zinc Chlorides With an Aryl Triflate", *Synth. Comm.*, 28(14):2725-2729 (1998).
Bates, R.B. & Janda, K.D., "High-Yield Benzyne Synthesis of Diaryl Ethers", *J. Org. Chem.*, 47:4374-4376 (1982).
Baudoin, O., et al., "Palladium-Catalyzed Borylation of Ortho-Substituted Phenyl Halides and Application to the One-Pot Synthesis of 2,2'-Disubstituted Biphenyls", *J. Org. Chem.*, 65:9268-9271 (2000).
Benaglia, M., et al., "Synthesis of Pyridylstannanes from Halopyridines and Hexamethyldistannane with Catalytic Palladium", *Tetrahedron Ltrs.*, 38(27):4737-4740 (1997).
Bernaerts, P., et al., "Histamine $H_3$ antagonist thioperamide dose-dependently enhances memory consolidation and reverses amnesia induced by dizocilpine or scopolamine in a one-trial inhibitory avoidance task in mice", *Bahav. Brain Res.*, 154:211-219 (2004).
Bienfait, B., et al., "β-Cyanocyclobutenone as a Highly Reactive Dienophile in Comparison to β-Cyanocyclopentenone", *Tetrahedron*, 47(38):8167-8176 (1991).
Bjenning, C., et al., "Peripherally administered Ciproxifan elevates Hypothalamic Histamine Levels and Potently Reduces Food intake in the Sprague Dawley rat", *Abstracts, Intn'l Sendai Histamine Symposium*, Sendai, Japan, #P30:449-452 (2000).

(Continued)

Primary Examiner—Golam M Shameem
(74) Attorney, Agent, or Firm—Portia Chen

(57) ABSTRACT

Compounds of formula (I)

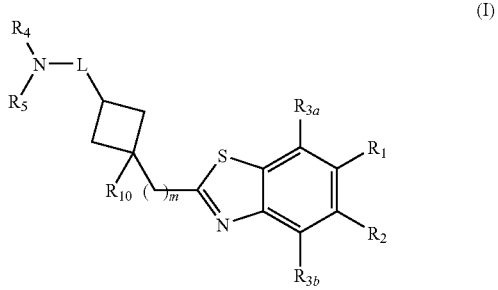

are useful in treating conditions or disorders prevented by or ameliorated by histamine-3 receptor ligands. Also disclosed are pharmaceutical compositions comprising the histamine-3 receptor ligands, methods for using such compounds and compositions, and a process for preparing compounds within the scope of formula (I).

18 Claims, No Drawings

OTHER PUBLICATIONS

Bogert, M.T. & Husted, H.G., "Researches on Thiazoles. XVIII. The Synthesis of 2-Phenylbenzothiazole-5-Carboxylic Acid and Derivatives", *J. of the Amer. Chem. Soc.*, 54:3394-3397 (1932).

Black, W.C., et al., "2,3-Diarylcyclopentenones as Orally Active, Highly Selective Cyclooxygenase2 Inhibitors", *J. Med. Chem.*, 42:1274-1281 (1999).

Browman, K.E., et al., "Enhancement of prepulse inhibition of startle in mice by the $H_3$ receptor antagonists thioperamide and ciproxifan", *Behav. Brain Res.*, 153:69-76 (2004).

Burger, A., et al., "2-(4-Imidazolyl)cyclopropylamine", *Univ. of Virg.*, 33-35 (1969).

Burns, H.D., et al., "Chapt.26. PET Ligands for Assessing Receptor Occupancy in Vivo", *Ann. Rep. In Medicinal Chem.*, 36:267-276 (2001).

Burns, H.D., et al., "Positron emission tomography neuroreceptor imaging as a tool in drug discovery, research and development", *Curr. Opin. In Chem. Biol.*, 3:388-394 (1999).

Carroll, F.I., et al., "Synthesis, Nicotinic Acetylcholine Receptor Binding, and Antinociceptive Properties of 2- exo '2-(2'-Substituted 5'-pyridinyl)-7-azabicyclo[2.2.1]heptanes. Epibatidine Analogues", *J. Med. Chem.*, 44:2229-2237 (2001).

Chen, Z., et al., "Effects of histamine on MK-801-induced memory deficits in radial maze performance in rats", *Brain Research*, 839:186-189 (1999).

Chen, Z., et al., "Pharmacological effects of carcinine on histaminergic neurons in the brain", *Brit. J. of Pharmacology*, 143:573-580 (2004).

Cheng, Y.-C. & Prusoff, W. H., "Relationship Between the Inhibition Constant ($K_I$) and the Concentration of Inhibitor Which Causes 50 Per Cent Inhibition ($I_{50}$) of an Enzymatic Reaction*", *Biochem. Pharmacology*, 22:3099-3108 (1973).

Clapham, J. & Kilpatrick, G.J., "Thioperamide, the selective histamine $H_3$ receptor antagonist, attenuates stimulant-induced locomotor activity in the mouse", *Eur. J. of Pharmacology*, 259:107-114 (1994).

Cowart, M., et al., "4-(2-[2-(R)-Methylpyrrolidin-1-yl]bensofuran-5-yl)benzonitrile and Related 2-Aminoethylbensofuran $H_3$ Receptor Antagonists Potently Enhance Cognition and Attention", *J. Med. Chem.*, 48:38-55 (2005).

Dannley, R.L. & Zazaris, D.A., "The Synthesis of 2-Aminobenzenethiol Hydrochlorides", *Can. J. Chem.*, 43:2610-2612 (1965).

Del Almeida, M.A.M.R. & Izquierdo, I., "Memory Facilitation by Histamine", *Arch. Int.. Pharmacodyn*, 283:193-198 (1986).

Delaunois, A., et al., "Modulation of acetylcholine, capsaicin and substance P effects by histamine $H_3$ receptors in isolated perfused rabbit lungs", *Eur. J. of Pharmacology*, 277:243-250 (1995).

Della, E. W., et al., "Bridgehead Carbocations: A Solvolytic Study of 1-Bromobicylco[1.1.1]pentane and Its Bridgehead-Substituted Derivatives", *J. Am. Chem. Soc.*, 116:6159-6166 (1994).

Dimitriadou, V., et al., "Functional relationship between mast cells and C-sensitive nerve fibres evidenced by histamine $H_3$-receptor modulation in rat lung and spleen", *Clin. Sci.*, 87:151-163 (1994).

Duméry, V. & Blozovski, D., "Development of amygdaloid cholinergic mediation of passive avoidance learning in the rat", *Exp. Brain Res.*, 67:61-69 (1987).

Dvorak, C.A., et al., "4-Phenoxypiperidines: Potent, Conformationally Restricted, Non-Imidazole Histamine $H_3$ Antagonists", *J. Med. Chem.*, 48:2229-2238 (2005).

Esbenshade, T.A., et al., "Pharmacological and behavioral properties of A-349821, a selective and potent human histamine $H_3$ receptor antagonist", *Biochem. Pharmacology*, 68:933-945 (2004).

Esbenshade, T.A., et al., "Pharmacological Properties of ABT-239 [4-(2-{2-[(2R)-2-Methylpyrroilidinyl]ethyl}-benzofuran-5-yl)benzonitrile]: 1. Potent and Selective Histamine $H_3$ Receptor Antagonist with Drug-Like Properties", *J. of Pharmacology & Ex. Ther.*, 313(1):165-175 (2005).

Fitzsimons, C., et al., "Histamine receptors signaling in epidermal tumor cell lines with H-ras gene alterations", *Infl. Res.*, 47(Suppl 1):S50-S51 (1998).

Fox, G.B., et al., "Effects of histamine $H_3$ receptor ligands GT-2331 and ciproxifan in a repeated acquitition avoidance response in the spontaneously hypertensive rat pup", *Beh. Brain Res.*, 131:151-161 (2002).

Fox, G.B., et al., "Identification of novel $H_3$ receptor ($H_3R$) antagonists with cognition enhancing properties in rats", *Infl. Res.*, 52(Suppl 1):S31-S32 (2003).

Fox, G.B., et al., "Two Novel and Selective Nonimidazole $H_3$ Receptor Antagonists A-304121 and A-317920: II. In Vivo Behavioral and Neurophysiological Characterization", *J. of Pharmacology & Exp. Ther.*, 305(2):897-908 (2003).

Fox, G.B., et al., "Pharmacological Properties of ABT-239 [4-(2-{2-[(2R)-2-Methylpyrrolidinyl]ethyl]-benzofuran-5-yl)benzonitrile]:II. Neurophysiological Characterization and Broad Preclinical Efficacy in Cognition and Schizophrenia of a Potent and Selective Histamine $H_3$ Receptor Antagonist", *J. of Pharma. & Exp. Ther.*, 313(1):176-190 (2005).

Furniss, B.S., et al., *Vogel's Textbook of Practical Organic Chemistry*, 5$^{th}$ Ed.:Table of Contents (1989).

Giles, M.E., et al., "Development of a Manufacturing Process for Sibenadet Hydrochloride, the Active Ingredient of Viozan", *Org. Proc. Res. & Dev.*, 8:628-642 (2004).

Glase, S.A., et al. "Chapter 2. Attention Deficit Hyperactivity Disorder: Pathophysiology and Design of New Treatments", *Ann. Rep. In Medicinal Chem.*, 37:11-20 (2002).

Haga, N. & Takayanagi, H., "Mechanisms of the Photochemical Rearrangement of Diphenyl Ethers", *J. Org. Chem.*, 61:735-745 (1996).

Hancock, A.A., et al., "Antiobesity effects of A-331440, a novel non-imidazole histamine $H_3$ receptor antagonist", *Eur. J. of Pharmacology*, 487:183-197 (2004).

Hancock, A.A., et al., "Histamine $H_3$ antagonists in models of obesity", *Infl. Res.*, 53(Suppl. 1):S47-S48 (2004).

Harada, C., et al., "Inhibitory effect of iodophenpropit, a selective histamine $H_3$ antagonist, on amygdaloid kindled seizures", *Brain Res.*, 63:143-146 (2004).

Hartwig, J.F., "Transition Metal Catalyzed Synthesis of Arylamines and Aryl Ethers from Aryl Halides and Triflates: Scope and Mechanism", *Angew. Chem. Int. Ed.*, 37:2046-2067 (1998).

Halpern, M.T., "GT-2331 Gliatech Inc". *Curr. Opin. In Centr. & Periph. Nerv. Syst. Invest. Drugs*, 1:524-527 (1999).

Hietala, J., "Lligand-receptor interactions as studied by PET:implications for drug development", *Ann. Medicine* (Helsinki), 31(6): 438-443 (1999).

Hriscu, A., et al., "Evaluarea Expreimentală a Eficacitătii Analgezice a Implicării Receptorilor Histaminergici in Patogenia Durerii", *Farmacia*, 49(2):23-30, 76 (2001).

Huang, Y.-W., et al., "Effect of the histamine $H_3$-antagonist clobenpropit on spatial memory deficits induce by Mk-801 as evaluated by radial maze in Sprague-Dawley rats", *Beh. Brain Res.*, 151:287-293 (2004).

Ishiyama, T., et al, "Palladium(0)-Catalyzed Cross-Coupling Reaction of Alkoxydiboron with Haloarenes: A Direct Procedure for Arylboronic Esters", *J. Org. Chem.*, 60:7508-7510 (1995).

Ishiyama, T., et al, "Synthesis of pinacol arylboronates via cross-coupling reaction of bis(pinacolato)diboron with chloroarenes catalyzed by palladium(0)-tricyclohexylphosphine complexes", *Tetradedron*, 57:9813-9816 (2001).

Itoh, E., et al., "Thioperamide, a Histamine $H_3$ Receptor Antagonist, Powerfully Suppresses Peptide YY-Induced Food Intake in Rats", *Soc. Of Biol. Psych.*, 45:475-481 (1999).

Jennings, L.D., "Cyclobutane Carboxamine Inhibitors of Fungal Melanin: Bioxsynthesis and their Evaluation as Fungicides", *Bioorg. & Medic. Chem.*, 8:897-907 (2000).

Kamei, C., et al., "Influence of certain $H_1$-blockers on the step-through active avoidance response in rats", *Psychopharmacology*, 102:312-318 (1990).

Kamei, C. & Tasaka, K., "Participation of Histamine in the Step-Through Active Avoidance Response and Its Inhibition by $H_1$-Blockers", *Japan. J. Pharmacol.*. 57:473-482 (1991).

Kiyomori, A., et al., "An Efficient Copper-atalyzed Coupling of Aryl Halides with Imidazoles", *Tetrahedron Ltrs.*, 40:2657-2660 (1999).

Klapars, A., et al, "A General and Efficient Copper Catalyst for the Amidation of Aryl Halides and the N-Arylation of Nitrogen Heterocycles", *J. Am. Chem. Soc.*, 123:7727-7729 (2001).

Komater, V.A., et al., "$H_3$ receptor blockade by thioperamide enhances cognition in rats without inducing locomotor sensitization", *Psychopharmacology*, 167:363-372 (2003).

Krische, M.J. & Lehn, J.-M., "Molecular-Recognition-Directed Self-Assembly of Pleated Sheets from 2-Aminopyrimidine Hydrogen-Bonding Motifs", *Helv. Chemica Acta*, 81:1909-1920 (1998).

Krueger, K.M.; et al., "G Protein-Dependent Pharmacology of Histamine $H_3$ Receptor ligands: Evidence for Heterogeneous Active State Receptor Conformations", *J. of Pharmacol. & Exp. Ther.*, 314(1):271-281 (2005).

Kuwabe, S.-I., et al., "Palladium-Catalyzed Intraolecular C-O Bond Formation", *J. Am. Chem. Soc.*, 123:12202-12206 (2001).

Kwong, F.Y., et al., "Copper-Catalyzed Coupling of Alkylamines and Aryl Iodides: An Efficient System Even in an Air Atmosphere", *Org. Ltrs.*, 4(4):581-584 (2002).

Lamberti, C., et al., "Antidepressant-like effects of endogenous histamine and of two histamine $H_1$ receptor agonists in the mouse forced swim test", *Brit. J. of Pharmacol.*, 123:1331-1336 (1998).

Lee, W. & Jenks, W.S., "Photophysics and Photosteromutation of Aryl Methyl Sulfoxides", *J. Org. Chem.*, 66:474-480 (2001).

Letsinger, R.L. & Dandegaonker, S.H., "Organoboron Compounds. IX. 8-Quinolineboronic Acid, its Preparation and Influence on Reactions of Chlorohydrins", *J. Amer. Chem. Soc.*, 81:498-501 (1959).

Leurs, R. & Timmerman, H., "The histamine $H_3$-receptor: A target for developing new drugs", *Prog. Drug. Res.*, 39:127-165 (1992).

Leurs, R., et al., "The medicinal chemistry and therapeutic potentials of ligands of the histamine $H_3$ receptor", *Prog. In Drug Res.*, 45:107-165 (1995).

Leurs, R., et al., "Histamine Homologues Discriminating between Two Functional $H_3$ Receptor Assays. Evidence for $H_3$ Receptor Heterogeneity?", *J. of Pharmacol. & Exp. Ther.*, 276(2):1009-1015 (1996).

Leurs, R. & Timmerman, Henk (editors), *The Histamine $H_3$ Receptor—A Target for New Drugs*, 30:Tbl of Contents (1998).

Li, G.Y., "The First Phosphine Oxide Ligand Precursors for Transition Metal Catalyzed Cross-Coupling Reactions: C-C, C-N, and C-S Bond Formation on Unactivated Aryl Chlorides", *Angew. Chem. Int. Ed.*, 40(8):1513-1516 (2001).

Li, G.Y., et al., "Highly Active, Air-Stable Versatile Palladium Catalysts for the C-C, C-N, and C-S Bond Formations via Cross-Coupling Reactions of Aryl Chlorides", *J. Org. Chem.*, 66:8677-8681 (2001).

Ligneau, X., et al., "Neurochemical and Behavioral Effects fo Ciproxifan, A Potent Histamine $H_3$-Receptor Antagonist", *J. of Pharmacol. & Exp. Ther.*, 287(2):658-666 (1993).

Lin, J.-S., et al., "Involvement of histaminergic neurons in arousal mechanisms demonstrated with $H_3$-receptor ligands in the cat", *Brain Res.*, 523:325-330 (1990).

Littke, A.F., et al., "Pd/P(t -Bu)$_3$: A Mild and General Catalyst for Stille Reactions of Aryl Chlorides and Aryl Bromides", *J. Am. Chem. Soc.*, 124:6343-6348 (2002).

Liu, G., et al., "Novel—Arylthio Cinnamides as Antagonists of Leukocyte Function-Associated Antigen- 1/Intracellular Adhesion Molecule-1 Interaction. 2. Mechanism of Inhibition and Structure-Based Improvement of Pharmaceutical Properties", *J. Med. Chem.*, 44:1202-1210 (2001).

Lozada, A.F., et al., "Plasticity of histamine $H_3$ receptor expression and binding in the vestibular nuclei after labyrinthectomy in rat", *BioMed Centr. Neurosci.*, 5:32 (2004).

Malmberg-Aiello, P., et al., "Role of histamine in rodent antinociception", *Br. J. Pharmacol.*, 111:1269-1279 (1994).

Mann, G. & Hartwig, J.F., "Palladium-Catalyzed Formation of Diaryl Ethrs from Aryl Bromides. Electron Poor Phosphines Enhance Reaction Yields", *Tetrahedron Ltrs.*, 38(46):8005-8008 (1997).

Marcoux, J.-F., et al., "A General Copper-Catalyzed Synthesis of Diaryl Ethers", *J. Am. Chem. Soc.*, 119:10539-10540 (1997).

Mazurkiewicz-Kwilecki, I.M. & Nsonwah, S., "Changes in the regional brain histamine and histidine levels in Postmortem brains of Alzheimer patients", *Can. J. Physiol. Pharmacol.*, 67:75-78 (1986).

McLeod, R.L., et al., "Combined Histamine $H_1$ and $H_3$ Receptor Blockade Produces Nasal Decongestion in an Experimental Medel of Nasal Congestion", *Amer. J. of Rhinology*, 13:391-399 (1999).

McLeod, R.L., et al., "Histamine $H_3$ Antagonists", *Prog. In Respir. Res.*, 31:133-136 (2001).

Meguro, K.-I., et al., "Effects of Thioperamide, a Histamine $H_3$ Antagonist, on the Step-Through Passive Avoidance Response and Histidine Decarboxylase Activity in Senescence-Accelerated Mice", *Pharmacol. Biochem. & Behav.*, 50(3):321-325 (1995).

Men'shchikov, F.A., et al., "Method of preparing 2- and 3-functionally substituted methylenecyclobutanes via the cycloaddition of allene with acrylic acid derivatives", *Chemical Abstracts*, 137:310640 (2006).

Mitchell, T.N., "Palladium-Catalysed Reactions of Organotin Compounds", *Synthesis*, 803-815 (1992).

Monti, J.M., et al., "Effects of selective activation or blockade of the histamine $H_3$ receptor on sleep and wakefulness", *Eur. J. of Pharmacol.*, 205:283-287 (1991).

Monti, J.M., et al., "Sleep and Walking during Acute Histamine $H_3$ Agonist BP 2.94 or $H_3$ Antagonist Carboperamide (MR 16155) Administration in Rats", *Amer. Col. of Neuropsychopharmacology*, 15(1):31-35 (1996).

Morisset, S., et al., "Atypical Neuroleptics Enhance Histamine Turnover in Brain Via 5-Hydroxytryptamine$_{2A}$ Receptor Blockade[1]", *J. of Pharmacol. & Exp. Ther.*, 288(2):590-596 (1999).

Moskal, J. & van Leusen, A.M., "Synthesis of aidehydes by a one-carbon homologation of ketones and aldehydes via α,β-unsaturated isocyanides", *Recl. Trav. Chim. Says-Bas*, 106:137-141 (1987).

Murakami, K., et al., "AQ-0145, a Newly Developed Histamine $H_3$ Antagonist, Decreased Seizure Susceptibility of Electrically Inuced Convulsions in Mice", *Meth. Find Exp. Clin. Pharmacol.*, 17(C):70-73 (1995).

Olivera, R., et al., "Dibenzoxepino[4,5-d]pyrazoles: a facile approach via the Ullmann-ether reaction", *Tetradedron Ltrs.*, 41:4353-4356 (2000).

O'Neill, A.B., et al., "Pharmacological Evaluation of the *In Vivo* Model of Vestibular Dysfunction in the Rat", *Meth. Find Exp. Clin. Pharmacol.*, 21(4):285-289 (1999).

O'Neill, B.T., et al., "Total Synthesis of (±)-Cytisine", *Org. Ltrs.*, 2(26):4201-4204 (2000).

Onodera, K., et al., "Neuropharmacology of the Histaminergic Neuron System in the Brain and It's Relationship with Behavioral Disorders", *Prog. In Neurobiol.*, 42:685-702 (1994).

Onodera, K., et al., "Improvement by FUB 181, a novel histamine $H_3$-receptor antagonist, of learning and memory in the elevated plus-maze test in mice", *Naunyn-Schmiedeberg's Arch. Pharmacol.*, 357:508-513 (1998).

Palomo, C., et al., "Phosphazene bases for the preparation of biaryl thioethers from aryl iodides and arenethuiols", *Tetrahedron Ltrs.*, 41:1283-1286 (2000).

Palucki, M., et al., "Palladium-Catalyzed Intermolecular Carbon-Oxygen Bond Formation: A New Synthesis of Aryl Ethers", *J. Am. Chem. Soc.*, 119:3395-3396 (1997).

Pan, J.B., et al., "Histaminergic Ligands Attenuate Barrel Rotation in Rats Following Unilateral Labyrinthectomy", *Meth. Find. Exp. Clin. Pharmacol.*, 20(9):771-777 (1998).

Panula, P., et al., "Neuronal Histamine deficit in Alzheimer's Disease", *Neuroscience*, 82(4):993-997 (1998).

Passani, M.B., et al., "Central histaminergic system and cognition", *Neuroscience & Biobeha. Rev.*, 24:107-113 (2000).

Pelter, A., et al., "The systhesis of homochiral ligands based on [2.2]paracyclophane", *Tetrahedron Ltrs.*, 42:8391-8394 (2001).

Penning, T.D., et al., "Structure-Activity Relationship Studies on 1-[2-(4-Phenylphenoxy)ethy]pyrrolidine (SC-22716), a Potent Inhibitor of Leukotriene $A_4$ ($LTA_4$) Hydrolase", *J. Med. Chem.*, 43:721-735 (2000).

Pérez-Garcia, C., et al., "Effects of histamine $H_3$ receptor ligands in experimental models of anxiety and depression", *Psychopharmacology*, 142:215-220 (1999).

Poste, G., et al., "Lipid vesicles as Carriers for Introducing Biologically Active Materials in to Cells", *Meth. In Cell Biol.*, XIV:33-71 (1976).

Prast, H., et al., "Histaminergic neurons facilitate social memory in rats", *Brain Res.*, 734:316-318 (1996).

*Pure Appl. Chem.*, "IUPAC Commission on Nomenclature of Organic Chemistry-Rules for the Nomenclature of Organic Chemistry", 45:13-30 (1976).

Rodriques, A.A., et al., "Interaction of clozapine with the histamine $H_3$ receptor in rat brain", *Brit. J. of Pharmacol.*, 1141523-1524 (1995).

Sakai, N., et al., "Effects of Thioperamide. A Histamine $H_3$ Receptor Antagonist. On Locomotor Activity and Brain Histamine Content in Mast Cell-Deficient W/W$^V$ Mice", *Life Sciences*, 48:2397-2404 (1991).

Sakata, T., et al., "Hypothalmic neuronal histamine modulates ad libitum feeding by rats", *Brain Research*, 537:303-306 (1990).

Sánchez-Lemus, E., et al., "Histamine $H_3$ receptor activation inhibits dopamine $D_1$ receptor-induced camp accumulation in rat striatal slices", *Neurosci. Ltrs.*, 364:179-184 (2004).

Satoh, T., et al., "Regioselective Arylation Reactions of Biphenyl-2-Ols, Naphthols, and Benzylic Compounds with Aryl Halides under Palladium Catalysis", *Bull. Chem. Soc. Jpn.*, 71(9):2239-2246 (1998).

Schopfer, U. & Schlapbach, A., "A general palladium-catalysed synthesis of aromatic and heteroaromatic thioethers", *Tetrahedron*, 57:3069-3073 (2001).

Schwartz, J.-C., et al., "Histamine", *Psychopharmacology: The 4$^{th}$ Gen. Of Prog.*, 397-405 (1995).

Schweitzer, J.B. & H.H. Holcomb, "Drugs under investigation for attention-deficit hyperactivity disorder", *Curr. Opin. In Invest. Drugs.*, 3(8):1207-1211 (2002).

Shaywitz, B.A., et al., "Dopaminergic but not noradrenergic mediation of hyperactivity and performance deficits in the developing rat pup", *Psychopharmacology*, 82:83-77 (1984).

Sindkhedkar, M.D., et al., "Aromatic interactions in the synthesis and conformation of two collapsible tetracationic cyclophanes", *Tetrahedron*, 57:2991-2996 (2001).

Stille, J.K., "The Palladium-Catalyzed Cross-Coupling Reactions of Organotin Reagents with Organic Electrophiles", *Angew. Chem. Int. Ed. Engl.*, 25:508-524 (1986).

Sugahara, M. & Ukita, T., "A Facile Copper-Catalyzed Ullmann Condensation: *N*-Arylation of Heterocyclic Compounds Containing an—NHCO-Moiety", *Chem. Pharm. Bull.*, 45(4):719-721 (1997).

Sugano, Y & Katzenellenbogen, J.A., "Synthesis of Tetradentate Bisamino-Bisthiol Complexes of Oxorhenium(V) as Structural Mimics of Steroids", *Bior. & Medicinal Chem. Ltrs.*, 6(4):361-366 (1996).

Szelag, A., "Role of histamine $H_3$-receptors in the proliferation of neoplastic cells in vitro", *Med. Sci. Monitor*, 4(5):747-7555 (1998).

Takagi, J., et al., "Iridium-catalyzed C-H coupling reaction of heteroaromatic compounds with bis(pinacolato)diboron: regioselective synthesis of heteroarylboronates", *Tetrahedron Ltrs.*, 43:5649-5651 (2002).

Takahashi, L., et al., "Syntheses of heterocyclic compounds of nitrogen", *Chemical Abstracts*, 71:41-44 (1951).

Tedford, C.E., et al., "Pharmacological Characterization of GT-2016, a Non-Thiourea-Containing Histamine $H_3$ Receptor Antagonist: In Vitro and In Vivo Studies", *J. Pharmacol. Exp. Ther.*, 275(2):598-604 (1995).

Torraca, K.E., et al., "An Efficient Intrmolecular Palladium-Catalyzed Synthesis of Aryl Ethers", *J. Amer. Chem. Soc.*, 123:10770-10771 (2001).

Toshimitsu, A., et al., "Preparation, Structure, and Reactivity of Pentacoordinate Disilanes Bearing an 8-Charcogeno-1-naphthyl Group and a Heteroatom on the Same Silicon Atom", *Het. Chem.*, 12(5):392-397 (2001).

Tozer, M.J. & Kalindjian, S.B., "Histamine $H_3$ receptor antagonists", *Exp. Opin. Ther. Pat.*, 10:1045-1055 (2000).

Vohora, D., et al., "Thiperamide, A Selective Histamine H3 Receptor Antagonist, Protects Against PTZ-Induced Seizures in Mice", *Life Sciences*, 66(22):297-301 (2000).

Wada, H., et al., "Is the histaminergic neuron system a regulatory center for whole-brain activity?", *Trends in Neurosci.*, 14(9):415-421 (1991).

Wang, Y., et al., Design and Synthesis of Ether Analogues as Potent and Selective $M_2$ Muscarinic Receptor Antagonists, *Bioorg. Medicinal Chem. Ltrs*, 11:891-894 (2001).

Weinstock, J., et al., "Synthesis and Evaluation of Non-Catechol D-1 and D-2 Dopamine Receptor Agonists: Benzimidazol-2-one, Benzoxazol-2-one, and the Highly Potent Benzothiazol-2-one 7-Ethylamines", *J. Med. Chem.*, 30:1166-1176 (1987).

Wilde, R.G., et al., "Acyl CoA:Cholesterol Acyltransferase (ACAT) Inhibitors: Ureas Bearing Heterocyclic Groups Bioisosteric for an Imidazole", *Biorg. & Medicinal Chem. Ltrs.*, 5(2):167-172 (1995).

Wolfe, J.P., et al., "Rational Development of Practical Catalysts for Aromatic Carbon-Nitrogen Bond Formation", *Acc. Chem. Res.*, 31:805-818 (1998).

Wolfe, J.P., et al., "Simple, Efficient Catalyst System for the Palladium-Catalyzed Amination of Aryl Chlorides, Bromides, and Triflates", *J. Org. Chem.*, 65:1158-1174 (2000).

Yamamoto, T. & Kurata, Y., "Ullmann condensation using copper or copper oxide as the reactant, Arylation of active hydrogen compounds (Imides, amides, amines, phenol, benzoic acid, and phenylacetylene)", *Can. J. Chem.*, 61:86-91 (1983).

Yan, G., et al., "Synthesis and Pharmacological Properties of 11-Hydroxy-3-(1', 1'-dimethylheptyl)hexahydrocannabinol: A High-Affinity Cannabinoid Agonist", *J. Med. Chem.*, 37:2619-2622 (1994).

Yang, B.H. & Buchwalk, S.L., "Palladium-catalyzed amination of aryl halides and sulfonates", *J. of Organometallic Chem.*, 576:125-146 (1999).

Yates, S.L., et al., "Identification and Pharmacological Characterization of a Series of New 1*H*-4-Substituted-Imidazoyl Histamine $H_3$ Receptor Ligands", *J. of Pharmacol. & Exp. Ther.*, 289(2):1151-1159 (1999).

Yates, S.I., et al., "Effects of a Novel Histamine H3 Receptor Antagonist, GT-2394, on Food Intake and Weight Gain in Sprague-Dawley Rats", *Abstracts. Soc. For Neurosci*, 102.10, p. 279 (2000).

Yawata, I., et al., "Role of Histaminergic neurons in development of epileptic seizures in EL mice", *Molec. Brain. Res.*, 132:13-17 (2004).

Yokoyama, H., et al., "Effect of thioperamide, a histamine $H_3$ receptor antagonist, on electrically induced convulsions in mice" *Eur. J. Pharmacol.*, 234(1):129-133 (1993).

Yokoyama, H. & Iinuma, K., "Histamine and Seizures", *CNS Drugs*, 5(5):321-330 (1995).

Zincke, T. & Müller, J., "Über 1.8-Amino-phenyl-mercaptan", *Chem. Ber.*, 46:775-786 (1913).

BENZOTHIAZOLE CYCLOBUTYL AMINE DERIVATIVES

This application claims the benefit of U.S. Provisional Patent Application No. 60/719,516, filed on Sep. 22, 2005, which is herein incorporated by reference in its entirety.

BACKGROUND OF THE INVENTION

1. Technical Field

The invention relates to benzothiazole cyclobutyl amine compounds, compositions comprising such compounds, methods for making the compounds, and methods of treating conditions and disorders using such compounds and compositions.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as histamine-3 receptors is believed to play a role in neurotransmission in the central nervous system.

The histamine-3 ($H_3$) receptor was first characterized pharmacologically on histaminergic nerve terminals (Nature, 302: 832-837 (1983)), where it regulates the release of neurotransmitters in both the central nervous system and peripheral organs, particularly the lungs, cardiovascular system and gastrointestinal tract. $H_3$ receptors are thought to be disposed presynaptically on histaminergic nerve endings, and also on neurons possessing other activity, such as adrenergic, cholinergic, serotoninergic, and dopaminergic activity. The existence of $H_3$ receptors has been confirmed by the development of selective $H_3$ receptor agonists and antagonists ((Nature, 327:117-123 (1987); Leurs and Timmerman, ed. "The History of $H_3$ Receptor: a Target for New Drugs," Elsevier (1998)).

The activity at the $H_3$ receptors can be modified or regulated by the administration of $H_3$ receptor ligands. The ligands can demonstrate antagonist, inverse agonist, agonist, or partial agonist activity. For example, $H_3$ receptors have been linked to conditions and disorders related to memory and cognition processes, neurological processes, cardiovascular function, and regulation of blood sugar, among other systemic activities. Although various classes of compounds demonstrating $H_3$ receptor-modulating activity exist, it would be beneficial to provide additional compounds demonstrating activity at the $H_3$ receptors that can be incorporated into pharmaceutical compositions useful for therapeutic methods.

SUMMARY OF THE INVENTION

The invention is directed to benzothiazole cyclobutyl amines and, more particularly, benzothiazole cyclobutyl amine derivatives having a compound of formula (I):

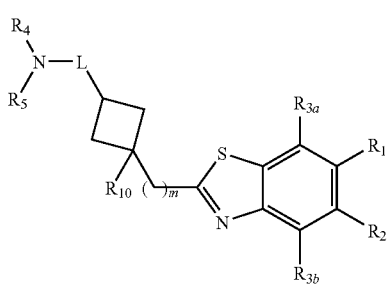

(I)

or a pharmaceutically acceptable salt, ester, amide, prodrug, or radiolabelled form thereof, wherein:

m is 0 or 1;

one of $R_1$ and $R_2$ is hydrogen, acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, haloalkoxy, haloalkyl, halogen, hydroxy, hydroxyalkyl, mercapto, nitro, alkylthio, —$NR_AR_B$, $(NR_AR_B)$carbonyl, —$SO_2N(R_{14a})(R_{14b})$, $N(R_{14a})SO_2(R_{14b})$, a group of the formula —$L_2$—$R_6$, or a group of the formula —$L_{3a}$—$R_{6a}$—$L_{3b}$—$R_{6b}$;

the other of $R_1$ and $R_2$ is selected from hydrogen, cyano, halogen, alkyl, cycloalkyl, fluoroalkyl, alkoxy, alkoxyalkyl, fluoroalkoxy, alkylthio, —$SO_2N(R_{14a})(R_{14b})$, and —$N(R_{14a})SO_2(R_{14b})$;

$R_{3a}$ and $R_{3b}$ are each independently selected from hydrogen, cyano, halogen, alkyl, cycloalkyl, fluoroalkyl, alkoxy, alkoxyalkyl, fluoroalkoxy, alkylthio, —$SO_2N(R_{14a})(R_{14b})$, and —$N(R_{14a})SO_2(R_{14b})$;

$R_4$ and $R_5$ are each independently selected from alkyl, fluoroalkyl, hydroxyalkyl, alkoxyalkyl, and cycloalkyl; or $R_4$ and $R_5$ taken together with the nitrogen atom to which each is attached form a non-aromatic ring;

$R_6$ is selected from aryl, heterocycle, and heterocyclealkyl;

$R_{6a}$ is selected from aryl and heterocycle;

$R_{6b}$ is selected from aryl and heterocycle;

L is a bond or alkylene;

$L_2$ is selected from a bond, —O—, alkylene, —C(=O)—, —S—, —$SO_2N(R_{14a})$—, —$N(R_{14a})SO_2$—, —C(O)N$(R_{14a})$—, —$N(R_{14a})C(O)$—, and —$N(R_{15})$—;

$L_{3a}$ and $L_{3b}$ are each independently selected from a bond, —O—, alkylene, —C(=O)—, —S—, —$SO_2N(R_{14a})$—, —$N(R_{14a})SO_2$—, —C(O)N$(R_{14a})$—, —$N(R_{14a})C(O)$—, and —$N(R_{15})$—;

$R_{10}$ is selected from hydrogen, cyano, fluoro, hydroxy, and alkyl;

$R_{14a}$ and $R_{14b}$ are each independently selected at each occurrence from hydrogen, alkyl, and cycloalkyl;

$R_{15}$ is selected from hydrogen, alkyl, acyl, alkoxycarbonyl and $(R_{14a})(R_{14b})$NC(O)—; and $R_A$ and $R_B$ are independently selected from hydrogen, alkyl, acyl, haloalkyl, alkoxycarbonyl, cycloalkyl, and formyl.

Another aspect of the invention relates to pharmaceutical compositions comprising compounds of the invention. Such compositions can be administered in accordance with a method of the invention, typically as part of a therapeutic regimen for treatment or prevention of conditions and disorders related to $H_3$ receptor activity.

Yet another aspect of the invention relates to a method of selectively modulating $H_3$ receptor activity. The method is useful for treating, or preventing conditions and disorders related to $H_3$ receptor modulation in mammals. More particularly, the method is useful for treating or preventing conditions and disorders related to memory and cognition processes, neurological processes, cardiovascular function, and body weight. Accordingly, the compounds and compositions of the invention are useful as a medicament for treating or preventing $H_3$ receptor modulated disease.

Yet another aspect of the invention relates to radiolabel pharmaceutical compositions useful as a radioligand. Radiolabelled forms of compounds of formula (I) can be provided as compositions of the invention and administered in accordance with a method of the invention, typically for assessing or diagnosing conditions and disorders related to $H_3$ receptor activity, for example in medical imaging. More particularly, positron-emitting isotopes of compounds of the invention may be used for medical imaging in PET (positron emitting tomography), wherein the localization of histamine $H_3$ receptors, and the extent to which these receptors are occupied by ligands, can be determined. In this use, the compounds of the invention possess at least one atom of a positron-emitting isotope selected from $^{11}C$, $^{18}F$, $^{15}O$, and $^{13}N$. Compounds of the invention may also incorporate isotopes that useful for sPECT imaging, for example $^{123}I$.

Processes for making compounds of the invention also are contemplated.

The compounds, compositions comprising the compounds, methods for making the compounds, methods for treating or preventing conditions and disorders by administering the compounds, radiolabelled forms of the compounds, and compositions containing radiolabelled forms of the compounds are further described herein.

DETAILED DESCRIPTION OF THE INVENTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. Each of the carbon atoms of the alkyl group is substituted with hydrogen or with 0, 1, or 2 substituents selected from acyl, acyloxy, alkoxy, alkoxyalkoxy, alkoxyalkyl, alkoxycarbonyl, alkoxyimino, alkoxysulfonyl, alkylcarbonyl, alkylsulfonyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, —$NR_AR_B$, ($NR_AR_B$)carbonyl, and ($NR_AR_B$)sulfonyl.

The term "alkylene" means a divalent group derived from a straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an —$NH_2$ group.

The term "aryl," as used herein, means phenyl, a bicyclic aryl, or a tricyclic aryl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl. The tricyclic aryl is a tricyclic aryl ring system such as anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, anthracenyl, phenanthrenyl, azulenyl, dihydroanthracenyl, fluorenyl, and tetrahydrophenanthrenyl.

The carbon atoms of the aryl groups of this invention are substituted with hydrogen or are optionally substituted with one or more substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_AR_B$, ($NR_AR_B$)carbonyl, —$SO_2N(R_{14a})(R_{14b})$, and $N(R_{14a})SO_2(R_{14b})$. Where the aryl group is a phenyl group, the number of substituents is 0, 1, 2, 3, 4, or 5. Where the aryl group is a bicyclic aryl, the number of substituents is 0, 1, 2, 3, 4, 5, 6, 7, 8, or 9. Where the aryl group is a tricyclic aryl, the number of substituents is 0, 1, 2, 3, 4, 5, 6, 7, 8, or 9.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(=O)— group.

The term "carboxy" as used herein means a —$CO_2H$ group, which may be protected as an ester group —$CO_2$-alkyl.

The term "cyano" as used herein means a —CN group, attached to the parent molecular moiety through the carbon.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

Each of the carbon atoms of the cycloalkyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_AR_B$, ($NR_AR_B$)carbonyl, —$SO_2N(R_{14a})(R_{14b})$, and —$N(R_{14a})SO_2(R_{14b})$.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkyl" as used herein means at least one fluoro group, as defined herein, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "fluoroalkoxy" as used herein means at least one fluoro group, as defined herein, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, heptafluoropropyloxy, and 2,2,2-trifluoroethoxy.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle", as used herein, refers to aromatic or non-aromatic cyclic groups that contain at least one heteroatom. Examples of aromatic heterocycles are, for example, heteroaryl groups as further defined below. Non-aromatic heterocycles are non-aromatic cyclic groups that contain at least one heteroatom; examples of non-aromatic heterocyclic groups or non-aromatic heterocycles are further defined below. Heterocyclic rings are connected to the parent molecular moiety through a carbon atom, or alternatively in the case of heterocyclic rings that contain a bivalent nitrogen atom having a free site for attachment, the heterocyclic ring may be connected to the parent molecular moiety though a nitrogen atom. Additionally, the heterocycles may be present as tautomers.

The term "heteroaryl", as used herein, refers to an aromatic ring containing one or more heteroatoms independently selected from nitrogen, oxygen, or sulfur, or a tautomer thereof. Such rings can be monocyclic or bicyclic as further described herein. Heteroaryl rings are connected to the parent molecular moiety, or to $L_2$, $L_{3a}$, or $L_{3b}$, wherein $L_2$, $L_{3a}$, or $L_{3b}$ are defined in formula (I), through a carbon or nitrogen atom.

The terms "monocyclic heteroaryl" or "5- or 6-membered heteroaryl ring", as used herein, refer to 5- or 6-membered aromatic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or S atom; one, two, or three N atoms are arranged in a suitable manner to provide an aromatic ring; or a ring wherein two carbon atoms in the ring are replaced with one O or S atom and one N atom. Such rings can include, but are not limited to, a six-membered aromatic ring wherein one to four of the ring carbon atoms are replaced by nitrogen atoms, five-membered rings containing a sulfur, oxygen, or nitrogen in the ring;

five-membered rings containing one to four nitrogen atoms; and five-membered rings containing an oxygen or sulfur and one to three nitrogen atoms. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, and pyrimidinonyl.

The term "bicyclic heteroaryl" or "8- to 12-membered bicyclic heteroaryl ring", as used herein, refers to an 8-, 9-, 10-, 11-, or 12-membered bicyclic aromatic ring containing at least 3 double bonds, and wherein the atoms of the ring include one or more heteroatoms independently selected from oxygen, sulfur, and nitrogen. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, and pyrrolopyrimidinyl.

Heteroaryl groups of the invention, whether monocyclic or bicyclic, may be substituted with hydrogen, or optionally substituted with one or more substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, —$NR_AR_B$, ($NR_AR_B$)carbonyl, —$SO_2N(R_{14a})$($R_{14b}$), and —$N(R_{14a})SO_2(R_{14b})$. Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the present invention may be present as tautomers.

The terms "non-aromatic heterocyclic ring" and "non-aromatic heterocycle", as used herein, refer to a 4- to 12-membered monocyclic or bicyclic ring containing at least one saturated carbon atom, and also containing one, two, three, four, or five heteroatoms independently selected from the group consisting of nitrogen, oxygen, and sulfur. Four- and five-membered rings may have zero or one double bond. Six-membered rings may have zero, one, or two double bonds. Seven- and eight-membered rings may have zero, one, two, or three double bonds. The non-aromatic heterocycle groups of the invention can be attached through a carbon atom or a nitrogen atom. The non-aromatic heterocycle groups may be present in tautomeric form. Representative examples of nitrogen-containing heterocycles include, but are not limited to, azepanyl, azetidinyl, aziridinyl, azocanyl, morpholinyl, piperazinyl, piperidinyl, pyrrolidinyl, pyrrolinyl, dihydrothiazolyl, dihydropyridinyl, and thiomorpholinyl. Representative examples of non-nitrogen containing non-aromatic heterocycles include, but are not limited to, dioxanyl, dithianyl, tetrahydrofuryl, dihydropyranyl, tetrahydropyranyl, and [1,3]dioxolanyl.

The non-aromatic heterocycles of the invention substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, —$NR_AR_B$, ($NR_AR_B$)carbonyl, —$SO_2N(R_{14a})(R_{14b})$, and —$N(R_{14a})SO_2(R_{14b})$.

Additional examples of heterocycles include, but are not limited to, isoindoline-1,3-dione, (Z)-1H-benzo[e][1,4]diazepin-5(4H)-one, pyrimidine-2,4(1H,3H)-dione, benzo[d]thiazol-2(3H)-one, pyridin-4(1H)-one, imidazolidin-2-one, 1H-imidazol-2(3H)-one, pyridazin-3(2H)-one, tetrahydropyrimidin-2(1H)-one, and 1H-benzo[d]imidazol-2(3H)-one.

The term "heterocyclealkyl" as used herein means a heterocycle group, as defined herein, appended to the parent molecular moiety through an alkyl group, as defined herein. Representative examples of heterocyclealkyl include, but are not limited to, 2-thienylmethyl, 2-thienylethyl, 2-furylethyl, and 2-furylmethyl.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyidimethylsilyl, t-butyidiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryidialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "($NR_AR_B$)alkyl" as used herein means an —$NR_AR_B$ group, as defined herein, appended to the parent molecular moiety through an alkyl group, as defined herein. $R_A$ and $R_B$ are independently selected from hydrogen, alkyl, acyl, cycloalkyl, and formyl. Representative examples of ($NR_AR_B$)alkyl include, but are not limited to, 2-(methylamino)ethyl, 2-(dimethylamino)ethyl, 2-(amino)ethyl, 2-(ethylmethylamino)ethyl, and the like.

The term "($NR_AR_B$)carbonyl" as used herein means an —$NR_AR_B$ group, as defined herein, appended to the parent molecular moiety through a carbonyl group, as defined herein. Representative examples of ($NR_AR_B$)carbonyl include, but are not limited to, aminocarbonyl, (methylamino)carbonyl, (dimethylamino)carbonyl, (ethylmethylamino)carbonyl, and the like.

The term "($NR_AR_B$)sulfonyl" as used herein means a —$NR_AR_B$ group, as defined herein, appended to the parent molecular moiety through a sulfonyl group, as defined herein. Representative examples of ($NR_AR_B$)sulfonyl include, but are not limited to, aminosulfonyl, (methylamino)sulfonyl, (dimethylamino)sulfonyl and (ethylmethylamino)sulfonyl.

The term "—N($R_{14a}$)$SO_2$($R_{14b}$)" as used herein means an amino group attached to the parent moiety to which is further appended with an $R_{14a}$ group as defined herein, and a $SO_2$ group to which is appended an ($R_{14b}$) group as defined herein. Representative examples of —N($R_{14a}$)$SO_2$($R_{14b}$) include, but are not limited to, N-methylmethanesulfonamide.

The term "—$SO_2$N($R_{14a}$)($R_{14b}$)" as used herein means a N($R_{14a}$)($R_{14b}$) group attached to a $SO_2$ group, appended to the parent moiety through the sulfonyl group. Representative examples of —$SO_2$N($R_{14a}$)($R_{14b}$) include, but are not limited to (dimethylamino)sulfonyl and N-cyclohexyl-N-methylsulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-OC=O)$_2$O, a diaryl anhydride, for example as represented by (aryl-OC=O)$_2$O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —S(O)$_2$— group.

As used herein, the term "antagonist" encompasses and describes compounds that prevent receptor activation by an $H_3$ receptor agonist alone, such as histamine, and also encompasses compounds known as "inverse agonists". Inverse agonists are compounds that not only prevent receptor activation by an $H_3$ receptor agonist, such as histamine, but also inhibit intrinsic $H_3$ receptor activity.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3H$ (tritium), $^{14}C$, $^{11}C$, $^{15}O$, $^{18}F$, $^{35}S$, $^{123}I$, and $^{125}I$.

Compounds of the Invention

Compounds of the invention can have the formula (I) as described in the Summary of the Invention In compounds of formula (I), m is 0 or 1. Preferably, m is 0.

L is a bond or L is alkylene. L is preferably a bond.

One of $R_1$ and $R_2$ in a compound of formula (I) is hydrogen, acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, haloalkoxy, haloalkyl, halogen, hydroxy, hydroxyalkyl, mercapto, nitro, alkylthio, —N$R_A R_B$, (N$R_A R_B$)carbonyl, —N($R_A$)alkylsulfonyl, (N$R_{14a}R_{14b}$)sulfonyl, or a group of the formula —$L_2$—$R_6$ or —$L_{3a}$—$R_{6a}$—$L_{3b}$—$R_{6b}$. The other group represented by $R_1$ or $R_2$ is hydrogen, cyano, halogen, alkyl, cycloalkyl, fluoroalkyl, alkoxy, alkoxyalkyl, fluoroalkoxy, alkylthio, $SO_2$N($R_{14a}$)($R_{14b}$), or N($R_{14a}$)$SO_2$($R_{14b}$), wherein $R_{14a}$ and $R_{14b}$ are each independently hydrogen, alkyl, or cycloalkyl, and more preferably are hydrogen or alkyl, particularly methyl. When $R_1$ or $R_2$ is not —$L_2$—$R_6$ or —$L_{3a}$—$R_{6a}$—$L_{3b}$—$R_{6b}$, the preferred group is hydrogen.

Preferably, $R_1$ is —$L_2$—$R_6$ or —$L_{3a}$—$R_{6a}$—$L_{3b}$—$R_{6b}$ and $R_2$ is hydrogen, cyano, halogen, alkyl, cycloalkyl, fluoroalkyl, alkoxy, alkoxyalkyl, and fluoroalkoxy. More preferably, $R_1$ is —$L_2$—$R_6$.

$L_2$ is selected from a bond, —O—, alkylene, —C(=O)—, —S—, —$SO_2$N($R_{14a}$)—, N($R_{14a}$)$SO_2$—, C(O)N($R_{14a}$)—, —N($R_{14a}$)C(O)—, and —N($R_{15}$)—. Preferably, $L_2$ is a bond.

Preferably, $R_6$ is a heterocycle. Examples of suitable heterocycles for $R_6$ include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, pyrimidinonyl, indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, pyrrolopyrimidinyl, azepanyl, azetidinyl, aziridinyl, azocanyl, morpholinyl, piperazinyl, piperidinyl, pyrrolidinyl, pyrrolinyl, dihydrothiazolyl, dihydropyridinyl, thiomorpholinyl, dioxanyl, dithianyl, tetrahydrofuryl, dihydropyranyl, tetrahydropyranyl, and [1,3]dioxolanyl.

Preferred heterocycles for $R_6$ are pyrazolyl, pyrimidinyl, pyrimidinonyl, pyridinyl, pyridazinonyl, and quinolinyl, wherein each ring is substituted with 0, 1, or 2 substituents selected from methoxy and methyl.

$L_{3a}$ and $L_{3b}$ are each independently selected from a bond, —O—, alkylene, —C(=O)—, —S—, —$SO_2$N($R_{14a}$)—, —N($R_{14a}$)$SO_2$—, —C(O)N($R_{14a}$)—, —N($R_{14a}$)C(O)—, and —N($R_{15}$)—. Preferably, $L_{3a}$ is a bond. $L_{3b}$ also is preferred to be a bond.

A preferred aryl group at $R_{6a}$ is cyanophenyl. Preferably, $R_{6a}$ is a heterocycle. Examples of suitable heterocycles for $R_{6a}$ include, but are not limited to pyrazinyl, pyrazolyl, pyridazinyl, pyridinyl, pyrimidinyl, pyrrolyl, pyridazinonyl, pyridonyl, pyrimidinonyl, pyrrolidinyl, pyrrolinyl and quinolinyl. More preferred heterocycles for $R_{6a}$ are pyrazolyl, pyrimidinyl, pyrimidinonyl, pyridinyl, pyridazinonyl, and quinolinyl wherein each ring is substituted with 0, 1, or 2 substituents selected from methoxy and methyl.

A preferred aryl group at $R_{6b}$ is cyanophenyl. Preferably, $R_{6b}$ is a heterocycle. Examples of suitable heterocycles for $R_{6b}$ include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, pyrimidinonyl, indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, pyrrolopyrimidinyl, azepanyl, azetidinyl, aziridinyl, azocanyl, morpholinyl, piperazinyl, piperidinyl, pyrrolidinyl, pyrrolinyl, dihydrothiazolyl, dihydropyridinyl, thiomorpholinyl, dioxanyl, dithianyl, tetrahydrofuryl, dihydropyranyl, tetrahydropyranyl, and

[1,3]dioxolanyl. More preferred heterocycles for $R_{6b}$ are pyrazinyl, pyrazolyl, pyridazinyl, pyridinyl, pyrimidinyl, pyrrolyl, pyridazinonyl, pyridonyl, pyrimidinonyl, pyrrolidinyl, pyrrolinyl and quionolyl, wherein each ring is substituted with 0, 1, or 2 substituents selected from methoxy and methyl.

$R_{3a}$ and $R_{3b}$ are each independently hydrogen, cyano, halogen, alkyl, cycloalkyl, fluoroalkyl, alkoxy, alkoxyalkyl, fluoroalkoxy, alkylthio, $SO_2N(R_{14a})(R_{14b})$, or —$N(R_{14a})SO_2$ $(R_{14b})$. $R_{3a}$ and $R_{3b}$ are both preferred to be hydrogen.

In one embodiment, $R_4$ and $R_5$ are each independently alkyl, fluoroalkyl, hydroxyalkyl, alkoxyalkyl, or cycloalkyl. In this embodiment, $R_4$ and $R_5$ are preferably alkyl or hydroxyalkyl, and more particularly methyl, ethyl, propyl, and hydroxyethyl. Groups selected for $R_4$ and $R_5$ need not be the same.

Alternatively, $R_4$ and $R_5$ are taken together with the nitrogen atom to which each is attached form a non-aromatic ring. The non-aromatic ring form can be any nitrogen-containing non-aromatic ring. Examples of non-aromatic rings suitable for the embodiment wherein $R_4$ and $R_5$ are taken together to form a ring include, but are not limited to, non-aromatic rings having the formulas:

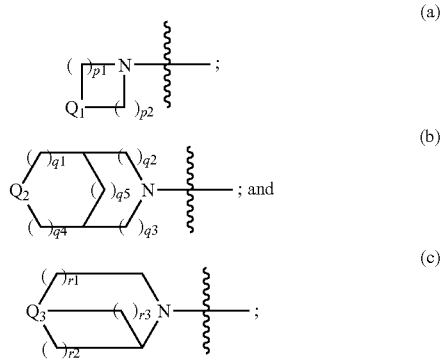

$Q_1$ is O, S, —$N(R_{20})$—, or C;

$Q_2$ is —$N(R_{20})$— or C;

$Q_3$ is N or C;

$R_{20}$ is selected from the group consisting of hydrogen, alkyl and alkylcarbonyl;

p1 and p2 are each independently 1, 2 or 3;

q1, q2, q3, q4, and q5 are each independently 0, 1, or 2; and r1, r2 and r3 are each independently 1 or 2;

wherein each carbon atom in the ring is substituted with hydrogen, or with 0, 1, or 2 substituents independently selected at each occurrence from the group consisting of hydroxy, fluoro, alkyl, hydroxyalkyl, fluoroalkyl, cycloalkyl, cyano, fluoroalkoxy, alkoxyalkyl, alkoxy, fluoroalkoxy, haloalkyl, and —$N(R_{21a})(R_{21b})$, wherein $R_{21a}$ and $R_{21b}$ are each independently selected from the group consisting of hydrogen, alkyl, and alkylcarbonyl.

Preferred groups for forming the ring of $R_4$ and $R_5$ have the formula (a) or (b). More particularly, $R_4$ and $R_5$ are taken together with the nitrogen atom to which each is attached to form azepanyl, azetidinyl, aziridinyl, azocanyl, morpholinyl, piperazinyl, piperidinyl, pyrrolidinyl, pyrrolinyl, and hexahydropyrrolo[3,4-b]pyrrolyl, wherein each group is substituted with 0, 1, or 2 substituents selected from alkyl, hydroxyalkyl, hydroxy, fluoro and fluoroalkyl.

Preferred rings of the formula (a) are piperidine, pyrrolidine, 4-fluoropiperidine, 4-hydroxypiperidine, 2-methylpiperidine, (2R)-methylpyrrolidine ring and (2S)-methylpyrrolidine ring.

A preferred ring of the formula (b) is

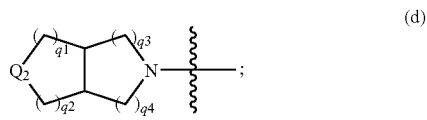

$Q_2$ is —$N(R_{20})$—;

wherein $q_1$, $q_2$, $q_3$, and $q_4$ are each 1; and $R_{20}$ is hydrogen or alkyl. In another embodiment $q_1$ is 0, $q_2$ is 2 and $q_3$ and $q_4$ are each 1.

Another embodiment of the invention is compounds of the formula (II):

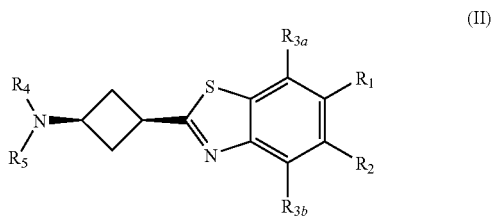

wherein $R_1$, $R_2$, $R_{3a}$, $R_{3b}$, $R_4$, and $R_5$ are as described for compounds of formula (I). In one embodiment, $R_1$ is —$L_2$—$R_6$, $R_2$ is hydrogen, $R_{3a}$ and $R_{3b}$ are both hydrogen, and $R_4$ and $R_5$ taken together form a non-aromatic ring. In another embodiment, $R_1$ is hydrogen, $R_2$ is —$L_2$—$R_6$, $R_{3a}$ and $R_{3b}$ are both hydrogen, and $R_4$ and $R_5$ taken together form a non-aromatic ring.

Another embodiment of the invention is compounds of the formula (III):

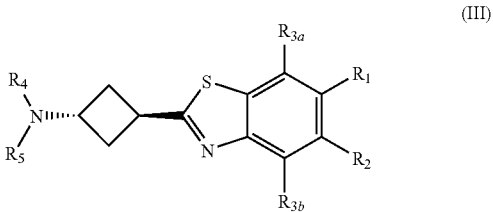

wherein $R_1$, $R_2$, $R_{3a}$, $R_{3b}$, $R_4$, and $R_5$ are as described for compounds of formula (I). In one embodiment, $R_1$ is —$L_2$—$R_6$, $R_2$ is hydrogen, $R_{3a}$ and $R_{3b}$ are both hydrogen, and $R_4$ and $R_5$ taken together form a non-aromatic ring. In another embodiment, $R_1$ is hydrogen, $R_2$ is —$L_2$—$R_6$, $R_{3a}$ and $R_{3b}$ are both hydrogen, and $R_4$ and $R_5$ taken together form a non-aromatic ring.

Suitable groups for each position in compounds of formula (I), for example, $R_1$, $R_2$, $R_{3a}$, $R_{3b}$, $R_4$, and $R_5$, and the integer represented by m, in all embodiments, each can be determined independently of substitutions in other positions of the compound. It is contemplated that a preferred group represented by one variable, for example $R_1$ is —$L_2R_6$ wherein $L_2$ is a defined for $R_1$ and $R_6$ is heterocycle, can be incorporated into compounds of formula (I) with a preferred group for another variable, for example wherein $R_4$ and $R_5$ is a group of formula (d) as previously described from $R_4$ and $R_5$.

One embodiment contemplated as part of the invention includes, but is not limited to, compounds of formula (I) wherein m is 0; L is a bond; $L_2$ is a bond, —O—, alkylene, —C(=O)—, —S—, —SO$_2$N(R$_{14a}$)—, N(R$_{14a}$)SO$_2$—, —C(O)N(R$_{14a}$)—, —N(R$_{14a}$)C(O)—, or —N(R$_{15}$)—, wherein $R_{14a}$, $R_{14b}$, and $R_{15}$ are as previously defined for compounds of formula (I); and $R_6$ is heterocycle.

One embodiment contemplated as part of the invention includes, but is not limited to, compounds of formula (I) wherein m is 0, L is a bond, $L_2$ is a bond, and $R_6$ is heterocycle.

Another specific embodiment contemplated as part of the invention includes, but is not limited to, compounds of formula (I) wherein m is 0; $L_2$ is a bond, —O—, alkylene, —C(=O)—, —S—, —SO$_2$N(R$_{14a}$)—, —N(R$_{14a}$)SO$_2$—, C(O)N(R$_{14a}$)—, —N(R$_{14a}$)C(O)—, or —N(R$_{15}$)—, wherein $R_{14a}$, $R_{14b}$, and $R_{15}$ are as previously defined for compounds of formula (I); $R_6$ is heterocycle; and $R_4$ and $R_5$ are taken together to form a non-aromatic ring of the structure (a), (b), or (c), as previously described for $R_4$ and $R_5$.

Another specific embodiment contemplated as part of the invention includes, but is not limited to, compounds of formula (I) wherein m is 0, $L_2$ is a bond, $R_6$ is heterocycle, and $R_4$ and $R_5$ are taken together to form a non-aromatic ring of the structure (a), (b), or (c), as previously described for $R_4$ and $R_5$.

Another specific embodiment contemplated as part of the invention includes, but is not limited to, compounds of formula (I) wherein m is 0, L is a bond, $R_6$ is heterocycle, and $R_4$ and $R_5$ are taken together to form a non-aromatic ring of the structure (a), (c), or (d), as previously described for $R_4$ and $R_5$.

Another embodiment of preferred compounds are compounds of formula (I) wherein $R_1$ or $R_2$ is $L_2R_6$, $L_2$ is a bond, and $R_6$ is a structure of formula:

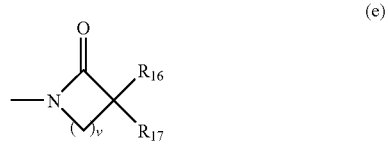

(e)

wherein $R_{16}$ and $R_{17}$ each are independently selected from hydrogen, alkyl, haloalkyl, cycloalkyl, alkoxyalkyl, aryl, and heteroaryl; or $R_{16}$ and $R_{17}$ taken together with the carbon atom to which each is attached form a 3- to 7-membered ring; v is 1, 2, 3, 4, 5, or 6; and all other variables are as defined for compounds of formula (I).

Specific embodiments contemplated as part of the invention also include, but are not limited to, compounds of formula (I), as defined, for example:
Trans-2-{3-[(2R)-2-methylpyrrolidin-1-yl]cyclobutyl}-6-pyrimidin-5-yl-1,3-benzothiazole;
Trans-6-(2,6-dimethylpyridin-3-yl)-2-{3-[(2R)-2-methylpyrrolidin-1-yl]cyclobutyl}-1,3-benzothiazole;
Trans-6-(2,4-dimethoxypyrimidin-5-yl)-2-{3-[(2R)-2-methylpyrrolidin-1-yl]cyclobutyl}-1,3-benzothiazole;
Trans-6-(2-methoxypyrimidin-5-yl)-2-{3-[(2R)-2-methylpyrrolidin-1-yl]cyclobutyl}-1,3-benzothiazole;
Trans-2-{3-[(2R)-2-methylpyrrolidin-1-yl]cyclobutyl}-6-pyridin-4-yl-1,3-benzothiazole;
Trans-6-(6-methoxypyridin-3-yl)-2-{3-[(2R)-2-methylpyrrolidin-1-yl]cyclobutyl}-1,3-benzothiazole;
Trans-2-{3-[(2R)-2-methylpyrrolidin-1-yl]cyclobutyl}-6-pyridin-3-yl-1,3-benzothiazole;
Trans-3-(2-{3-[(2R)-2-methylpyrrolidin-1-yl]cyclobutyl}-1,3-benzothiazol-6-yl)quinoline;
Trans-6-(6-fluoropyridin-3-yl)-2-{3-[(2R)-2-methylpyrrolidin-1-yl]cyclobutyl}-1,3-benzothiazole;
Trans-4-(2-{3-[(2R)-2-methylpyrrolidin-1-yl]cyclobutyl}-1,3-benzothiazol-6-yl)benzonitrile;
Trans-2-{3-[(2S)-2-methylpyrrolidin-1-yl]cyclobutyl}-6-pyrimidin-5-yl-1,3-benzothiazole;
Trans-6-(2,4-dimethoxypyrimidin-5-yl)-2-{3-[(2S)-2-methylpyrrolidin-1-yl]cyclobutyl}-1,3-benzothiazole;
Trans-6-(2,6-dimethylpyridin-3-yl)-2-{3-[(2S)-2-methylpyrrolidin-1-yl]cyclobutyl}-1,3-benzothiazole;
Trans-6-(2-methoxypyrimidin-5-yl)-2-{3-[(2S)-2-methylpyrrolidin-1-yl]cyclobutyl}-1,3-benzothiazole;
Trans-6-(6-methoxypyridin-3-yl)-2-{3-[(2S)-2-methylpyrrolidin-1-yl]cyclobutyl}-1,3-benzothiazole;
Trans-3-(2-{3-[(2S)-2-methylpyrrolidin-1-yl]cyclobutyl}-1,3-benzothiazol-6-yl)quinoline;
Cis-2-{3-[(2R)-2-methylpyrrolidin-1-yl]cyclobutyl}-6-pyrimidin-5-yl-1,3-benzothiazole;
Cis-6-(2,6-dimethylpyridin-3-yl)-2-{3-[(2R)-2-methylpyrrolidin-1-yl]cyclobutyl}-1,3-benzothiazole;
Cis-2-{3-[(2S)-2-methylpyrrolidin-1-yl]cyclobutyl}-6-pyrimidin-5-yl-1,3-benzothiazole;
Cis-6-(2,4-dimethoxypyrimidin-5-yl)-2-{3-[(2S)-2-methylpyrrolidin-1-yl]cyclobutyl}-1,3-benzothiazole;
Cis-6-(2,6-dimethylpyridin-3-yl)-2-{3-[(2S)-2-methylpyrrolidin-1-yl]cyclobutyl}-1,3-benzothiazole;
Trans-2-(2-{3-[(2R)-2-methylpyrrolidin-1-yl]cyclobutyl}-1,3-benzothiazol-6-yl)pyridazin-3(2H)-one;
Trans-6-methyl-2-(2-{3-[(2R)-2-methylpyrrolidin-1-yl]cyclobutyl}-1,3-benzothiazol-6-yl)pyridazin-3(2H)-one;
Trans-5-methyl-1-(2-{3-[(2R)-2-methylpyrrolidin-1-yl]cyclobutyl}-1,3-benzothiazol-6-yl)pyridin-2(1H)-one;
Trans-3-methyl-1-(2-{3-[(2R)-2-methylpyrrolidin-1-yl]cyclobutyl}-1,3-benzothiazol-6-yl)pyridin-2(1H)-one;
Trans-2-(2-{3-[(2S)-2-methylpyrrolidin-1-yl]cyclobutyl}-1,3-benzothiazol-6-yl)pyridazin-3(2H)-one;
Trans-6-methyl-2-(2-{3-[(2S)-2-methylpyrrolidin-1-yl]cyclobutyl}-1,3-benzothiazol-6-yl)pyridazin-3(2H)-one;
Trans-5-methyl-1-(2-{3-[(2S)-2-methylpyrrolidin-1-yl]cyclobutyl}-1,3-benzothiazol-6-yl)pyridin-2(1H)-one;
Trans-3-methyl-1-(2-{3-[(2S)-2-methylpyrrolidin-1-yl]cyclobutyl}-1,3-benzothiazol-6-yl)pyridin-2(1H)-one;
Cis-6-pyrimidin-5-yl-2-(3-pyrrolidin-1-ylcyclobutyl)-1,3-benzothiazole;
Cis-6-(2-methoxypyrimidin-5-yl)-2-(3-pyrrolidin-1-ylcyclobutyl)-1,3-benzothiazole;
Cis-2-(3-piperidin-1-ylcyclobutyl)-6-pyrimidin-5-yl-1,3-benzothiazole
Cis-6-(2-methoxypyrimidin-5-yl)-2-(3-piperidin-1-ylcyclobutyl)-1,3-benzothiazole;
Cis-2-(3-azepan-1-ylcyclobutyl)-6-pyrimidin-5-yl-1,3-benzothiazole;
Cis-2-(3-morpholin-4-ylcyclobutyl)-6-pyrimidin-5-yl-1,3-benzothiazole;
Cis-{(2S)-1-[3-(6-pyrimidin-5-yl-1,3-benzothiazol-2-yl)cyclobutyl]pyrrolidin-2-yl}methanol;
Cis-((2S)-1-{3-[6-(2-methoxypyrimidin-5-yl)-1,3-benzothiazol-2-yl]cyclobutyl}pyrrolidin-2-yl)methanol;
Cis-2-{3-[(3aR,6aR)-hexahydropyrrolo[3,4-b]pyrrol-5(1H)-yl]cyclobutyl}-6-pyrimidin-5-yl-1,3-benzothiazole;
Cis-2-{3-[(3aR,6aR)-hexahydropyrrolo[3,4-b]pyrrol-5(1H)-yl]cyclobutyl}-6-(2-methoxypyrimidin-5-yl)-1,3-benzothiazole;
Cis-2-{3-[(2R)-2-methylpiperidin-1-yl]cyclobutyl}-6-pyrimidin-5-yl-1,3-benzothiazole;
Cis-N-isopropyl-N-methyl-N-[3-(6-pyrimidin-5-yl-1,3-benzothiazol-2-yl)cyclobutyl]amine;

Cis-{1-[3-(6-pyrimidin-5-yl-1,3-benzothiazol-2-yl)cyclobutyl]piperidin-4-yl}methanol;
Trans-{1-[3-(6-pyrimidin-5-yl-1,3-benzothiazol-2-yl)cyclobutyl]piperidin-4-yl}methanol;
Trans-2-(3-piperidin-1-ylcyclobutyl)-6-pyrimidin-5-yl-1,3-benzothiazole;
Trans-6-(2,6-dimethylpyridin-3-yl)-2-(3-piperidin-1-ylcyclobutyl)-1,3-benzothiazole;
Trans-6-(6-methoxypyridin-3-yl)-2-(3-piperidin-1-ylcyclobutyl)-1,3-benzothiazole;
Trans-6-(2-methoxypyrimidin-5-yl)-2-(3-piperidin-1-ylcyclobutyl)-1,3-benzothiazole;
Trans-2-[2-(3-piperidin-1-ylcyclobutyl)-1,3-benzothiazol-6-yl]pyridazin-3(2H)-one;
Cis-2-[2-(3-piperidin-1-ylcyclobutyl)-1,3-benzothiazol-6-yl]pyridazin-3(2H)-one;
Trans-6-methyl-2-[2-(3-piperidin-1-ylcyclobutyl)-1,3-benzothiazol-6-yl]pyridazin-3(2H)-one;
Trans-3-methyl-1-[2-(3-piperidin-1-ylcyclobutyl)-1,3-benzothiazol-6-yl]pyridin-2(1H)-one;
Trans-6-(1-methyl-1H-pyrazol-4-yl)-2-(3-piperidin-1-ylcyclobutyl)-1,3-benzothiazole;
Trans-N-isopropyl-N-methyl-{3-[6-(6-pyrimidin-5-yl-1,3-benzothiazol-2-yl)cyclobutyl]amine;
Trans-N-isopropyl-N-{3-[6-(2-methoxypyrimidin-5-yl)-1,3-benzothiazol-2-yl]cyclobutyl}-N-methylamine;
Trans-N-isopropyl-N-{3-[6-6-methoxypyridin-3-yl)-1,3-benzothiazol-2-yl]cyclobutyl}-N-methylamine;
Trans-N-isopropyl-N-{3-[6-(2-methoxypyridin-3-yl)-1,3-benzothiazol-2-yl]cyclobutyl}-N-methylamine;
Trans-N-{3-[6-(2,6-dimethylpyridin-3-yl)-1,3-benzothiazol-2-yl]cyclobutyl}-N-isopropyl-N-methylamine;
Trans-2-(2-{3-[isopropyl(methyl)amino]cyclobutyl}-1,3-benzothiazol-6-yl)pyridazin-3(2H)-one;
Trans-2-(2-{3-[isopropyl(methyl)amino]cyclobutyl}-1,3-benzothiazol-6-yl)-6-methylpyridazin-3(2H)-one;
Trans-1-(2-{3-[isopropyl(methyl)amino]cyclobutyl}-1,3-benzothiazol-6-yl)-3-methylpyridin-2(1H)-one;
Trans-1-(2-{3-[isopropyl(methyl)amino]cyclobutyl}-1,3-benzothiazol-6-yl)-5-methylpyridin-2(1H)-one;
Trans-2-(3-azetidin-1-ylcyclobutyl)-6-pyrimidin-5-yl-1,3-benzothiazole;
Trans-6-pyrimidin-5-yl-2-(3-pyrrolidin-1-ylcyclobutyl)-1,3-benzothiazole;
Trans-6-(2,6-dimethylpyridin-3-yl)-2-(3-pyrrolidin-1-ylcyclobutyl)-1,3-benzothiazole;
Trans-6-(2-methoxypyrimidin-5-yl)-2-(3-pyrrolidin-1-ylcyclobutyl)-1,3-benzothiazole;
Trans-6-(2,4-dimethoxypyrimidin-5-yl)-2-(3-pyrrolidin-1-ylcyclobutyl)-1,3-benzothiazole;
Trans-6-(6-methoxypyridin-3-yl)-2-(3-pyrrolidin-1-ylcyclobutyl)-1,3-benzothiazole;
Trans-2-[2-(3-pyrrolidin-1-ylcyclobutyl)-1,3-benzothiazol-6-yl]pyridazin-3(2H)-one;
Trans-6-methyl-2-[2-(3-pyrrolidin-1-ylcyclobutyl)-1,3-benzothiazol-6-yl]pyridazin-3(2H)-one;
Trans-5-methyl-1-[2-(3-pyrrolidin-1-ylcyclobutyl)-1,3-benzothiazol-6-yl]pyridin-2(1H)-one;
Trans-3-methyl-1-[2-(3-pyrrolidin-1-ylcyclobutyl)-1,3-benzothiazol-6-yl]pyridin-2(1H)-one;
Trans-2-(3-azepan-1-ylcyclobutyl)-6-pyrimidin-5-yl-1,3-benzothiazole;
Trans-2-(3-morpholin-4-ylcyclobutyl)-6-pyrimidin-5-yl-1,3-benzothiazole;
Trans-2-{3-[(2S)-2-(fluoromethyl)pyrrolidin-1-yl]cyclobutyl}-6-pyrimidin-5-yl-1,3-benzothiazole;
Trans-{(2S)-1-[3-(6-pyrimidin-5-yl-1,3-benzothiazol-2-yl)cyclobutyl]pyrrolidin-2-yl}methanol;
Trans-((2S)-1-{3-[6-(2,6-dimethylpyridin-3-yl)-1,3-benzothiazol-2-yl]cyclobutyl}pyrrolidin-2-yl)methanol;
Trans-2-[3-(2-methylpiperidin-1-yl)cyclobutyl]-6-pyrimidin-5-yl-1,3-benzothiazole;
Trans-2-(3-hexahydropyrrolo[3,4-b]pyrrol-5(1H)-ylcyclobutyl)-6-pyrimidin-5-yl-1,3-benzothiazole;
Trans-2-[3-(4-fluoropiperidin-1-yl)cyclobutyl]-6-pyrimidin-5-yl-1,3-benzothiazole;
Trans-2-[3-(4-fluoropiperidin-1-yl)cyclobutyl]-6-(2-methoxypyrimidin-5-yl)-1,3-benzothiazole;
Trans-6-(2,6-dimethylpyridin-3-yl)-2-[3-(4-fluoropiperidin-1-yl)cyclobutyl]-1,3-benzothiazole;
Trans-(3R)-1-[3-(6-pyrimidin-5-yl-1,3-benzothiazol-2-yl)cyclobutyl]piperidin-3-ol;
Trans-N-ethyl-N-propyl-N-[3-(6-pyrimidin-5-yl-1,3-benzothiazol-2-yl)cyclobutyl]amine;
Trans-Diethyl-[3-(6-pyrimidin-5-yl-benzothiazol-2-yl)-cyclobutyl]-amine;
Trans-Diethyl-{3-[6-(2-methoxy-pyrimidin-5-yl)-benzothiazol-2-yl]-cyclobutyl}-amine;
Trans-{3-[6-(2-Methoxy-pyrimidin-5-yl)-benzothiazol-2-yl]-cyclobutyl}-methyl-propyl-amine;
Trans-{3-[6-(2,6-Dimethyl-pyridin-3-yl)-benzothiazol-2-yl]-cyclobutyl}-methyl-propyl-amine;
Trans-Methyl-{3-[6-(1-methyl-1H-pyrazol-4-yl)-benzothiazol-2-yl]-cyclobutyl}-propyl-amine;
Trans-2-(Ethyl-{3-[6-(2-methoxy-pyrimidin-5-yl)-benzothiazol-2-yl]-cyclobutyl}-amino)-ethanol;
Trans-2-({3-[6-(2,6-Dimethyl-pyridin-3-yl)-benzothiazol-2-yl]-cyclobutyl}-ethyl-amino)-ethanol;
6-Pyrimidin-5-yl-2-(3-pyrrolidin-1-ylmethyl-cyclobutyl)-benzothiazole;
Trans-5-(2,6-Dimethyl-pyridin-3-yl)-2-[3-(2-methyl-pyrrolidin-1-yl)-cyclobutyl]-benzothiazole;
Trans-5-(2,4-Dimethoxy-pyrimidin-5-yl)-2-[3-(2-methyl-pyrrolidin-1-yl)-cyclobutyl]-benzothiazole;
Trans-6-(1-Methyl-1H-pyrazol-4-yl)-2-[3-(2-methyl-pyrrolidin-1-yl)-cyclobutyl]-benzothiazole;
Trans-2-[3-(4-Fluoro-piperidin-1-yl)-cyclobutyl]-6-(1-methyl-1H-pyrazol-4-yl)-benzothiazole;
Trans-2-(3-azetidin-1-ylcyclobutyl)-6-(2-methoxypyrimidin-5-yl)-1,3-benzothiazole;
Trans-2-(3-azetidin-1-ylcyclobutyl)-6-(2,6-dimethylpyridin-3-yl)-1,3-benzothiazole;
Trans-2-(3-azetidin-1-ylcyclobutyl)-6-(1-methyl-1H-pyrazol-4-yl)-1,3-benzothiazole;
Trans-2-(3-azepan-1-ylcyclobutyl)-6-(2-methoxypyrimidin-5-yl)-1,3-benzothiazole;
Trans-2-(3-azepan-1-ylcyclobutyl)-6-(2,6-dimethylpyridin-3-yl)-1,3-benzothiazole;
Trans-2-(3-azepan-1-ylcyclobutyl)-6-(1-methyl-1H-pyrazol-4-yl)-1,3-benzothiazole;
Cis-N-[2-(3-Piperidin-1-yl-cyclobutyl)-benzothiazole-6-yl]-acetamide;
Cis-2-Chloro-N-[2-(3-Piperidin-1-yl-cyclobutyl)-benzothiazole-6-yl]-acetamide;
Cis-N-[2-(3-Piperidin-1-yl-cyclobutyl)-benzothiazole-6-yl]-propionamide;
Cis-N-[2-(3-Piperidin-1-yl-cyclobutyl)-benzothiazole-6-yl]-isobutyramide;
Cis-Cyclopropanecarboxylic acid[2-(3-Piperidin-1-yl-cyclobutyl)-benzothiazole-6-yl]-amide;
Cis-Cyclobutanecarboxylic acid[2-(3-Piperidin-1-yl-cyclobutyl)-benzothiazole-6-yl]-amide;
Cis-Cyclopentanecarboxylic acid[2-(3-Piperidin-1-yl-cyclobutyl)-benzothiazole-6-yl]-amide;
Cis-Cyclohexanecarboxylic acid[2-(3-Piperidin-1-yl-cyclobutyl)-benzothiazole-6-yl]-amide;
Cis-Furan-2-carboxylic acid[2-(3-Piperidin-1-yl-cyclobutyl)-benzothiazole-6-yl]-amide;
Cis-4-Cyano-N-[2-(3-Piperidin-1-yl-cyclobutyl)-benzothiazole-6-yl]-benzamide;

Cis-4-Cyano-N-[2-(3-Piperidin-1-yl-cyclobutyl)-benzothiazole-6-yl]-benzenesulfonamide;
Cis-Thiophene-2-sulfonic acid-[2-(3-Piperidin-1-yl-cyclobutyl)-benzothiazole-6-yl]-amide;
113 Cis-Thiophene-2-carboxylic acid-[2-(3-Piperidin-1-yl-cyclobutyl)-benzothiazole-6-yl]-amide;
Cis-Thiophene-2-carboxylic acid-[2-(3-Piperidin-1-yl-cyclobutyl)-benzothiazole-6-yl]-amide;
Cis-[2-(3-Piperidin-1-yl-cyclobutyl)-benzothiazole-6-yl]-carbamic acid isobutyl ester;
Cis-Morpholine-4-carboxylic acid-[2-(3-Piperidin-1-yl-cyclobutyl)-benzothiazole-6-yl]-amide;
Cis-Pyrazine-2-carboxylic acid-[2-(3-Piperidin-1-yl-cyclobutyl)-benzothiazole-6-yl]-amide;
Cis-N-[2-(3-Piperidin-1-yl-cyclobutyl)-benzothiazole-6-yl]-2-thiophen-3-yl-acetamide;
Cis-N-[2-(3-Piperidin-1-yl-cyclobutyl)-benzothiazole-6-yl]-3-thiophen-2-yl-propionamide;
Cis-3-Furan-2-yl-N-[2-(3-Piperidin-1-yl-cyclobutyl)-benzothiazole-6-yl]-propionamide;
Cis-Pyrimidine-5-carboxylic acid-[2-(3-Piperidin-1-yl-cyclobutyl)-benzothiazole-6-yl]-amide;
Trans-4-Cyano-N-[2-(3-Piperidin-1-yl-cyclobutyl)-benzothiazole-6-yl]-benzamide;
Trans-N-[2-(3-Piperidin-1-yl-cyclobutyl)-benzothiazole-6-yl]-propionamide;
Trans-N-[2-(3-Piperidin-1-yl-cyclobutyl)-benzothiazole-6-yl]-isobutyramide;
Trans-[2-(3-Piperidin-1-yl-cyclobutyl)-benzothiazole-6-yl]-carbamic acid isobutyl ester;
Trans-Cyclopropanecarboxylic acid[2-(3-Piperidin-1-yl-cyclobutyl)-benzothiazole-6-yl]-amide;
Trans-Cyclobutanecarboxylic acid[2-(3-Piperidin-1-yl-cyclobutyl)-benzothiazole-6-yl]-amide;
Trans-Cyclopentanecarboxylic acid[2-(3-Piperidin-1-yl-cyclobutyl)-benzothiazole-6-yl]-amide;
Trans-Cyclohexanecarboxylic acid[2-(3-Piperidin-1-yl-cyclobutyl)-benzothiazole-6-yl]-amide;
Trans-Furan-2-carboxylic acid[2-(3-Piperidin-1-yl-cyclobutyl)-benzothiazole-6-yl]-amide;
Trans-Morpholine-4-carboxylic acid-[2-(3-Piperidin-1-yl-cyclobutyl)-benzothiazole-6-yl]-amide;
Trans-Pyrimidine-5-carboxylic acid-[2-(3-Piperidin-1-yl-cyclobutyl)-benzothiazole-6-yl]-amide;
Trans-Pyrazine-2-carboxylic acid-[2-(3-Piperidin-1-yl-cyclobutyl)-benzothiazole-6-yl]-amide;
Racemic-[2-(3-Piperidin-1-yl-cyclobutyl)-benzothiazole-6-yl]-pyrimidin-5-yl-amine;
Racemic-[2-(3-Piperidin-1-yl-cyclobutyl)-benzothiazole-6-yl]-pyrimidin-2-yl-amine;
Racemic-(5-bromo-pyrimidin-2-yl)-[2-(3-Piperidin-1-yl-cyclobutyl)-benzothiazole-6-yl]-amine;
Racemic-(5-methyl-pyridin-2-yl)-[2-(3-Piperidin-1-yl-cyclobutyl)-benzothiazole-6-yl]-amine;
Racemic-6-[2-(3-Piperidin-1-yl-cyclobutyl)-benzothiazole-6-ylamino]-nicotinonitrile;
Racemic-6-[2-(3-Piperidin-1-yl-cyclobutyl)-benzothiazole-6-ylamino]-nicotinonitrile;
2{Trans-3-[(S)-2-methylpiperidin-1-yl]cyclobutyl}-1,3-benzothiazol-6-yl-azetidin-2-one;
2-{Trans-3-[(S)-2-methylpiperidin-1-yl]cyclobutyl}-1,3-benzothiazol-6-yl-pyrrolidin-2-one;
2{Trans-3-[(S)-2-methylpiperidin-1-yl]cyclobutyl}-1,3-benzothiazol-6-yl-piperidin-2-one;
2{Trans-3-[(S)-2-methylpiperidin-1-yl]cyclobutyl}-1,3-benzothiazol-6-yl-homopyrrolidin-2-one;
2-{Trans-3-[(S)-2-methylpiperidin-1-yl]cyclobutyl}-1,3-benzothiazole-6-carboxamide;
N-Isopropyl-2-{trans-3-[(S)-2-methylpiperidin-1-yl]cyclobutyl}-1,3-benzothiazole-6-carboxamide;
N-cyclopropyl-2-{trans-3-[(S)-2-methylpiperidin-1-yl]cyclobutyl}-1,3-benzothiazole-6-carboxamide;
N-phenyl-2-{trans-3-[(S)-2-methylpiperidin-1-yl]cyclobutyl}-1,3-benzothiazole-6-carboxamide;
N-thiazol-2-yl-2-{trans-3-[(S)-2-methylpiperidin-1-yl]cyclobutyl}-1,3-benzothiazole-6-carboxamide;
N-benzyl-2-{trans-3-[(S)-2-methylpiperidin-1-yl]cyclobutyl}-1,3-benzothiazole-6-carboxamide;
N-(2-phenethyl)-2-{trans-3-[(S)-2-methylpiperidin-1-yl]cyclobutyl}-1,3-benzothiazole-6-carboxamide;
N,N-dimethyl-2-{trans-3-[(S)-2-methylpiperidin-1-yl]cyclobutyl}-1,3-benzothiazole-6-carboxamide;
(Pyrrolidin-1-yl)-2-{trans-3-[(S)-2-methylpiperidin-1-yl]cyclobutyl}-1,3-benzothiazole-6-methanone;
2-[Trans-3-(piperidin-1-yl)cyclobutyl]-1,3-benzothiazol-6-yl-3-methyl-pyrrolidin-2-one;
2-[Trans-3-(piperidin-1-yl)cyclobutyl]-1,3-benzothiazol-6-yl-oxazolidin-2-one; and
2-[Trans-3-(piperidin-1-yl)cyclobutyl]-1,3-benzothiazol-6-yl-3-methylimidazolidin-2-one;
Trans-6-bromo-2-{3-[(2R)-2-methylpyrrolidin-1-yl]cyclobutyl}-1,3-benzothiazole;
Trans-6-bromo-2-{3-[(2S)-2-methylpyrrolidin-1-yl]cyclobutyl}-1,3-benzothiazole;
Cis-6-bromo-2-{3-[(2R)-2-methylpyrrolidin-1-yl]cyclobutyl}-1,3-benzothiazole;
Cis-6-bromo-2-(3-pyrrolidin-1-ylcyclobutyl)-1,3-benzothiazole;
Cis-6-bromo-2-(3-piperidin-1-ylcyclobutyl)-1,3-benzothiazole;
Cis-2-(3-azepan-1-ylcyclobutyl)-6-bromo-1,3-benzothiazole;
Cis-{(2S)-1-[3-(6-bromo-1,3-benzothiazol-2-yl)cyclobutyl]pyrrolidin-2-yl}methanol;
Cis-tert-butyl(3aR,6aR)-5-[3-(6-bromo-1,3-benzothiazol-2-yl)cyclobutyl]hexahydropyrrolo[3,4-b]pyrrole-1(2H)-carboxylate;
Cis-6-bromo-2-{3-[(2R)-2-methylpiperidin-1-yl]cyclobutyl}-1,3-benzothiazole;
Cis-N-[3-(6-bromo-1,3-benzothiazol-2-yl)cyclobutyl]-N-isopropyl-N-methylamine;
Cis-{1-[3-(6-bromo-1,3-benzothiazol-2-yl)cyclobutyl]piperidin-4-yl}methanol;
Trans-{1-[3-(6-bromo-1,3-benzothiazol-2-yl)cyclobutyl]piperidin-4-yl}methanol;
Trans-6-bromo-2-(3-piperidin-1-ylcyclobutyl)-1,3-benzothiazole;
Trans-N-[3-(6-bromo-1,3-benzothiazol-2-yl)cyclobutyl]-N-isopropyl-N-methylamine;
Trans-2-(3-azetidin-1-ylcyclobutyl)-6-bromo-1,3-benzothiazole;
Trans-6-bromo-2-(3-pyrrolidin-1-ylcyclobutyl)-1,3-benzothiazole;
Trans-2-(3-azepan-1-ylcyclobutyl)-6-bromo-1,3-benzothiazole;
Trans-6-bromo-2-(3-morpholin-4-ylcyclobutyl)-1,3-benzothiazole;
Trans-6-bromo-2-{3-[(2S)-2-(fluoromethyl)pyrrolidin-1-yl]cyclobutyl}-1,3-benzothiazol;
Trans-{(2S)-1-[3-(6-bromo-1,3-benzothiazol-2-yl)cyclobutyl]pyrrolidin-2-yl}methanol;
Trans-6-bromo-2-[3-(2-methylpiperidin-1-yl)cyclobutyl]-1,3-benzothiazole;
Trans-tert-butyl 5-[3-(6-bromo-1,3-benzothiazol-2-yl)cyclobutyl]hexahydropyrrolo[3,4-b]pyrrole-1(2H)-carboxylate;
Trans-6-bromo-2-[3-(4-fluoropiperidin-1-yl)cyclobutyl]-1,3-benzothiazole;
Trans-[3-(6-Bromo-benzothiazol-2-yl)-cyclobutyl]-diethylamine;

Trans-[3-(6-Bromo-benzothiazol-2-yl)-cyclobutyl]-methyl-propyl-amine;
Trans-2-{[3-(6-Bromo-benzothiazol-2-yl)-cyclobutyl]-ethyl-amino}-ethanol;
6-Bromo-2-(3-pyrrolidin-1-ylmethyl-cyclobutyl)-benzothiazole and
Trans-5-Chloro-2-[3-(2-methyl-pyrrolidin-1-yl)-cyclobutyl]-benzothiazole.

Preferred compounds of formula (I), (II), or (III) include at least:
Trans-2-(3-piperidin-1-ylcyclobutyl)-6-pyrimidin-5-yl-1,3-benzothiazole;
Trans-Diethyl-{3-[6-(2-methoxy-pyrimidin-5-yl)-benzothiazol-2-yl]-cyclobutyl}-amine;
Trans-2-(Ethyl-{3-[6-(2-methoxy-pyrimidin-5-yl)-benzothiazol-2-yl]-cyclobutyl}-amino)-ethanol;
Trans-2-[2-(3-piperidin-1-ylcyclobutyl)-1,3-benzothiazol-6-yl]pyridazin-3(2H)-one; and
Cis-2-[2-(3-piperidin-1-ylcyclobutyl)-1,3-benzothiazol-6-yl]pyridazin-3(2H)-one.

Compound names are assigned by using AutoNom naming software, which is provided by MDL Information Systems GmbH (formerly known as Beilstein Informationssysteme) of Frankfurt, Germany, and is part of the CHEMDRAW® ULTRA v. 6.0.2 software suite.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Fumiss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutanes may be present in the cis or trans configuration, and may be present as a single isomer or a mixture of the cis and trans isomers. Individual cis or trans isomers of compounds of the invention may be prepared synthetically from commercially available starting materials using selective organic transformations, or by prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen and deuterium, or $^{12}C$ and $^{13}C$.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: BINAP for 2,2'-bis(diphenylphosphino)-1,1'-binaphthyl; Boc for butyloxycarbonyl; EtOAc for ethyl acetate; HPLC for high pressure liquid chromatography; IPA for isopropyl alcohol; Me for methyl; MeOH for methanol; Ms for methanesulfonyl; Pd for palladium; tBu for tert-butyl; TEA for triethylamine; TFA for trifluoroacetic acid; THF for tetrahydrofuran; and Ts for para-toluenesulfonyl; rt for "room temperature" or ambient temperature suitably ranging 20-30° C. Microwave heating was accomplished in a commercial microwave apparatus.

The compounds of this invention can be prepared by a variety of synthetic procedures. Representative procedures are shown in, but are not limited to, Schemes 1-5.

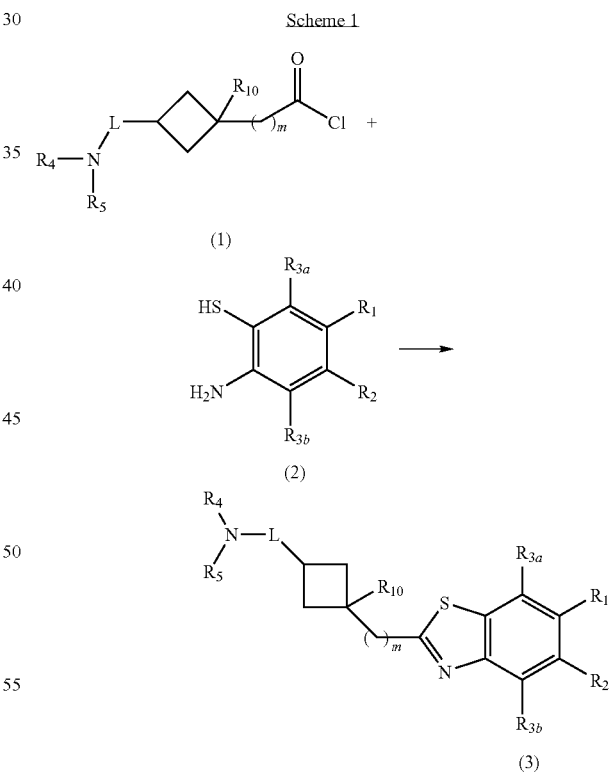

Compounds of formula (3), wherein m, $R_1$, $R_2$, $R_{3a}$, $R_{3b}$, $R_4$, $R_5$, L are as defined in formula (I), can be prepared as described in Scheme 1. Acid chlorides of formula (1), purchased or prepared using methodologies known to those of ordinary skill in the art, when treated with compounds of formula (2) will provide compounds of formula (3) which are representative of the compounds of the present invention.

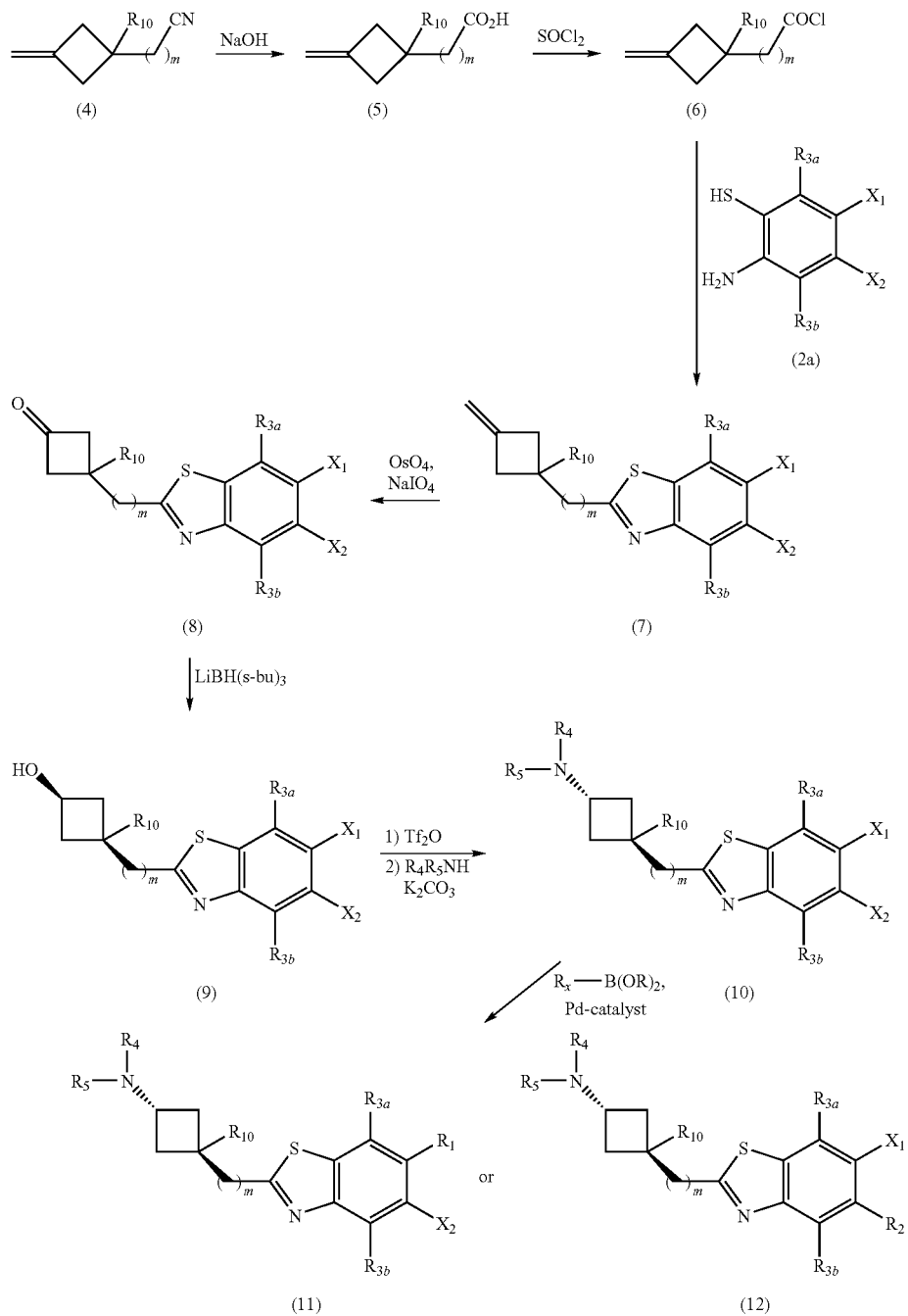

Scheme 2

Compounds of formula (4) containing a nitrile group when treated with sodium hydroxide under aqueous conditions will provide carboxylic acids of formula (5). Carboxylic acid compounds of formula (5) when treated with sulfonyl chloride or oxalyl chloride will provide acid chlorides of formula (6). Compounds of formula (6) undergo a condensation to benzothiazole compounds of formula (7) when treated with compounds of formula (2a). Compounds (2a) are defined as in formula (1) for $R_{3a}$, $R_{3b}$, and wherein at least one of $X_1$ and $X_2$ is chloro, iodo, or bromo, and the other is hydrogen, acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, haloalkoxy, haloalkyl, halogen, hydroxy, hydroxyalkyl, mercapto, nitro, alkylthio, —$NR_AR_B$, ($NR_A R_B$)carbonyl, —$SO_2N(R_{14a})(R_{14b})$, $N(R_{14a})SO_2(R_{14b})$. Compounds of formula (7) when treated with osmium tetroxide or potassium osmate and sodium periodate will provide the cyclobutanone compound of formula (8). The reduction of compounds of formula (8) using hydride reducing reagents such as, but not limited to lithium tri-sec-butylborohydride (L-Selectride), in solvents such as but not limited to THF, provides compounds of formula (9). Compounds of formula (9) when treated with triflic anhydride, mesyl chloride or tosyl chloride in the presence of a base such as but not limited to potassium carbonate, triethylamine, diisopropylethylamine and the like, followed by treatment with an amine of formula $R_4R_5NH$, wherein $R_4$ and $R_5$ are as defined in formula (I), will provide the compound of formula (10).

There are many suitable and readily available amines of formula $R_4R_5NH$, wherein $R_4$ and $R_5$ are as defined in formula (I). Examples of such amines $R_4R_5NH$ are exemplified, but not limited to, those shown in Table 1.

TABLE 1

Examples of readily available amines of formula $R_4R_5NH$.

| Amines | Structures | Commercial Source, Chemical Abstracts Number (CAS #), or Literature Reference |
|---|---|---|
| 2-(R)-methyl-pyrrolidine L-tartrate | 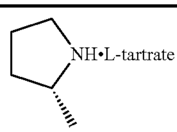 | WO 2004043458; Y. Pu et al., Organic Process Research & Development, 9(1), 45-50, 2005 |
| 2-(S)-methyl-pyrrolidine L-tartrate | 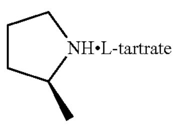 | Kim, Mahn-Joo, et al., Bioorg. Med. Chem. Lett. 6(1):71-76 (1996); Tetrahedron, 37:1861-1869 (1981). |
| L-pyrolinol | 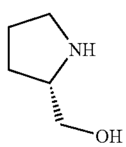 | CAS# 23356-96-9, Aldrich |
| hexahydro-pyrrolo[3,4-b]pyrrole-1-carboxylic acid tert-butyl ester | 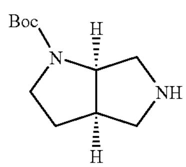 | Q. Li, et al., J. Med. Chem.; 39(16), 3070-3088, 1996 |
| 2-(R)-methyl-piperidine | 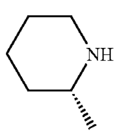 | Clariant Life Science Molecules Sandycroft Deeside Clwyd CH5 2PX UNITED KINGDOM |
| S-(+)-2-fluoromethyl-pyrrolidine | 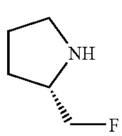 | CAS # 460748-85-0, prepared according to the procedure that described in: WO 2004043458 |
| 2-methyl-piperidine | 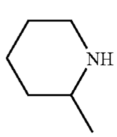 | CAS # 109-05-7, Aldrich |
| 4-fluoro-piperidine hydrochloride | 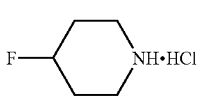 | ABCR GmbH & CO. KG P.O. Box 21 01 35 76151 Karlsruhe GERMANY |
| (R)-3-hydroxy-piperidine hydrochloride | 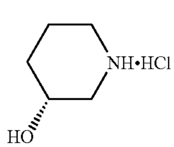 | CAS #198976-43-1, Aldrich Chemical Company, Inc. 1001 West Saint Paul Avenue Milwaukee, WI 53233 USA |

The Suzuki reaction can be used to convert compounds of formula (10) containing an $X_1$ group that is I, Br or Cl into compounds of formula (11). Similarly, the Suzuki reaction will convert compounds of formula (10) which contains an $X_2$ group that is I, Br or Cl into compounds of formula (12). The Suzuki reaction is between a halogen compound such as that of formula (10) and a boronic acid or boronic ester of formula $R_x$—$B(OR)_2$ wherein $R_x$ is aryl, heteroaryl, heterocyclyl, alkyl, alkenyl, or cycloalkyl and R is hydrogen or alkyl, and is conducted in the presence of a metal catalyst such as, but not limited to, palladium diacetate, $PdCl_2(PPh_3)_2$, or $Pd(PPh_3)_4$, optionally with a palladium ligand added such as 2-(dicyclohexylphosphino)biphenyl, tri-t-Butylphosphine, or tris(2-furyl)phosphine and a base such as, but not limited to aqueous $K_3PO_4$ or $Na_2CO_3$, or KF. Alternatively, pinacol borane reagents such as, but not limited to, those represented by the formula

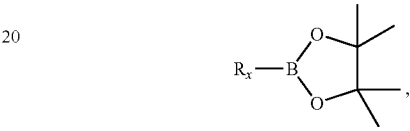

can be used in place of boronic acids or esters in the Suzuki reaction. References describing the methodology may be found in the following: N. Miyaura et al., Chem. Rev. 95:2457 (1995) or references cited within the article.

There are many aryl, heteroaryl, and heterocyclic boronic acids and boronic acid esters that are available commercially or that can be prepared as described in the scientific literature of synthetic organic chemistry. Typical examples of boronic acid and boronic acid ester reagents for the synthesis of compounds of formula (I) are shown in Table 2.

TABLE 2

Examples of Boronic Acid and Boronic Acid Ester Reagents

| Boronic Acid or Boronic Acid Ester | Commercial Source, Chemical Abstracts Number (CAS #), or Literature Reference |
|---|---|
| 2-pyrimidinone-5-boronic acid | CAS #373384-19-1 |
| 2-methoxypyrimidine-5-boronic acid | Frontier Scientific, Inc., Logan, UT, USA |
| 1H-pyrimidine-2,4-dione-5-boranic acid | Specs, Fleminglaan, the Netherlands CAS #70523-22-7; Schinazi, Raymond F.; Prusoff, William H., Synthesis of 5-(dihydroxyboryl)-2'-deoxyuridine and related boron-containing pyrimidines, Journal of Organic Chemistry (1985), 50(6), 841-7. |
| pyridine-3-boronic acid | CAS #1692-25-7, Frontier Scientific, Inc., Logan, UT, USA |
| 2,4-dimethoxypyrimidine-5-boronic acid | CAS #89641-18-9, Frontier Scientific, Inc., Logan, UT, USA |
| 2-methoxy-5-pyridine boronic acid | Digital Specialty Chemicals, Dublin, NH; CAS #163105-89-3; New shelf-stable halo- and alkoxy-substituted pyridylboronic acids and their Suzuki cross-coupling reactions to yield heteroarylpyridines, Parry, Paul R.; Bryce, Martin R.; Tarbit, Brian, Department of Chemistry, Synthesis (2003), (7), 1035-1038; Functionalized Pyridylboronic Acids and Their Suzuki Cross-Coupling |

TABLE 2-continued

Examples of Boronic Acid and Boronic Acid Ester Reagents

| | |
|---|---|
| | Reactions To Yield Novel Heteroarylpyridines, Parry, Paul R.; Wang, Changsheng; Batsanov, Andrei S.; Bryce, Martin R.; Tarbit, Brian, Journal of Organic Chemistry (2002), 67(21), 7541-7543. |
| pyrimidine-5-boronic acid | CAS #109299-78-7, S. Gronowitz, et al., "On the synthesis of various thienyl- and selenienyl-pyrimidines", Chem. Scr. 26(2): 305-309 (1986). |
| pyrimidine-5-boronic acid, pinacol ester | Umemoto, et al., Angew. Chem. Int. Ed. 40(14): 2620-2622 (2001). |
| 2-methylpyridine-5-boronic acidhydrate | SYNCHEM OHG Heinrich-Plett-Strassse 40; Kassel, D-34132; Germany; CAS #659742-21-9 |
| 2H-Pyran,3,6-dihydro-4-(4,4,5,5-tetramethyl-1,3,2-dioxaborolan-2-yl) | CAS # 287944-16-5; Murata, Miki; Oyama, Takashi; Watanabe, Shinji; Masuda, Yuzuru, Synthesis of alkenylboronates via palladium-catalyzed borylation of alkenyl triflates (or iodides) with pinacolborane. Synthesis(2000), (6), 778-780. |
| 1(2H)-Pyridinecarboxylic acid, 3,6-dihydro-4-(4,4,5,5-tetramethyl-1,3,2-dioxaborolan-2-yl)-,1,1-dimethylethyl ester | CAS # 286961-14-6; A versatile synthesis of 4-aryltetrahydropyridines via palladium mediated Suzuki cross-coupling with cyclic vinyl boronates, Eastwood, Paul R., Discovery Chemistry, Aventis Pharma, Essex, UK., Tetrahedron Letters (2000), 41(19), 3705-3708. |
| (5-cyano-3-pyridinyl)-boronic acid | CAS #497147-93-0; Chemstep Institut du PIN - University Bordeaux 1 351 cours de la liberation Talence Cedex, 33450 France |
| Thianthrene-1-boronic acid | Aldrich Chemical Company, Inc. |
| Benzoxazole-5-boronic acid | Cat # 110831, Asymchem Laboratories, Inc. |
| Benzothiazole-5-boronic acid | Cat # 1464, Digital Specialty Chemicals, Inc. |
| 4-Methyl-7-(4,4,5,5-tetramethyl-1,3,2-dioxaborolan-2-yl)-3,4-dihydro-2h-1,4-benzoxazine | Cat # CC13539CB, Acros Organics USA |
| 10-Methyl-3-(4,4,5,5-tetramethyl-[1,3,2]dioxaborolan-2-yl)-10H-phenothiazine | Kraemer, C. S.; et. al. Synthesis 2002, 9, 1163-1170. |
| (1,4-Dihydro-4,4-dimethyl-2-oxo-2H-3,1-benzoxazin-6-yl)boronic acid | Zhang, P.; et. al. J. Med. Chem. 2002, 45, 4379-4382. |

Boronic acids or boronic acid esters of formula $R_x$—B(OR)$_2$ and

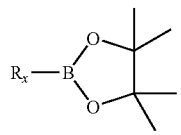

can be prepared from corresponding halides or triflates of $R_x$ via either: (1) metal exchange with an organo lithium agent followed with addition of alkyl borate or pinacolborate or, (2) cross coupling with a reagent such as, but not limited to, bis(pinacolato)diboron (CAS #73183-34-3) or bis(pinacolato)borane. References describing the first method are: B. T. O'Neill, et al., Organic Letters, 2:4201 (2000); M. D. Sindkhedkar, et al., Tetrahedron, 57:2991 (2001); W. C. Black, et al., J. Med. Chem., 42:1274 (1999); R. L. Letsinger et al., J. Amer. Chem. Soc., 81:498-501 (1959); and F. I. Carroll et al., J. Med. Chem., 2229-2237 (2001). References describing the second method are: T. Ishiyama et al., Tetrahedron, 57:9813-9816 (2001); T. Ishiyama et al., J. Org. Chem., 60:7508-7510 (1995); and Takagi et al., Tetrahedron Letters, 43:5649-5651 (2002).

Other methods for preparing boronic acids and boronic acid esters is described in O. Baudoin, et al., J. Org. Chem., 65:9268-9271 (2000), wherein an aryl or heteroaryl halides or triflate are treated with a dialkyloxyborane such as pinacolborane, in the presence of triethylamine and palladium (II) acetate in dioxane.

Alternatively, utilizing other coupling methods such as Stille coupling, compounds of formula (10), can be converted into the compound of formula (11) and (12) by treatment with organostannanes of formula $(R_y)_3SnR_x$ wherein $R_y$ is alkyl or aryl, and $R_x$ is aryl, heteroaryl, heterocyclyl, alkyl or alkenyl, or cycloalkyl, in the presence of a palladium source such as tris(dibenzylidineacetone)dipalladium (CAS # 52409-22-0) or palladium diacetate (CAS # 3375-31-3), and a ligand such as tri(2-furyl)phosphine (CAS # 5518-52-5) or triphenylarsine (CAS # 603-32-7). The reaction can be performed in a solvent such as DMF at a temperature from about 25° C. to about 150° C. Such methods are described, for instance, in J. K. Stille Angew. Chem. Int. Ed. 25:508 (1986) and T. N. Mitchell, Synthesis, 803 (1992).

While many stannanes are commercially available or described in the literature, it is also possible to prepare new stannanes from arylhalides, aryltriflates, heteroarylhalides, and heteroaryltriflates by reaction with hexa-alkyl distannanes of formula $((R_x)_3Sn)_2$ wherein $R_x$ is alkyl or aryl, with aryl, heteroaryl, or heterocyclic halides and triflates in the presence of a palladium source like $Pd(Ph_3P)_4$. Example of hexa-alkyl distannanes include, but not limited to, hexamethyldistannane (CAS # 661-69-8). Such methods are described, for instance in Krische, et. al., Helvetica Chimica Acta 81(11):1909-1920 (1998), and in Benaglia, et al., Tetrahedron Letters 38:4737-4740 (1997). Alternatively, aryl, heteroaryl, or heterocyclic organolithium and magnesium reagents can be treated with $Bu_3SnCl$ to provide Stille reagents. These reagents can be reacted with compounds of formula (10) to provide compounds of formula (11) and (12) under Stille conditions. A reference describing the Stille reaction is A. F. Littke et al., J. Amer. Chem. Soc. 124:6343-6348 (2002).

Compounds of formulas (11) wherein m, $R_{3a}$, $R_{3b}$, $R_4$, and $R_5$ are as defined in formula (I), alkylthio, and $R_1$ is —$L_2$—$R_6$, wherein $L_2$ is a bond, and $R_6$ is a nitrogen-containing heterocyclic ring linked to the parent moiety through the nitrogen, may be prepared as follows. The treatment of a compound of formulas (10) wherein $X_1$ is I, Br or Cl, with a heterocycle of formula H—$R_6$, wherein H is a hydrogen on the nitrogen atom contained in the heterocycle, in the presence of a base such as, but not limited to, sodium t-butoxide or cesium carbonate, a metal catalyst such as, but not limited to copper metal or CuI, palladium diacetate, and optionally with a ligand such as, but not limited to, BINAP or tri-tertbutylphosphine will provide compounds of formula (11). Similarly, the treatment of compounds of formula (10) wherein m, $R_{3a}$, $R_{3b}$, $R_4$, and $R_5$ are as defined in formula (I), and $X_2$ is I, Br or Cl with a heterocycle of formula H—$R_6$, wherein H is a hydrogen on the nitrogen atom contained in the heteroaryl or heterocycle using the same conditions will provide compounds of formula (12). These reactions are typically conducted in a solvent such as, but not limited to, dioxane, toluene or pyridine. References that describe these methods may be found in the following: J. Hartwig et al., Angew. Chem. Int. Ed. 37:2046-2067 (1998); J. P. Wolfe et al., Acc. Chem. Res., 13:805-818 (1998); M. Sugahara et al., Chem. Pharm. Bull., 45:719-721 (1997); J. P. Wolfe et al., J. Org. Chem., 65:1158-1174 (2000); F. Y. Kwong et al., Org. Lett., 4:581-584 (2002); A. Klapars et al., J. Amer. Chem. Soc., 123:7727-7729 (2001); B. H. Yang et al., J. Organomet. Chem., 576:125-146 (1999); and A. Kiyomori et al., Tet. Lett., 40:2657-2640 (1999).

Compounds of formulas (11) wherein m, $R_3$, $R_{3a}$, $R_{3b}$, $R_4$, and $R_5$ are as defined in formula (I), and $R_1$ is —$L_2$—$R_6$, wherein $L_2$ is —NH— or —N(alkyl)-, and $R_6$ is as defined for a compound of formula (I) can be prepared as follows. The treatment of compounds of formula (10) wherein $X_1$ is I, Br or Cl with a compound of formula $H_2N$—$R_6$ or HN(alkyl)-$R_6$ and a base such as, but not limited to, sodium t-butoxide or cesium carbonate in the presence of a metal catalyst such as, but not limited to, copper metal or CuI, palladium diacetate, and also optionally with a ligand such as, but not limited to, BINAP, or tri-tert-butylphosphine under heated conditions will provide compounds of formula (11). Similarly, compounds of formulas (12) wherein m, $R_3$, $R_{3a}$, $R_{3b}$, $R_4$, and $R_5$ are as defined in formula (I), and $R_2$ is —$L_2$—$R_6$, wherein $L_2$ is —NH— or —N(alkyl)-, and $R_6$ is as defined for a compound of formula (I) can be prepared by heating compounds of formula (10) wherein $X_2$ is I, Br or Cl with a compound of formula $H_2N$—$R_6$ or HN(alkyl)-$R_6$ utilizing the same conditions. The reaction can be performed in a solvent such as dioxane, toluene, or pyridine. References that describe these methodologies may be found in the following: J. Hartwig, et al., Angew. Chem. Int. Ed., 37:2046-2067 (1998); J. P. Wolfe et al., Acc. Chem. Res., 13:805-818 (1998); J. P. Wolfe et al., J. Org. Chem., 65:1158-1174 (2000); F. Y. Kwong et al., Org. Lett., 4:581-584 (2002); and B. H. Yang et al., J. Organomet. Chem., 576:125-146 (1999).

Compounds of formulas (11) wherein m, $R_3$, $R_{3a}$, $R_{3b}$, $R_4$ and $R_5$ are as defined in formula (I), and $R_1$ is $L_2$—$R_6$, wherein $L_2$ is oxygen and $R_6$ is as defined in formula (I) can be prepared as follows. The treatment of compounds of formula (10) wherein $X_1$ is I, Br or Cl, with a compound of formula HO—$R_6$ using a base such as, but not limited to, sodium hydride in a solvent such as toluene or N,N-dimethylformamide, in the presence of a metal containing catalyst such as CuI or palladium diacetate under heated conditions will provide compounds of formula (11). Similarly, compounds of formulas (12) wherein m, $R_3$, $R_{3a}$, $R_{3b}$, $R_4$ and $R_5$ are as defined in formula (I), and $R_2$ is $L_2$—$R_6$, wherein $L_2$ is oxygen and $R_6$ is as defined in formula (I) can be prepared by heating compounds of formula (10) wherein $X_2$ is I, Br or Cl with a compound of formula HO—$R_6$ utilizing the same conditions. References that describe these methodologies may be found in the following: J. Hartwig et al., Angew. Chem. Int. Ed., 37:2046-2067 (1998); K. E. Torraca et al., J. Amer. Chem. Soc., 123:10770-10771 (2001); S. Kuwabe et al., J. Amer. Chem. Soc., 123:12202-12206 (2001); K. E. Toracca et al., J. Am. Chem. Soc., 122:12907-12908 (2000); R. Olivera et al., Tet. Lett., 41:4353-4356 (2000); J.-F. Marcoux et al., J. Am. Chem. Soc., 119:10539-10540 (1997); A. Aranyos et al., J. Amer. Chem. Soc., 121:4369-4378 (1999); T. Satoh et al., Bull. Chem. Soc. Jpn., 71:2239-2246 (1998); J. F. Hartwig, Tetrahedron Lett., 38:2239-2246 (1997); M. Palucki et al., J. Amer. Chem. Soc., 119:3395-3396 (1997); N. Haga et al, J. Org. Chem., 61:735-745 (1996); R. Bates et al., J. Org. Chem., 47:4374-4376 (1982); T. Yamamoto et al., Can. J. Chem., 61:86-91 (1983); A. Aranyos et al., J. Amer. Chem. Soc., 121:4369-4378 (1999); and E. Baston et al., Synth. Commun., 28:2725-2730 (1998).

Compounds of formulas (11) wherein m, $R_3$, $R_{3a}$, $R_{3b}$, $R_4$ and $R_5$ are as defined in formula (I), and $R_1$ is $L_2$—$R_6$, wherein $L_2$ is sulfur and $R_6$ is as defined for a compound of formula (I) can be prepared by heating compounds of formula (10) wherein $X_1$ is I, Br or Cl, with a compound of formula HS—$R_6$ in the presence of a base, with or without a metal catalyst such as CuI or palladium diacetate, in a solvent such as dimethylformamide or toluene. Similarly, compounds of formula (12) wherein m, $R_3$, $R_{3a}$, $R_{3b}$, $R_4$ and $R_5$ are as defined in formula (I), and $R_2$ is $L_2$—$R_6$, wherein $L_2$ is sulfur and $R_6$ is as defined in formula (I) can be prepared by heating compounds of formula (10) wherein $X_2$ is I, Br or Cl with a compound of formula HS—$R_6$ utilizing the same conditions. References that describe these methodologies may be found in the following: G. Y. Li et al., J. Org. Chem., 66:8677-8681 (2001); Y. Wang et al., Bioorg. Med. Chem. Lett., 11:891-894 (2001); G. Liu et al., J. Med. Chem., 44:1202-1210 (2001); G. Y. Li et al., Angew. Chem. Int. Ed., 40:1513-1516 (2001); U. Schopfer et al., Tetrahedron, 57:3069-3074 (2001); and C. Palomo et al., Tet. Lett., 41:1283-1286 (2000); A. Pelter et al., Tet. Lett., 42:8391-8394 (2001); W. Lee et al., J. Org. Chem., 66:474-480 (2001); and A. Toshimitsu et al., Het. Chem., 12:392-397 (2001).

Scheme 3

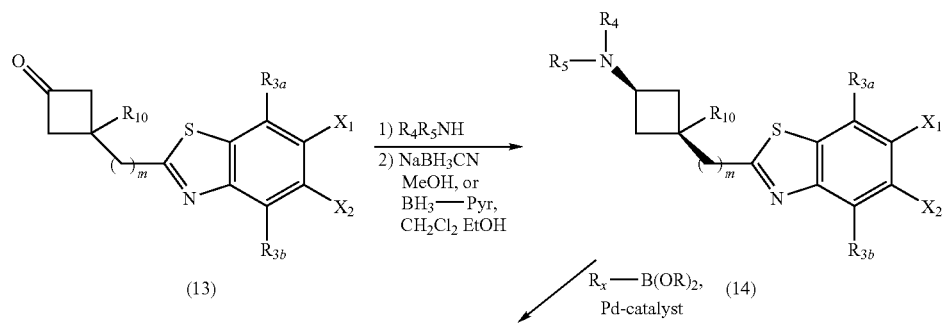

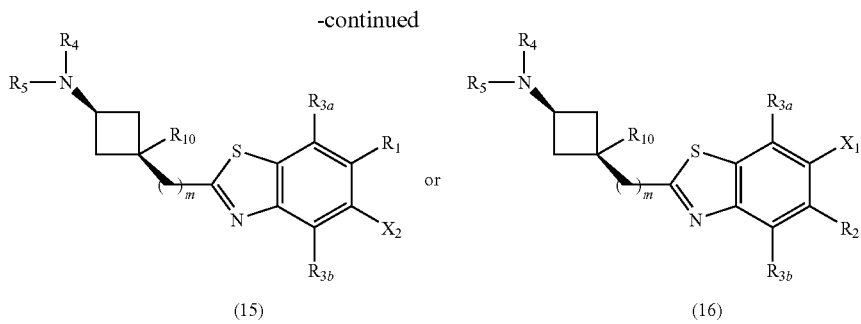

As shown in Scheme 3, compounds of formula (13) when treated with an amine of formula $R_4R_5NH$ followed by treatment with either sodium cyanoborohydride in methanol, sodium triacetoxyborohydride in dichloromethane, or borane-pyridine complex in a mixture of solvents such as but not limited to dichloromethane and ethanol will provide compounds of formula (14). Compounds of formula (14) wherein m, $R_{3a}$, $R_{3b}$, $R_4$ and $R_5$ are as defined in Formula (I), $R_2$ is selected from the group consisting of hydrogen, alkoxy, halogen, cyano, or alkylthio, and $X_1$ is I, Br or Cl may be treated according to the conditions describing the conversion of compounds of formula (10) into compounds of formula (11), to obtain compounds of formula (15). Similarly, compounds of formula (14), wherein, $R_{3a}$, $R_{3b}$, $R_4$ and $R_5$ are as defined in Formula (I), $R_1$ is selected from the group consisting of hydrogen, alkoxy, halogen, cyano, or alkylthio, and $X_2$ is I, Br or Cl may be treated according to the conditions describing the conversion of compounds of formula (10) into compounds of formula (12), to obtain compounds of formula (16).

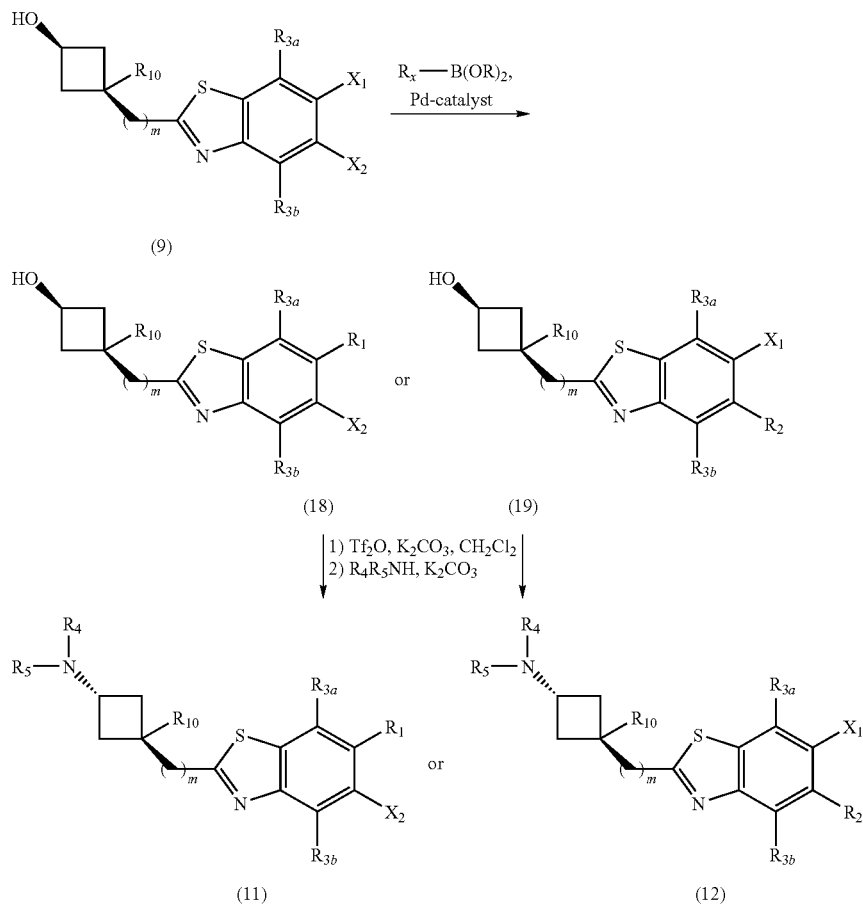

Scheme 4 shows an alternative route to the generation of compounds of formula (11) from compounds of formula (9), a base such as but not limited to potassium carbonate will produce compounds of formula (12).

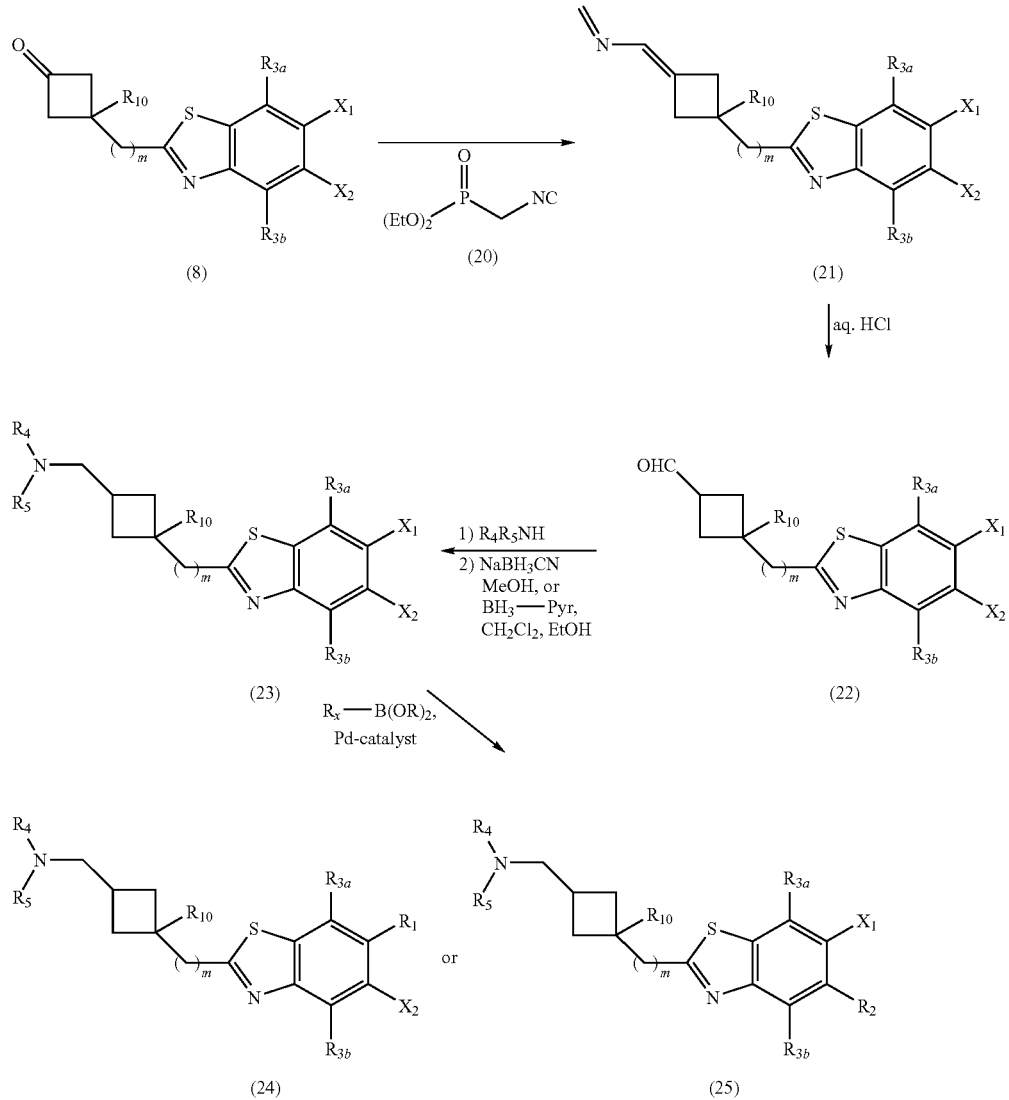

wherein m, $R_{3a}$, $R_{3b}$, $R_4$ and $R_5$ are as defined in Formula (I), and $X_1$ is I, Br or Cl. Treatment of (9) with a boronic acid or ester and palladium under Suzuki conditions will provide compounds of formula (18). The treatment of compounds of formula (18) with triflic anhydride and a base such as, but not limited to, potassium carbonate in dichloromethane, followed by treatment with an amine of formula $R_4R_5NH$ and a base such as, but not limited to, potassium carbonate will produce compounds of formula (11). Similarly, compounds of formula (9) wherein m, $R_{3a}$, $R_{3b}$, $R_4$ and $R_5$ are as defined in Formula (I), and $X_2$ is I, Br or Cl when treated with a boronic acid or ester and palladium under Suzuki reaction conditions will provide compounds of formula (19). Compounds of formula (19) when treated with triflic anhydride and a base such as but not limited to potassium carbonate in dichloromethane followed by treatment with an amine of formula $R_4R_5NH$ and As outlined in Scheme 5, compounds of formula (8) when treated with a solution containing the anion of diethyl isocyanomethylphosphonate (itself generated from the phosphonic ester reagents of formula (20) and a base such as but not limited to sodium hydroxide or sodium methoxide) will provide compounds of formula (21). The use of this reaction methodology is described in Moskal, et al. Recl. Trav. Pay Chem B. vol. 106(5), 137-141 (1987) and Yan, et al. J. Medical Chemistry vol. 37(16), 2619-2622 (1994). The hydrolysis of compounds of formula (21) under acidic conditions will provide aldehydes of formula (22). The aldehyde of compounds of formula (22) when treated with an amine $R_4R_5NH$, wherein $R_4$ and $R_5$ are as defined in formula (I), followed by treatment with sodium cyanoborohydride in methanol, sodium triacetoxyborohydride in dichloromethane, or borane-pyridine complex in a mixture of dichloromethane and methanol will provided compounds of formula (23). The compounds of formula (23) when treated according to the conditions in Scheme 2 describing the Suzuki reaction will provide compounds of formula (24) or (25) depending on the appropriate substitution of $X_1$ or $X_2$.

when treated with sodium borohydride or another appropriate reducing agent known to one skilled in the art will provide compounds of formula (31). Compounds of formula (31) when treated with trifluoromethanesulfonic anhydride (also known as triflic anhydride) in the presence of a base such as

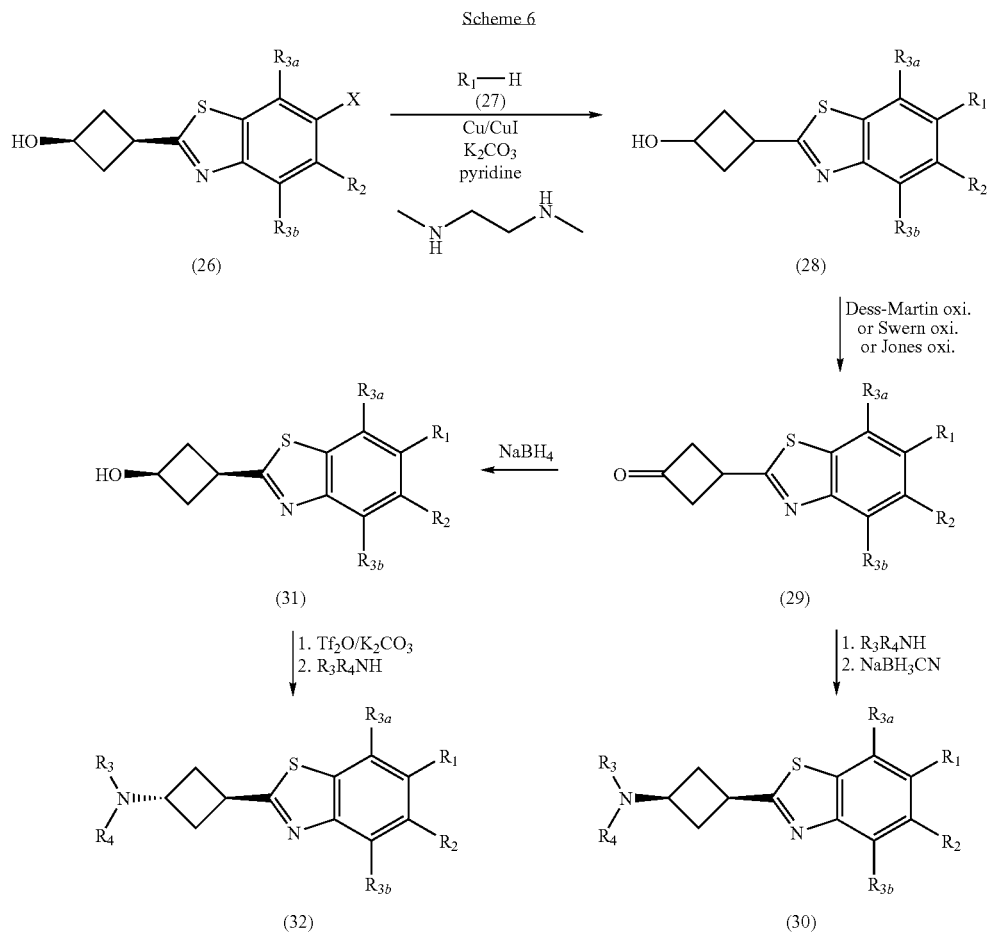

As outlined in Scheme 6, compounds of formula (26), wherein X is bromo or iodo and $R_2$, $R_{3a}$ and $R_{3b}$ are as defined in formula (I), when treated with a compound of formula (27), wherein $R_1$ is either a group of the formula —$L_2$—$R_6$ or a group of the formula —$L_{3a}$—$R_{6a}$—$L_{3b}$—$R_{6b}$, wherein $L_2$ and $L_{3a}$ are a bond, $R_6$ and $R_{6a}$ are heterocycle (wherein the heterocycle contains a reactive nitrogen such as pyridazin-3(2H)-one or pyridine-2(1H)-one) and $L_{3b}$ and $R_{6a}$ are defined in formula (I), in the presence of copper powder, copper iodide, potassium carbonate and pyridine under heated conditions will provide compounds of formula (28). Compounds of formula (28) when subjected to oxidative conditions such as but not limited to Dess-Martin periodinane ([87413-09-0], Aldrich Chemical Company), Swern oxidation or Jones oxidation as known to one skilled in the art, will provide compounds of formula (29). Compounds of formula (29) when treated with an amine of formula $R_3R_4NH$ followed by the addition of sodium cyanoborohydride will provide compounds of formula (30). Alternatively, reducing agents described in Scheme 3 for the conversion of compounds of formula (13) into compounds of formula (14) may also be used for this transformation. Compounds of formula (29)

but not limited to potassium carbonate followed by the treatment with an amine of formula $R_3R_4NH$ will provide compounds of formula (32). Both compounds of formula (30) and (32) are representative of compounds of the present invention but contain different stereochemical configurations.

Cyclobutane nitrile compounds (4) are available by known routes or are commercially available. For example, 3-methylene cyclobutanecarbonitrile (CAS number 15760-35-7) is commercially available from Maybridge Plc, Trevilleft, Tintagel, Cornwall, PL34 0HW, United Kingdom, and from Ryan Scientific, Inc., PO Box 845, Isle of Palms, S.C., 29451, USA. 1-methyl-3-methylenecyclobutanecarbonitrile (CAS number 32082-16-9) is available through methods described in "Methods of preparing 2- and 3-functionally substituted methylenecyclobutanes via the cycloaddition of allene with acrylic acid derivatives" by Men'shchikov, V. A. (Otkrytoe Aktsionernoe Obshchestvo "Vserossiiskii Nauchno-Issledovatel'skii Institut Organicheskogo Sinteza", Russia), and found in Chemical Abstracts Number 137:310640; and Russian patent application RU 2000-103966. Synthesis of 1-methyl-3-methylenecyclobutanecarbonitrile is also described in "Cyclobutane Carboxamide Inhibitors of Fungal Melanin: Biosynthesis and their Evaluation as Fungicides" Jennings, et al. Bioorganic & Medicinal Chemistry 8 (2000) 897-907; this reference also describes the synthesis of 3-methylene-1 (trifluoromethyl)cyclobutanecarbonitrile, 1-chloro-3 methylenecyclobutanecarbonitrile, and describes a general method of synthesis of 1-substituted analogs of (4). 1-chloro-3-methylenecyclobutanecarbonitrile is also available by methods described in Bienfait, et al. Tetrahedron (1991), 47(38), 8167-76. The conversion of chloro compounds such as 1-chloro-3-methylenecyclobutanecarbonitrile to fluoro compounds such as 1-fluoro-3-methylenecyclobutanecarbonitrile is well-known, for example by treatment with fluoride ion. Compounds (4) can be converted to compounds (5) and to compounds of the invention of general formula (I) by the routes described in Schemes 1-5 and described herein.

Cyclobutane carboxylic acid compounds (5) are also available by known routes or are commercially available. For example, 1-hydroxy-3-methylenecyclobutanecarboxylic acid is described in Della, et al. Journal of the American Chemical Society (1994), 116(14), 6159-6166. Other compounds (5) have been described in Jennings, et al. Bioorganic & Medicinal Chemistry 8 (2000) 897-907, for example 1-methyl-3-methylenecyclobutanecarboxylic acid and 1-ethyl-3-methylenecyclobutanecarboxylic acid; this reference provides a general method for the conversion of the commercially available 3-methylenecyclobutanecarboxylic acid (Chemical Abstracts number 15760-35-7, available from Ryan Scientific, Inc., PO Box 845, Isle of Palms, S.C., 29451, USA, and other sources) to a variety of 1-substituted 3-methylenecyclobutanecarboxylic acids. In this transformation, the 3-methylenecyclobutanecarboxylic acid is deprotonated with a base such as lithium di-isopropyl amide or other base, in a solvent such as THF, followed by treatment with an electrophilic reagent. Suitable electrophilic reagents are ethyl iodide, TosMIC (toluene methyl isocyanide), CNBr, and the like.

Esters of cyclobutane carboxylic acid compounds (5) are available by known routes or are commercially available, and these may be hydrolyzed to the cyclobutane carboxylic acid compounds (5) under basic conditions (NaOH) or acid conditions (HCl). For example, cyclobutanecarboxylic acid, 1-cyano-3-methylene-, methyl ester (Chemical abstracts number 116546-99-7) is available for hydrolysis to 1-cyano-3-methylenecyclobutanecarboxylic acid.

2-aminobenzenethiol compounds of formula (2) are available from a variety of routes or are commercially available. Examples of compounds (2) include 2-amino-5-(dimethylamino)benzenethiol (Chemical Abstracts number 860766-72-9, see Zincke, Th.; Muller, Joh. Marburg, Ber. (1913), 46, 775-86); Benzenethiol, 2-amino-5-chloro-3-methoxy-, hydrochloride (Chemical Abstracts number 859032-36-3, see Takahashi, Torizo; Shibasaki, Juichiro; Okada, Jutaro. Syntheses of heterocyclic compounds of nitrogen. L. Yakugaku Zasshi (1951), 71, 41-4.); Herz, Richard; 2-amino-5-(phenylamino)benzenethiol (Chemical Abstracts number 858833-38-2; see Friedlaender, Paul. Aryl mercaptan derivatives. (1923), DE 491224); 4-amino-3-mercaptobenzonitrile (Chemical Abstracts numer 802559-53-1, see Bogert, Marston T.; Husted, Helen G. Thiazoles. XVIII. Synthesis of 2-phenylbenzothiazole-5-carboxylic acid and derivatives. Journal of the American Chemical Society (1932), 54, 3394-7); 2-amino-5-ethoxybenzenethiol (Chemical Abstracts number 785727-27-7, see Wilde, Richard G.; Billheimer, Jeffrey T.; Germain, Sandra J.; Gillies, Peter J.; Higley, C. Anne; Kezar, Hollis S., III; Maduskuie, Thomas P.; Shimshick, Edward S.; Wexler, Ruth R. Acyl CoA: cholesterol acyltransferase (ACAT) inhibitors: ureas bearing heterocyclic groups bioisosteric for an imidazole. Bioorganic & Medicinal Chemistry Letters (1995), 5(2), 167-72); 2-amino-5-(piperidin-1-ylsulfonyl)benzenethiol (Chem. Abstracts number 749216-22-6, commercially available from Enamine, 23 Alexandra Matrosova Street, Kiev, 01103); 3-amino-4-mercapto-benzoic acid methyl ester, described in Dannley, et al. Canadian J. Chem. vol. 43; (1965) 2610-2612); 2-amino-5-benzyloxy-benzenethiol, described in Sugano, et al., Bioorg. Med. Chem. Lett. vol. 6 (1996), pp. 361-366.

Additionally, 2-aminobenzenethiol compounds of formula (2) are available by basic hydrolysis of benzo[d]thiazol-2 (3H)-ones, as described in Example 1a, or acid hydrolysis. A wide variety of benzo[d]thiazol-2(3H)-ones have been described, and methods of preparation are known to those skilled in the art of organic synthesis. Examples of general methods of preparation of benzo[d]thiazol-2(3H)-ones from anilines (which are themselves widely available commercially) can be found in "Development of a Manufacturing Process for Sibenadet Hydrochloride, the Active Ingredient of Viozan" Giles, et al. Organic Process Research & Development, vol. 8(4), 628-642 (2004), and "Synthesis and Evaluation of Non-Catechol D-1 and D-2 Dopamine Receptor Agonists: Benzimidazol-2-one, Benzoxazol-2-one, and the Highly Potent Benzothiazol-2-one 7-Ethylamines" Weinstock, et al., Journal of Medicinal Chemistry (1987), 30, pp 1166-1176.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzensulfonic, carbonic, fumaric, maleic, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner.

Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl trifilate, for example with methyliodide, benzyl iodide, cyclopentyl iodide. They also may be prepared by reaction of the compound with an acid such as hydrochloric acid and an alkylcarboxylic acid such as acetic acid, or with acid and an arylcarboxylic acid such as benzoic acid.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

Methods of the Invention

The compounds and compositions of the invention are useful for treating and preventing certain diseases and disorders in humans and animals. As an important consequence of the ability of the compounds of the invention to modulate the effects of histamine-3 receptors in cells, the compounds described in the invention can affect physiological processes in humans and animals. In this way, the compounds and compositions described in the invention are useful for treating and preventing diseases and disorders modulated by histamine-3 receptors. Typically, treatment or prevention of such diseases and disorders can be effected by selectively modulating the histamine-3 receptors in a mammal, by administering a compound or composition of the invention, either alone or in combination with another active agent as part of a therapeutic regimen.

The compounds of the invention, including but not limited to those specified in the examples, possess an affinity for the histamine-3 receptors and therefore, the compounds of the invention may be useful for the treatment and prevention of diseases or conditions such as attention-deficit hyperactivity disorder (ADHD), deficits in attention, dementia, and diseases with deficits of memory, learning, schizophrenia, cognitive deficits of schizophrenia, cognitive deficits and dysfunction in psychiatric disorders, Alzheimer's disease, mild cognitive impairment, epilepsy, seizures, allergic rhinitis, and asthma, motion sickness, dizziness, Meniere's disease, vestibular disorders, vertigo, obesity, diabetes, type II diabetes, Syndrome X, insulin resistance syndrome, metabolic syndrome, pain, including neuropathic pain, neuropathy, sleep disorders, narcolepsy, pathological sleepiness, jet lag, drug abuse, mood alteration, bipolar disorder, depression, obsessive compulsive disorder, Tourette's syndrome, Parkinson's disease, and medullary thyroid carcinoma, melanoma, and polycystic ovary syndrome. The ability of histamine-3 receptor modulators, and consequently the compounds of the invention, to prevent or treat such disorders is demonstrated by examples found in the following references.

The ability of the compounds of the invention, including, but not limited to, those specified in the examples, to treat attention-deficit hyperactivity disorder (ADHD), and deficits in attention, may be demonstrated by Cowart, et al. *J. Med. Chem.* 2005, 48, 38-55; Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190; "Effects of histamine $H_3$ receptor ligands GT-2331 and ciproxifan in a repeated acquisition avoidance response in the spontaneously hypertensive rat pup." Fox, G. B., et al. Behavioural Brain Research (2002), 131(1,2), 151-161; Yates, et al. JPET (1999) 289, 1151-1159 "Identification and Pharmacological Characterization of a Series of New 1H-4-Substituted-Imidazoyl Histamine $H_3$ Receptor Ligands"; Ligneau, et al. Journal of Pharmacology and Experimental Therapeutics (1998), 287, 658-666; Tozer, M. Expert Opinion Therapeutic Patents (2000) 10, p. 1045; M. T. Halpern, "GT-2331" Current Opinion in Central and Peripheral Nervous System Investigational Drugs (1999) 1, pages 524-527; Shaywitz et al., Psychopharmacology, 82:73-77 (1984); Dumery and Blozovski, Exp. Brain Res., 67:61-69 (1987); Tedford et al., J. Pharmacol. Exp. Ther., 275:598-604 (1995); Tedford et al., Soc. Neurosci. Abstr., 22:22 (1996); and Fox, et al., Behav. Brain Res., 131:151-161 (2002); Glase, S. A., et al. "Attention deficit hyperactivity disorder: pathophysiology and design of new treatments." Annual Reports in Medicinal Chemistry (2002), 37 11-20; Schweitzer, J. B., and Holcomb, H. H. "Drugs under investigation for attention-deficit hyperactivity disorder" Current Opinion in Investigative Drugs (2002) 3, p. 1207.

The ability of the compounds of the invention, including, but not limited to, those specified in the examples, to treat dementia, and diseases with deficits of memory and learning, may be demonstrated by "Two novel and selective nonimidazole $H_3$ receptor antagonists A-304121 and A-317920: II. In vivo behavioral and neurophysiological characterization." Fox, G. B., et al. Journal of pharmacology and experimental therapeutics (2003 June), 305(3), 897-908; "Identification of novel $H_3$ receptor ($H_3R$) antagonist with cognition enhancing properties in rats." Fox, G. B.; Inflammation Research (2003), 52(Suppl. 1), S31-S32; Bernaerts, P., et al. "Histamine $H_3$ antagonist thioperamide dose-dependently enhances memory consolidation and reverses amnesia induced by dizocilpine or scopolamine in a one-trial inhibitory avoidance task in mice" Behavioural Brain Research 154 (2004) 211-219; Onodera, et al. Nauyn-Schmiedebergs' Arch. Pharmacol. (1998), 357, 508-513; Prast, et al. Brain Research (1996) 734, 316-318; Chen, et al. Brain Research (1999) 839, 186-189 "Effects of histamine on MK-801-induced memory deficits in radial maze performance in rats"; Passani, et al. "Central histaminergic system and cognition" Neuroscience and Biobehavioral Reviews (2000) 24, p 107-113.

The ability of the compounds of the invention, including, but not limited to, those specified in the examples, to treat schizophrenia, cognitive deficits of schizophrenia, and cognitive deficits, may be demonstrated by Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190 and by "Enhancement of prepulse inhibition of startle in mice by the $H_3$ receptor antagonists thioperamide and ciproxifan." Browman, Kaitlin E., et al. Behavioural Brain Research (2004), 153(1), 69-76; "$H_3$ receptor blockade by thioperamide enhances cognition in rats without inducing locomotor sensitization."; Komater, V. A., et al. Psychopharmacology (Berlin, Germany) (2003), 167(4), 363-372; M Rodrigues, F P Jansen, R Leurs, H Timmerman and G D Prell "Interaction of clozapine with the histamine $H_3$ receptor in rat brain" British Journal of Pharmacology (1995), 114(8), pp. 1523-1524; Passani, et al. "Central histaminergic system and cognition" Neuroscience and Biobehavioral Reviews (2000) 24, p 107-113; Morriset, S., et al. "Atypical Neuroleptics Enhance Histamine Turnover in Brain Via 5-Hydroxytryptamine$_{2A}$ Receptor Blockade" Journal of Pharmacology and Experimental Therapeutics (1999) 288, pages 590-596.

The ability of the compounds of the invention, including, but not limited to, those specified in the examples, to treat dysfunction in psychiatric disorders, Alzheimer's disease, and mild cognitive impairment may be demonstrated by Meguro, et al. Pharmacology, Biochemistry and Behavior (1995) 50(3), 321-325; Esbenshade, T., et al. "Pharmacological and behavioral properties of A-349821, a selective and potent human histamine H3 receptor antagonist" Biochemical Pharmacology 68 (2004) 933-945; Huang, Y.-W., et al. "Effect of the histamine H3-antagonist clobenpropit on spatial memory deficits induced by MK-801 as evaluated by radial maze in Sprague-Dawley rats" Behavioural Brain Research 151 (2004) 287-293; Mazurkiewicz-Kwilecki and Nsonwah, Can. J. Physiol. Pharmacol. (1989) 67, p. 75-78; P. Panula, et al., Neuroscience (1997) 82, 993-997; Haas, et al., Behav. Brain Res. (1995) 66, p. 4144; De Almeida and Izquierdo, Arch. Int. Pharmacodyn. (1986), 283, p. 193-198; Kamei et al., Psychopharmacology, (1990) 102, p. 312-318; Kamei and Sakata, Jpn. J. Pharmacol. (1991), 57, p. 437-482; Schwartz et al., Psychopharmacology, The Fourth Generation of Progress. Bloom and Kupfer (eds). Raven Press, New York, (1995) 397; and Wada, et al., Trends in Neurosci. (1991) 14, p. 415.

The ability of the compounds of the invention, including, but not limited to, those specified in the examples, to treat epilepsy, and seizures, may be demonstrated by Harada, C., et al. "Inhibitory effect of iodophenpropit, a selective histamine H3 antagonist, on amygdaloid kindled seizures" Brain Research Bulletin (2004) 63 p, 143-146; as well as by Yokoyama, et al., Eur. J. Pharmacol. (1993) 234, p. 129-133; Yokoyama, et al. European Journal of Pharmacology (1994) 260, p. 23; Yokoyama and Iinuma, CNS Drugs (1996) 5, p. 321; Vohora, Life Sciences (2000) 66, p. 297-301; Onodera et al., Prog. Neurobiol. (1994) 42, p. 685; Chen, Z., et al. "Pharmacological effects of carcinine on histaminergic neurons in the brain" British Journal of Pharmacology (2004) 143, 573-580; R. Leurs, R. C. Vollinga and H. Timmerman, "The medicinal chemistry and therapeutic potential of ligands of the histamine $H_3$ receptor", Progress in Drug Research (1995) 45, p. 170-165; Leurs and Timmerman, Prog. Drug Res. (1992) 39, p. 127; H. Yokoyama and K. Iinuma, "Histamine and Seizures: Implications for the treatment of epilepsy", CNS Drugs, 5(5): 321-330 (1995); and K. Hurukami, H. Yokoyama, K. Onodera, K. Iinuma and T. Watanabe, "AQ-0145, A newly developed histamine $H_3$ antagonist, decreased seizure susceptibility of electrically induced convulsions in mice", Meth. Find. Exp. Clin. Pharmacol., 17(C):70-73 (1995); Yawata, et al. "Role of histaminergic neurons in development of epileptic seizures in EL mice" Molecular Brain Research 132 (2004) 13-17.

The ability of the compounds of the invention, including, but not limited to, those specified in the examples, to treat allergic rhinitis, and asthma, may be demonstrated by McLeod, R. L., Mingo, G. G., Herczku, C., DeGennaro-Culver, F., Kreutner, W., Egan, R. W., Hey, J. A., "Combined histamine H1 and H3 receptor blockade produces nasal decongestion in an experimental model of nasal congestion" Am. J. Rhinol. (1999a) 13, p. 391-399; McLeod, Robbie L.; Egan, Robert W.; Cuss, Francis M.; Bolser, Donald C.; Hey, John A. (Allergy, Schering-Plough Research Institute, Kenilworth, N.J., USA.) Progress in Respiratory Research (2001), 31 (in New Drugs for Asthma, Allergy and COPD), pp. 133-136; A. Delaunois A., et al., "Modulation of acetylcholine, capsaicin and substance P effects by histamine $H_3$ receptors in isolated perfused rabbit lungs," European Journal of Pharmacology (1995) 277, p. 243-250; Dimitriadou, et al., "Functional relationship between mast cells and C-sensitive nerve fibres evidenced by histamine $H_3$-receptor modulation in rat lung and spleen," Clinical Science (1994), 87, p. 151-163.

The ability of the compounds of the invention, including, but not limited to, those specified in the examples, to treat motion sickness, dizziness, Meniere's disease, vestibular disorders, and vertigo, may be demonstrated by Pan, et al. Methods and Findings in Clinical Pharmacology (1998), 20(9), 771-777; O'Neill, et al. Methods and Findings in Clinical Pharmacology (1999) 21(4), 285-289; and by R. Leurs, R. C. Vollinga and H. Timmerman, "The medicinal chemistry and therapeutic potential of ligands of the histamine $H_3$ receptor," Progress in Drug Research (1995), 45, p. 170-165, Lozada, et al. "Plasticity of histamine $H_3$ receptor expression and binding in the vestibular nuclei after labyrinthectomy in rat" BioMedCentral Neuroscience 2004, 5:32.

The ability of the compounds of the invention, including, but not limited to, those specified in the examples, to treat obesity, diabetes, type II diabetes, Syndrome X, insulin resistance syndrome, and metabolic syndrome, may be demonstrated by Hancock, A. A. "Antiobesity effects of A-331440, a novel non-imidazole histamine H3 receptor antagonist" European Journal of Pharmacology (2004) 487, 183-197;

Hancock, A. A., et al. "Histamine $H_3$ antagonists in models of obesity" Inflamm. res. (2004) 53, *Supplement* 1 S47-S48; as well as by E. Itoh, M. Fujimiay, and A. Inui, "Thioperamide, A histamine $H_3$ receptor antagonist, powerfully suppresses peptide YY-induced food intake in rats," Biol. Psych. (1999) 45(4), p. 475-481; S. I. Yates, et al., "Effects of a novel histamine $H_3$ receptor antagonist, GT-2394, on food intake and weight gain in Sprague-Dawley rats," Abstracts, Society for Neuroscience, 102.10:219 (November, 2000); and C. Bjenning, et al., "Peripherally administered ciproxifan elevates hypothalamic histamine levels and potently reduces food intake in the Sprague Dawley rat," Abstracts, International Sendai Histamine Symposium, Sendai, Japan, #P39 (November, 2000); Sakata T; et al. "Hypothalamic neuronal histamine modulates ad libitum feeding by rats." Brain research (1990 Dec. 24), 537(1-2), 303-6.

The ability of the compounds of the invention, including, but not limited to, those specified in the examples, to treat pain, including neuropathic pain and neuropathy, may be demonstrated by Malmberg-Aiello, Petra; Lamberti, Claudia; Ghelardini, Carla; Giotti, Alberto; Bartolini, Alessandro. British Journal of Pharmacology (1994), 111(4), 1269-1279; Hriscu, Anisoara; Gherase, Florenta; Pavelescu, M.; Hriscu, E. "Experimental evaluation of the analgesic efficacy of some antihistamines as proof of the histaminergic receptor involvement in pain." Farmacia, (2001), 49(2), 23-30, 76.

The ability of the compounds of the invention, including, but not limited to, those specified in the examples, to treat sleep disorders, including narcolepsy and pathological sleepiness, and jet lag, may be demonstrated by Barbier, A. J., et al. "Acute wake-promoting actions of JNJ-5207852, a novel, diamine-based $H_3$ antagonist" British Journal of Pharmacology (2004) 1-13; Monti et al., Neuropsychopharmacology (1996) 15, 31-35; Lin et al., Brain Res. (1990) 523, p. 325-330; Monti, et al., Neuropsychopharmacology (1996) 15, p. 31-35; Ligneau, et al. Journal of Pharmacology and Experimental Therapeutics (1998), 287, 658-666; Sakai, et al., Life Sci. (1991) 48, p. 2397-2404; Mazurkiewicz-Kwilecki and Nsonwah, Can. J. Physiol. Pharmacol., (1989) 67, p. 75-78; P. Panula, et al., Neuroscience (1998) 44, 465-481; Wada, et al., Trends in Neuroscience (1991) 14, p. 415; and Monti, et al., Eur. J. Pharmacol. (1991), 205, p. 283; Dvorak, C., et al. "4-Phenoxypiperidines: Potent, Conformationally Restricted, Non-Imidazole Histamine $H_3$ Antagonists" Journal of Medicinal Chemistry (2005) 48, 2229-2238.

The ability of the compounds of the invention, including, but not limited to, those specified in the examples, to treat drug abuse. Amphetamine is an abused stimulant in humans. It, and similar abused drugs stimulate locomotor activity in animals, and it has been found that the $H_3$ antagonist thioperamide suppresses the locomotor stimulation induced by amphetamine; therefore $H_3$ antagonists are likely to be useful for treating drug abuse as may be demonstrated by Clapham J.; Kilpatrick G. J. "Thioperamide, the selective histamine $H_3$ receptor antagonist, attenuates stimulant-induced locomotor activity in the mouse", European journal of pharmacology (1994), 259(2), 107-14.

The ability of the compounds of the invention, including, but not limited to, those specified in the examples, to treat mood alteration, bipolar disorder, depression, obsessive compulsive disorder, and Tourette's syndrome, may be demonstrated by Lamberti, et al. British Journal of Pharmacology (1998) 123, 1331-1336; Perez-Garcia C, et. al., Psychopharmacology (Berlin) (1999) 142(2): 215-20.

The ability of the compounds of the invention, including, but not limited to, those specified in the examples, to treat Parkinson's disease (a disease wherein patients have deficits in ability to initiate movements, and patients' brain have low dopamine levels) may be demonstrated by Sánchez-Lemus, E., et al. "Histamine $H_3$ receptor activation inhibits dopamine $D_1$ receptor-induced cAMP accumulation in rat striatal slices" Neuroscience Letters (2004) 364, p. 179-184; Sakai, et al., Life Sci. (1991) 48, 2397-2404; Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist" Journal of Pharmacology and Experimental Therapeutics, 313:176-190, 2005; Chen, Z., et al. "Pharmacological effects of carcinine on histaminergic neurons in the brain" British Journal of Pharmacology (2004) 143, 573-580.

The ability of the compounds of the invention, including, but not limited to, those specified in the examples, to treat medullary thyroid carcinoma, melanoma, polycystic ovary syndrome, may be demonstrated by Polish Med. Sci. Mon. (1998) 4(5): 747; Adam Szelag, "Role of histamine $H_3$-receptors in the proliferation of neoplastic cells in vitro," Med. Sci. Monitor (1998) 4(5): 747-755; and C. H. Fitzsimons, et al., "Histamine receptors signalling in epidermal tumor cell lines with H-ras gene alterations," Inflammation Res. (1998) 47 (Suppl 1):S50-S51.

Compounds of the invention are particularly useful for treating and preventing a condition or disorder affecting memory or cognition, for example Alzheimer's disease, attention-deficit hyperactivity disorder, schizophrenia, or the cognitive deficits of schizophrenia.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 30 mg/kg/day. For purposes of oral administration, more preferable doses can be in the range of from about 0.0003 to about 1 mg/kg/day. If desired, the effective daily dose can be divided into multiple doses for purposes of administration; consequently, single dose compositions may contain such amounts or submultiples thereof to make up the daily dose.

Compounds and compositions of the invention also are useful as diagnostic tools. The ability of PET (positron emitting tomography) and sPECT to probe the degree of receptor occupancy in humans and animals by endogenous ligands (such as histamine for the histamine $H_3$ receptor) or drugs (such with a clinically used drug that affects brain histamine levels) is widely recognized. This constitutes the use of PET as a biomarker to assess efficacy of pharmacological interventions with drugs. The topic and use of positron-emitting ligands for these purposes has been generally reviewed, for example in "PET ligands for assessing receptor occupancy in vivo" Burns, et al. Annual Reports in Medicinal Chemistry (2001), 36, 267-276; "Ligand-receptor interactions as studied by PET: implications for drug development" by Jarmo Hietala, Annals of Medicine (Helsinki) (1999), 31(6), 438-443; "Positron emission tomography neuroreceptor imaging as a tool in drug discovery, research and development" Burns, et al. Current Opinion in Chemical Biology (1999), 3(4), 388-394. The compounds of the invention, synthesized with $^{11}C$, $^{18}F$, or other positron-emitting isotopes are suitable ligand tools for PET; a number of positron-emitting reagents have been synthesized, are available, and are known to those skilled in the art. Especially suitable compounds of the invention for this use are those wherein a $^{11}CH_3$ group can be incorporated in by reaction with $^{11}CH_3I$. Also, especially suitable compounds of the use are those wherein a $^{18}F$ group can be incorporated into the compound by reaction with $^{18}F$-fluoride anion. The incorporation of $^{11}CH_3I$ can be carried out according to a method such as that described in Example 51, substituting $^{11}CH_3I$ for the $^{12}CH_3I$ used in Example 51. In a like manner, other analogs, wherein compounds of formula (1), wherein $R_6$, $R_{6a}$, or $R_{6b}$ are pyrazol-4-yl or pyrazol-2-yl can be treated with base and $^{11}CH_3I$ to prepare ligands for use in PET studies. For incorporation of $^{18}F$ into compounds or compositions of the invention, compounds of formula (I), wherein $R_4R_5N$ is 4-hydroxypiperidine or 4-hydroxymethylpyrrolidine, can be treated with methanesulfonic anhydride or triflic anhydride and a base in an inert solvent such as dichloromethane, and the resulting compound (a methanesulfonate or triflate) can be treated with $^{18}F$-fluoride by methods well known to skilled in the art of synthetic organic chemistry or medicinal chemistry. Among compounds of the invention that are suitable for use as ligands for PET studies are $^{18}F$ and $^{11}C$ isotopes of compounds of the invention, including, but not limited to Trans-6-(1-($^{11}C$)methyl-1H-pyrazol-4-yl)-2-(3-piperidin-1-ylcyclobutyl)-1,3-benzothiazole;

Trans-2-{3-[(2S)-2-(($^{18}F$)fluoromethyl)pyrrolidin-1-yl]cyclobutyl}-6-pyrimidin-5-yl-1,3-benzothiazole;

Trans-2-{3-[(2S)-2-(($^{18}F$)fluoromethyl)pyrrolidin-1-yl]cyclobutyl}-6-pyrimidin-5-yl-1,3-benzothiazole;

Trans-2-[3-(4-($^{18}F$)fluoropiperidin-1-yl)cyclobutyl]-6-(2-methoxypyrimidin-5-yl)-1,3-benzothiazole;

Trans-6-(2,6-dimethylpyridin-3-yl)-2-[3-(4-($^{18}F$)fluoropiperidin-1-yl)cyclobutyl]-1,3-benzothiazole;

Trans-Methyl-{3-[6-(1-($^{11}C$)methyl-1H-pyrazol-4-yl)-benzothiazol-2-yl]-cyclobutyl}-propyl-amine;

Trans-6-(1-($^{11}C$)Methyl-1H-pyrazol-4-yl)-2-[3-(2-methylpyrrolidin-1-yl)-cyclobutyl]-benzothiazole;

Trans-2-[3-(4-($^{18}F$)Fluoro-piperidin-1-yl)-cyclobutyl]-6-(1-methyl-1H-pyrazol-4-yl)-benzothiazole; and Trans-2-[3-(4-(Fluoro-piperidin-1-yl)-cyclobutyl]-6-(1-($^{11}C$)methyl-1H-pyrazol-4-yl)-benzothiazole.

The compounds and processes of the invention will be better understood by reference to the following examples, which are intended as an illustration of and not a limitation upon the scope of the invention.

REFERENCE EXAMPLES

Reference Example 1

3-methylenecyclobutanecarboxylic acid

3-Methylenecyclobutanecarbonitrile (CAS# 15760-35-7, 33.84 g, 0.368 mole), sodium hydroxide (38 g, 0.95 mole) and water (50 mL) were mixed and heated at 110° C. for 30 min to give a two-phase mixture. Tetrabutylammonium hydroxide (40 wt. % in water, 0.7 mL) was added and the organic phase became brown. Within 10 minutes, gas was evolved, and the two phases became well mixed to give a light brown homogeneous solution. Heating was continued at 110° C. for two days. The mixture was cooled to room temperature and then to 0° C. Concentrated hydrochloric acid (95 mL) was added very slowly to adjust the pH to 0.5-1.0. A white slurry was formed, which was extracted with ether (500 mL×2). The organic layer was dried (over $Na_2SO_4$), and concentrated to give an oil. This oil was distilled and collected at 108° C.-110° C. to give a colorless liquid (27.74 g, 68% yield). 1H NMR (300 MHz, CDCl$_3$) δ ppm 4.77-4.88 (m, 2H), 3.10-3.24 (m, 1H), 2.86-3.09 (m, 4H).

Reference Example 2

3-methylenecyclobutanecarboxylic acid chloride

In a 50 mL round-bottom flask equipped with a dropping funnel and water condenser with drying tube, the carboxylic acid prepared above (26.19 g, 0.234 mole) was charged. Thionyl chloride (20.5 mL, 0.281 mole, 1.2 equiv) was added dropwise. The mixture was heated at reflux (oil bath temperature 90° C.) for 3 h then cooled to room temperature. The condenser was replaced with a distillation head and the mixture was distilled under vacuum. A clear colorless liquid was collected at 43-45° C. (23 g, 75% yield). 1H NMR (300 MHz, CDCl$_3$) δ ppm 4.85-4.93 (m, 2H), 3.50-3.63 (m, 1H), 2.95-3.19 (m, 4H).

EXAMPLES

Example 1

Trans-2-{3-[(2R)-2-methylpyrrolidin-1-yl]cyclobutyl}-6-pyrimidin-5-yl-1,3-benzothiazole Example 1A 2-Amino-5-bromo-benzenethiol 6-Bromo-2-benzothiazolinone (4.65 g, 20.0 mmole) and sodium hydroxide (15.4 g, 0.385 mole) were mixed in 40 ml water. The mixture was stirred at room temperature for 30 minutes to form a slurry, was then heated at 100° C. and became a clear solution. The mixture continued to stir at 100° C. overnight after which it was cooled to room temperature. While cooling in an ice bath, the pH of the solution was adjusted to 6 with acetic acid (22 ml). The resulting solid was collected by filtration, washed three times (3×) with water and dried under vacuum to give 4.60 g of title compound. $^1$H NMR (300 MHz, DMSO-d$_6$) δ ppm 7.23 (s, 1H), 6.98 (d, J=7.80 Hz, 1H), 6.59 (d, J=8.82 Hz, 1H), 5.41 (br, 2H). MS: (M+H)$^+$=203/205, (M+H)$^+$=406.

Example 1B

6-Bromo-2-(3-methylene-cyclobutyl)-benzothiazole

The product of Example 1A (1.0 g, 4.90 mmole) was weighed into a 100 ml round bottom flask and pyrridium p-toluenesulfonate (0.37 g, 1.47 mmole) was added. The flask was placed on high vacuum overnight. Para-xylene (50 ml) was added followed by tiethylamine (0.68 ml, 4.9 mmole). The mixture was rapidly stirred at 50° C. to give an almost clear solution. A solution of 3-methylene-cyclobutanecarbonyl chloride (0.64 g, 4.9 mmole) (prepared according to literature procedure, JACS, 1959, 81, 2723-2728) in 10 ml xylene was then added dropwise over 15 minutes. The temperature was raised to 140° C. for 7 hours. The mixture was cooled to room temperature, followed by the addition of ethyl acetate (100 ml). The resulting solution was washed with saturated sodium bicarbonate, and the organic layer was dried ($Na_2SO_4$), and concentrated to give an oil. The crude product was purified by chromatography (20% hexane in dichloromethane) to give the title compound (1.03 g, 75%). $^1$H NMR (300 MHz, $CDCl_3$) δ ppm 7.98 (d, J=2.03 Hz, 1H), 7.83 (d, J=8.82 Hz, 1H), 7.55 (dd, J=8.82, 2.03 Hz, 1H), 4.83-4.98 (m, 2H), 3.83-4.04 (m, 1H), 3.10-3.35 (m, 4H). MS: $(M+H)^+$=279/281.

Example 1C

3-(6-Bromo-benzothiazol-2-yl)-cyclobutanone

The product of Example 1B (931 mg, 3.33 mmole) and osmium tetraoxide (28 mg, cat.) were dissolved in 30 ml THF and 15 ml water. The solution was cooled to 0° C. Sodium periodate (1.5 g, 7.0 mmole) was added in small portions. The mixture was stirred at room temperature overnight. The solution was quenched with water, and extracted three times with dichloromethane. The combined organics were dried over sodium sulfate and concentrated to give the crude product, which was purified by chromatography (20% hexane in dichloromethane) to give the title compound (710 mg, 76%). $^1$H NMR (500 MHz, $CDCl_3$) δ ppm 8.00 (d, J=1.87 Hz, 1H), 7.84 (d, J=8.74 Hz, 1H), 7.59 (dd, J=8.73, 1.87 Hz, 1H), 3.96-4.10 (m, 1H), 3.54-3.76 (m, 4H). MS: $(M+H)^+$=281/283

Example 1D

Cis-3-(6-Bromo-benzothiazol-2-yl)-cyclobutanol

The product of Example 1C (710 mg, 2.52 mmole) was dissolved in 50 ml anhydrous THF and cooled to 0° C. L-selectride (1.0M in THF, 3.02 ml, 3.02 mmole) was added slowly. The mixture was stirred at 0° C. for 10 minutes, then warmed to room temperature for 30 minutes. It was then quenched with 1 N sodium hydroxide (20 ml) and extracted three times with ethyl acetate. The organics were combined, dried over sodium sulfate and concentrated to give the crude product, which was used in the next step without further purification.

Example 1E

Trans-6-bromo-2-{3-[(2R)-2-methylpyrrolidin-1-yl]cyclobutyl}-1,3-benzothiazole The product of Example 1D (2.52 mmole) was dissolved in anhydrous dichloromethane (20 ml). Potassium carbonate (696 mg, 5.04 mmole) was added followed by trifluoromethanesulfonic anhydride (551 µl, 3.27 mmole). The mixture was allowed to stir at room temperature for 2 hours, then another portion of potassium carbonate (1.74 g, 12.6 mmole) was added, followed by 2-(R)-methylpyrrolidine L-tartrate (prepared according to the procedure that described in: R. Altenbach et al., WO 2004043458, and Y. Pu et al., Organic Process Research & Development, 9(1), 45-50, 2005) (1.18 g, 5.04 mmole). The resulting mixture was stirred at room temperature overnight. It was then quenched with water, and extracted three times with dichloromethane. The organic layers were combined, washed with brine, dried over sodium sulfate, and concentrated. The crude product was purified by column chromatography (0.5% ammonium hydroxide and 5% methanol in dichloromethane) to give 394 mg (45%) of title compound. $^1$H NMR (400 MHz, $CDCl_3$) δ ppm 7.97 (d, J=1.84 Hz, 1H), 7.83 (d, J=8.90 Hz, 1H), 7.55 (dd, J=8.75, 1.99 Hz, 1H), 3.75-3.88 (m, 1H), 3.40-3.56 (m, 1H), 3.00-3.10 (m, 1H), 2.61-2.79 (m, 3H), 2.42-2.57 (m, 2H), 2.23-2.37 (m, 1H), 1.88-2.02 (m, 1H), 1.77-1.88 (m, 1H), 1.61-1.76 (m, 1H), 1.39-1.54 (m, 1H), 1.11 (d, J=6.14 Hz, 3H). MS: $(M+H)^+$=351/353.

Example 1F

Trans-2-{3-[(2R)-2-methylpyrrolidin-1-yl]cyclobutyl}-6-pyrimidin-5-yl-1,3-benzothiazole A solution of the product of Example 1E (40 mg, 0.114 mmole), pyrimidine-5-boronic acid (CAS # 109299-78-7) (21 mg, 0.169 mmole), dichlorobis(triphenylphosphine)palladium(II) (8 mg, 0.01 mmole) and potassium carbonate (47 mg, 0.34 mmole) in 1 ml isopropanol was heated at 85° C. overnight with stirring. The reaction was then quenched with water and extracted three times with dichloromethane. The combined organic layers were washed with brine, dried over sodium sulfate, filtered, and concentrated. The crude product was purified by column chromatography (eluted by 0.35% ammonium hydroxide and 3.5% methanol in dichloromethane) to give 33 mg (82%/o yield) of title compound. $^1$H NMR (400 MHz, $CDCl_3$) δ ppm 9.23 (s, 1H), 9.02 (s, 2H), 8.12 (d, J=8.59 Hz, 1H), 8.06 (d, J=1.84 Hz, 1H), 7.67 (dd, J=8.44, 1.99 Hz, 1H), 3.83-3.94 (m, 1H), 3.46-3.62 (m, 1H), 2.99-3.14 (m, 1H), 2.64-2.85 (m, 3H), 2.43-2.64 (m, 2H), 2.23-2.40 (m, 1H), 1.89-2.03 (m, 1H), 1.78-1.91 (m, 1H), 1.67-1.78 (m, 1H), 1.42-1.56 (m, 1H), 1.14 (d, J=4.91 Hz, 3H). MS: $(M+H)^+$=351.

Example 2

Trans-6-(2,6-dimethylpyridin-3-yl)-2-{3-[(2R)-2-methylpyrrolidin-1-yl]cyclobutyl}-1,3-benzothiazole

Example 2A

2,6-Dimethyl-3-(4,4,5,5-tetramethyl-[1,3,2]dioxaborolan-2-yl)-pyridine

A solution of 3-bromo-2,6-dimethylpyridine (5.10 g, 27.4 mmol) in anhydrous ether (160 ml) cooled to −78° C. under a nitrogen atmosphere was treated dropwise with n-butyl lithium (4.1 ml, 10 M in hexane) and stirred at −78° C. for 45 minutes. 2-isopropoxy-4,4,5,5-tetramethyl-[1,3,2]dioxaborolane (10.2 g, 54.8 mmol) in 20 ml of ether was added dropwise at −78° C. and stirred at −78° C. for 3 hours. The mixture was quenched with 10 ml of isopropanol, and allowed to warm to room temperature. 150 ml of saturated aqueous NaCl solution was added. The aqueous phase was separated and extracted with dichloromethane (100 ml×6). The combined organic phases were dried and concentrated to provide the title compound as light brown oil (6.29 g, 98.4%).

¹H NMR (300 MHz, CDCl₃) δ ppm 7.92 (d, J=7.46 Hz, 1H) 6.96 (d, J=7.80 Hz, 1H) 2.73 (s, 3H) 2.53 (s, 3H) 1.34 (s, 12H). MS: (M+H)⁺=234.

Example 2B

Trans-6-(2,6-dimethylpyridin-3-yl)-2-{3-[(2R)-2-methylpyrrolidin-1-yl]cyclobutyl}-1,3-benzothiazole The title compound was prepared according to the procedure described in Example 1F, substituting the product of Example 2A for pyrimidine-5-boronic acid. ¹H NMR (400 MHz, CDCl₃) δ ppm 8.02 (d, J=8.29 Hz, 1H) 7.76 (d, J=1.84 Hz, 1H) 7.46 (d, J=7.67 Hz, 1H) 7.39 (dd, J=8.44, 1.69 Hz, 1H) 7.07 (d, J=7.67 Hz, 1H) 3.82-3.93 (m, 1H) 3.47-3.58 (m, 1H) 2.98-3.13 (m, 1H) 2.64-2.84 (m, 3H) 2.59 (s, 3H) 2.50 (s, 3H) 2.43-2.59 (m, 2H) 2.26-2.40 (m, 1H) 1.89-2.03 (m, 1H) 1.78-1.88 (m, 1H) 1.61-1.75 (m, 1H) 1.40-1.54 (m, 1H) 1.13 (t, J=5.37 Hz, 3H). MS: (M+H)⁺=378.

Example 3

Trans-6-(2,4-dimethoxypyrimidin-5-yl)-2-{3-[(2R)-2-methylpyrrolidin-1-yl]cyclobutyl}-1,3-benzothiazole The title compound was prepared according to the procedure described in Example 1F, substituting 2,6-dimethoxy-5-pyrimidineboronic acid (CAS # 89641-18-9) for pyrimidine-5-boronic acid. ¹H NMR (400 MHz, CDCl₃) δ ppm 8.32 (s, 1H) 8.02 (d, J=8.59 Hz, 1H) 7.97 (d, J=1.84 Hz, 1H) 7.57 (dd, J=8.44, 1.69 Hz, 1H) 4.06 (s, 3H) 4.05 (s, 3H) 3.82-3.92 (m, 1H) 3.45-3.59 (m, 1H) 3.02-3.13 (m, 1H) 2.65-2.82 (m, 3H) 2.47-2.62 (m, 2H) 2.25-2.41 (m, 1H) 1.90-2.02 (m, 1H) 1.77-1.89 (m, 1H) 1.67-1.76 (m, 1H) 1.53-1.66 (m, 1H) 1.14 (d, J=5.83 Hz, 3H). MS: (M+H)⁺=411.

Example 4

Trans-6-(2-methoxypyrimidin-5-yl)-2-{3-[(2R)-2-methylpyrrolidin-1-yl]cyclobutyl}-1,3-benzothiazole The title compound was prepared according to the procedure described in Example 1F, substituting 2-methoxypyrimidine-5-boronic acid (Frontier Scientific, Inc., Logan, Utah, USA) for pyrimidine-5-boronic acid. ¹H NMR (500 MHz, CDCl₃) δ ppm 8.77 (s, 2H) 8.08 (d, J=8.42 Hz, 1H) 7.98 (d, J=1.56 Hz, 1H) 7.57 (dd, 1H) 4.09 (s, 3H) 3.83-3.95 (m, 1H) 3.50-3.62 (m, 1H) 3.03-3.15 (m, 1H) 2.67-2.85 (m, 2H) 2.46-2.64 (m, 2H) 2.29-2.40 (m, 1H) 1.92-2.03 (m, 1H) 1.82-1.89 (m, 1H) 1.65-1.79 (m, 1H) 1.44-1.63 (m, 2H) 1.15 (s, 3H). MS: (M+H)⁺=381.

Example 5

Trans-2-{3-[(2R)-2-methylpyrrolidin-1-yl]cyclobutyl}-6-pyridin-4-yl-1,3-benzothiazole The title compound was prepared according to the procedure described in Example 1F, substituting pyridine-4-boronic acid for pyrimidine-5-boronic acid. ¹H NMR (500 MHz, CDCl₃) δ ppm 8.69 (d, J=6.24 Hz, 2H) 8.12 (d, J=1.87 Hz, 1H) 8.08 (d, J=8.42 Hz, 1H) 7.73 (dd, J=8.42, 1.87 Hz, 1H) 7.56 (dd, J=4.52, 1.72 Hz, 2H) 3.85-3.93 (m, 1H) 3.49-3.59 (m, 1H) 3.01-3.13 (m, 1H) 2.69-2.84 (m, 2H) 2.46-2.61 (m, 2H) 2.28-2.42 (m, 1H) 1.92-2.01 (m, 1H) 1.79-1.88 (m, 1H) 1.69-1.78 (m, 1H) 1.57-1.66 (m, 1H) 1.45-1.55 (m, 1H) 1.14 (d, J=5.62 Hz, 3H). MS: (M+H)⁺=350.

Example 6

Trans-6-(6-methoxypyridin-3-yl)-2-{3-[(2R)-2-methylpyrrolidin-1-yl]cyclobutyl}-1,3-benzothiazole The title compound was prepared according to the procedure described in Example 1F substituting 2-methoxypyridine-5-boronic acid for pyrimidine-5-boronic acid. ¹H NMR (300 MHz, CDCl₃) δ ppm 8.00 (d, J=8.48 Hz, 1H) 7.87 (d, J=2.03 Hz, 1H) 7.67 (dd, J=9.15, 2.71 Hz, 1H) 7.56 (d, J=2.71 Hz, 1H) 7.49 (dd, J=8.48, 2.03 Hz, 1H) 6.70 (d, J=9.15 Hz, 1H) 3.82-3.95 (m, 1H) 3.65 (s, 3H) 3.48-3.60 (m, 1H) 3.01-3.21 (m, 1H) 2.65-2.87 (m, 2H) 2.45-2.64 (m, 2H) 2.28-2.44 (m, 1H) 1.92-2.05 (m, 1H) 1.62-1.91 (m, 3H) 1.46-1.60 (m, 1H) 1.15 (s, 3H). MS: (M+H)⁺=380.

Example 7

Trans-2-{3-[(2R)-2-methylpyrrolidin-1-yl]cyclobutyl}-6-pyridin-3-yl-1,3-benzothiazole The title compound was prepared according to the procedure described in Example 1F, substituting pyridine-3-boronic acid for pyrimidine-5-boronic acid. ¹H NMR (300 MHz, CDCl₃) δ ppm 8.91 (d, J=1.70 Hz, 1H) 8.62 (dd, J=4.92, 1.53 Hz, 1H) 8.02-8.15 (m, 2H) 7.89-7.97 (m, 1H) 7.68 (dd, J=8.48, 1.70 Hz, 1H) 7.34-7.44 (m, 1H) 3.79-3.96 (m, 1H) 3.46-3.62 (m, 1H) 3.02-3.16 (m, 1H) 2.65-2.88 (m, 2H) 2.47-2.63 (m, 2H) 2.27-2.44 (m, 1H) 1.64-2.06 (m, 4H) 1.41-1.59 (m, 1H) 1.14 (t, J=6.95 Hz, 3H). MS: (M+H)⁺=350.

Example 8

Trans-3-(2-{3-[(2R)-2-methylpyrrolidin-1-yl]cyclobutyl}-1,3-benzothiazol-6-yl)quinoline The title compound was prepared according to the procedure described in Example 1F, substituting 3-(4,4,5,5-Tetramethyl-[1,3,2]dioxaborolan-2-yl)-quinoline (CAS #171364-85-5) for pyrimidine-5-boronic acid. ¹H NMR (300 MHz, CDCl₃) δ ppm 9.24 (d, J=2.37 Hz, 1H) 8.37 (d, J=2.03 Hz, 1H) 8.08-8.23 (m, 3H) 7.91 (d, J=7.46 Hz, 1H) 7.82 (dd, J=8.48, 1.70 Hz, 1H) 7.72-7.79 (m, 1H) 7.61 (t, J=7.46 Hz, 1H) 3.87-4.00 (m, 1H) 3.46-3.64 (m, 1H) 3.01-3.15 (m, 1H) 2.73-2.83 (m, 2H) 2.58-2.69 (m, 2H) 2.32-2.45 (m, 1H) 1.70-2.12 (m, 5H) 1.55 (s, 3H). MS: (M+H)⁺=400.

Example 9

Trans-6-(6-fluoropyridin-3-yl)-2-{3-[(2R)-2-methylpyrrolidin-1-yl]cyclobutyl}-1,3-benzothiazole The title compound was prepared according to the procedure described in Example 1F, substituting 2-fluoro-5-(4,4,5,5-tetramethyl-[1,3,2]dioxaborolan-2-yl)-pyridine (available from Aldrich) for pyrimidine-5-boronic acid. ¹H NMR (300 MHz, CDCl₃) δ ppm 8.48 (d, J=2.71 Hz, 1H) 8.07 (d, J=8.48 Hz, 1H) 7.98-8.04 (m, 2 H) 7.62 (dd, J=8.48, 2.03 Hz, 1H) 7.04 (dd, J=8.48, 2.71 Hz, 1H) 3.84-3.97 (m, 1H) 3.46-3.68

(m, 1H) 2.95-3.22 (m, 1H) 2.68-2.87 (m, 2H) 2.51-2.64 (m, 2H) 2.24-2.44 (m, 1H) 1.47-2.08 (m, 5H) 1.17 (s, 3H). MS: (M+H)$^+$=368.

Example 10

Trans-4-(2-{3-[(2R)-2-methylpyrrolidin-1-yl]cyclobutyl}-1,3-benzothiazol-6-yl)benzonitrile The title compound was prepared according to the procedure described in Example 1F, substituting 4-cyanophenylboronic acid for pyrimidine-5-boronic acid. $^1$H NMR (300 MHz, CDCl$_3$) δ ppm 8.05-8.06 (m, 2H) 7.75 (s, 4H) 7.68 (dd, J=8.82, 1.70 Hz, 1H) 3.83-3.94 (m, 1H) 3.46-3.58 (m, 1H) 3.01-3.15 (m, 1H) 2.65-2.86 (m, 2H) 2.45-2.63 (m, 2H) 2.27-2.42 (m, 1H) 1.65-2.03 (m, 4H) 1.42-1.57 (m, 1H) 1.14 (d, J=6.10 Hz, 3H). MS: (M+H)$^+$=374.

Example 11

Trans-2-{3-[(2S)-2-methylpyrrolidin-1-yl]cyclobutyl}-6-pyrimidin-5-yl-1,3-benzothiazole

Example 11A

Trans-6-bromo-2-{3-[(2S)-2-methylpyrrolidin-1-yl]cyclobutyl}-1,3-benzothiazole

The title compound was prepared according to the procedure described in Example 1E, substituting 2-(S)-methylpyrrolidine for 2-(R)-methylpyrrolidine. $^1$H NMR (500 MHz, CDCl$_3$) δ ppm 7.98 (d, J=1.87 Hz, 1H) 7.82 (d, J=8.74 Hz, 1H) 7.56 (dd, J=8.73, 2.18 Hz, 1H) 3.87 (t, J=9.83 Hz, 1H) 3.65-3.80 (m, 1H) 3.22-3.39 (m, 1H) 2.82-3.00 (m, 3H) 2.69-2.78 (m, 1H) 2.56-2.66 (m, 2H) 2.04-2.14 (m, 1H) 1.89-2.03 (m, 1H) 1.78-1.89 (m, 1H) 1.61-1.72 (m, 1H) 1.27 (d, J=4.37 Hz, 3H). MS: (M+H)$^+$=351/353.

Example 11B

Trans-2-{3-[(2S)-2-methylpyrrolidin-1-yl]cyclobutyl}-6-pyrimidin-5-yl-1,3-benzothiazole The title compound was prepared according to the procedure described in Example 1F, substituting Example 11A for Example 1E. $^1$H NMR (500 MHz, CDCl$_3$) δ ppm 9.24 (s, 1H) 8.97-9.08 (s, 2H) 8.12 (d, J=8.54 Hz, 1H) 8.07 (d, J=1.53 Hz, 1H) 7.67 (dd, J=8.54, 1.83 Hz, 1H) 3.86-3.96 (m, 1H) 3.49-3.68 (m, 1H) 3.03-3.21 (m, 1H) 2.69-2.87 (m, 3H) 2.53-2.66 (m, 2H) 2.26-2.44 (m, 1H) 1.94-2.08 (m, 1H) 1.80-1.94 (m, 1H) 1.68-1.81 (m, 1H) 1.53-1.64 (m, 1H) 1.16 (s, 3H). MS: (M+H)$^+$=351.

Example 12

Trans-6-(2,4-dimethoxypyrimidin-5-yl)-2-{3-[(2S)-2-methylpyrrolidin-1-yl]cyclobutyl}-1,3-benzothiazole The title compound was prepared according to the procedure described in Example 1F, substituting the product of Example 11A for the product of Example 1E and substituting 2,6-dimethoxy-5-pyrimidineboronic acid for pyrimidine-5-boronic acid. $^1$H NMR (500 MHz, CDCl$_3$) δ ppm 8.32 (s, 1H) 8.02 (d, J=8.54 Hz, 1H) 7.98 (d, J=1.53 Hz, 1H) 7.57 (dd, J=8.39, 1.68 Hz, 1H) 4.06 (s, 3H) 4.05 (s, 3H) 3.83-3.95 (m, 1H) 3.51-3.72 (m, 1H) 3.10-3.29 (m, 1H) 2.68-2.80 (m, 3H) 2.40-2.65 (m, 3H) 1.49-2.13 (m, 4H) 1.10-1.27 (s, 3H). MS: (M+H)$^+$=411.

Example 13

Trans-6-(2,6-dimethylpyridin-3-yl)-2-{3-[(2S)-2-methylpyrrolidin-1-yl]cyclobutyl}-1,3-benzothiazole The title compound was prepared according to the procedure described in Example 1F, substituting the Example 11A for the Example 1E and substituting the product of Example 2A for pyrimidine-5-boronic acid. $^1$H NMR (500 MHz, CDCl$_3$) δ ppm 8.02 (d, J=8.24 Hz, 1H) 7.77 (d, J=1.22 Hz, 1H) 7.46 (d, J=7.63 Hz, 1H) 7.40 (dd, J=8.39, 1.68 Hz, 1H) 7.07 (d, J=7.63 Hz, 1H) 3.83-3.95 (m, 1H) 3.49-3.65 (m, 1H) 3.04-3.18 (m, 1H) 2.69-2.83 (m, 3H) 2.59 (s, 3H) 2.53 (s, 3H) 2.39-2.63 (m, 3H) 1.95-2.03 (m, 1H) 1.81-1.94 (m, 1H) 1.69-1.80 (m, 1H) 1.58-1.68 (m, 1H) 1.16 (s, 3H). MS: (M+H)$^+$=378.

Example 14

Trans-6-(2-methoxypyrimidin-5-yl)-2-{3-[(2S)-2-methylpyrrolidin-1-yl]cyclobutyl}-1,3-benzothiazole The title compound was prepared according to the procedure described in Example 1F, except for substituting the product of Example 11A for the product of Example 1E and substituting 2-methoxypyrimidine-5-boronic acid for pyrimidine-5-boronic acid. $^1$H NMR (500 MHz, CDCl$_3$) δ ppm 8.77 (s, 2H) 8.08 (d, J=8.42 Hz, 1H) 7.98 (d, J=1.87 Hz, 1H) 7.60 (dd, J=8.58, 1.72 Hz, 1H) 4.09 (s, 3H) 3.84-3.98 (m, 1H) 3.47-3.65 (m, 1H) 2.99-3.18 (m, 1H) 2.66-2.80 (m, 2H) 2.44-2.62 (m, 2H) 2.27-2.44 (m, 1H) 1.92-2.04 (m, 1H) 1.80-1.92 (m, 1H) 1.67-1.78 (m, 1H) 1.44-1.64 (m, 2H) 1.14 (s, 3H). MS: (M+H)$^+$=378.

Example 15

Trans-6-(6-methoxypyridin-3-yl)-2-{3-[(2S)-2-methylpyrrolidin-1-yl]cyclobutyl}-1,3-benzothiazole The title compound was prepared according to the procedure described in Example 1F, except for substituting the product of Example 11A for the product of Example 1E and substituting 6-methoxy-3-pyridineboronic acid for pyrimidine-5-boronic acid. $^1$H NMR (500 MHz, CDCl$_3$) δ ppm 8.43 (d, J=2.18 Hz, 1H) 8.03 (d, J=8.42 Hz, 1H) 7.97 (d, J=1.56 Hz, 1H) 7.83 (dd, J=8.58, 2.65 Hz, 1H) 7.61 (dd, J=8.42, 1.56 Hz, 1H) 6.84 (d, J=8.73 Hz, 1H) 4.00 (s, 3H) 3.81-3.92 (m, 1H) 3.47-3.58 (m, 1H) 2.97-3.15 (m, 1H) 2.66-2.85 (m, 2H) 2.44-2.64 (m, 2H) 2.26-2.39 (m, 1H) 1.92-2.03 (m, 1H) 1.79-1.89 (m, 1H) 1.67-1.77 (m, 1H) 1.46-1.64 (m, 2H) 1.14 (d, J=5.30 Hz, 3H). MS: (M+H)$^+$=380.

Example 16

Trans-3-(2-{3-[(2S)-2-methylpyrrolidin-1-yl]cyclobutyl}-1,3-benzothiazol-6-yl)quinoline The title compound was prepared according to the procedure described in Example 1F, substituting the product of Example 11A for the product of Example 1E and substituting 3-(4,4,5,5-tetramethyl-[1,3,2]dioxaborolan-2-yl)-quinoline for pyrimidine-5-boronic acid. $^1$H NMR (500 MHz, CDCl$_3$) δ ppm 9.24 (d, J=2.50 Hz, 1H) 8.37 (d, J=2.50 Hz, 1H)

8.09-8.21 (m, 3H) 7.90 (d, J=8.11 Hz, 1H) 7.81 (dd, J=8.42, 1.87 Hz, 1H) 7.71-7.78 (m, 1H) 7.54-7.66 (m, 1H) 3.82-3.99 (m, 1H) 3.46-3.64 (m, 1H) 2.98-3.16 (m, 1H) 2.65-2.86 (m, 2H) 2.42-2.64 (m, 2H) 2.28-2.41 (m, 1H) 1.92-2.05 (m, 1H) 1.81-1.89 (m, 1H) 1.69-1.78 (m, 1H) 1.44-1.63 (m, 2H) 1.16 (s, 3H). MS: (M+H)$^+$=400.

Example 17

Cis-2-{3-[(2R)-2-methylpyrrolidin-1-yl]cyclobutyl}-6-pyrimidin-5-yl-1,3-benzothiazole Example 17A Cis 6-bromo-2-{3-[(2R)-2-methylpyrrolidin-1-yl]cyclobutyl}-1,3-benzothiazole The product of Example 1C (500 mg, 1.77 mmole) was dissolved in 6 ml dichloromethane and 4 ml ethanol. 2-(R)-methylpyrrolidine (1.04 g, 4.43 mmole, toluene extract from 50% sodium hydroxide) was added and stirred at room temperature for 30 minutes. Then borane-pyridine (358 µl, 3.54 mmole) was added. The mixture was stirred at room temperature overnight. The reaction was quenched with saturated sodium bicarbonate and extracted with dichloromethane. The combined organic layers were washed with brine, dried over sodium sulfate, filtered, and concentrated under reduced pressure to give the crude product which was purified by column chromatography (0.4% ammonium hydroxide and 4% methanol in dichloromethane) to give 45 mg (9% yield) of the title compound. $^1$H NMR (500 MHz, CDCl$_3$) δ ppm 7.98 (d, J=1.83 Hz, 1H) 7.80 (d, J=8.85 Hz, 1H) 7.54 (dd, J=8.54, 1.83 Hz, 1H) 3.54-3.65 (m, 1H) 3.15-3.29 (m, 1H) 3.00-3.13 (m, 1H) 2.73-2.86 (m, 1H) 2.56-2.69 (m, 2H) 2.32-2.57 (m, 3H) 1.92-2.05 (m, 1H) 1.79-1.90 (m, 1H) 1.67-1.78 (m, 1H) 1.46-1.57 (m, 1H) 1.17 (s, 3H). MS: (M+H)$^+$=351/353.

Example 17B

Cis-2-{3-[(2R)-2-methylpyrrolidin-1-yl]cyclobutyl}-6-pyrimidin-5-yl-1,3-benzothiazole The title compound was prepared according to the procedure described in Example 1F, substituting Example the product of 17A for the product of Example 1E. $^1$H NMR (400 MHz, CDCl$_3$) δ ppm 9.23 (s, 1H) 9.01 (s, 2H) 8.03-8.13 (m, 2H) 7.65 (dd, J=8.44, 1.69 Hz, 1H) 3.57-3.74 (m, 1H) 3.17-3.31 (m, 1H) 3.01-3.12 (m, 1H) 2.76-2.88 (m, 1H) 2.61-2.70 (m, 1H) 2.44-2.59 (m, 3H) 2.30-2.40 (m, 1H) 1.91-2.05 (m, 1H) 1.78-1.89 (m, 1H) 1.67-1.79 (m, 1H) 1.44-1.62 (m, 1H) 1.17 (s, 3H). MS: (M+H)$^+$=351.

Example 18

Cis-6-(2,6-dimethylpyridin-3-yl)-2-{3-[(2R)-2-methylpyrrolidin-1-yl]cyclobutyl}-1,3-benzothiazole The title compound was prepared according to the procedure described in Example 1F, substituting the product of Example 17A for the product of Example 1E and substituting the product of Example 2A for pyrimidine-5-boronic acid. $^1$H NMR (400 MHz, CDCl$_3$) δ ppm 7.99 (d, J=8.29 Hz, 1H) 7.76 (d, J=1.84 Hz, 1H) 7.45 (d, J=7.67 Hz, 1H) 7.38 (dd, J=8.44, 1.69 Hz, 1H) 7.06 (d, J=7.36 Hz, 1H) 3.57-3.70 (m, 1H) 3.14-3.29 (m, 1H) 2.99-3.13 (m, 1H) 2.73-2.85 (m, 1H) 2.59 (s, 3H) 2.49 (s, 3H) 2.28-2.67 (m, 5H) 1.91-2.01 (m, 1H) 1.77-1.88 (m, 1H) 1.59-1.73 (m, 1H) 1.43-1.53 (m, 1H) 1.15 (s, 3H). MS: (M+H)$^+$=378.

Example 19

Cis-2-{3-[(2S)-2-methylpyrrolidin-1-yl]cyclobutyl}-6-pyrimidin-5-yl-1,3-benzothiazole Example 19A Cis-6-bromo-2-{3-[(2S)-2-methylpyrrolidin-1-yl]cyclobutyl}-1,3-benzothiazole The product of Example 1C (500 mg, 1.77 mmole) was dissolved in 6 ml dichloromethane and 4 ml ethanol. 2-(S)-methylpyrrolidine (1.04 g, 4.43 mmole, toluene extract from 50% sodium hydroxide) was then added and the solution was stirred at room temperature for 30 minutes. Borane-pyridine (358 µl, 3.54 mmole) was added, and the mixture was stirred at room temperature overnight. The reaction was quenched with saturated sodium bicarbonate and extracted three times with dichloromethane. The combined organic layers were washed with brine, dried over sodium sulfate, filtered, and concentrated to give the crude product which was purified by column chromatography (0.4% ammonium hydroxide and 4% methanol in dichloromethane) to give 98 mg (16% yield) of the title compound. $^1$H NMR (500 MHz, CDCl$_3$) δ ppm 7.98 (d, J=2.14 Hz, 1H) 7.80 (d, J=8.85 Hz, 1H) 7.54 (dd, J=8.54, 1.83 Hz, 1H) 3.54-3.65 (m, 1H) 3.15-3.29 (m, 1H) 3.00-3.12 (m, 1H) 2.74-2.85 (m, 1H) 2.58-2.68 (m, 1H) 2.43-2.56 (m, 3H) 2.30-2.39 (m, 1H) 1.92-2.02 (m, 1H) 1.78-1.89 (m, 1H) 1.70-1.76 (m, 1H) 1.44-1.59 (m, 1H) 1.16 (s, 3H). MS: (M+H)$^+$=351/353.

Example 19B

Cis-2-{3-[(2S)-2-methylpyrrolidin-1-yl]cyclobutyl}-6-pyrimidin-5-yl-1,3-benzothiazole The title compound was prepared according to the procedure described in Example 1F, substituting the product of Example 19A for the product of Example 1E. $^1$H NMR (400 MHz, CDCl$_3$) δ ppm 9.23 (s, 1H) 9.01 (s, 2H) 8.00-8.13 (m, 2H) 7.65 (dd, J=8.44, 1.69 Hz, 1H) 3.58-3.75 (m, 1H) 3.15-3.28 (m, 1H) 3.00-3.12 (m, 1H) 2.75-2.86 (m, 1H) 2.60-2.71 (m, 1H) 2.43-2.58 (m, 3H) 2.30-2.42 (m, 1H) 1.91-2.05 (m, 1H) 1.76-1.90 (m, 1H) 1.66-1.76 (m, 1H) 1.40-1.56 (m, 1H) 1.16 (s, 3H). MS: (M+H)$^+$=351.

Example 20

Cis-6-(2,4-dimethoxypyrimidin-5-yl)-2-{3-[(2S)-2-methylpyrrolidin-1-yl]cyclobutyl}-1,3-benzothiazole The title compound was prepared according to the procedure described in Example 1F, substituting the product of Example 19A for the product of Example 1E and substituting 2,6-dimethoxy-5-pyrimidineboronic acid for pyrimidine-5-boronic acid. $^1$H NMR (400 MHz, CDCl$_3$) δ ppm 8.31 (s, 1H) 7.91-8.03 (m, 2H) 7.55 (dd, J=8.44, 1.69 Hz, 1H) 4.06 (s, 3H) 4.05 (s, 3H) 3.55-3.70 (m, 1H) 3.15-3.29 (m, 1H) 3.02-3.14 (m, 1H) 2.72-2.88 (m, 1H) 2.60-2.71 (m, 1H) 2.43-2.56 (m, 3H) 2.30-2.40 (m, 1H) 1.91-2.02 (m, 1H) 1.79-1.88 (m, 1H) 1.66-1.77 (m, 1H) 1.44-1.55 (m, 1H) 1.16 (s, 3H). MS: (M+H)$^+$=411.

Example 21

Cis-6-(2,6-dimethylpyridin-3-yl)-2-{3-[(2S)-2-methylpyrrolidin-1-yl]cyclobutyl}-1,3-benzothiazole The title compound was prepared according to the procedure described in Example 1F, substituting the product of Example 19A for the product of Example 1E and substituting the product of Example 2A for pyrimidine-5-boronic acid. $^1$H NMR (400 MHz, CDCl$_3$) δ ppm 7.99 (d, J=8.29 Hz, 1H) 7.76 (d, J=1.53 Hz, 1H) 7.45 (d, J=7.67 Hz, 1H) 7.38 (dd, J=8.44, 1.69 Hz, 1H) 7.06 (d, J=7.67 Hz, 1H) 3.58-3.70 (m, 1H) 3.16-3.30 (m, 1H) 3.00-3.13 (m, 1H) 2.69-2.86 (m, 1H) 2.59-2.68 (m, 1H) 2.59 (s, 3H) 2.49 (s, 3H) 2.42-2.52 (m, 3H) 1.91-2.03 (m, 1H) 1.78-1.87 (m, 1H) 1.67-1.77 (m, 1H) 1.42-1.57 (m, 1H) 1.16 (s, 3H). MS: (M+H)$^+$=378.

Example 22

Trans-2-(2-{3-[(2R)-2-methylpyrrolidin-1-yl]cyclobutyl}-1,3-benzothiazol-6-yl)pyridazin-3(2H)-one The product of Example 1E (30 mg, 0.085 mmole), 3(2H)-pyridazinone (CAS # 504-30-3) (16 mg, 0.17 mmole), copper (11 mg, 0.17 mmole), and potassium carbonate (71 mg, 0.51 mmole) were mixed in degassed pyridine (1 ml) and the mixture was heated at reflux overnight. The reaction was quenched with water and extracted three times with dichloromethane. The combined organic layers were washed with brine, dried over sodium sulfate, filtered, and concentrated under reduced pressure to give the crude product which was purified by column chromatography (0.35% ammonium hydroxide and 3.5% methanol in dichloromethane) to give 23 mg (74% yield) of title compound. $^1$H NMR (500 MHz, CDCl$_3$) δ ppm 8.15 (m, 1H) 8.05 (m, 1H) 7.92 (dd, J=3.74, 1.87 Hz, 1H) 7.69 (dd, J=8.73, 2.18 Hz, 1H) 7.20-7.32 (m, 1H) 7.08 (dd, J=9.51, 1.72 Hz, 1H) 3.86-3.99 (m, 1H) 3.58-3.70 (m, 1H) 3.15-3.27 (m, 1H) 3.01-3.13 (m, 1H) 2.74-2.87 (m, 1H) 2.28-2.71 (m, 4H) 1.90-2.03 (m, 1H) 1.79-1.90 (m, 1H) 1.66-1.78 (m, 1H) 1.44-1.65 (m, 1H) 1.16 (s, 3H) MS: (M+H)$^+$=367.

Example 23

Trans-6-methyl-2-(2-{3-[(2R-2-methylpyrrolidin-1-yl]cyclobutyl}-1,3-benzothiazol-6-yl)pyridazin-3(2H)-one The title compound was prepared according to the procedure described in Example 22, substituting 6-methyl-3(2H)-pyridazinone (CAS #13327-27-0) for 3(2H)-pyridazinone. $^1$H NMR (500 MHz, CDCl$_3$) δ ppm 8.12 (d, J=1.87 Hz, 1H) 8.01 (d, J=8.74 Hz, 1H) 7.68 (dd, J=8.73, 2.18 Hz, 1H) 7.16 (d, J=9.36 Hz, 1H) 7.00 (d, J=9.67 Hz, 1H) 3.55-3.70 (m, 1H) 3.15-3.25 (m, 1H) 3.02-3.14 (m, 1H) 2.74-2.84 (m, 1H) 2.59-2.69 (m, 1H) 2.45-2.56 (m, 2H) 2.40 (s, 3H) 2.30-2.37 (m, 1H) 1.91-2.02 (m, 1H) 1.78-1.87 (m, 1H) 1.69-1.77 (m, 1H) 1.55-1.67 (m, 1H) 1.46-1.52 (m, 1H) 1.16 (d, J=1.87 Hz, 3H). MS: (M+H)$^+$=381.

Example 24

Trans-5-methyl-1-(2-{3-[(2R)-2-methylpyrrolidin-1-yl]cyclobutyl}-1,3-benzothiazol-6-yl)pyridin-2(1H)-one The title compound was prepared according to the procedure described in Example 22, substituting 5-methyl-2(1H)-pyridone (CAS #1003-68-5) for 3(2H)-pyridazinone. $^1$H NMR (500 MHz, CDCl$_3$) δ ppm 8.03 (m, 1H) 7.88 (d, J=1.87 Hz, 1H) 7.42 (dd, J=8.58, 2.03 Hz, 1H) 7.25-7.32 (m, 1H) 7.15 (s, 1H) 6.62 (d, J=9.36 Hz, 1H) 3.57-3.69 (m, 1H) 3.15-3.25 (m, 1H) 3.01-3.11 (m, 1H) 2.73-2.83 (m, 1H) 2.58-2.67 (m, 1H) 2.42-2.54 (m, 2H) 2.31-2.39 (m, 1H) 2.12 (s, 3H) 1.91-2.03 (m, 1H) 1.78-1.89 (m, 1H) 1.66-1.75 (m, 1H) 1.56-1.65 (m, 1H) 1.44-1.53 (m, 1H) 1.15 (d, J=4.06 Hz, 3H). MS: (M+H)$^+$=380.

Example 25

Trans-3-methyl-1-(2-{3-[(2R)-2-methylpyrrolidin-1-yl]cyclobutyl}-1,3-benzothiazol-6-yl)pyridin-2(1H)-one The title compound was prepared according to the procedure described in Example 22, substituting 3-methyl-2-pyridone (CAS #1003-56-1) for 3(2H)-pyridazinone. $^1$H NMR (500 MHz, CDCl$_3$) δ ppm 8.02 (d, J=8.42 Hz, 1H) 7.89 (d, J=2.50 Hz, 1H) 7.42 (dd, J=8.73, 2.18 Hz, 1H) 7.21-7.33 (m, 2H) 6.18 (t, J=6.71 Hz, 1H) 3.57-3.67 (m, 1H) 3.15-3.25 (m, 1H) 3.01-3.11 (m, 1H) 2.74-2.83 (m, 1H) 2.58-2.65 (m, 1H) 2.43-2.55 (m, 2H) 2.29-2.40 (m, 1H) 2.20 (s, 3H) 1.90-2.01 (m, 1H) 1.80-1.89 (m, 1H) 1.66-1.75 (m, 1H) 1.46-1.62 (m, 2H) 1.15 (s, 3H). MS: (M+H)$^+$=380.

Example 26

Trans-2-(2-{3-[(2S)-2-methylpyrrolidin-1-yl]cyclobutyl}-1,3-benzothiazol-6-yl)pyridazin-3(2H)-one The title compound was prepared according to the procedure described in Example 22, substituting the product of Example 11A for the product of Example 1E. $^1$H NMR (500 MHz, CDCl$_3$) δ ppm 8.15 (d, J=2.18 Hz, 1H) 8.03 (d, J=8.73 Hz, 1H) 7.92 (dd, J=3.74, 1.56 Hz, 1H) 7.69 (dd, J=8.73, 2.18 Hz, 1H) 7.23-7.30 (m, 1H) 7.08 (dd, J=9.51, 1.72 Hz, 1H) 3.58-3.68 (m, 1H) 3.16-3.26 (m, 1H) 3.01-3.11 (m, 1H) 2.75-2.84 (m, 1H) 2.59-2.68 (m, 1H) 2.45-2.57 (m, 2H) 2.31-2.41 (m, 1H) 1.92-2.01 (m, 1H) 1.79-1.90 (m, 1H) 1.68-1.76 (m, 1H) 1.47-1.62 (m, 2H) 1.16 (s, 3H). MS: (M+H)$^+$=367.

Example 27

Trans-6-methyl-2-(2-{3-[(2S)-2-methylpyrrolidin-1-yl]cyclobutyl}-1,3-benzothiazol-6-yl)pyridazin-3(2H)-one The title compound was prepared according to the procedure described in Example 22, substituting the product of Example 11A for the product of Example 1E, and substituting 6-methyl-3(2H)-pyridazinone for 3(2H)-pyridazinone. $^1$H NMR (500 MHz, CDCl$_3$) δ ppm 8.12 (m, 1H) 8.00 (m, 1H) 7.67 (dd, J=8.73, 1.87 Hz, 1H) 7.16 (m, 1H) 7.01 (m, 1H) 3.57-3.67 (m, 1H) 3.15-3.24 (m, 1H) 3.02-3.11 (m, 1H) 2.73-2.86 (m, 1H) 2.56-2.68 (m, 1H) 2.45-2.55 (m, 2H) 2.41 (s, 3H) 2.30-2.37 (m, 1H) 1.92-2.04 (m, 1H) 1.77-1.87 (m, 1H) 1.67-1.74 (m, 1H) 1.44-1.61 (m, 2H) 1.15 (s, 3H). MS: (M+H)$^+$=381.

Example 28

Trans-5-methyl-1-(2-{3-[(2S)-2-methylpyrrolidin-1-yl]cyclobutyl}-1,3-benzothiazol-6-yl)pyridin-2(1H)-one The title compound was prepared according to the procedure described in Example 22, substituting the product of Example 11A for the product of Example 1E and substituting 5-methyl-2(1H)-pyridone for 3(2H)-pyridazinone. $^1$H NMR (500 MHz, CDCl$_3$) δ ppm 8.02 (d, J=8.42 Hz, 1H) 7.88 (d, J=2.18 Hz, 1H) 7.42 (dd, J=8.58, 2.03 Hz, 1H) 7.28 (dd, J=9.36, 2.50 Hz, 1H) 7.15 (s, 1H) 6.62 (d, J=9.36 Hz, 1H) 3.59-3.69 (m, 1H) 3.15-3.25 (m, 1H) 3.01-3.10 (m, 1H) 2.77-2.85 (m, 1H) 2.60-2.67 (m, 1H) 2.33-2.56 (m, 3H) 2.12 (s, 3H) 1.93-2.03 (m, 1H) 1.79-1.88 (m, 1H) 1.68-1.77 (m, 1H) 1.45-1.64 (m, 2H) 1.16 (s, 3H). MS: $(M+H)^+=380$.

Example 29

Trans-3-methyl-1-(2-{3-[(2S)-2-methylpyrrolidin-1-yl]cyclobutyl}-1,3-benzothiazol-6-yl)pyridin-2(1H)-one The title compound was prepared according to the procedure described in Example 22, substituting the product of Example 11A for the product of Example 1E and substituting 3-methyl-2-pyridone for 3(2H)-pyridazinone. $^1$H NMR (500 MHz, CDCl$_3$) δ ppm 8.02 (d, J=8.74 Hz, 1H) 7.89 (d, J=1.87 Hz, 1H) 7.42 (dd, J=8.73, 2.18 Hz, 1H) 7.25-7.31 (m, 2H) 6.18 (t, J=6.86 Hz, 1H) 3.57-3.68 (m, 1H) 3.15-3.25 (m, 1H) 3.02-3.10 (m, 1H) 2.72-2.85 (m, 1H) 2.59-2.68 (m, 1H) 2.44-2.53 (m, 2H) 2.31-2.43 (m, 1H) 2.20 (s, 3H) 1.91-2.02 (m, 1H) 1.79-1.88 (m, 1H) 1.65-1.76 (m, 1H) 1.44-1.64 (m, 2H) 1.15 (s, 3H). MS: $(M+H)^+=380$.

Example 30

Cis-6-pyrimidin-5-yl-2-(3-pyrrolidin-1-ylcyclobutyl)-1,3-benzothiazole

Example 30A

Cis-6-bromo-2-(3-pyrrolidin-1-ylcyclobutyl)-1,3-benzothiazole

Pyrrolidine (295 μl, 3.54 mmol) was added to a solution of the product of Example 1C (100 mg, 0.354 mmole) in 2 ml methanol and the mixture was stirred at room temperature for 1 hour. Sodium cyanoborohydride (56 mg, 0.891 mmole) was added and the resulting mixture was stirred at room temperature overnight. The reaction was quenched with water and extracted three times with dichloromethane. The combined organic layers were washed with brine, dried over sodium sulfate, filtered, and concentrated to give the crude product which was purified by column chromatography (0.5% ammonium hydroxide and 5% methanol in dichloromethane) to give 65 mg (55%) of the title compound. $^1$H NMR (400 MHz, CDCl$_3$) for the cis isomer δ ppm 7.97 (d, J=1.84 Hz, 1H) 7.80 (d, J=8.90 Hz, 1H) 7.54 (dd, J=8.75, 1.99 Hz, 1H) 3.56-3.66 (m, 1H) 3.05-3.19 (m, 1H) 2.55-2.75 (m, 6H) 2.41-2.53 (m, 2H) 1.75-1.92 (m, 4H). MS: $(M+H)^+=337/339$.

Example 30B

Cis-6-pyrimidin-5-yl-2-(3-pyrrolidin-1-ylcyclobutyl)-1,3-benzothiazole

The title compound was prepared according to the procedure described in Example 1F, substituting the product of Example 30A for the product of Example 1E. $^1$H NMR (400 MHz, CDCl$_3$) δ ppm 9.23 (s, 1H) 9.01 (s, 2H) 8.08 (d, J=8.59 Hz, 1H) 8.05 (d, J=1.53 Hz, 1H) 7.65 (dd, J=8.59, 1.84 Hz, 1H) 3.59-3.74 (m, 1H) 3.02-3.16 (m, 1H) 2.66-2.79 (m, 2H) 2.51-2.63 (m, 4H) 2.38-2.49 (m, 2H) 1.84 (s, 4H). MS: $(M+H)^+=337$.

Example 31

Cis-6-(2-methoxypyrimidin-5-yl)-2-(3-pyrrolidin-1-ylcyclobutyl)-1,3-benzothiazole The title compound was prepared according to the procedure described in Example 1F, substituting the product of Example 30A for the product of Example 1E and substituting 2-methoxypyrimidine-5-boronic acid for pyrimidine-5-boronic acid. $^1$H NMR (400 MHz, CDCl$_3$) δ ppm 8.77 (s, 2H) 8.04 (d, J=8.90 Hz, 1H) 7.98 (d, J=1.23 Hz, 1H) 7.58 (dd, J=8.44, 1.99 Hz, 1H) 4.08 (s, 3H) 3.60-3.72 (m, 1H) 3.04-3.14 (m, 1H) 2.65-2.78 (m, 2H) 2.51-2.63 (m, 4H) 2.38-2.51 (m, 2H) 1.84 (s, 4H). MS: $(M+H)^+=367$.

Example 32

Cis-2-(3-piperidin-1-ylcyclobutyl)-6-pyrimidin-5-yl-1,3-benzothiazole

Example 32A

Cis-6-bromo-2-(3-piperidin-1-ylcyclobutyl)-1,3-benzothiazole

The title compound was prepared according to the procedure described in Example 17A, substituting piperidine for 2-(R)-methylpyrrolidine. $^1$H NMR (500 MHz, CDCl$_3$) δ ppm 7.97 (d, J=1.87 Hz, 1H) 7.79 (d, J=8.73 Hz, 1H) 7.53 (dd, J=8.73, 1.87 Hz, 1H) 3.50-3.61 (m, 1H) 2.79 (s, 1H) 2.61-2.71 (m, 2H) 2.23-2.43 (m, 6H) 1.52-1.71 (m, 6H). MS: $(M+H)^+=351/353$.

Example 32B

Cis-2-(3-piperidin-1-ylcyclobutyl)-6-pyrimidin-5-yl-1,3-benzothiazole

The title compound was prepared according to the procedure described in Example 1F, substituting the product of Example 32A for the product of Example 1E. $^1$H NMR (500 MHz, CDCl$_3$) δ ppm 9.23 (s, 1H) 9.01 (s, 2H) 8.08 (d, J=9.05 Hz, 1H) 8.05 (d, J=1.25 Hz, 1H) 7.64 (dd, J=8.42, 1.87 Hz, 1H) 3.56-3.68 (m, 1H) 2.80-2.88 (m, 1H) 2.66-2.77 (m, 2H) 2.22-2.47 (m, 6H) 1.52-1.74 (m, 6H). MS: $(M+H)^+=351$.

Example 33

Cis-6-(2-methoxypyrimidin-5-yl)-2-(3-piperidin-1-ylcyclobutyl)-1,3-benzothiazole The title compound was prepared according to the procedure described in Example 1F, substituting the product of Example 32A for the product of Example 1E, and substituting 2-methoxypyrimidine-5-boronic acid for pyrimidine-5-boronic acid. $^1$H NMR (500 MHz, CDCl$_3$) δ ppm 8.77 (s, 2H) 8.04 (d, J=8.42 Hz, 1H) 7.98 (s, 1H) 7.58 (dd, J=8.42, 1.87

Hz, 1H) 4.08 (s, 3H) 3.55-3.68 (m, 1H) 2.79-2.91 (m, 1H) 2.66-2.77 (m, 2H) 2.23-2.49 (m, 6H) 1.52-1.73 (m, 6H). MS: (M+H)$^+$=381.

Example 34

Cis-2-(3-azepan-1-ylcyclobutyl)-6-pyrimidin-5-yl-1,3-benzothiazole

Example 34A

Cis-2-(3-azepan-1-ylcyclobutyl)-6-bromo-1,3-benzothiazole

The title compound was prepared according to the procedure described in Example 17A, except for substituting hexamethyleneimine for 2-(R)-methylpyrrolidine. $^1$H NMR (500 MHz, CDCl$_3$) δ ppm 7.97 (d, J=1.87 Hz, 1H) 7.80 (d, J=8.74 Hz, 1H) 7.53 (dd, J=8.58, 2.03 Hz, 1H) 3.45-3.57 (m, 1H) 3.02-3.15 (m, 1H) 2.64-2.73 (m, 2H) 2.48-2.62 (m, 4H) 2.20-2.37 (m, 2H) 1.51-1.75 (m, 8H). MS: (M+H)$^+$=365/367.

Example 34B

Cis-2-(3-azepan-1-ylcyclobutyl)-6-pyrimidin-5-yl-1,3-benzothiazole

The title compound was prepared according to the procedure described in Example 1F, substituting the product of Example 34A for the compound of Example 1E. $^1$H NMR (400 MHz, CDCl$_3$) δ ppm 9.23 (s, 1H) 9.01 (s, 2H) 8.09 (d, J=8.29 Hz, 1H) 8.05 (d, J=1.23 Hz, 1H) 7.65 (dd, J=8.44, 1.69 Hz, 1H) 3.45-3.67 (m, 1H) 3.04-3.21 (m, 1H) 2.67-2.77 (m, 2H) 2.46-2.65 (m, 4H) 2.26-2.43 (m, 2H) 1.53-1.78 (m, 8H). MS: (M+H)$^+$=365.

Example 35

Cis-2-(3-morpholin-4-ylcyclobutyl)-6-pyrimidin-5-yl-1,3-benzothiazole

Example 35A

Cis-6-bromo-2-(3-morpholin-4-ylcyclobutyl)-1,3-benzothiazole

The title compound was prepared according to the procedure described in Example 17A, substituting morpholine for 2-(R)-methylpyrrolidine. $^1$H NMR (500 MHz, CDCl$_3$) δ ppm 7.97 (d, J=1.87 Hz, 1H) 7.81 (d, J=8.74 Hz, 1H) 7.54 (dd, J=8.58, 2.03 Hz, 1H) 4.01 (d, J=15.29 Hz, 1H) 3.68-3.80 (m, 2H) 3.51-3.62 (m, 1H) 3.14 (d, J=13.73 Hz, 1H) 2.81-2.98 (m, 2H) 2.64-2.72 (m, 1H) 2.25-2.48 (m, 4H) 1.58 (s, 2H). MS: [M+H)$^+$=353/355.

Example 35B

Cis-2-(3-morpholin-4-ylcyclobutyl)-6-pyrimidin-5-yl-1,3-benzothiazole

The title compound was prepared according to the procedure described in Example 1F, substituting the product of Example 35A for the product of Example 1E. $^1$H NMR (400 MHz, CDCl$_3$) δ ppm 9.23 (s, 1H) 9.01 (s, 2H) 8.10 (d, J=8.29 Hz, 1H) 8.06 (d, J=1.53 Hz, 1H) 7.66 (dd, J=8.29, 1.84 Hz, 1H) 3.60-3.87 (m, 3 H) 2.80-3.01 (m, 1H) 2.66-2.78 (m, 2H) 2.30-2.51 (m, 4H) 1.58 (s, 4H). MS: (M+H)$^+$=353.

Example 36

Cis-{(2S)-1-[3-(6-pyrimidin-5-yl-1,3-benzothiazol-2-yl)cyclobutyl]pyrrolidin-2-yl}methanol

Example 36A

Cis-{(2S)-1-[3-(6-bromo-1,3-benzothiazol-2-yl)cyclobutyl]pyrrolidin-2-yl}methanol The title compound was prepared according to the procedure described in Example 30A, substituting L-prolinol for pyrrolidine. $^1$H NMR (400 MHz, CDCl$_3$) δ ppm 7.97 (d, J=2.15 Hz, 1H) 7.81 (d, J=8.59 Hz, 1H) 7.55 (dd, J=8.59, 1.84 Hz, 1H) 3.50-3.63 (m, 2H) 3.39 (dd, J=10.59, 3.22 Hz, 1H) 3.22-3.32 (m, 1H) 3.00-3.13 (m, 1H) 2.70-2.84 (m, 2H) 2.58-2.70 (m, 1H) 2.34-2.53 (m, 3H) 1.86-2.01 (m, 1H) 1.68-1.82 (m, 3H). MS: (M+H)$^+$=367/369.

Example 36B

Cis-[(2S)-1-[3-(6-pyrimidin-5-yl-1,3-benzothiazol-2-yl)cyclobutyl]pyrrolidin-2-yl]methanol The title compound was prepared according to the procedure described in Example 1F, substituting the compound of Example 36A for the product of Example 1E. $^1$H NMR (400 MHz, CDCl$_3$) δ ppm 9.23 (s, 1H) 9.01 (s, 2H) 8.10 (d, J=8.90 Hz, 1H) 8.05 (d, J=1.23 Hz, 1H) 7.66 (dd, J=8.44, 1.99 Hz, 1H) 3.53-3.68 (m, 2H) 3.38-3.46 (m, 1H) 3.26-3.35 (m, 1H) 3.02-3.14 (m, 1H) 2.74-2.86 (m, 2H) 2.63-2.73 (m, 1H) 2.40-2.57 (m, 3H) 1.86-1.99 (m, 1H) 1.71-1.84 (m, 2H) 1.49-1.70 (m, 1H). MS: (M+H)$^+$=367.

Example 37

Cis-((2S)-1-{3-[6-(2-methoxypyrimidin-5-yl)-1,3-benzothiazol-2-yl]cyclobutyl}pyrrolidin-2-yl)methanol The title compound was prepared according to the procedure described in Example 1F, substituting the product of Example 36A for the product of Example 1E and substituting 2-methoxypyrimidine-5-boronic acid for pyrimidine-5-boronic acid. $^1$H NMR (400 MHz, CDCl$_3$) δ ppm 8.77 (s, 2H) 8.06 (d, J=8.59 Hz, 1H) 7.98 (d, J=1.53 Hz, 1H) 7.59 (dd, J=8.59, 1.84 Hz, 1H) 4.08 (s, 3H) 3.55-3.68 (m, J=7.67 Hz, 2H) 3.36-3.47 (m, 1H) 3.25-3.35 (m, 1H) 3.03-3.14 (m, 1H) 2.72-2.87 (m, 2H) 2.61-2.72 (m, 1H) 2.40-2.54 (m, 3H) 1.87-2.01 (m, 1H) 1.69-1.85 (m, 2H) 1.51-1.70 (m, 1H). MS: (M+H)$^+$=397.

Example 38

Cis-2-{3-[(3aR,6aR)-hexahydropyrrolo[3,4-b]pyrrol-5(1H)-yl]cyclobutyl}-6-pyrimidin-5-yl-1,3-benzothiazole

Example 38A

Cis-tert-butyl(3aR,6aR)-5-[3-(6-bromo-1,3-benzothiazol-2-yl)cyclobutyl]hexahydropyrrolo[3,4-b]pyrrole-1(2H)-carboxylate The title compound was prepared according to the procedure described in Example 30A, substituting hexahydro-pyrrolo[3,4-b]pyrrole-1-carboxylic acid tert-butyl ester (prepared according to the procedure that described in: Q. Li et al., J. Med. Chem.; 39(16), 3070-3088, 1996) for pyrrolidine. $^1$H NMR (400 MHz, CDCl$_3$) δ ppm 7.97 (d, J=1.53 Hz, 1H) 7.81 (d, J=8.59 Hz, 1H) 7.54 (dd, J=8.59, 1.84 Hz, 1H) 4.13-4.28 (m, 2H) 3.50-3.63 (m, 2H) 3.33-3.46 (m, 2H) 2.93-3.01 (m, 1H) 2.78-2.88 (m, 1H) 2.27-2.71 (m, 6H) 1.90-2.02 (m, 1H) 1.66-1.78 (m, 1H) 1.45-1.48 (s, 9H). MS: (M+H)$^+$=478/480.

Example 38B

Cis-tert-butyl (3aR,6aR)-5-[3-(6-pyrimidin-5-yl-1,3-benzothiazol-2-yl)cyclobutyl]hexahydropyrrolo[3,4-b]pyrrole-1(2H)-carboxylate The title compound was prepared according to the procedure described in Example 1F, substituting the product of Example 38A for the compound of Example 1E. $^1$H NMR (500 MHz, CDCl$_3$) δ ppm 9.23 (s, 1H) 9.01 (s, 2H) 8.09 (d, J=8.42 Hz, 1H) 8.05 (d, J=1.25 Hz, 1H) 7.65 (dd, J=8.42, 1.87 Hz, 1H) 4.15-4.30 (m, 2H) 3.53-3.71 (m, 2H) 3.35-3.49 (m, 2H) 2.95-3.07 (m, 1H) 2.81-2.91 (m, 1H) 2.58-2.76 (m, 3H) 2.29-2.52 (m, 3H) 1.91-2.03 (m, 1H) 1.68-1.80 (m, 1H) 1.39-1.52 (s, 9H). MS: (M+H)$^+$=478.

Example 38C

Cis-2-{3-[(3aR,6aR)-hexahydropyrrolo[3,4-b]pyrrol-5(1H)-yl]cyclobutyl}-6-pyrimidin-5-yl-1,3-benzothiazole The title compound was prepared by mixing the product of Example 38B with 1:1 mixture of TFA and dichloromethane. After 2 hours, the solvent was removed under reduced pressure, the residue was basified with saturated sodium bicarbonate and extracted three times with dichloromethane. The combined organic layers were washed with brine, dried over sodium sulfate, filtered, and concentrated under reduced pressure. The resulting residue was purified by column chromatography (0.5% ammonium hydroxide and 5% methanol in dichloromethane) to provide the title compound. $^1$H NMR (500 MHz, CDCl$_3$) δ ppm 9.19-9.26 (s, 1H) 9.01 (s, 2H) 8.09 (d, J=8.54 Hz, 1H) 8.05 (d, J=1.53 Hz, 1H) 7.65 (dd, J=8.54, 1.83 Hz, 1H) 3.81-3.92 (m, 1H) 3.60-3.71 (m, 1H) 3.03-3.12 (m, 1H) 2.95-3.03 (m, 1H) 2.87-2.95 (m, 1H) 2.72-2.79 (m, 1H) 2.64-2.71 (m, 2H) 2.50-2.62 (m, 3H) 2.32-2.46 (m, 3H) 1.91-2.00 (m, 1H) 1.57-1.67 (m, 1H). MS: (M+H)$^+$=378.

Example 39

Cis-2-{3-[(3aR,6aR)-hexahydropyrrolo[3,4-b]pyrrol-5(1H)-yl]cyclobutyl}-6-(2-methoxypyrimidin-5-yl)-1,3-benzothiazole Example 39A Cis-tert-butyl (3aR,6aR)-5-{3-[6-(2-methoxypyrimidin-5-yl)-1,3-benzothiazol-2-yl]cyclobutyl}hexahydropyrrolo[3,4-b]pyrrole-1(2H)-carboxylate The title compound was prepared according to the procedure described in Example 1F, substituting the product of Example 38A for the product of Example 1E and substituting 2-methoxypyrimidine-5-boronic acid for pyrimidine-5-boronic acid. $^1$H NMR (500 MHz, CDCl$_3$) δ ppm 8.77 (s, 2H) 8.05 (d, J=8.42 Hz, 1H) 7.97 (s, 1H) 7.58 (dd, J=8.42, 1.56 Hz, 1H) 4.14-4.29 (m, 2H) 4.08 (s, 3H) 3.54-3.70 (m, 2H) 3.34-3.49 (m, 2H) 2.93-3.05 (m, 1H) 2.77-2.91 (m, 1H) 2.52-2.75 (m, 3H) 2.28-2.50 (m, 3H) 1.90-2.02 (m, 1H) 1.66-1.81 (m, 1H) 1.46 (s, 9H). MS: (M+H)$^+$=508.

Example 39B

Cis-2-{3-[(3aR,6aR)-hexahydropyrrolo[3,4-b]pyrrol-5(1H)-yl]cyclobutyl}-6-(2-methoxypyrimidin-5-yl)-1,3-benzothiazole The title compound was prepared according to the procedure described in Example 38C, substituting the product of Example 39A for the product of Example 38B. $^1$H NMR (500 MHz, CDCl$_3$) δ ppm 8.77 (s, 2H) 8.05 (d, J=8.54 Hz, 1H) 7.97 (s, 1H) 7.58 (dd, J=8.54, 1.83 Hz, 1H) 4.08 (s, 3H) 3.85-3.98 (m, 1H) 3.60-3.70 (m, 1H) 3.08-3.16 (m, 1H) 2.90-3.02 (m, 2H) 2.73-2.81 (m, 1H) 2.61-2.71 (m, 2H) 2.49-2.60 (m, 3H) 2.31-2.47 (m, 3H) 1.93-2.05 (m, 1H) 1.58-1.74 (m, 1H). MS: (M+H)$^+$=408.

Example 40

Cis-2-{3-[(2R)-2-methylpiperidin-1-yl]cyclobutyl}-6-pyrimidin-5-yl-1,3-benzothiazole Example 40A Cis-6-bromo-2-{3-[(2R)-2-methylpiperidin-1-yl]cyclobutyl}-1,3-benzothiazole The title compound was prepared according to the procedure described in Example 30A, substituting 2-(R)-methylpiperidine (available from Clariant) for pyrrolidine. $^1$H NMR (500 MHz, CDCl$_3$) δ ppm 7.97 (d, J=2.18 Hz, 1H) 7.80 (d, J=8.73 Hz, 1H) 7.53 (dd, J=8.58, 2.03 Hz, 1H) 3.43-3.57 (m, 1H) 3.07-3.18 (m, 1H) 2.67-2.81 (m, 2H) 2.51-2.66 (m, 2H) 2.37-2.50 (m, 2H) 2.27-2.38 (m, 1H) 2.08 (m, 1H) 1.50-1.68 (m, 4H) 1.29-1.42 (m, 1H) 1.06 (d, J=4.99 Hz, 3H). MS: (M+H)$^+$=365/367.

Example 40B

Cis-2-{3-[(2R)-2-methylpiperidin-1-yl]cyclobutyl}-6-pyrimidin-5-yl-1,3-benzothiazole The title compound was prepared according to the procedure described in Example 1F, substituting the product of Example 40A for the product of Example 1E. $^1$H NMR (400 MHz, CDCl$_3$) δ ppm 9.17 (s, 1H) 9.15 (s, 2H) 8.39 (s, 1H) 8.11 (d, J=8.59 Hz, 1H) 7.89 (dd, J=8.29, 1.53 Hz, 1H) 3.92-4.13 (m, 2H) 3.75-3.90 (m, 2H) 3.52-3.63 (m, 1H) 3.03-3.18 (m, 1H) 2.83-3.01 (m, 3H) 2.66-2.83 (m, 2H) 1.83-2.06 (m, 2H) 1.56-1.80 (m, 2H) 1.41 (dd, J=18.72, 6.75 Hz, 3H). MS: (M+H)$^+$=365.

Example 41

Cis-N-isopropyl-N-methyl-N-[3-(6-pyrimidin-5-yl-1,3-benzothiazol-2-yl)cyclobutyl]amine Example 41A Cis-N-[3-(6-bromo-1,3-benzothiazol-2-yl)cyclobutyl]-N-isopropyl-N-methylamine The title compound was prepared according to the procedure described in Example 30A, substituting isopropylmethylamine for pyrrolidine. $^1$H NMR (500 MHz, CDCl$_3$) δ ppm 7.97 (d, J=1.87 Hz, 1H) 7.80 (d, J=8.42 Hz, 1H) 7.53 (dd, J=8.58, 2.03 Hz, 1H) 3.47-3.58 (m, 1H) 3.12-3.23 (m, 1H) 2.89-3.01 (m, 1H) 2.60-2.71 (m, 2H) 2.23-2.38 (m, 2H) 2.12 (s, 3H) 1.01 (d, J=6.55 Hz, 6H). MS: (M+H)$^+$=339/341.

Example 41B

Cis-N-isopropyl-N-methyl-N-[3-(6-pyrimidin-5-yl-1,3-benzothiazol-2-yl)cyclobutyl]amine The title compound was prepared according to the procedure described in Example 1F, substituting the product of Example 41A for the product of Example 1E. $^1$H NMR (400 MHz, Solvent) δ ppm 9.17 (s, 1H) 9.15 (s, 2H) 8.39 (d, J=1.53 Hz, 1H) 8.11 (d, J=8.59 Hz, 1H) 7.89 (dd, J=8.59, 1.84 Hz, 1H) 3.96-4.10 (m, 1H) 3.77-3.91 (m, 1H) 3.60-3.78 (m, 1H) 2.86-3.07 (m, 3H) 2.69-2.82 (m, 1H) 2.71 (s, 3H) 1.36 (dd, J=30.84, 6.29 Hz, 6H). MS: (M+H)$^+$=339.

Example 42

Cis-{1-[3-(6-pyrimidin-5-yl-1,3-benzothiazol-2-yl)cyclobutyl]piperidin-4-yl}methanol

Example 42A

Cis-{1-[3-(6-bromo-1,3-benzothiazol-2-yl)cyclobutyl]piperidin-4-yl}methanol

The title compound was prepared according to the procedure described in Example 30A, substituting 4-piperidinemethanol for pyrrolidine. $^1$H NMR (500 MHz, CDCl$_3$) δ ppm 7.97 (d, J=1.83 Hz, 1H) 7.80 (d, J=8.85 Hz, 1H) 7.54 (dd, J=8.70, 1.98 Hz, 1H) 3.54-3.60 (m, 1H) 3.51 (d, J=6.41 Hz, 2H) 2.94 (d, J=10.37 Hz, 2H) 2.77-2.86 (m, 1H) 2.65-2.72 (m, 2H) 2.26-2.35 (m, 2H) 1.73-1.87 (m, 4H) 1.47-1.57 (m, 2H) 1.23-1.34 (m, 2H). MS: (M+H)$^+$=381/383.

Example 42B

Cis-{1-[3-(6-pyrimidin-5-yl-1,3-benzothiazol-2-yl)cyclobutyl]piperidin-4-yl}methanol The title compound was prepared according to the procedure described in Example 1F, substituting the product of Example 42A for the product of Example 1E. $^1$H NMR (400 MHz, CDCl$_3$) δ ppm 9.23 (s, 1H) 9.02 (s, 2H) 8.03-8.12 (m, 2H) 7.65 (dd, J=8.59, 1.84 Hz, 1H) 3.60-3.71 (m, 1H) 3.53 (d, J=6.44 Hz, 2H) 3.04-3.17 (m, 2H) 2.61-3.03 (m, 6H) 2.46-2.59 (m, 2H) 1.91-2.04 (m, 1H) 1.73-1.89 (m, 2H) 1.52-1.67 (m, 1H) 1.34-1.49 (m, 1H). MS: (M+H)$^+$=381.

Example 43

Trans-{1-[3-(6-pyrimidin-5-yl-1,3-benzothiazol-2-yl)cyclobutyl]piperidin-4-yl}methanol

Example 43A

Trans-{1-[3-(6-bromo-1,3-benzothiazol-2-yl)cyclobutyl]piperidin-4-yl}methanol

The product of Example 1D (0.177 mmole) was dissolved in anhydrous dichloromethane (2 ml). Potassium carbonate (50 mg, 0.362 mmole) was added followed by trifluoromethanesulfonic anhydride (40 µl, 0.238 mmole). The mixture was allowed to stir at room temperature for 2 hours, then another portion of potassium carbonate (100 mg, 0.724 mmole) was added, followed by 4-piperidinemethanol (61 mg, 0.530 mmole). The resulting mixture was stirred at room temperature overnight. It was then quenched with water, and extracted three times with dichloromethane. The organic layers were combined, washed with brine, dried over sodium sulfate, and concentrated. The crude product was purified by column chromatography (0.3% ammonium hydroxide and 3% methanol in dichloromethane) to give 29 mg (43%) of title compound. $^1$H NMR (500 MHz, CDCl$_3$) δ ppm 7.98 (d, J=1.83 Hz, 1H) 7.83 (d, J=8.54 Hz, 1H) 7.56 (dd, J=8.54, 1.83 Hz, 1H) 3.74-3.86 (m, 1H) 3.52 (d, J=6.10 Hz, 2H) 3.08-3.19 (m, 1H) 2.95 (d, J=10.68 Hz, 2H) 2.51-2.62 (m, 4H) 1.79 (d, J=10.68 Hz, 4H) 1.48-1.59 (m, 2H) 1.25-1.38 (m, 2H). MS: (M+H)$^+$=381/383.

Example 43B

Trans-{1-[3-(6-pyrimidin-5-yl-1,3-benzothiazol-2-yl)cyclobutyl]piperidin-4-yl}methanol The title compound was prepared according to the procedure described in Example 1F, substituting the product of Example 43A for the product of Example 1E. $^1$H NMR (400 MHz, CDCl$_3$) δ ppm 9.24 (s, 1H) 9.02 (s, 2H) 8.11 (d, J=8.29 Hz, 1H) 8.06 (d, J=1.53 Hz, 1H) 7.67 (dd, J=8.59, 1.84 Hz, 1H) 3.86-3.94 (m, 1H) 3.54 (t, J=6.44 Hz, 2H) 3.30-3.51 (m, 3H) 3.15-3.24 (m, 2H) 2.84-2.98 (m, 2H) 2.63-2.76 (m, 2H) 1.97-2.12 (m, 2H) 1.77-1.90 (m, 2H) 1.44-1.68 (m, 2H). MS: (M+H)$^+$=381.

Example 44

Trans-2-(3-piperidin-1-ylcyclobutyl)-6-pyrimidin-5-yl-1,3-benzothiazole

Example 44A

Trans-6-bromo-2-(3-piperidin-1-ylcyclobutyl)-1,3-benzothiazole

The title compound was prepared according to the procedure described in Example 43A, substituting piperidine for 4-piperidinemethanol. $^1$H NMR (400 MHz, CDCl$_3$) δ ppm 7.97 (d, J=2.15 Hz, 1H) 7.82 (d, J=8.59 Hz, 1H) 7.55 (dd, J=8.59, 1.84 Hz, 1H) 3.73-3.87 (m, 1H) 3.05-3.18 (m, 1H) 2.49-2.66 (m, 4H) 2.19-2.44 (m, 4H) 1.55-1.71 (m, 4H) 1.39-1.54 (m, 2H). MS: (M+H)$^+$=351/353.

Example 44B

Trans-2-(3-piperidin-1-ylcyclobutyl)-6-pyrimidin-5-yl-1,3-benzothiazole

The title compound was prepared according to the procedure described in Example 1F, substituting the product of Example 44A for the product of Example 1E. $^1$H NMR (400 MHz, CDCl$_3$) δ ppm 9.23 (s, 1H) 9.01 (s, 2H) 8.11 (d, J=8.29 Hz, 1H) 8.06 (d, J=1.53 Hz, 1H) 7.66 (dd, J=8.29, 1.84 Hz, 1H) 3.80-3.94 (m, 1H) 3.09-3.21 (m, 1H) 2.56-2.68 (m, 4H) 2.27-2.42 (m, 4H) 1.58-1.70 (m, 4H) 1.42-1.55 (m, 2H). MS: (M+H)$^+$=351.

Example 45

Trans-6-(2,6-dimethylpyridin-3-yl)-2-(3-piperidin-1-ylcyclobutyl)-1,3-benzothiazole The title compound was prepared according to the procedure described in Example 1F, substituting the product of Example 44A for the product of Example 1E and substituting the product of Example 2A for pyrimidine-5-boronic acid. $^1$H NMR (500 MHz, CDCl$_3$) δ ppm 8.02 (d, J=8.24 Hz, 1H) 7.76 (s, 1H) 7.47 (d, J=7.63 Hz, 1H) 7.40 (dd, J=8.54, 1.53 Hz, 1H) 7.08 (d, J=7.63 Hz, 1H) 3.83-3.92 (m, 1H) 3.42-3.53 (m, 1H) 2.92-3.04 (m, 1H) 2.62-2.74 (m, 3H) 2.60 (s, 3H) 2.50 (s, 3H) 2.08 (s, 4H) 1.71-1.83 (m, 4H) 1.50-1.61 (m, 2H). MS: (M+H)$^+$=378.

Example 46

Trans-6-(6-methoxypyridin-3-yl)-2-(3-piperidin-1-ylcyclobutyl)-1,3-benzothiazole The title compound was prepared according to the procedure described in Example 1F, substituting the product of Example 44A for the product of Example 1E, and substituting 6-methoxypyridine-3-boronic acid for pyrimidine-5-boronic acid. $^1$H NMR (500 MHz, CDCl$_3$) δ ppm 8.43 (d, J=2.44 Hz, 1H) 8.03 (d, J=8.54 Hz, 1H) 7.97 (d, J=1.53 Hz, 1H) 7.84 (dd, J=8.70, 2.59 Hz, 1H) 7.62 (dd, J=8.54, 1.83 Hz, 1H) 6.85 (d, J=8.54 Hz, 1H) 4.00 (s, 3H) 3.82-3.93 (m, 1H) 3.36-3.48 (m, 1H) 2.87-2.98 (m, 2H) 2.52-2.71 (m, 4H) 2.08 (s, 2H) 1.67-1.82 (m, 4H) 1.48-1.58 (m, 2H). MS: (M+H)$^+$=380.

Example 47

Trans-6-(2-methoxypyrimidin-5-yl)-2-(3-piperidin-1-ylcyclobutyl)-1,3-benzothiazole The title compound was prepared according to the procedure described in Example 1F, except for substituting the compound of Example 44A for the compound of Example 1E, and substituting 2-methoxypyrimidine-5-boronic acid for pyrimidine-5-boronic acid. $^1$H NMR (500 MHz, CDCl$_3$) δ ppm 8.78 (s, 2H) 8.07 (d, J=8.54 Hz, 1H) 7.98 (d, J=1.53 Hz, 1H) 7.60 (dd, J=8.39, 1.68 Hz, 1H) 4.09 (s, 3H) 3.80-3.92 (m, 1H) 3.07-3.24 (m, 1H) 2.55-2.73 (m, 4H) 2.26-2.47 (m, 4H) 1.57-1.80 (m, 4H) 1.43-1.53 (m, 2H). MS: (M+H)$^+$=381.

Example 48A

Trans-2-[2-(3-piperidin-1-ylcyclobutyl)-1,3-benzothiazol-6-yl]pyridazin-3(2H)-one The title compound was prepared according to the procedure described in Example 22, substituting the product of Example 44A for the product of Example 1E. In this preparation, two isomeric products were obtained which represented the cis- and trans-configurations of the cyclobutane ring. The product that had a RF of 0.28 on TLC (TLC conditions 0.5% ammonium hydroxide and 5% methanol in dichloromethane on silica gel) was separated and purified by column chromatography on silica gel, eluting with 0.5% ammonium hydroxide and 5% methanol in dichloromethane to give an off-white solid, which corresponded to the trans isomer: mp 139-140° C. $^1$H NMR (500 MHz, CDCl$_3$) δ ppm 8.15 (d, J=2.14 Hz, 1H) 8.05 (d, J=8.85 Hz, 1H) 7.93 (dd, J=3.81, 1.68 Hz, 1H) 7.70 (dd, J=8.85, 2.14 Hz, 1H) 7.24-7.31 (m, 1H) 7.09 (dd, J=9.46, 1.83 Hz, 1H) 3.80-3.92 (m, 1H) 3.10-3.19 (m, 1H) 2.53-2.70 (m, 4H) 2.21-2.47 (m, 4H) 1.58-1.72 (m, 4H) 1.42-1.55 (m, 2H). MS: (M+H)$^+$=367.

Alternative Method of Preparing Example 48A

The title compound was prepared according to the procedure described in Example 1E, except for substituting the product of Example 48E for the product of Example 1D, and substituting piperidine for 2-(R)-methylpyrrolidine L-tartrate. The NMR and mass spectra confirmed a match with the spectrum of the product prepared in the previous method.

Salt Preparations of Example 48A

A methanolic solution of the title compound when treated with hydrochloric acid (1:1 molar ratio), followed by concentration of the solution, gave a solid of m.p. 256-259° C. A methanolic solution of the title compound when treated with sulfuric acid (1:1 molar ratio), followed by concentration of the solution, gave a solid of m.p. 86-92° C. A methanolic solution of the title compound when treated with ortho-phosphoric acid (1:1 molar ratio), followed by concentration of the solution, gave a solid of m.p. 110-113° C. A methanolic solution of the title compound when treated with L-tartaric acid (1:1 molar ratio), followed by concentration of the solution, gave a solid of m.p. 94-97° C.

Example 48B

Cis-2-[2-(3-piperidin-1-ylcyclobutyl)-1,3-benzothiazol-6-yl]pyridazin-3(2H)-one

The titled compound was prepared as described in Example 48A to isolate the other isomer that had a RF of 0.32 on TLC (TLC conditions 0.5% ammonium hydroxide and 5% methanol in dichloromethane on silica gel) corresponded to the cis-isomer as an off-white solid, mp 127-128° C. $^1$H NMR (400 MHz, CDCl$_3$) δ ppm 8.14 (t, J=2.61 Hz, 1H) 8.02 (d, J=8.59 Hz, 1H) 7.92 (dd, J=3.68, 1.53 Hz, 1H) 7.66-7.70 (m, 1H) 7.23-7.30 (m, 1H) 7.08 (dd, J=9.36, 1.69 Hz, 1H) 3.52-3.65 (m, 1H) 2.75-2.86 (m, 1H) 2.62-2.73 (m, 2H) 2.25-2.41 (m, 6H) 1.55-1.66 (m, 4H) 1.41-1.52 (m, 2H). MS: (M+H)$^+$=367.

Salt Preparations of Example 48B

A methanolic solution of the title compound when treated with hydrochloric acid (1:1 molar ratio), followed by concentration of the solution, gave a solid of m.p. 258-261° C. A methanolic solution of the title compound when treated with sulfuric acid (1:1 molar ratio), followed by concentration of the solution, gave a solid of m.p. 105-110° C. A methanolic solution of the title compound when treated with ortho-phosphoric acid (1:1 molar ratio), followed by concentration of the solution, gave a solid of m.p. 206-209° C. A methanolic solution of the title compound when treated with L-tartaric acid (1:1 molar ratio), followed by concentration of the solution, gave a solid of m.p. 136-140° C.

Alternative Preparation of Example 48B

Example 48C

2-[2-(3-hydroxy-cyclobutyl)-1,3-benzothiazol-6-yl]-2H-pyridazin-3-one

The product of Example 1D (cis-3-(6-Bromo-benzothiazol-2-yl)-cyclobutanol) (2.25 g, 7.93 mmole), 3(2H)-pyridazinone (CAS # 504-30-3) (1.52 g, 15.83 mmole), copper (500 mg, 7.93 mmole), potassium carbonate (3.28 g, 23.77 mmole), and copper(I) iodide (211 mg, 1.11 mmole) were mixed in degassed pyridine (50 ml) and placed under vacuum for 15 minutes then refilled with nitrogen. N,N'-dimethylethylene diamine (240 μl, 196 mg, 2.22 mmole) was added and the mixture was heated at reflux overnight. The mixture was diluted with water and extracted three times with dichloromethane. The combined organic layers were washed with brine, dried over sodium sulfate, filtered, and concentrated under reduced pressure to give the crude product which was purified by column chromatography (0.4% ammonium hydroxide and 4% methanol in dichloromethane) to provide the title compound. $^1$H NMR (400 MHz, CDCl$_3$) δ ppm 8.15 (d, J=2.15 Hz, 1H) 8.04 (d, J=8.90 Hz, 1H) 7.92 (dd, J=3.68, 1.53 Hz, 1H) 7.70 (dd, J=8.59, 2.15 Hz, 1H) 7.24-7.30 (m, 1H) 7.04-7.11 (m, 1H) 4.68-4.81 (m, 0.3H) 4.31-4.43 (m, 0.7H) 3.87-3.98 (m, 0.3H) 3.39-3.51 (m, 0.7H) 2.90-3.01 (m, 1.4H) 2.77-2.87 (m, 0.6H) 2.51-2.62 (m, 0.6H) 2.33-2.45 (m, 2.1H) 2.07 (d, J=5.22 Hz, 0.3H). MS: (M+H)$^+$=300.

Example 48D

2-[2-(3-oxo-cyclobutyl)-1,3-benzothiazol-6-yl]-2H-pyridazin-3-one

The product of Example 48C (1.63 g, 5.45 mmole) was dissolved in 50 ml anhydrous dichloromethane. Dess-Martin periodinane (3.0 g, 7.07 mmole, [87413-09-0]) was added. After 3 hours at room temperature, the mixture was diluted with water and extracted three times with dichloromethane. The combined organic layers were washed with brine, dried over sodium sulfate, filtered, and concentrated under reduced pressure to provide the crude product which was purified by column chromatography (0.25% ammonium hydroxide and 2.5% methanol in dichloromethane) to provide the title compound. $^1$H NMR (300 MHz, CDCl$_3$) δ ppm 8.20 (d, J=2.03 Hz, 1H) 8.07 (d, J=8.82 Hz, 1H) 7.94 (dd, J=3.73, 1.70 Hz, 1H) 7.75 (dd, J=8.82, 2.37 Hz, 1H) 7.26-7.31 (m, 1H) 7.09 (dd, J=9.49, 1.70 Hz, 1H) 4.01-4.15 (m, 1H) 3.54-3.79 (m, 5H). MS: (M+H)$^+$=298.

Example 48E

Cis-2-[2-(3-hydroxy-cyclobutyl)-1,3-benzothiazol-6-yl]-2H-pyridazin-3-one

The product of 48D (213 mg, 0.72 mmole) was dissolved in 6 ml of methanol and 3 ml of dichloromethane and cooled in an ice bath. Sodium borohydride (60 mg, 1.62 mmole) was added and the mixture was stirred at this temperature for 30 minutes. The mixture was diluted with water, stirred for 1 hour and extracted three times with dichloromethane. The combined organic layers were washed with brine, dried over sodium sulfate, filtered, and concentrated under reduced pressure to provide the title compound. $^1$H NMR (300 MHz, CDCl$_3$) δ ppm 8.16 (d, J=2.37 Hz, 1H) 8.05 (d, J=8.82 Hz, 1H) 7.93 (dd, J=3.73, 1.70 Hz, 1H) 7.70 (dd, J=8.82, 2.03 Hz, 1H) 7.25-7.30 (m, 1H) 7.08 (dd, J=9.49, 1.70 Hz, 1H) 4.38 (m, 1H) 3.37-3.54 (m, 1H) 2.90-3.05 (m, 2H) 2.31-2.46 (m, 2H) 2.19-2.28 (m, 1H). MS: (M+H)$^+$=300.

Example 48B

Cis-2-[2-(3-piperidin-1-ylcyclobutyl)-1,3-benzothiazol-6-yl]pyridazin-3(2H)-one

The title compound was prepared according to the procedure described in Example 30A, except for substituting the product of Example 48D for the product of Example 1C, and substituting piperidine for pyrrolidine. The NMR and mass spectra confirmed a match with the spectrum of the product prepared in the previous method.

Example 49

Trans-6-methyl-2-[2-(3-piperidin-1-ylcyclobutyl)-1,3-benzothiazol-6-yl]pyridazin-3(2H)-one The title compound was prepared according to the procedure described in Example 22, substituting the product of Example 44A for the product of Example 1E and substituting 6-methyl-3(2H)-pyridazinone for 3(2H)-pyridazinone. $^1$H NMR (400 MHz, CDCl$_3$) δ ppm 8.12 (d, J=2.15 Hz, 1H) 8.01 (d, J=8.90 Hz, 1H) 7.67 (dd, J=8.90, 2.15 Hz, 1H) 7.16 (d, J=9.51 Hz, 1H) 7.00 (d, J=9.51 Hz, 1H) 3.52-3.64 (m, 1H) 2.72-2.86 (m, 1H) 2.53-2.73 (m, 2H) 2.40 (s, 3H) 2.24-2.38 (m, 4H) 1.65-1.75 (m, 2H) 1.54-1.65 (m, 4H) 1.46 (d, J=4.91 Hz, 2H). MS: (M+H)$^+$=381.

Example 50

Trans-3-methyl-1-[2-(3-piperidin-1-ylcyclobutyl)-1,3-benzothiazol-6-yl]pyridin-2(1H)-one The title compound was prepared according to the procedure described in Example 22, substituting the product of Example 44A for the product of Example 1E and substituting 3-methyl-2-pyridone for 3(2H)-pyridazinone. $^1$H NMR (400 MHz, CDCl$_3$) δ ppm 8.02 (d, J=8.59 Hz, 1H) 7.89 (d, J=2.15 Hz, 1H) 7.42 (dd, J=8.75, 1.99 Hz, 1H) 7.22-7.34 (m, 2H) 6.19 (t, J=6.75 Hz, 1H) 3.53-3.68 (m, 1H) 2.80-2.94 (m, 1H) 2.51-2.91 (m, 3H) 2.32-2.50 (m, 4H) 2.20 (s, 3H) 1.99-2.12 (m, 1H) 1.58-1.73 (m, 4H) 1.43-1.54 (m, 2H). MS: (M+H)$^+$=380.

Example 51

Trans-6-(1-methyl-1H-pyrazol-4-yl)-2-(3-piperidin-1-ylcyclobutyl)-1,3-benzothiazole

Example 51A

Trans-2-(3-piperidin-1-ylcyclobutyl)-6-(1-trityl-1H-pyrazol-4-yl)-1,3-benzothiazole)

The product of Example 44A (120 mg, 0.34 mmole), 4-(4,4,5,5-tetramethyl-[1,3,2]dioxaborolan-2-yl)-1-trityl-1H-pyrazole (224 mg, 0.51 mmole), dichlorobis-(triphenylphosphine)palladium(II) (14.0 mg, 0.020 mmole), 2-(dicyclohexyl-phosphino)biphenyl (7.0 mg, 0.020 mmole), sodium carbonate (1 M solution, 0.51 ml, 0.51 mmole) and 1.5 ml of ethanol/dioxane (1:1) were combined under N$_2$ in a capped, sealed vial. The vial was sealed and was placed a commercial (i.e. Emrys Creator) microwave for 10 minutes at 140° C. The reaction mixture was quenched with water and extracted with dichloromethane (4×5 ml). The combined organic layers were washed with brine, dried over sodium sulfate, filtered, and concentrated to give the crude product which was purified by column chromatography (1% ammonium hydroxide and 10% methanol in dichloromethane) to give 138.1 mg (70% yield) of title compound. $^1$H NMR (300 MHz, CDCl$_3$) δ ppm 7.99 (s, 1H), 7.89 (d, J=8.31 Hz, 1H), 7.88 (d, J=2.03 Hz, 1H), 7.68 (s, 1H), 7.53 (dd, J=8.31, 1.87 Hz, 1H), 7.52-7.35 (m, 9H), 7.19-7.23 (m, 6H), 3.93 (m, 1H 3.42 (m, 1H) 2.61-2.73 (m, 2H) 2.26-2.52 (m, 4H) 1.73-1.90 (m, 4H) 1.43-1.58 (m, 4H). MS: (M+H)$^+$=581.

Example 51B

Trans-2-(3-piperidin-1-ylcyclobutyl)-6-(1H-pyrazol-4-yl)-1,3-benzothiazole

The product of Example 51A (135.0 mg, 0.23 mmole) was dissolved in formic acid (88%, 2 ml) and stirred at room temperature for 2 hours. The reaction mixture concentrated was under reduced pressure. The solid residue was then treated with saturated aqueous sodium bicarbonate and extracted with dichloromethane (4×5 ml). The combined organic layers were washed with brine, dried over sodium sulfate, filtered, and concentrated to give the crude product which was purified by column chromatography (1% ammonium hydroxide and 10% methanol in dichloromethane) to give 71.2 mg (90.5%) of title compound. MS: (M+H)$^+$=339.

Example 51C

Trans-6-(1-methyl-1H-pyrazol-4-yl)-2-(3-piperidin-1-ylcyclobutyl)-1,3-benzothiazole The product of Example 51B (34.0 mg, 0.10 mmole) was dissolved in DMF (2 ml) and then cooled to 0° C. NaH (60%, 44.0 mg, 1.1 mmol) was added under N$_2$, and the reaction was stirred at 0° C. for 0.5 hours. Iodomethane (6.8 μl, 0.11 mmole) was added, and the reaction mixture was stirred at 0° C. for 1 hour, and then slowly raised to room temperature. The mixture was quenched with saturated aqueous sodium bicarbonate and extracted with dichloromethane (4×5 ml). The combined organic layers were washed with brine, dried over sodium sulfate, filtered, and concentrated to give the crude product which was purified by column chromatography (10% methanol in dichloromethane) to give 23.8 mg (67.6%) of title compound. $^1$H NMR (300 MHz, CDCl$_3$) δ ppm 7.94 (d, J=8.48 1H) 7.93 (d, J=2.03 1H) 7.80 (s, 1H) 7.66, (s, 1H) 7.56 (dd, J=8.48, 2.03 1H) 3.80 (s, 3H) 3.87 (m, 1H) 3.27 (m, 1H) 2.38-2.62 (m, 4H) 1.49-1.76 (m, 6H). MS: (M+H)$^+$=353.

Example 52

Trans-N-isopropyl-N-methyl-N-[3-(6-pyrimidin-5-yl-1,3-benzothiazol-2-yl)cyclobutyl]amine

Example 52A

Trans-N-[3-(6-bromo-1,3-benzothiazol-2-yl)cyclobutyl]-N-isopropyl-N-methylamine

The title compound was prepared according to the procedure described in Example 43A, substituting isopropyl-methylamine for 4-piperidinemethanol. $^1$H NMR (300 MHz, CDCl$_3$) δ ppm 7.99 (d, J=1.36 Hz, 1H) 7.83 (d, J=9.15 Hz, 1H) 7.57 (dd, J=8.81, 2.03 Hz, 1H) 3.80-3.96 (m, 2H) 3.28-3.42 (m, 1H) 2.90-3.10 (m, 2H) 2.58-2.77 (m, 2H) 2.40 (s, 3H) 1.23 (d, J=5.76 Hz, 6H). MS: (M+H)$^+$=339/341.

Example 52B

Trans-N-isopropyl-N-methyl-N-[3-(6-pyrimidin-5-yl-1,3-benzothiazol-2-yl)cyclobutyl]amine The title compound was prepared according to the procedure described in Example 1F, substituting the product of Example 52A for the product of Example 1E. $^1$H NMR (300 MHz, CDCl$_3$) δ ppm 9.24 (s, 1H) 9.02 (s, 2H) 8.12 (d, J=8.48 Hz, 1H) 8.07 (d, J=1.70 Hz, 1H) 7.67 (dd, J=8.48, 1.70 Hz, 1H) 3.78-3.93 (m, 1H) 3.61 (m, 1H) 3.06 (m, 1H) 2.67-2.81 (m, 1H) 2.61 (t, J=9.16 Hz, 2H) 2.11-2.26 (m, 2H) 1.48-1.75 (m, 4H) 0.94-1.17 (m, 4H). MS: (M+H)$^+$=339.

Example 53

Trans-N-isopropyl-N-{3-[6-(2-methoxypyrimidin-5-yl)-1,3-benzothiazol-2-yl]cyclobutyl}-N-methylamine The title compound was prepared according to the procedure described in Example 1F, substituting the product of Example 52A for the product of Example 1E and substituting 2-methoxypyrimidine-5-boronic acid for pyrimidine-5-boronic acid. $^1$H NMR (500 MHz, CDCl$_3$) δ ppm 8.77 (s, 2H) 8.07 (d, J=8.42 Hz, 1H) 7.98 (d, J=1.87 Hz, 1H) 7.60 (dd, J=8.42, 1.87 Hz, 2H) 4.09 (s, 3H) 3.76-3.89 (m, 1H) 3.51-3.66 (m, 1H) 2.95-3.05 (m, 1H) 2.53-2.74 (m, 4H) 2.14 (s, 3H) 1.03 (d, J=6.55 Hz, 6H). MS: (M+H)$^+$=369.

Example 54

Trans-N-isopropyl-N-{3-[6-(6-methoxypyridin-3-yl)-1,3-benzothiazol-2-yl]cyclobutyl}-N-methylamine The title compound was prepared according to the procedure described in Example 1F, substituting the product of Example 52A for the product of Example 1E and substituting 6-methoxypyridine-3-boronic acid for pyrimidine-5-boronic acid. $^1$H NMR (300 MHz, CDCl$_3$) δ ppm 8.00 (d, J=8.48 Hz, 1H) 7.87 (d, J=1.70 Hz, 1H) 7.68 (dd, J=9.16, 2.71 Hz, 1H) 7.49 (dd, J=8.48, 1.70 Hz, 1H) 7.39-7.44 (m, 1H) 6.70 (d, J=9.49 Hz, 1H) 3.75-3.88 (m, 1H) 3.65 (s, 3H) 3.56-3.63 (m, 1H) 3.00-3.16 (m, 1H) 2.66-2.80 (m, 2H) 2.52-2.65 (m, 2H) 2.18 (s, 3H) 1.05 (d, J=6.44 Hz, 6H). MS: (M+H)$^+$=368.

Example 55

Trans-N-isopropyl-N-{3-[6-(2-methoxypyridin-3-yl)-1,3-benzothiazol-2-yl]cyclobutyl}-N-methylamine The title compound was prepared according to the procedure described in Example 1F, substituting the product of Example 52A for the product of Example 1E and substituting 2-methoxypyridine-3-boronic acid for pyrimidine-5-boronic acid. $^1$H NMR (500 MHz, CDCl$_3$) δ ppm 8.19 (dd, J=4.99, 1.87 Hz, 1H) 7.97-8.05 (m, 2H) 7.66 (dd, J=7.18, 1.87 Hz, 1H) 7.63 (dd, J=8.42, 1.87 Hz, 1H) 7.00 (dd, J=7.49, 4.99 Hz, 1H) 3.99 (s, 3H) 3.78-3.85 (m, 1H) 3.53-3.63 (m, 1H) 2.92-3.09 (m, 1H) 2.63-2.73 (m, 2H) 2.52-2.61 (m, 3H) 2.14 (d, J=5.93 Hz, 3H) 0.96-1.08 (m, 6H). MS: (M+H)$^+$=368.

Example 56

Trans-N-{3-[6-(2,6-dimethylpyridin-3-yl)-1,3-benzothiazol-2-yl]cyclobutyl}-N-isopropyl-N-methylamine The title compound was prepared according to the procedure described in Example 1F, except for substituting the product of Example 52A for the product of Example 1E and

Example 57

Trans-2-(2-{3-[isopropyl(methyl)amino]cyclobutyl}-1,3-benzothiazol-6-yl)pyridazin-3(2H)-one The title compound was prepared according to the procedure described in Example 22, except for substituting the product of Example 52A for the product of Example 1E. $^1$H NMR (400 MHz, CDCl$_3$) δ ppm 8.14 (d, J=1.84 Hz, 1H) 8.03 (d, J=8.59 Hz, 1H) 7.92 (dd, J=3.68, 1.53 Hz, 1H) 7.68 (dd, J=8.90, 2.15 Hz, 1H) 7.24-7.29 (m, 1H) 7.08 (dd, J=9.51, 1.53 Hz, 1H) 3.53-3.65 (m, 1H) 3.13-3.28 (m, 1H) 2.90-3.06 (m, 1H) 2.61-2.74 (m, 2H) 2.28-2.45 (m, 2H) 2.15 (s, 3H) 1.04 (d, J=6.14 Hz, 6H). MS: (M+H)$^+$=355.

Example 58

Trans-2-(2-{3-[isopropyl(methyl)amino]cyclobutyl}-1,3-benzothiazol-6-yl)-6-methylpyridazin-3(2H)-one The title compound was prepared according to the procedure described in Example 22, except for substituting the product of Example 52A for the product of Example 1E and substituting 6-methyl-3(2H)-pyridazinone for 3(2H)-pyridazinone. $^1$H NMR (400 MHz, CDCl$_3$) δ ppm 8.12 (d, J=1.84 Hz, 1H) 8.01 (d, J=8.90 Hz, 1H) 7.67 (dd, J=8.59, 2.15 Hz, 1H) 7.16 (d, J=9.51 Hz, 1H) 7.00 (d, J=9.51 Hz, 1H) 3.49-3.66 (m, 1H) 3.12-3.28 (m, 1H) 2.91-3.06 (m, 1H) 2.61-2.75 (m, 2H) 2.40 (s, 3H) 2.29-2.40 (m, 2H) 2.14 (s, 3H) 1.03 (d, J=6.75 Hz, 6H). MS: (M+H)$^+$=369.

Example 59

Trans-1-(2-{3-[isopropyl(methyl)amino]cyclobutyl}-1,3-benzothiazol-6-yl)-3-methylpyridin-2(1H)-one The title compound was prepared according to the procedure described in Example 22, except for substituting the product of Example 52A for the product of Example 1E and substituting 3-methyl-2-pyridone for 3(2H)-pyridazinone. $^1$H NMR (400 MHz, CDCl$_3$) δ ppm 8.02 (d, J=8.59 Hz, 1H) 7.89 (d, J=1.84 Hz, 1H) 7.42 (dd, J=8.75, 1.99 Hz, 1H) 7.23-7.34 (m, 2H) 6.18 (t, J=6.75 Hz, 1H) 3.52-3.63 (m, 1H) 3.12-3.27 (m, 1H) 2.90-3.03 (m, 1H) 2.55-2.73 (m, 2H) 2.25-2.44 (m, 2H) 2.20 (s, 3H) 2.13 (s, 3H) 1.02 (d, J=6.44 Hz, 6H). MS: (M+H)$^+$=368.

Example 60

Trans-1-(2-{3-[isopropyl(methyl)amino]cyclobutyl}-1,3-benzothiazol-6-yl)-5-methylpyridin-2(1H)-one The title compound was prepared according to the procedure described in Example 22, except for substituting the product of Example 52A for the product of Example 1E and substituting 5-methyl-2-pyridone for 3(2H)-pyridazinone. $^1$H NMR (400 MHz, CDCl$_3$) δ ppm 8.02 (d, J=8.59 Hz, 1H) 7.88 (d, J=2.15 Hz, 1H) 7.42 (dd, J=8.59, 1.84 Hz, 1H) 7.26-7.30 (m, 1H) 7.15 (s, 1H) 6.62 (d, J=9.21 Hz, 1H) 3.51-3.64 (m, 1H) 3.13-3.27 (m, 1H) 2.90-3.02 (m, 1H) 2.62-2.72 (m, 2H) 2.28-2.40 (m, 2H) 2.13 (s, 3H) 2.12 (s, 3H) 1.02 (d, J=6.44 Hz, 6H). MS: (M+H)$^+$=368.

Example 61

Trans-2-(3-azetidin-1-ylcyclobutyl)-6-pyrimidin-5-yl-1,3-benzothiazole

Example 61A

Trans-2-(3-azetidin-1-ylcyclobutyl)-6-bromo-1,3-benzothiazole

The title compound was prepared according to the procedure described in Example 43A, except for substituting azetidine for 4-piperidinemethanol. $^1$H NMR (300 MHz, CDCl$_3$) δ ppm 7.97 (d, J=2.03 Hz, 1H) 7.82 (d, J=8.48 Hz, 1H) 7.56 (dd, J=8.48, 2.03 Hz, 1H) 3.95-4.09 (m, 1H) 3.80-3.91 (m, 1H) 3.55-3.75 (m, 2H) 3.19-3.36 (m, 2H) 2.78-2.94 (m, 2H) 2.44-2.62 (m, 2H) 2.05-2.23 (m, 2H). MS: (M+H)$^+$=323/325.

Example 61B

Trans-2-(3-azetidin-1-ylcyclobutyl)-6-pyrimidin-5-yl-1,3-benzothiazole

The title compound was prepared according to the procedure described in Example 1F, except for substituting the product of Example 61A for the product of Example 1E. $^1$H NMR (400 MHz, CDCl$_3$) δ ppm 9.23 (s, 1H) 9.01 (s, 2H) 8.11 (d, J=8.29 Hz, 1H) 8.05 (d, J=1.53 Hz, 1H) 7.66 (dd, J=8.44, 1.69 Hz, 1H) 3.98-4.12 (m, 1H) 3.60-3.74 (m, 1H) 3.26-3.45 (m, 4H) 2.53-2.69 (m, 2H) 2.42-2.54 (m, 2H) 2.16 (m, 2H). MS: (M+H)$^+$=323.

Example 62

Trans-6-pyrimidin-5-yl-2-(3-pyrrolidin-1-ylcyclobutyl)-1,3-benzothiazole

Example 62A

Trans-6-bromo-2-(3-pyrrolidin-1-ylcyclobutyl)-1,3-benzothiazole

The title compound was prepared according to the procedure described in Example 43A, except for substituting pyrrolidine for 4-piperidinemethanol. $^1$H NMR (300 MHz, CDCl$_3$) δ ppm 7.98 (d, J=2.03 Hz, 1H) 7.82 (d, J=8.82 Hz, 1H) 7.56 (dd, J=8.65, 1.87 Hz, 1H) 3.90-4.04 (m, 1H) 3.47 (d, J=7.12 Hz, 1H) 2.55-2.90 (m, 8H) 1.93 (m, 4H). MS: (M+H)$^+$=337/339.

Example 62B

Trans-6-pyrimidin-5-yl-2-(3-pyrrolidin-1-ylcyclobutyl)-1,3-benzothiazole

The title compound was prepared according to the procedure described in Example 1F, substituting the product of Example 62A for the product of Example 1E. $^1$H NMR (400 MHz, CDCl$_3$) δ ppm 9.23 (s, 1H) 9.01 (s, 2H) 8.11 (d, J=8.59 Hz, 1H) 8.06 (d, J=1.84 Hz, 1H) 7.66 (dd, J=8.59, 1.84 Hz, 1H) 3.91-4.09 (m, 1H) 3.20-3.40 (m, 1H) 2.60-2.74 (m, 4H) 2.50-2.58 (m, 4H) 1.78-1.92 (m, 4H). MS: (M+H)$^+$=337.

Example 63

Trans-6-(2,6-dimethylpyridin-3-yl)-2-(3-pyrrolidin-1-ylcyclobutyl)-1,3-benzothiazole The title compound was prepared according to the procedure described in Example 1F, substituting the product of Example 62A for the product of Example 1E and substituting the product of Example 2A for pyrimidine-5-boronic acid. $^1$H NMR (300 MHz, CDCl$_3$) δ ppm 8.02 (d, J=8.48 Hz, 1H) 7.76 (d, J=1.36 Hz, 1H) 7.45 (d, J=7.80 Hz, 1H) 7.40 (dd, J=8.31, 1.86 Hz, 1H) 7.07 (d, J=7.80 Hz, 1H) 3.95-4.07 (m, 1H) 3.25-3.45 (m, 1H) 2.59 (s, 3H) 2.50 (s, 3H) 2.43-2.78 (m, 6H) 1.77-2.00 (m, 4H) 1.47-1.68 (m, 2H). MS: (M+H)$^+$=364.

Example 64

Trans-6-(2-methoxypyrimidin-5-yl)-2-(3-pyrrolidin-1-ylcyclobutyl)-1,3-benzothiazole The title compound was prepared according to the procedure described in Example 1F, substituting the product of Example 62A for the product of Example 1E and substituting 2-methoxypyrimidine-5-boronic acid for pyrimidine-5-boronic acid. $^1$H NMR (300 MHz, CDCl$_3$) δ ppm 8.78 (s, 1H) 8.07 (d, J=8.48 Hz, 1H) 7.98 (d, J=1.70 Hz, 1H) 7.60 (dd, J=8.48, 2.03 Hz, 1H) 4.08 (s, 3H) 3.93-4.07 (m, 1H) 3.26-3.45 (m, 1H) 2.50-2.80 (m, 6H) 1.78-1.96 (m, 4H) 1.59 (m, 2H). MS: (M+H)$^+$=367.

Example 65

Trans-6-(2,4-dimethoxypyrimidin-5-yl)-2-(3-pyrrolidin-1-ylcyclobutyl)-1,3-benzothiazole The title compound was prepared according to the procedure described in Example 1F, substituting the product of Example 62A for the product of Example 1E and substituting 2,6-dimethoxy-5-pyrimidineboronic acid for pyrimidine-5-boronic acid. $^1$H NMR (300 MHz, CDCl$_3$) δ ppm 8.32 (s, 1H) 8.02 (d, J=8.48 Hz, 1H) 7.97 (d, J=1.70 Hz, 1H) 7.57 (dd, J=8.65, 1.86 Hz, 1H) 4.03-4.10 (s, 3H) 3.95-4.03 (m, 1H) 3.26-3.42 (m, 1H) 2.43-2.78 (m, 6H) 1.79-1.98 (m, 4H) 1.45-1.66 (m, 2H). MS: (M+H)$^+$=397.

Example 66

Trans-6-(6-methoxypyridin-3-yl)-2-(3-pyrrolidin-1-ylcyclobutyl)-1,3-benzothiazole The title compound was prepared according to the procedure described in Example 1F, substituting the product of Example 62A for the product of Example 1E and substituting 6-methoxy-3-pyridineboronic acid for pyrimidine-5-boronic acid. $^1$H NMR (300 MHz, CDCl$_3$) δ ppm 8.43 (d, J=2.37 Hz, 1H) 8.03 (d, J=8.48 Hz, 1H) 7.97 (s, 1H), 7.83 (dd, J=8.65, 2.54 Hz, 1H) 7.61 (dd, J=8.48, 2.03 Hz, 1H) 6.85 (d, J=9.15 Hz, 1H) 4.01-4.10 (m, J=6.78 Hz, 1H) 4.00 (s, 3H) 3.35-3.70 (m, 1H) 2.68 (s, 6H) 1.93 (s, 2H) 1.93 (s, 4H) 1.46-1.65 (m, 2H). MS: (M+H)$^+$=366.

Example 67

Trans-2-[2-(3-pyrrolidin-1-ylcyclobutyl)-1,3-benzothiazol-6-yl]pyridazin-3(2H)-one The title compound was prepared according to the procedure described in Example 22, substituting the product of Example 62A for the product of Example 1E. $^1$H NMR (300 MHz, CDCl$_3$) δ ppm 8.15 (t, J=1.86 Hz, 1H) 8.04 (dd, J=8.65, 7.63 Hz, 1H) 7.89-7.95 (dt, 1H) 7.72 (td, 1H) 7.21-7.31 (m, 1H) 7.04-7.15 (dt, 1H) 4.03 (m, 1H) 3.65 (m, 1H) 2.46-2.77 (m, 6H) 1.75-2.00 (m, 4H) 1.49-1.62 (m, 2H). MS: (M+H)$^+$=353.

Example 68

Trans-6-methyl-2-[2-(3-pyrrolidin-1-ylcyclobutyl)-1,3-benzothiazol-6-yl]pyridazin-3(2H)-one The title compound was prepared according to the procedure described in Example 22, substituting the product of Example 62A for the product of Example 1E and substituting 6-methyl-3(2H)-pyridazinone for 3(2H)-pyridazinone. $^1$H NMR (300 MHz, CDCl$_3$) δ ppm 8.12 (t, J=2.03 Hz, 1H) 8.03 (t, J=8.48 Hz, 1H) 7.66 (dd, J=8.48, 2.37 Hz, 1H) 7.17 (d, J=9.49, 1H) 7.00 (d, J=9.49 Hz, 1H) 3.56-3.72 (m, 1H) 3.07 (m, 1H) 2.48-2.78 (m, 6H) 2.41 (s, 3H) 1.87-1.96 (m, 2H) 1.77-1.87 (m, 2H) 1.49-1.73 (m, 2H). MS: (M+H)$^+$=367.

Example 69

Trans-5-methyl-1-[2-(3-pyrrolidin-1-ylcyclobutyl)-1,3-benzothiazol-6-yl]pyridin-2(1H)-one The title compound was prepared according to the procedure described in Example 22, substituting the product of Example 62A for the product of Example 1E and substituting 5-methyl-2(1H)-pyridone for 3(2H)-pyridazinone. $^1$H NMR (300 MHz, CDCl$_3$) δ ppm 8.03 (d, J=9.15 Hz, 1H) 7.87-7.90 (m, 1H) 7.44 (td, J=9.00, 2.03 Hz, 1H) 7.29 (dt, J=9.00, 2.37 Hz, 2H) 7.15 (s, 1H) 6.63 (d, J=9.15 Hz, 1H) 3.61-3.73 (m, 1H) 3.03-3.16 (m, 1H) 2.43-2.78 (m, 6H) 2.12 (s, 3H) 1.81-1.91 (m, 4H) 1.51-1.61 (m, 2H). MS: (M+H)$^+$=366.

Example 70

Trans-3-methyl-1-[2-(3-pyrrolidin-1-ylcyclobutyl)-1,3-benzothiazol-6-yl]pyridin-2(1H)-one The title compound was prepared according to the procedure described in Example 22, substituting the product of Example 62A for the product of Example 1E and substituting 3-methyl-2-pyridone for 3(2H)-pyridazinone. $^1$H NMR (300 MHz, CDCl$_3$) δ ppm 8.03 (t, J=8.31 Hz, 1H) 7.89 (d, J=2.03 Hz, 1H) 7.44 (t, 1H) 7.27-7.33 (m, 1H) 6.18 (q, 2H) 3.55-3.75 (m, 1H) 3.03-3.15 (m, 1H) 2.39-2.76 (m, 6H) 2.21 (s, 3H) 1.79-1.99 (m, 4H) 1.50-1.70 (m, 2H). MS: (M+H)$^+$=366.

Example 71

Trans-2-(3-azepan-1-ylcyclobutyl)-6-pyrimidin-5-yl-1,3-benzothiazole

Example 71A

Trans-2-(3-azepan-1-ylcyclobutyl)-6-bromo-1,3-benzothiazole

The title compound was prepared according to the procedure described in Example 43A, substituting hexamethyleneimine for 4-piperidinemethanol. $^1$H NMR (500 MHz, CDCl$_3$) δ ppm 7.98 (d, J=1.83 Hz, 1H) 7.82 (d, J=8.54 Hz, 1H) 7.56

(dd, J=8.54, 1.83 Hz, 1H) 3.73-3.85 (m, 1H) 3.29-3.42 (m, 1H) 2.46-2.62 (m, 8H) 1.52-1.74 (m, 8H). MS: (M+H)$^+$=365/367.

Example 71B

Trans-2-(3-azepan-1-ylcyclobutyl)-6-pyrimidin-5-yl-1,3-benzothiazole

The title compound was prepared according to the procedure described in Example 1F, except for substituting the product of Example 71A for the product of Example 1E. $^1$H NMR (400 MHz, CDCl$_3$) δ ppm 9.23 (s, 1H) 9.01 (s, 2H) 8.11 (d, J=7.98 Hz, 1H) 8.06 (d, J=1.84 Hz, 1H) 7.66 (dd, J=8.29, 1.84 Hz, 1H) 3.73-3.95 (m, J=6.29, 6.29 Hz, 1H) 3.34-3.50 (m, 1H) 2.48-2.69 (m, 8H) 1.59-1.82 (m, 8H). MS: (M+H)$^+$=365.

Example 72

Trans-2-(3-morpholin-4-ylcyclobutyl)-6-pyrimidin-5-yl-1,3-benzothiazole

Example 72A

Trans-6-bromo-2-(3-morpholin-4-ylcyclobutyl)-1,3-benzothiazole

The title compound was prepared according to the procedure described in Example 43A, substituting morpholine for 4-piperidinemethanol. $^1$H NMR (300 MHz, CDCl$_3$) δ ppm 7.98 (d, J=2.03 Hz, 1H) 7.84 (d, J=8.65 Hz, 1H) 7.56 (dd, J=8.65, 1.86 Hz, 1H) 3.82-3.92 (m, 1H) 3.68-3.82 (m, 4H) 3.08-3.27 (m, 1H) 2.58 (m, 4H) 2.31-2.49 (m, 4H). MS: (M+H)$^+$=353/355.

Example 72B

Trans-2-(3-morpholin-4-ylcyclobutyl)-6-pyrimidin-5-yl-1,3-benzothiazole

The title compound was prepared according to the procedure described in Example 1F, substituting the product of Example 72A for the product of Example 1E. $^1$H NMR (400 MHz, CDCl$_3$) δ ppm 9.24 (s, 1H) 8.99-9.05 (s, 2H) 8.12 (d, J=8.59 Hz, 1H) 8.06 (d, J=1.23 Hz, 1H) 7.67 (dd, J=8.59, 1.84 Hz, 1H) 3.86-3.97 (m, 1H) 3.71-3.82 (m, 4H) 3.15-3.24 (m, 1H) 2.35-2.67 (m, 8H). MS: (M+H)$^+$=353.

Example 73

Trans-2-{3-[(2S)-2-(fluoromethyl)pyrrolidin-1-yl]cyclobutyl}-6-pyrimidin-5-yl-1,3-benzothiazole

Example 73A

Trans-6-bromo-2-{3-[(2S)-2-(fluoromethyl)pyrrolidin-1-yl]cyclobutyl}-1,3-benzothiazole The title compound was prepared according to the procedure described in Example 43A, substituting S(+)-2-fluoromethylpyrrolidine (CAS#460748-85-0, prepared according to the procedure that described in: R. Altenbach et al., WO 2004043458) for 4-piperidinemethanol. $^1$H NMR (300 MHz, CDCl$_3$) δ ppm 7.98 (d, J=1.70 Hz, 1H) 7.83 (d, J=8.81 Hz, 1H) 7.56 (dd, J=8.65, 1.86 Hz, 1H) 4.30-4.46 (m, 1H) 4.14-4.29 (m, 1H) 3.78-3.91 (m, 1H) 3.55-3.70 (m, 1H) 2.98-3.13 (m, 1H) 2.82-2.95 (m, 1H) 2.53-2.72 (m, 4H) 2.39-2.50 (m, 1H) 1.70-1.97 (m, 2H) 1.50-1.59 (m, 2H). MS: (M+H)$^+$=369/371.

Example 73B

Trans-2-{3-[(2S)-2-(fluoromethyl)pyrrolidin-1-yl]cyclobutyl}-6-pyrimidin-5-yl-1,3-benzothiazole The title compound was prepared according to the procedure described in Example 1F, substituting the product of Example 73A for the product of Example 1E. $^1$H NMR (300 MHz, CDCl$_3$) δ ppm 9.24 (s, 1H) 9.02 (s, 2H) 8.12 (d, J=8.48 Hz, 1H) 8.06 (d, J=1.70 Hz, 1H) 7.67 (dd, J=8.48, 1.70 Hz, 1H) 4.06-4.50 (m, 1H) 3.82-4.03 (m, 1H) 3.54-3.76 (m, 1H) 3.00-3.18 (m, 1H) 2.79-2.95 (m, 1H) 2.55-2.74 (m, 3H) 2.34-2.54 (m, 1H) 1.70-1.97 (m, 2H) 1.45-1.61 (m, 4H). MS: (M+H)$^+$=369.

Example 74

Trans-{(2S)-1-[3-(6-pyrimidin-5-yl-1,3-benzothiazol-2-yl)cyclobutyl]pyrrolidin-2-yl}methanol

Example 74A

Trans-{(2S)-1-[3-(6-bromo-1,3-benzothiazol-2-yl)cyclobutyl]pyrrolidin-2-yl}methanol The title compound was prepared according to the procedure described in Example 43A, substituting S(+)-2-hydroxymethylpyrrolidine for 4-piperidinemethanol. $^1$H NMR (300 MHz, CDCl$_3$) δ ppm 7.99 (d, J=2.03 Hz, 1H) 7.82 (d, J=8.48 Hz, 1H) 7.57 (dd, J=8.48, 2.03 Hz, 1H) 4.05-4.17 (m, 1H) 3.28-3.95 (m, 5H) 2.51-2.87 (m, 4H) 1.70-2.18 (m, 4H) 1.41-1.65 (m, 2H). MS: (M+H)$^+$=367/369.

Example 74B

Trans-{(2S)-1-[3-(6-pyrimidin-5-yl-1,3-benzothiazol-2-yl)cyclobutyl]pyrrolidin-2-yl}methanol The title compound was prepared according to the procedure described in Example 1F, substituting the product of Example 74A for the product of Example 1E. $^1$H NMR (300 MHz, CDCl$_3$) δ ppm 9.24 (s, 1H) 9.02 (s, 2H) 8.11 (d, J=8.48 Hz, 1H) 8.07 (d, J=2.03 Hz, 1H) 7.68 (dd, J=8.48, 1.70 Hz, 1H) 3.89-4.04 (m, 1H) 3.55-3.74 (m, 2H) 3.26-3.47 (m, 1H) 2.62-2.88 (m, 4H) 2.42-2.60 (m, 1H) 1.72-2.08 (m, 5H) 1.48-1.67 (m, 2H). MS: (M+H)$^+$=367.

Example 75

Trans-((2S)-1-{3-[6-(2,6-dimethylpyridin-3-yl)-1,3-benzothiazol-2-yl]cyclobutyl}pyrrolidin-2-yl)methanol The title compound was prepared according to the procedure described in Example 1F, substituting the product of Example 74A for the product of Example 1E and substituting the product of Example 2A for pyrimidine-5-boronic acid. $^1$H NMR (300 MHz, CDCl$_3$) δ ppm 8.02 (d, J=8.81 Hz, 1H) 7.77 (d, J=1.36 Hz, 1H) 7.45 (d, J=7.80 Hz, 1H) 7.40 (dd, J=8.48, 1.70 Hz, 1H) 7.07 (d, J=7.80 Hz, 1H) 3.83-4.00 (m, 1H) 3.52-3.75 (m, 2H) 3.32-3.47 (m, 1H) 2.99-3.17 (m, 1H) 2.63-2.80 (m, 3H) 2.59 (s, 3H) 2.50 (s, 3H) 1.70-2.08 (m, 5H) 1.46-1.65 (m, 2H). MS: (M+H)$^+$=394.

Example 76

Trans-2-[3-(2-methylpiperidin-1-yl)cyclobutyl]-6-pyrimidin-5-yl-1,3-benzothiazole

Example 76A

Trans-6-bromo-2-[3-(2-methylpiperidin-1-yl)cyclobutyl]-1,3-benzothiazole

The title compound was prepared according to the procedure described in Example 43A, substituting 2-methylpiperidine (CAS # 109-05-7) for 4-piperidinemethanol. $^1$H NMR (300 MHz, CDCl$_3$) δ ppm 7.98 (d, J=1.70 Hz, 1H) 7.83 (d, J=8.81 Hz, 1H) 7.56 (dd, J=8.65, 1.86 Hz, 1H) 3.78-3.90 (m, 1H) 2.81-3.11 (m, 2H) 2.56-2.77 (m, 4H) 1.38-1.93 (m, 8H) 1.24 (s, 3H). MS: (M+H)$^+$=365/367.

Example 76B

Trans-2-[3-(2-methylpiperidin-1-yl)cyclobutyl]-6-pyrimidin-5-yl-1,3-benzothiazole The title compound was prepared according to the procedure described in Example 1F, substituting the product of Example 76A for the product of Example 1E. $^1$H NMR (500 MHz, CDCl$_3$) δ ppm 9.24 (s, 1H) 8.99-9.04 (m, 2H) 8.12 (d, J=8.24 Hz, 1H) 8.07 (d, J=1.83 Hz, 1H) 7.68 (dd, J=8.39, 1.68 Hz, 1H) 3.78-3.90 (m, 1H) 3.51-3.67 (m, 1H) 2.53-2.80 (m, 5H) 1.61 (m, 6H) 1.35-1.50 (m, 2H) 1.09 (s, 3H). MS: (M+H)$^+$=365.

Example 77

Trans-2-(3-hexahydropyrrolo[3,4-b]pyrrol-5(1H)-ylcyclobutyl)-6-pyrimidin-5-yl-1,3-benzothiazole

Example 77A

Trans-tert-butyl 5-[3-(6-bromo-1,3-benzothiazol-2-yl)cyclobutyl]hexahydropyrrolo[3,4-b]pyrrole-1(2H)-carboxylate The title compound was prepared according to the procedure described in Example 43A, substituting hexahydro-pyrrolo[3,4-b]pyrrole-1-carboxylic acid tert-butyl ester (prepared according to the procedure that described in: Q. Li et al., J. Med. Chem.; 39(16), 3070-3088, 1996) for 4-piperidinemethanol. $^1$H NMR (300 MHz, CDCl$_3$) δ ppm 7.97 (d, J=1.70 Hz, 1H) 7.82 (d, J=8.81 Hz, 1H) 7.56 (dd, J=8.82, 2.03 Hz, 1H) 4.10-4.37 (m, 2H) 3.85-4.02 (m, 1H) 3.49 (m 2H) 3.11-3.29 (m, 1H) 2.95-3.07 (m, 1H) 2.79-2.94 (m, 1H) 2.31-2.67 (m, 6H) 1.90-2.11 (m, 1H) 1.65-1.86 (m, 1H) 1.46 (s, 9H). MS: (M+H)$^+$=478/480.

Example 77B

Trans-tert-butyl 5-[3-(6-pyrimidin-5-yl-1,3-benzothiazol-2-yl)cyclobutyl]hexahydropyrrolo[3,4-b]pyrrole-1(2H)-carboxylate The title compound was prepared according to the procedure described in Example 1F, substituting the product of Example 77A for the product of Example 1E. $^1$H NMR (300 MHz, CDCl$_3$) δ ppm 9.23 (s, 1H) 9.01 (s, 2H) 8.11 (d, J=8.48 Hz, 1H) 8.06 (d, J=1.36 Hz, 1H) 7.67 (dd, J=8.42, 1.87 Hz, 1H) 4.15-4.30 (m, 1H) 3.91-4.06 (m, 2H) 3.43 (m, 3H) 3.12-3.26 (m, 1H) 2.79-2.92 (m, 1H) 2.66-2.76 (m, 1H) 2.49-2.62 (m, 4H) 2.31-2.45 (m, 1H) 1.90-2.08 (m, 1H) 1.67-1.83 (m, 1H) 1.44-1.47 (m, 9H). MS: (M+H)$^+$=478.

Example 77C

Trans-2-(3-hexahydropyrrolo[3,4-b]pyrrol-5(1H)-ylcyclobutyl)-6-pyrimidin-5-yl-1,3-benzothiazole The title compound was prepared according to the procedure described in Example 38C, substituting the product of Example 77B for the product Example 38B. $^1$H NMR (300 MHz, CDCl$_3$) δ ppm 9.23 (s, 1H) 9.01 (s, 2H) 8.11 (d, J=8.81 Hz, 1H) 8.05 (d, J=1.36 Hz, 1H) 7.66 (dd, J=8.48, 2.03 Hz, 1H) 3.94-4.06 (m, 2H) 3.55-3.81 (m, 1H) 3.14-3.27 (m, 2H) 3.02-3.15 (m, 1H) 2.75-2.96 (m, 3H) 2.45-2.68 (m, 6H) 1.96-2.13 (m, 1H) 1.67-1.82 (m, 1H). MS: (M+H)$^+$=378.

Example 78

Trans-2-[3-(4-fluoropiperidin-1-yl)cyclobutyl]-6-pyrimidin-5-yl-1,3-benzothiazole

Example 78A

Trans-6-bromo-2-[3-(4-fluoropiperidin-1-yl)cyclobutyl]-1,3-benzothiazole

The title compound was prepared according to the procedure described in Example 43A, substituting 4-fluoropiperidine hydrochloride (available from ABCR) for 4-piperidinemethanol. $^1$H NMR (300 MHz, CDCl$_3$) δ ppm 7.98 (d, J=2.03 Hz, 1H) 7.83 (d, J=8.48 Hz, 1H) 7.56 (dd, J=8.48, 2.03 Hz, 1H) 4.73 (m, 1H), 3.83 (m, 1H) 3.20 (m, 1H) 2.38-2.60 (m, 6H) 1.92 (m, 4H) 1.59 (m, 2H). MS: (M+H)$^+$=369/371.

Example 78B

Trans-2-[3-(4-fluoropiperidin-1-yl)cyclobutyl]-6-pyrimidin-5-yl-1,3-benzothiazole The title compound was prepared according to the procedure described in Example 1F, substituting the product of Example 78A for the product of Example 1E. $^1$H NMR (300 MHz, CDCl$_3$) δ ppm 9.24 (s, 1H) 9.00 (s, 2H) 8.11 (d, J=8.48 Hz, 1H) 8.06 (d, J=1.70 Hz, 1H) 7.67 (dd, J=8.48, 1.70 Hz, 1H) 4.65-4.80 (m, 1H) 3.89 (m, 1H) 3.20 (m, 1H) 2.36-2.63 (m, 8H) 1.93 (m, 4H). MS: (M+H)$^+$=369.

Example 79

Trans-2-[3-(4-fluoropiperidin-1-yl)cyclobutyl]-6-(2-methoxypyrimidin-5-yl)-1,3-benzothiazole The title compound was prepared according to the procedure described in Example 1F, substituting the product of Example 78A for the product of Example 1E, and substituting 2-methoxypyrimidine-5-boronic acid for pyrimidine-5-boronic acid. $^1$NMR (300 MHz, CDCl$_3$) δ ppm 8.78 (s, 2H) 8.07 (d, J=8.48 Hz, 1H) 7.99 (d, J=1.70 Hz, 1H) 7.61 (dd, J=8.48, 1.70 Hz, 1H) 4.71 (m, 1H) 4.09 (s, 3H) 3.90 (m, 1H) 3.23 (m, 1H) 2.62 (m, 6H) 2.35 (m, 2H) 1.93 (m, 4H). MS: (M+H)$^+$=399.

Example 80

Trans-6-(2,6-dimethylpyridin-3-yl)-2-[3-(4-fluoropiperidin-1-yl)cyclobutyl]-1,3-benzothiazole The title compound was prepared according to the procedure described in Example 1F, substituting the product of Example 78A for the product of Example 1E, and substituting the product of Example 2A for pyrimidine-5-boronic acid. $^1$H NMR (300 MHz, CDCl$_3$) δ ppm 8.02 (d, J=8.48 Hz, 1H) 7.77 (d, J=1.70 Hz, 1H) 7.46 (d, J=7.80 Hz, 1H) 7.40 (dd, J=8.48, 1.70 Hz, 1H) 7.07 (d, J=7.80 Hz, 1H) 4.65-4.80 (m, 1H) 3.89 (m, 1H) 3.21 (m, 1H) 2.36-2.63 (m, 8H) 2.59 (s, 3H) 2.50 (s, 3H) 1.86-2.05 (m, 4H). MS: (M+H)$^+$=396.

Example 81

Trans-(3R)-1-[3-(6-pyrimidin-5-yl-1,3-benzothiazol-2-yl)cyclobutyl]piperidin-3-ol

Example 81A

Cis-3-(6-pyrimidin-5-yl-1,3-benzothiazol-2-yl)cyclobutanol

The product of Example 1D (100 mg, 0.35 mmole), pyrimidine-5-boronic acid (65 mg, 0.53 mmole), dichlorobis(triphenylphosphine)palladium(II) (14.8 mg, 0.0021 mmole), 2-(dicyclohexyl-phosphino)biphenyl (7.4 mg, 0.021 mmole), sodium carbonate (1 M solution, 0.53 ml, 0.53 mmole) and 2 ml of ethanol/dioxane (1:1) were mixed under N$_2$ in a capped, sealed vial. The vial was sealed heated in the microwave for 10 minutes at 140° C. using a commercial microwave heating apparatus (i.e. the Emrys Creator). The reaction mixture was quenched with water and extracted with dichloromethane (4×5 ml). The combined organic layers were washed with brine, dried over sodium sulfate, filtered, and concentrated under reduced pressure to give the crude product which was purified by column chromatography (10% methanol in dichloromethane) to give 80.4 mg (84.6% yield) of title compound. $^1$H NMR (300 MHz, CDCl$_3$) δ ppm 9.25 (s, 1H), 9.03 (s, 2H), 8.14 (d, J=8.48 Hz, 1H), 8.07 (d, J=1.70 Hz, 1H), 7.67 (dd, J=8.48, 2.03 Hz, 1H), 4.40 (m, 1H), 3.50 (m, 1H), 3.01 (m, 2H), 2.46 (m, 2H), 2.17 (brs, 1H). MS: (M+H)$^+$=284.

Example 81B

Trans-(3R)-1-[3-(6-pyrimidin-5-yl-1,3-benzothiazol-2-yl)cyclobutyl]piperidin-3-ol The title compound was prepared according to the procedure described in Example 43A, substituting (R)-3-hydroxypiperidine hydrochloride (CAS #198976-43-1) for 4-piperidinemethanol and substituting Example 81A for Example 1D. $^1$H NMR (300 MHz, CDCl$_3$) δ ppm 9.28 (s, 1H) 9.11 (s, 2H) 8.12 (d, J=9.0 Hz, 1H) 8.10 (s, 1H) 7.71 (d, J=9.0 Hz, 1H) 4.28 (m, 1H) 3.96 (m, 1H) 3.83 (m, 1H) 3.65 (m, 2H) 3.50 (m, 2H) 3.34-2.51 (m, 6H) 2.60-1.07 (m, 4H). MS: (M+H)$^+$=367.

Example 82

Trans-N-ethyl-N-propyl-N-[3-(6-pyrimidin-5-yl-1,3-benzothiazol-2-yl)cyclobutyl]amine The title compound was prepared according to the procedure described in Example 43A, substituting N-ethyl-N-propylamine for 4-piperidinemethanol and substituting Example 81A for Example 1D. $^1$H NMR (300 MHz, CDCl$_3$) δ ppm 9.27 (s, 1H) 9.07 (s, 2H) 8.12 (d, J=9.0 Hz, 1H) 8.11 (s, 1H) 7.71 (d, J=9.0 Hz, 1H) 4.14 (m, 1H) 4.00 (m, 1H) 3.22 (m, 1H) 3.10 (m, 2H) 2.90-2.73 (m, 4H) 1.77 (m, 2H) 1.36 (t, 3H) 1.04 (t, 3H). MS: (M+H)$^+$=353.

Example 83

Trans-Diethyl-[3-(6-pyrimidin-5-yl-benzothiazol-2-yl)-cyclobutyl]-amine

Example 83A

Trans-[3-(6-Bromo-benzothiazol-2-yl)-cyclobutyl]-diethyl-amine

The title compound was prepared according to the procedure described in Example 43A, substituting diethylamine for 4-piperidinemethanol. 1H NMR (300 MHz, CHLOROFORM-D) δ ppm 7.98 (d, J=2.03 Hz, 1H), 7.83 (d, J=8.82 Hz, 1H), 7.56 (dd, J=8.65, 1.86 Hz, 1H), 3.74-3.87 (m, 1H), 3.53-3.70 (m, 1H), 2.45-2.82 (m, 6H) 1.56 (m, 2H) 1.00-1.17 (m, 6H). (M+H)$^+$=341/343.

Example 83B

Trans-Diethyl-[3-(6-pyrimidin-5-yl-benzothiazol-2-yl)-cyclobutyl]-amine

The title compound was prepared according to the procedure described in Example 81A, substituting Example 83A for Example 1D. 1H NMR (400 MHz, CHLOROFORM-D) δ ppm 9.23 (s, 1H), 9.01 (s, 2H), 8.12 (d, J=8.29 Hz, 1H), 8.06 (d, J=1.84 Hz, 1H), 7.67 (dd, J=8.59, 1.84 Hz, 1H), 3.81-3.91 (m, 1H), 3.55-3.68 (m, 1H), 2.57-2.75 (m, 8H), 1.06 (t, J=6.90 Hz, 6H). MS: (M+H)$^+$=339.

Example 84

Trans-Diethyl-{3-[6-(2-methoxy-pyrimidin-5-yl)-benzothiazol-2-yl]-cyclobutyl}-amine The title compound was prepared according to the procedure described in Example 81A, substituting Example 83A for Example 1D, and substituting 2-methoxypyrimidine-5-boronic acid for pyrimidine-5-boronic acid. 1H NMR (400 MHz, CHLOROFORM-D) d ppm 8.77 (s, 2H), 8.07 (d, J=8.29 Hz, 1H), 7.98 (d, J=1.84 Hz, 1H), 7.60 (dd, J=8.44, 1.69 Hz, 1H), 4.09 (s, 3H), 3.79-3.91 (m, 1H), 3.55-3.67 (m, 1H), 2.53-2.80 (m, 8H) 1.06 (t, J=6.90 Hz, 6H). MS: (M+H)$^+$=369.

Example 85

Trans-{3-[6-(2-Methoxy-pyrimidin-5-yl)-benzothiazol-2-yl]-cyclobutyl}-methyl-propyl-amine

Example 85A

Trans-[3-(6-Bromo-benzothiazol-2-yl)-cyclobutyl]-methyl-propyl-amine

The title compound was prepared according to the procedure described in Example 43A, substituting N-methyl-N-propylamine for 4-piperidinemethanol. 1H NMR (400 MHz, CHLOROFORM-D) δ ppm 7.97 (d, J=1.84 Hz, 1H), 7.82 (d, J=8.90 Hz, 1H), 7.55 (dd, J=8.75, 1.99 Hz, 1H), 3.74-3.83 (m, 1H), 3.15-3.27 (m, 1H), 2.56 (t, J=7.06 Hz, 4H), 2.20-2.28 (m, 2H), 2.16 (s, 3H), 1.46-1.56 (m, 2H), 0.91 (t, J=7.36 Hz, 3H). MS: (M+H)$^+$=339/341.

Example 85B

Trans-{3-[6-(2-Methoxy-pyrimidin-5-yl)-benzothiazol-2-yl]-cyclobutyl}-methyl-propyl-amine The title compound was prepared according to the procedure described in Example 81A, substituting Example 85A for Example 1D, and substituting 2-methoxypyrimidine-5-boronic acid for pyrimidine-5-boronic acid. 1H NMR (400 MHz, CHLOROFORM-D) δ ppm 8.77 (s, 2H), 8.07 (d, J=8.59 Hz, 1H), 7.98 (d, J=1.84 Hz, 1H), 7.60 (dd, J=8.29, 1.84 Hz, 1H), 4.08 (s, 3H), 3.80-3.90 (m, 1H), 3.22-3.32 (m, 1H), 2.57-2.66 (m, 4H), 2.24-2.32 (m, 2H), 2.19 (s, 3H), 1.48-1.59 (m, 2H), 0.92 (t, J=7.36 Hz, 3H). MS: (M+H)$^+$=369.

Example 86

Trans-{3-[6-(2,6-Dimethyl-pyridin-3-yl)-benzothiazol-2-yl]-cyclobutyl}-methyl-propyl-amine The title compound was prepared according to the procedure described in Example 81A, substituting Example 85A for Example 1D, and substituting the product of Example 2A for pyrimidine-5-boronic acid. 1H NMR (500 MHz, CHLOROFORM-D) δ ppm 8.02 (d, J=8.54 Hz, 1H), 7.77 (d, J=1.22 Hz, 1H), 7.46 (d, J=7.93 Hz, 1H), 7.40 (dd, J=8.24, 1.83 Hz, 1H), 7.07 (d, J=7.63 Hz, 1H), 3.82-3.91 (m, 1H), 3.27-3.41 (m, 1H), 2.68-2.77 (m, 2H), 2.61-2.67 (m, 2H), 2.59 (s, 3H), 2.50 (s, 3H), 2.31-2.39 (m, 2H), 2.25 (s, 3H), 1.53-1.63 (m, 2H), 0.94 (t, J=7.32 Hz, 3H). (M+H)$^+$=366.

Example 87

Trans-Methyl-{3-[6-(1-methyl-1H-pyrazol-4-yl)-benzothiazol-2-yl]-cyclobutyl}-propyl-amine The title compound was prepared according to the procedure described in Example 81A, substituting Example 85A for Example 1D, and substituting 1-methyl-4-(4,4,5,5-tetramethyl-1,3,2-dioxaborolan-2-yl)-1H-pyrazole (Available from Boron Molecular) for pyrimidine-5-boronic acid. 1H NMR (400 MHz, CHLOROFORM-D) δ ppm 7.94 (d, J=8.59 Hz, 1H), 7.92 (d, J=1.23 Hz, 1H), 7.80 (s, 1H), 7.65 (s, 1H), 7.56 (dd, J=8.59, 1.84 Hz, 1H), 3.97 (s, 3H), 3.79-3.89 (m, 1H), 3.26-3.42 (m, 1H), 2.56-2.78 (m, 4H), 2.31-2.41 (m, 2H), 2.26 (s, 3H), 1.53-1.64 (m, 2H), 0.94 (t, J=7.36 Hz, 3H). (M+H)$^+$=341.

Example 88

Trans-2-(Ethyl-{3-[6-(2-methoxy-pyrimidin-5-yl)-benzothiazol-2-yl]-cyclobutyl}-amino)-ethanol Example 88A Trans-2-{[3-(6-Bromo-benzothiazol-2-yl)-cyclobutyl]-ethyl-amino}-ethanol The title compound was prepared according to the procedure described in Example 43A, substituting 2-(ethylamino) ethanol for 4-piperidinemethanol. 1H NMR (400 MHz, CHLOROFORM-D) δ ppm 7.98 (d, J=2.15 Hz, 1H), 7.83 (d, J=8.59 Hz, 1H), 7.56 (dd, J=8.75, 1.99 Hz, 1H), 3.72-3.80 (m, 1H), 3.62-3.71 (m, 1H), 3.58 (t, J=5.37 Hz, 2H), 2.53-2.68 (m, 8H), 1.03 (t, J=7.06 Hz, 3H). (M+H)$^+$=355/357.

Example 88B

Trans-2-(Ethyl-{3-[6-(2-methoxy-pyrimidin-5-yl)-benzothiazol-2-yl]-cyclobutyl}-amino)-ethanol The title compound was prepared according to the procedure described in Example 81A, substituting Example 88A for Example 1D, and substituting 2-methoxypyrimidine-5-boronic acid for pyrimidine-5-boronic acid. 1H NMR (400 MHz, CHLOROFORM-D) δ ppm 8.77 (s, 2H), 8.07 (d, J=8.29 Hz, 1H), 7.98 (d, J=1.53 Hz, 1H), 7.60 (dd, J=8.29, 1.84 Hz, 1H), 4.09 (s, 3H), 3.78-3.88 (m, 1H), 3.65-3.76 (m, 1H), 3.60 (t, J=5.52 Hz, 2H), 2.53-2.71 (m, 8H), 1.05 (t, J=7.21 Hz, 3H). MS: (M+H)$^+$=385.

Example 89

Trans-2-({3-[6-(2,6-Dimethyl-pyridin-3-yl)-benzothiazol-2-yl]-cyclobutyl}-ethyl-amino)-ethanol The title compound was prepared according to the procedure described in Example 81A, substituting Example 88A for Example 1D, and substituting the product of Example 2A for pyrimidine-5-boronic acid. 1H NMR (500 MHz, CHLOROFORM-D) δ ppm 8.02 (d, J=8.54 Hz, 1H), 7.77 (d, J=1.22 Hz, 1H), 7.46 (d, J=7.63 Hz, 1H), 7.41 (dd, J=8.24, 1.53 Hz, 1H), 7.07 (d, J=7.93 Hz, 1H), 3.78-3.90 (m, 2H), 3.71 (t, J=5.03 Hz, 2H), 2.79-2.88 (m, 4H), 2.75-2.79 (m, 2H), 2.65-2.71 (m, 2H), 2.59 (s, 3H), 2.50 (s, 3H), 1.14 (t, J=7.17 Hz, 3H). MS: (M+H)$^+$=382.

Example 90

6-Pyrimidin-5-yl-2-(3-pyrrolidin-1-ylmethyl-cyclobutyl)-benzothiazole

Example 90A

[3-(6-Bromo-benzothiazol-2-yl)-cyclobutyl]-methanol

The product of Example 1B (600.0 mg, 2.14 mmole) was dissolved in 4 ml of THF and cooled to 0° C. BH$_3$.THF (1 M in THF, 5.35 ml, 5.35 mmole) was added to it and the mixture was allowed to warm to room temperature and stirred for 2 hours. The mixture was cooled to 0° C., 30% H$_2$O$_2$ (2.5 ml) and 3M NaOH were successively added dropwise. The mixture was slowly warmed to room temperature and stirred for 5 hours. The mixture was quenched with brine, and extracted three times with dichloromethane. The combined organics were washed with sodium bisulfite and brine, dried over sodium sulfate, filtered and concentrated to the crude product, which was purified by chromatography (5% methanol in dichloromethane) to provide the title compound (268.9 mg, 42.1%). $^1$H NMR (300 MHz, CDCl$_3$) 7.98 (d, J=2.0 Hz, 1H) 7.83 (d, J=8.8 Hz, 1H) 7.56 (dd, J=8.7, 1.9 Hz, 1H) 3.79 (m, 2H) 3.66 (m, 1H) 2.55-2.70 (m, 3H) 2.42 (m, 1H) 2.26 (m, 1H). MS: (M+H)$^+$=298/300.

Example 90B

6-Bromo-2-(3-pyrrolidin-1-ylmethyl-cyclobutyl)-benzothiazole

The title compound was prepared according to the procedure described in Example 43A, except for substituting pyrrolidine for 4-piperidinemethanol and substituting Example 90A for Example 1D. $^1$H NMR (300 MHz, CDCl$_3$) δ ppm 7.98 (d, J=2.03 Hz, 1H) 7.82 (d, J=8.48 Hz, 1H) 7.56 (dd, J=8.48, 2.03 Hz, 1H) 3.81-3.94 (m, 3H) 3.25-3.35 (m, 3H) 2.76-2.92 (m, 4H) 2.09-2.57 (m, 6H). MS: (M+H)$^+$=351/353.

Example 90C

6-Pyrimidin-5-yl-2-(3-pyrrolidin-1-ylmethyl-cyclobutyl)-benzothiazole

The title compound was prepared according to the procedure described in Example 1F, except for substituting the product of Example 90B for the product of Example 1E. MS: (M+H)$^+$=351.

Example 91

Trans-5-(2,6-Dimethyl-pyridin-3-yl)-2-[3-(2-methyl-pyrrolidin-1-yl)-cyclobutyl]-benzothiazole

Example 91A

2-Amino-4-chloro-benzenethiol

The title compound was prepared according to the procedure described in Example 1A, substituting 5-chloro-2-benzothiazolinone for 6-bromo-2-benzothiazolinone. 1H NMR (300 MHz, CHLOROFORM-D) δ ppm 7.03 (d, J=8.48 Hz, 1H), 6.71 (d, J=2.03 Hz, 1H), 6.56 (dd, J=8.31, 2.20 Hz, 1H), 4.43 (br, 2H). MS: (M+H)$^+$=160, (M+H)$^+$=316 (dimmer).

Example 91B

5-Chloro-2-(3-methylene-cyclobutyl)-benzothiazole

The title compound was prepared according to the procedure described in Example 1B, substituting 91A for 1A (42% yield). 1H NMR (500 MHz, CHLOROFORM-D) δ ppm 7.96 (d, J=2.18 Hz, 1H), 7.75 (d, J=8.42 Hz, 1H), 7.33 (dd, J=8.58, 2.03 Hz, 1H), 4.88-4.95 (m, 1H), 4.76-4.82 (m, 1H), 3.90-4.00 (m, 1H), 3.14-3.30 (m, 2H), 2.90-3.12 (m, 2H). (M+H)$^+$=236.

Example 91C 3-(5-Chloro-benzothiazol-2-yl)-cyclobutanone

The title compound was prepared according to the procedure described in Example 1C, substituting 91B for 1B (46% yield). 1H NMR (500 MHz, CHLOROFORM-D) δ ppm 7.99 (d, J=1.87 Hz, 1H), 7.77 (d, J=8.42 Hz, 1H), 7.37 (dd, J=8.58, 2.03 Hz, 1H), 4.00-4.11 (m, 1H), 3.56-3.75 (m, 4H). (M+H)$^+$=238.

Example 91D

Cis-3-(5-chloro-benzothiazol-2-yl)-cyclobutanol

The title compound was prepared according to the procedure described in Example 1D, substituting 91C for 1C. Crude product was used in the next step without purification.

Example 91E

Trans-5-Chloro-2-[3-(2-methyl-pyrrolidin-1-yl)-cyclobutyl]-benzothiazole

The title compound was prepared according to the procedure described in Example 1E, substituting 91 D for 1 D. 1H NMR (500 MHz, CHLOROFORM-D) δ ppm 7.98 (d, J=1.83 Hz, 1H), 7.75 (d, J=8.54 Hz, 1H), 7.33 (dd, J=8.54, 2.14 Hz, 1H), 3.78-3.88 (m, 1H), 3.44-3.56 (m, 1H), 3.01-3.11 (m, 1H), 2.62-2.81 (m, 3H), 2.44-2.58 (m, 2H), 2.25-2.37 (m, 1H), 1.91-2.01 (m, 1H), 1.78-1.88 (m, 1H), 1.67-1.76 (m, 1H), 1.43-1.54 (m, 1H), 1.13 (d, J=5.80 Hz, 3H). (M+H)$^+$=307.

Example 91F

Trans-5-(2,6-Dimethyl-pyridin-3-yl)-2-[3-(2-methyl-pyrrolidin-1-yl)-cyclobutyl]-benzothiazole In a 4 ml vial, the product of Example 91E (30 mg, 0.098 mmole), potassium fluoride (19 mg, 0.323 mmole) and tris(dibenzylideneacetone)dipalladium (5.3 mg, 0.0075 mmole) were charged and dried on high vacuum for 30 min. The product of Example 2A (34 mg, 0.147 mmole) was added followed by dioxane (1 ml) under nitrogen atmosphere. Tri-t-butylphosphine (10 wt % in hexane, 45 ul, 0.0147 mmole) was added last and the vial was sealed and heated at 85° C. overnight then 95° C. for 7 h. TLC (TLC conditions: 1% ammonium hydroxide and 10% methanol in dichloromethane on silica gel) showed a new spot besides the starting material. The reaction mixture was quenched with water and extracted three times with dichloromethane. The combined organic layers were washed with brine, dried over sodium sulfate, filtered, and concentrated. The crude product was purified by column chromatography (eluted by 0.35% ammonium hydroxide and 3.5% methanol in dichloromethane) to give 6 mg (16% yield) of title compound. 1H NMR (300 MHz, CHLOROFORM-D) δ ppm 7.93 (d, J=1.36 Hz, 1H), 7.89 (d, J=8.14 Hz, 1H), 7.47 (d, J=7.80 Hz, 1H), 7.30 (dd, J=8.48, 1.70 Hz, 1H), 7.08 (d, J=7.80 Hz, 1H), 3.80-3.94 (m, 1H), 3.46-3.60 (m, 1H), 3.02-3.15 (m, 1H), 2.66-2.84 (m, 3H), 2.60-2.61 (s, 3H), 2.50-2.54 (s, 3H), 2.26-2.40 (m, 2H), 1.62-2.04 (m, 4H), 1.43-1.58 (m, 1H), 1.15 (d, J=5.76 Hz, 3H). (M+H)$^+$=378.

Example 92

Trans-5-(2,4-Dimethoxy-pyrimidin-5-yl)-2-[3-(2-methyl-pyrrolidin-1-yl)-cyclobutyl]-benzothiazole The title compound was prepared according to the procedure described in Example 91F, substituting 2,6-dimethoxy-5-pyrimidineboronic acid for Example 2A. 1H NMR (400 MHz, CHLOROFORM-D) δ ppm 8.34 (s, 1H), 8.13 (s, 1H), 7.89 (d, J=8.29 Hz, 1H), 7.48 (dd, J=8.29, 1.84 Hz, 1H), 4.06 (s, 3H), 4.05 (s, 3H), 3.81-3.92 (m, 1H), 3.46-3.61 (m, 1H), 2.99-3.17 (m, 1H), 2.63-2.86 (m, 3H), 2.48-2.62 (m, 2H), 2.27-2.41 (m, 1H), 1.45-2.03 (m, 4H), 1.14 (s, 3H). (M+H)$^+$=411.

Example 93

Trans-6-(1-Methyl-1H-pyrazol-4-yl)-2-[3-(2-methyl-pyrrolidin-1-yl)-cyclobutyl]-benzothiazole The title compound was prepared according to the procedure described in Example 51A-C, substituting Example 1E for Example 44A. 1H NMR (400 MHz, CHLOROFORM-D) d ppm 7.90-7.98 (m, 2H) 7.80 (s, 1H) 7.65 (s, 1H) 7.56 (dd, J=8.44, 1.69 Hz, 1H) 3.97 (s, 3H) 3.80-3.92 (m, 1H) 3.50-3.63 (m, 1H) 3.01-3.22 (m, 1H) 2.67-2.89 (m, 2H) 2.50-2.64 (m, 2H) 2.31-2.45 (m, 1H) 1.93-2.04 (m, 1H) 1.81-1.91 (m, 1H) 1.65-1.81 (m, 2H) 1.46-1.58 (m, 1H) 1.17 (d, J=4.60 Hz, 3H). $(M+H)^+=353$.

Example 94

Trans-2-[3-(4-Fluoro-piperidin-1-yl)-cyclobutyl]-6-(1-methyl-1H-pyrazol-4-yl benzothiazole The title compound was prepared according to the procedure described in Example 51A-C, substituting Example 78A for Example 44A. 1H NMR (400 MHz, CHLOROFORM-D) d ppm 7.88-7.98 (m, 2H) 7.80 (s, 1H) 7.65 (s, 1H) 7.56 (d, J=8.29 Hz, 1H) 4.60-4.80 (m, 1H) 3.97 (s, 3H) 3.76-3.89 (m, 1H) 3.11-3.24 (m, 1H) 2.44-2.65 (m, 5H) 2.25-2.39 (m, 2H) 1.80-2.04 (m, 3H) 1.52-1.62 (m, 2H). $(M+H)^+=371$.

Example 95

Trans-2-(3-azetidin-1-ylcyclobutyl)-6-(2-methoxy-pyrimidin-5-yl)-1,3-benzothiazole The title compound was prepared according to the procedure described in Example 1F, except for substituting the product of Example 61A for the product of Example 1E, and substituting 2-methoxypyrimidine-5-boronic acid (Frontier Scientific, Inc., Logan, Utah, USA) for pyrimidine-5-boronic acid. 1H NMR (300 MHz, $CDCl_3$) δ ppm 8.77 (s, 2H) 8.07 (d, J=8.48 Hz, 1H) 7.97 (d, J=2.03 Hz, 1H) 7.59 (dd, J=8.48, 2.03 Hz, 1H) 4.08 (s, 3H) 3.93-4.06 (m, 1H) 3.18-3.34 (m, 5 H) 2.49-2.61 (m, 1H) 2.34-2.47 (m, 3H) 2.03-2.19 (m, 2H). MS: $(M+H)^+=353$.

Example 96

Trans-2-(3-azetidin-1-ylcyclobutyl)-6-(2,6-dimethylpyridin-3-yl)-1,3-benzothiazole The title compound was prepared according to the procedure described in Example 1F, except for substituting the product of Example 61A for the product of Example 1E, and substituting Example 2A (2,6-dimethyl-3-(4,4,5,5-tetramethyl-[1,3,2]dioxaborolan-2-yl)-pyridine) for pyrimidine-5-boronic acid. $^1$H NMR (300 MHz, $CDCl_3$) δ ppm 8.01 (d, J=8.48 Hz, 1H) 7.75 (d, J=1.36 Hz, 1H) 7.45 (d, J=7.80 Hz, 1H) 7.39 (dd, J=8.48, 1.70 Hz, 1H) 7.06 (d, J=7.80 Hz, 1H) 3.96-4.08 (m, 1H) 3.19-3.40 (m, 5H) 2.59 (s, 3H) 2.49 (s, 3H) 2.37-2.56 (m, 4H) 2.07-2.19 (m, 2H). MS: $(M+H)^+=350$.

Example 97

Trans-2-(3-azetidin-1-ylcyclobutyl)-6-(1-methyl-1H-pyrazol-4-yl)-1,3-benzothiazole The title compound was prepared according to the procedure described in Example 1F, except for substituting the product of Example 61A for the product of Example 1E, and substituting 1-methyl-1H-pyrazoleboronic acid pinacol ester for pyrimidine-5-boronic acid. $^1$H NMR (300 MHz, $CDCl_3$) δ ppm 7.89-7.97 (m, 2H) 7.80 (s, 1H) 7.65 (s, 1H) 7.55 (dd, J=8.31, 1.86 Hz, 1H) 3.97 (s, 3H) 3.92-4.07 (m, 1H) 3.21-3.45 (m, 5H) 2.36-2.62 (m, 4H) 2.06-2.24 (m, 2H). MS: $(M+H)^+=325$.

Example 98

Trans-2-(3-azepan-1-ylcyclobutyl)-6-(2-methoxypyrimidin-5-yl)-1,3-benzothiazole

The title compound was prepared according to the procedure described in Example 1F, except for substituting the product of Example 71A for the product of Example 1E, and substituting 2-methoxypyrimidine-5-boronic acid (Frontier Scientific, Inc., Logan, Utah, USA) for pyrimidine-5-boronic acid. $^1$H NMR (500 MHz, $CDCl_3$) δ ppm 8.78 (s, 2H) 8.07 (d, J=8.24 Hz, 1H) 7.98 (d, J=1.83 Hz, 1H) 7.59 (dd, J=8.39, 1.68 Hz, 1H) 4.09 (s, 3H) 3.78-3.86 (m, 1H) 3.33-3.44 (m, 1H) 2.45-2.65 (m, 8H) 1.58-1.75 (m, 8H). MS: $(M+H)^+=395$.

Example 99

Trans-2-(3-azepan-1-ylcyclobutyl)-6-(2,6-dimethylpyridin-3-yl)-1,3-benzothiazole The title compound was prepared according to the procedure described in Example 1F, except for substituting the product of Example 71A for the product of Example 1E, and substituting Example 2A (2,6-dimethyl-3-(4,4,5,5-tetramethyl-[1,3,2]dioxaborolan-2-yl)-pyridine) for pyrimidine-5-boronic acid. $^1$H NMR (500 MHz, $CDCl_3$) δ ppm 8.02 (d, J=8.54 Hz, 1H) 7.76 (d, J=1.53 Hz, 1H) 7.46 (d, J=7.63 Hz, 1H) 7.39 (dd, J=8.24, 1.83 Hz, 1H) 7.07 (d, J=7.63 Hz, 1H) 3.78-3.86 (m, 1H) 3.32-3.43 (m, 1H) 2.59 (s, 6H) 2.45-2.56 (m, 8H) 1.58-1.73 (m, 8H). MS: $(M+H)^+=392$.

Example 100

Trans-2-(3-azepan-1-ylcyclobutyl)-6-(1-methyl-1H-pyrazol-4-yl)-1,3-benzothiazole The title compound was prepared according to the procedure described in Example 1F, except for substituting the product of Example 71A for the product of Example 1E, and substituting 1-methyl-4-1H-pyrazoleboronic acid pinacol ester for pyrimidine-5-boronic acid. $^1$H NMR (500 MHz, $CDCl_3$) δ ppm 7.89-7.97 (m, 2H) 7.80 (s, 1H) 7.65 (s, 1H) 7.55 (dd, J=8.39, 1.68 Hz, 1H) 3.97 (s, 3H) 3.74-3.83 (m, 1H) 3.30-3.41 (m, 1H) 2.46-2.61 (m, 8H) 1.56-1.71 (m, 8H). MS: $(M+H)^+=367$.

Example 101

Cis-N-[2-(3-Piperidin-1-yl-cyclobutyl)-benzothiazol-6-yl]-acetamide

Example 101A

Cis-2-(3-Piperidin-1-yl-cyclobutyl)-benzothiazole-6-ylamine

The product of Example 44A (trans-6-bromo-2-(3-piperidin-1-ylcyclobutyl)-1,3-benzothiazole) (658 mg, 1.875 mmole), tris(dibenzylideneacetone)dipalladium (0) (34 mg, 0.037 mmole), racemic-2,2'-bis(diphenylphosphino)-1,1'-binaphthyl (BINAP, 70 mg, 0.113 mmole) and sodium tert-butoxide (249 mg, 2.62 mmole) were charged in a tube and sealed. The system was vacuumed for 2 hours and refilled with nitrogen. Toluene (10 mL) was added followed by benzophenone imine (409 mg, 377 µl, 2.25 mmole). The sealed tube was heated in an oil bath (temp 95° C.) for 18 hours. TLC (TLC conditions: 0.5% ammonium hydroxide and 5% methanol in dichloromethane on silica gel) confirmed the completion of the reaction with two new spots. The reaction was quenched with water and the mixture was extracted three times with dichloromethane. The organic layers were dried (over $Na_2SO_4$), filtered and concentrated under reduced pressure to give the crude product as the benzophenone imine. The crude product was dissolved in tetrahydrofuran (10 mL) and 2N HCl (4 mL). The mixture was stirred at room temperature for 2 hours. TLC (TLC conditions: 0.5% ammonium hydroxide and 5% methanol in dichloromethane on silica gel) indicated complete conversion of the starting material (imine) to two new products. The mixture was basified with 2N NaOH (6 mL) and extracted three times with dichloromethane. The organic layers were dried (over $Na_2SO_4$), filtered and concentrated under reduced pressure to give the crude product. The crude product was purified by column chromatography (0.4% ammonium hydroxide and 4% methanol in dichloromethane). The product with a Rf value of 0.3 (TLC conditions: 0.5% ammonium hydroxide and 5% methanol in dichloromethane on silica gel) corresponded to the cis-product (270 mg). $^1$H NMR (300 MHz, $CDCl_3$) δ ppm 7.71 (d, J=8.82 Hz, 1H) 7.08 (d, J=2.03 Hz, 1H) 6.79 (dd, J=8.82, 2.37 Hz, 1H) 3.75 (s, 2H) 3.42-3.57 (m, 1H) 2.68-2.82 (m, 1H) 2.55-2.69 (m, 2H) 2.16-2.39 (m, 6H) 1.52-1.65 (m, 4H) 1.39-1.51 (m, 2H). MS: $(M+H)^+$=288.

Example 101B

Trans-2-(3-Piperidin-1-yl-cyclobutyl)-benzothiazole-6-ylamine

In the above preparation, the product with a Rf value of 0.2 (TLC conditions: 0.5% ammonium hydroxide and 5% methanol in dichloromethane on silica gel) corresponded to the trans-isomer (100 mg). $^1$H NMR (300 MHz, $CDCl_3$) δ ppm 7.74 (d, J=8.82 Hz, 1H) 7.09 (d, J=2.37 Hz, 1H) 6.80 (dd, J=8.65, 2.20 Hz, 1H) 3.67-3.83 (m, 3H) 2.99-3.15 (m, 1H) 2.46-2.60 (m, 4H) 2.21-2.38 (m, 4H) 1.53-1.68 (m, 4H) 1.39-1.51 (m, 2H). MS: $(M+H)^+$=288.

Example 101C

Cis-N-[2-(3-Piperidin-1-yl-cyclobutyl)-benzothiazole-6-yl]-acetamide

The product of Example 101A (20 mg, 0.070 mmole) was dissolved in anhydrous dichloromethane (1.5 mL). To the solution was added triethylamine (35.6 mg, 49 μL, 0.35 mmole) and acetyl chloride (10 μL, 0.14 mmole). The mixture was stirred at room temperature overnight then diluted with water. The aqueous layer was extracted three times with dichloromethane and the combined organic layers were concentrated to give the crude product. The crude product was purified by column chromatography (0.5% ammonium hydroxide and 5% methanol in dichloromethane) to give the title compound. $^1$H NMR (500 MHz, $CDCl_3$) δ ppm 8.39 (d, J=2.14 Hz, 1H) 7.84 (d, J=8.54 Hz, 1H) 7.37 (s, 1H) 7.22 (dd, J=8.85, 2.14 Hz, 1H) 3.48-3.59 (m, 1H) 2.72-2.83 (m, 1H) 2.60-2.70 (m, 2H) 2.24-2.39 (m, 6H) 2.21 (s, 3H) 1.54-1.64 (m, 4H) 1.40-1.51 (m, 2H). MS: $(M+H)^+$=330.

Example 102

Cis-2-Chloro-N-[2-(3-Piperidin-1-yl-cyclobutyl)-benzothiazole-6-yl]-acetamide

The title compound was prepared according to the procedure described in Example 101C, except for substituting chloroacetyl chloride for acetyl chloride. $^1$H NMR (500 MHz, $CDCl_3$) δ ppm 8.38 (d, J=1.83 Hz, 1H) 8.36 (s, 1H) 7.90 (d, J=8.85 Hz, 1H) 7.35 (dd, J=8.85, 2.14 Hz, 1H) 4.23 (s, 2H) 3.49-3.61 (m, 1H) 2.74-2.84 (m, 1H) 2.61-2.72 (m, 2H) 2.20-2.41 (m, 6H) 1.54-1.63 (m, 4H) 1.40-1.52 (m, 2H). MS: $(M+H)^+$=364.

Example 103

Cis-N-[2-(3-Piperidin-1-yl-cyclobutyl)-benzothiazole-6-yl]-propionamide

The title compound was prepared according to the procedure described in Example 101C, except for substituting propionyl chloride for acetyl chloride. $^1$H NMR (500 MHz, $CDCl_3$) δ ppm 8.43 (s, 1H) 7.84 (d, J=8.54 Hz, 1H) 7.30 (d, 1H) 7.23 (dd, J=8.54, 2.14 Hz, 1H) 3.48-3.60 (m, 1H) 2.72-2.84 (m, 1H) 2.61-2.70 (m, 2H) 2.43 (q, J=7.53 Hz, 2H) 2.22-2.38 (m, 6H) 1.54-1.64 (m, 4H) 1.39-1.51 (m, 2H) 1.27 (t, J=7.63 Hz, 3H). MS: $(M+H)^+$=344.

Example 104

Cis-N-[2-(3-Piperidin-1-yl-cyclobutyl)-benzothiazole-6-yl]-isobutyramide

The title compound was prepared according to the procedure described in Example 101C, except for substituting isobutyryl chloride for acetyl chloride. $^1$H NMR (500 MHz, $CDCl_3$) δ ppm 8.46 (d, J=1.83 Hz, 1H) 7.85 (d, J=8.54 Hz, 1H) 7.29 (s, 1H) 7.23 (dd, J=8.85, 2.14 Hz, 1H) 3.48-3.58 (m, 1H) 2.71-2.82 (m, 1H) 2.61-2.70 (m, 2H) 2.48-2.59 (m, 1H) 2.22-2.39 (m, 6H) 1.54-1.64 (m, 4H) 1.39-1.51 (m, 2H) 1.28 (d, J=7.02 Hz, 6H). MS: $(M+H)^+$=358.

Example 105

Cis-Cyclopropanecarboxylic acid[2-(3-Piperidin-1-yl-cyclobutyl)-benzothiazole-6-yl]-amide The title compound was prepared according to the procedure described in Example 101C, except for substituting cyclopropane carbonyl chloride for acetyl chloride. 1H NMR (500 MHz, $CDCl_3$) δ ppm 8.42 (s, 1H) 7.84 (d, J=8.54 Hz, 1H) 7.56 (s, 1H) 7.24 (dd, J=8.70, 1.98 Hz, 1H) 3.48-3.58 (m, 1H) 2.73-2.81 (m, 1H) 2.60-2.70 (m, 2H) 2.23-2.39 (m, 6H) 1.56-1.64 (m, 4H) 1.49-1.56 (m, 1H) 1.40-1.49 (m, 2H) 1.08-1.15 (m, 2H) 0.83-0.91 (m, 2H). MS: $(M+H)^+$=356.

Example 106

Cis-Cyclobutanecarboxylic acid[2-(3-Piperidin-1-yl-cyclobutyl)-benzothiazole-6-yl]-amide The title compound was prepared according to the procedure described in Example 101C, except for substituting cyclobutane carbonyl chloride for acetyl chloride. $^1$H NMR (500 MHz, $CDCl_3$) δ ppm 8.46 (d, J=2.14 Hz, 1H) 7.84 (d, J=8.85 Hz, 1H) 7.22 (dd, J=8.54, 2.14 Hz, 1H) 7.15 (s, 1H) 3.48-3.60 (m, 1H) 3.13-3.23 (m, 1H) 2.72-2.83 (m, 1H) 2.61-2.70 (m, 2H) 2.37-2.46 (m, 2H) 2.19-2.36 (m, 8H) 1.89-2.09 (m, 2H) 1.54-1.64 (m, 4H) 1.40-1.50 (m, J=4.88 Hz, 2H). MS: $(M+H)^+$=370.

Example 107

Cis-Cyclopentanecarboxylic acid[2-(3-Piperidin-1-yl-cyclobutyl)-benzothiazole-6-yl]-amide The title compound was prepared according to the procedure described in Example 101C, except for substituting cyclopentane carbonyl chloride for acetyl chloride. $^1$H NMR (500 MHz, CDCl$_3$) δ ppm 8.46 (d, J=2.14 Hz, 1H) 7.84 (d, J=8.54 Hz, 1H) 7.32 (s, 1H) 7.22 (dd, J=8.85, 2.14 Hz, 1H) 3.48-3.60 (m, 1H) 2.61-2.83 (m, 4H) 2.22-2.40 (m, 6H) 1.87-2.01 (m, 4H) 1.78-1.86 (m, 2H) 1.55-1.68 (m, 6H) 1.40-1.50 (m, 2H). MS: (M+H)$^+$=384.

Example 108

Cis-Cyclohexanecarboxylic acid[2-(3-Piperidin-1-yl-cyclobutyl)-benzothiazole-6-yl]-amide The title compound was prepared according to the procedure described in Example 101C, except for substituting cyclohexane carbonyl chloride for acetyl chloride. $^1$H NMR (500 MHz, CDCl$_3$) δ ppm 8.46 (d, J=1.83 Hz, 1H) 7.84 (d, J=8.85 Hz, 1H) 7.30 (s, 1H) 7.22 (dd, J=8.54, 2.14 Hz, 1H) 3.47-3.59 (m, 1H) 2.72-2.81 (m, 1H) 2.61-2.70 (m, 2H) 2.21-2.40 (m, 6H) 1.93-2.02 (m, 2H) 1.82-1.90 (m, 2H) 1.67-1.74 (m, 1H) 1.52-1.64 (m, 6H) 1.40-1.50 (m, 2H) 1.21-1.40 (m, 4H). MS: (M+H)$^+$=384.

Example 109

Cis-Furan-2-carboxylic acid[2-(3-Piperidin-1-yl-cyclobutyl)-benzothiazole-6-yl]-amide The title compound was prepared according to the procedure described in Example 101C, except for substituting 2-furoyl chloride for acetyl chloride. $^1$H NMR (500 MHz, CDCl$_3$) δ ppm 8.53 (d, J=2.14 Hz, 1H) 8.19 (s, 1H) 7.90 (d, J=8.54 Hz, 1H) 7.54 (s, 1H) 7.40 (dd, J=8.70, 2.29 Hz, 1H) 7.24-7.31 (m, 1H) 6.58 (dd, J=3.51, 1.68 Hz, 1H) 3.50-3.62 (m, 1H) 2.74-2.83 (m, 1H) 2.61-2.71 (m, 2H) 2.24-2.41 (m, 6H) 1.55-1.64 (m, 4H) 1.41-1.51 (m, 2H). MS: (M+H)$^+$=382.

Example 110

Cis-4-Cyano-N-[2-(3-Piperidin-1-yl-cyclobutyl)-benzothiazole-6-yl]-benzamide

The title compound was prepared according to the procedure described in Example 101C, except for substituting 4-cyanobenzoyl chloride for acetyl chloride. $^1$H NMR (400 MHz, CDCl$_3$) δ ppm 8.50 (d, J=2.15 Hz, 1H) 7.96-8.02 (m, 3H) 7.92 (d, J=8.59 Hz, 1H) 7.81 (d, J=8.59 Hz, 2H) 7.39 (dd, J=8.75, 2.30 Hz, 1H) 3.49-3.62 (m, 1H) 2.73-2.85 (m, 1H) 2.62-2.73 (m, 2H) 2.24-2.38 (m, 6H) 1.54-1.64 (m, 4H) 1.41-1.51 (m, 2H). MS: (M+H)$^+$=417.

Example 111

Cis-4-Cyano-N-[2-(3-Piperidin-1-yl-cyclobutyl)-benzothiazole-6-yl]-benzenesulfonamide The title compound was prepared according to the procedure described in Example 101C, except for substituting 4-cyanobenzenesulfonyl chloride for acetyl chloride. $^1$H NMR (500 MHz, CDCl$_3$) δ ppm 8.07 (d, J=8.54 Hz, 2H) 7.94 (d, J=8.54 Hz, 1H) 7.87-7.91 (m, 3H) 7.51 (d, J=2.14 Hz, 1H) 7.02 (dd, J=8.54, 2.14 Hz, 1H) 3.57-3.64 (m, 1H) 2.76-2.86 (m, 1H) 2.64-2.75 (m, 2H) 2.24-2.41 (m, 6H) 1.56-1.65 (m, 4H) 1.41-1.51 (m, 2H). MS: (M+H)$^+$=453.

Example 112

Cis-Thiophene-2-sulfonic acid-[2-(3-Piperidin-1-yl-cyclobutyl)-benzothiazole-6-yl]-amide The title compound was prepared according to the procedure described in Example 101C, except for substituting thiophene-2-sulfonyl chloride for acetyl chloride. $^1$H NMR (500 MHz, CDCl$_3$) δ ppm 7.91 (d, J=8.85 Hz, 1H) 7.79 (dd, J=3.97, 1.22 Hz, 1H) 7.75 (dd, J=5.03, 1.37 Hz, 1H) 7.63 (d, J=2.14 Hz, 1H) 7.16 (dd, J=5.03, 3.81 Hz, 2H) 7.12 (dd, J=8.54, 2.14 Hz, 1H) 3.53-3.64 (m, 1H) 2.75-2.83 (m, 1H) 2.62-2.73 (m, 2H) 2.23-2.39 (m, 6H) 1.55-1.63 (m, 4H) 1.40-1.51 (m, 2H). MS: (M+H)$^+$=434.

Example 113

Cis-Thiophene-2-carboxylic acid-[2-(3-Piperidin-1-yl-cyclobutyl)-benzothiazole-6-yl]-amide The title compound was prepared according to the procedure described in Example 101C, except for substituting 2-thiophene carbonyl chloride for acetyl chloride. $^1$H NMR (500 MHz, CDCl$_3$) δ ppm 8.49 (d, J=2.14 Hz, 1H) 7.90 (d, J=8.54 Hz, 1H) 7.81 (s, 1H) 7.63-7.69 (m, 1H) 7.55-7.59 (m, 1H) 7.37 (dd, J=8.54, 2.14 Hz, 1H) 7.15 (dd, J=5.03, 3.81 Hz, 1H) 3.50-3.60 (m, 1H) 2.73-2.83 (m, 1H) 2.61-2.72 (m, 2H) 2.23-2.39 (m, 6H) 1.55-1.63 (m, 4H) 1.41-1.50 (m, 2H). MS: (M+H)$^+$=398.

Example 114

Cis-Thiophene-2-carboxylic acid-[2-(3-Piperidin-1-yl-cyclobutyl)-benzothiazole-6-yl]-amide The title compound was prepared according to the procedure described in Example 101C, except for substituting 2-thiophene acetyl chloride for acetyl chloride. $^1$H NMR (500 MHz, CDCl$_3$) δ ppm 8.33 (d, J=1.83 Hz, 1H) 7.82 (d, J=8.54 Hz, 1H) 7.44 (s, 1H) 7.33 (dd, J=4.58, 1.83 Hz, 1H) 7.15 (dd, J=8.54, 2.14 Hz, 1H) 7.01-7.09 (m, 2H) 3.98 (s, 2H) 3.47-3.58 (m, 1H) 2.71-2.82 (m, 1H) 2.64 (m, 2H) 2.21-2.38 (m, 6H) 1.52-1.65 (m, 4H) 1.45 (s, 2H). MS: (M+H)$^+$=412.

Example 115

Cis-[2-(3-Piperidin-1-yl-cyclobutyl)-benzothiazole-6-yl]-carbamic acid isobutyl ester The title compound was prepared according to the procedure described in Example 101C, except for substituting isobutylchloroformate for acetyl chloride. $^1$H NMR (500 MHz, CDCl$_3$) δ ppm 8.18 (s, 1H) 7.84 (d, J=8.54 Hz, 1H) 7.19 (dd, J=8.85, 2.14 Hz, 1H) 6.72 (s, 1H) 3.98 (d, J=6.71 Hz, 2H) 3.48-3.59 (m, 1H) 2.72-2.82 (m, 1H) 2.61-2.70 (m, 2H) 2.22-2.38 (m, 6H) 1.94-2.05 (m, 1H) 1.54-1.64 (m, 4H) 1.41-1.51 (m, 2H) 0.98 (d, J=6.71 Hz, 6H). MS: (M+H)$^+$=388.

Example 116

Cis-Morpholine-4-carboxylic acid-[2-(3-Piperidin-1-yl-cyclobutyl)-benzothiazole-6-yl]-amide The title compound was prepared according to the procedure described in Example 101C, except for substituting 4-morpholine carbonyl chloride for acetyl chloride. $^1$H NMR (500 MHz, CDCl$_3$) δ ppm 8.15 (d, J=2.14 Hz, 1H) 7.82 (d, J=8.85 Hz, 1H) 7.17 (dd, J=8.85, 2.14 Hz, 1H) 6.51 (s, 1H) 3.72-3.79 (m, 4H) 3.49-3.53 (m, 4H) 3.36-3.44 (m, 1H) 2.72-2.80 (m, 1H) 2.60-2.69 (m, 2H) 2.20-2.39 (m, 6H) 1.54-1.62 (m, 4H) 1.39-1.51 (m, 2H). MS: (M+H)$^+$=401.

Example 117

Cis-Pyrazine-2-carboxylic acid-[2-(3-Piperidin-1-yl-cyclobutyl)-benzothiazole-6-yl]-amide The product of Example 101A (59 mg, 0.206 mmole) was dissolved in anhydrous dichloromethane (2.0 mL). To the solution was added 2-pyrazine carboxylic acid (51 mg, 0.412 mmole), 1-[3-(dimethylamino)propyl]-3-ethylcarbodiimide hydrochloride (79 mg, 0.412 mmole) and 1-hydroxybenzotriazole hydrate (28 mg, 0.206 mmole). The mixture was stirred at room temperature overnight then diluted with water. The pH of the mixture was was adjusted to pH 9 with 1 N NaOH and extracted three times with dichloromethane. The combined organic layers were concentrated to give the crude product. The crude product was purified by column chromatography (0.6% ammonium hydroxide and 6% methanol in dichloromethane) to provide the title compound. $^1$H NMR (500 MHz, CDCl$_3$) δ ppm 9.81 (s, 1H) 9.54 (d, J=1.53 Hz, 1H) 8.83 (d, J=2.44 Hz, 1H) 8.66 (d, J=2.14 Hz, 1H) 8.58-8.63 (m, 1H) 7.94 (d, J=8.85 Hz, 1H) 7.52 (dd, J=8.85, 2.14 Hz, 1H) 3.52-3.62 (m, 1H) 2.74-2.84 (m, 1H) 2.61-2.72 (m, 2H) 2.24-2.41 (m, 6H) 1.55-1.64 (m, 4H) 1.40-1.52 (m, 2H). MS: (M+H)$^+$=394.

Example 118

Cis-N-[2-(3-Piperidin-1-yl-cyclobutyl)-benzothiazole-6-yl]-2-thiophen-3-yl-acetamide The title compound was prepared according to the procedure described in Example 117, except for substituting 3-thiopheneacetic acid for 2-pyrazine carboxylic acid. $^1$H NMR (500 MHz, CDCl$_3$) δ ppm 8.34 (d, J=2.14 Hz, 1H) 7.81 (d, J=8.54 Hz, 1H) 7.42 (dd, J=4.88, 3.05 Hz, 1H) 7.26-7.32 (m, 1H) 7.13 (dd, J=8.70, 2.29 Hz, 1H) 7.10 (d, J=4.88 Hz, 1H) 3.81 (s, 2H) 3.47-3.57 (m, 1H) 2.73-2.81 (m, 1H) 2.61-2.69 (m, 2H) 2.23-2.40 (m, 6H) 1.54-1.63 (m, 4H) 1.40-1.50 (m, 2H). MS: (M+H)$^+$=412.

Example 119

Cis-N-[2-(3-Piperidin-1-yl-cyclobutyl)-benzothiazole-6-yl]-3-thiophen-2-yl-propionamide The title compound was prepared according to the procedure described in Example 117, except for substituting 3-(2-thienyl)propanoic acid for 2-pyrazine carboxylic acid. $^1$H NMR (500 MHz, CDCl$_3$) δ ppm 8.37 (d, J=1.83 Hz, 1H) 7.83 (d, J=8.54 Hz, 1H) 7.23 (s, 1H) 7.11-7.19 (m, 2H) 6.93 (dd, J=5.03, 3.51 Hz, 1H) 6.88 (d, J=2.75 Hz, 1H) 3.47-3.59 (m, 1H) 3.30 (t, J=7.32 Hz, 2H) 2.71-2.82 (m, 3H) 2.60-2.70 (m, 2H) 2.22-2.40 (m, 6H) 1.54-1.65 (m, 4H) 1.40-1.50 (m, 2H). MS: (M+H)$^+$=426.

Example 120

Cis-3-Furan-2-yl-N-[2-(3-Piperidin-1-yl-cyclobutyl)-benzothiazole-6-yl]-propionamide The title compound was prepared according to the procedure described in Example 117, except for substituting 3-(2-furyl)propanoic acid for 2-pyrazine carboxylic acid. $^1$H NMR (500 MHz, CDCl$_3$) δ ppm 8.38 (d, J=1.53 Hz, 1H) 7.83 (d, J=8.54 Hz, 1H) 7.34 (s, 1H) 7.25-7.30 (m, 1H) 7.16 (dd, J=8.54, 2.14 Hz, 1H) 6.27-6.34 (m, 1H) 6.09 (d, J=2.75 Hz, 1H) 3.47-3.59 (m, 1H) 3.10 (t, J=7.32 Hz, 2H) 2.70-2.83 (m, 3H) 2.60-2.69 (m, 2H) 2.22-2.40 (m, 6H) 1.54-1.65 (m, 4H) 1.40-1.51 (m, 2H). MS: (M+H)$^+$=410.

Example 121

Cis-Pyrimidine-5-carboxylic acid-[2-(3-Piperidin-1-yl-cyclobutyl)-benzothiazole-6-yl]-amide The title compound was prepared according to the procedure described in Example 117, except for substituting 5-pyrimidinecarboxylic acid for 2-pyrazine carboxylic acid. $^1$H NMR (500 MHz, CDCl$_3$) δ ppm 9.39 (s, 1H) 9.25 (s, 2H) 8.49 (s, 1H) 7.99-8.07 (m, 1H) 7.93 (d, J=8.85 Hz, 1H) 7.41 (dd, J=8.85, 2.14 Hz, 1H) 3.52-3.63 (m, 1H) 2.73-2.84 (m, 1H) 2.63-2.73 (m, 2H) 2.22-2.42 (m, 6H) 1.54-1.64 (m, 4H) 1.41-1.51 (m, 2H). MS: (M+H)$^+$=394.

Example 122

Trans-4-Cyano-N-[2-(3-Piperidin-1-yl-cyclobutyl)-benzothiazole-6-yl]-benzamide

The title compound was prepared according to the procedure described in Example 101C, except for substituting Example 101B for Example 101A and substituting 4-cyanobenzoyl chloride for acetyl chloride. $^1$H NMR (400 MHz, CDCl$_3$) δ ppm 8.51 (s, 1H) 8.00 (d, J=8.59 Hz, 2H) 7.91-7.98 (m, 2H) 7.78-7.84 (m, 2H) 7.40 (dd, J=8.90, 2.15 Hz, 1H) 3.76-3.88 (m, 1H) 3.05-3.16 (m, 1H) 2.49-2.61 (m, 4H) 2.23-2.37 (m, 4H) 1.54-1.66 (m, 4H) 1.40-1.53 (m, 2H). MS: (M+H)$^+$=417.

Example 123

Trans-N-[2-(3-Piperidin-1-yl-cyclobutyl)-benzothiazole-6-yl]-Propionamide

The title compound was prepared according to the procedure described in Example 101C, except for substituting Example 101B for Example 101A and substituting propionyl chloride for acetyl chloride. $^1$H NMR (500 MHz, CDCl$_3$) δ ppm 8.44 (d, J=1.53 Hz, 1H) 7.87 (d, J=8.85 Hz, 1H) 7.21-7.33 (m, 2H) 3.74-3.85 (m, 1H) 3.03-3.16 (m, 1H) 2.49-2.62 (m, 4H) 2.44 (q, J=7.63 Hz, 2H) 2.21-2.38 (m, 4H) 1.56-1.63 (m, 4H) 1.41-1.52 (m, 2H) 1.28 (t, J=7.63 Hz, 3H). MS: (M+H)$^+$=344.

Example 124

Trans-N-[2-(3-Piperidin-1-yl-cyclobutyl)-benzothiazole-6-yl]-isobutyramide

The title compound was prepared according to the procedure described in Example 101C, except for substituting Example 101B for Example 101A and substituting isobutyryl chloride for acetyl chloride. ¹H NMR (500 MHz, CDCl$_3$) δ ppm 8.46 (d, J=1.83 Hz, 1H) 7.87 (d, J=8.85 Hz, 1H) 7.29 (s, 1H) 7.24-7.26 (m, 1H) 3.77-3.85 (m, 1H) 3.04-3.14 (m, 1H) 2.49-2.61 (m, 5H) 2.22-2.37 (m, 4H) 1.56-1.64 (m, 4H) 1.42-1.52 (m, 2H) 1.29 (d, J=6.71 Hz, 6H). MS: (M+H)$^+$=358.

Example 125

Trans-[2-(3-Piperidin-1-yl-cyclobutyl)-benzothiazole-6-yl]-carbamic acid isobutyl ester The title compound was prepared according to the procedure described in Example 101C, except for substituting Example 101B for Example 101A and substituting isobutyl-chloroformate for acetyl chloride. ¹H NMR (500 MHz, CDCl$_3$) δ ppm 8.18 (s, 1H) 7.87 (d, J=8.54 Hz, 1H) 7.21 (dd, J=8.85, 2.14 Hz, 1H) 6.73 (s, 1H) 3.98 (d, J=6.41 Hz, 2H) 3.74-3.84 (m, 1H) 3.04-3.13 (m, 1H) 2.48-2.60 (m, 4H) 2.19-2.38 (m, 4H) 1.95-2.07 (m, 1H) 1.55-1.68 (m, 4H) 1.42-1.51 (m, 2H) 0.98 (d, J=6.71 Hz, 6H). MS: (M+H)$^+$=388.

Example 126

Trans-Cyclopropanecarboxylic acid[2-(3-Piperidin-1-yl-cyclobutyl)-benzothiazole-6-yl]-amide The title compound was prepared according to the procedure described in Example 101C, except for substituting Example 101B for Example 101A and substituting cyclopropane carbonyl chloride for acetyl chloride. ¹H NMR (500 MHz, CDCl$_3$) δ ppm 8.42 (s, 1H) 7.87 (d, J=8.85 Hz, 1H) 7.52 (s, 1H) 7.22-7.30 (m, 1H) 3.74-3.85 (m, 1H) 3.03-3.15 (m, 1H) 2.49-2.61 (m, 4H) 2.19-2.39 (m, 4H) 1.57-1.64 (m, 4H) 1.50-1.57 (m, 1H) 1.41-1.48 (m, 2H) 1.08-1.15 (m, 2H) 0.82-0.94 (m, 2H). MS: (M+H)$^+$=356.

Example 127

Trans-Cyclobutanecarboxylic acid[2-(3-Piperidin-1-yl-cyclobutyl)-benzothiazole-6-yl]-amide The title compound was prepared according to the procedure described in Example 101C, except for substituting Example 101B for Example 101A and substituting cyclobutane carbonyl chloride for acetyl chloride. ¹H NMR (500 MHz, CDCl$_3$) δ ppm 8.46 (d, J=1.83 Hz, 1H) 7.87 (d, J=8.85 Hz, 1H) 7.24 (dd, J=8.85, 2.14 Hz, 1H) 7.16 (s, 1H) 3.75-3.84 (m, 1H) 3.14-3.23 (m, 1H) 3.04-3.14 (m, 1H) 2.50-2.61 (m, 4H) 2.37-2.47 (m, 2H) 2.21-2.37 (m, 6H) 1.91-2.08 (m, 2H) 1.56-1.64 (m, 4H) 1.42-1.51 (m, 2H). MS: (M+H)$^+$=370.

Example 128

Trans-Cyclopentanecarboxylic acid[2-(3-Piperidin-1-yl-cyclobutyl)-benzothiazole-6-yl]-amide The title compound was prepared according to the procedure described in Example 101C, except for substituting Example 101B for Example 101A and substituting cyclopentane carbonyl chloride for acetyl chloride. ¹H NMR (500 MHz, CDCl$_3$) δ ppm 8.46 (d, J=1.83 Hz, 1H) 7.87 (d, J=8.85 Hz, 1H) 7.31 (s, 1H) 7.24 (dd, J=8.85, 2.14 Hz, 1H) 3.74-3.84 (m, 1H) 3.03-3.13 (m, 1H) 2.67-2.76 (m, 1H) 2.51-2.61 (m, 4H) 2.23-2.39 (m, 4H) 1.88-2.01 (m, 4H) 1.76-1.86 (m, 2H) 1.56-1.65 (m, 6H) 1.42-1.51 (m, 2H). MS: (M+H)$^+$=384.

Example 129

Trans-Cyclohexanecarboxylic acid[2-(3-Piperidin-1-yl-cyclobutyl)-benzothiazole-6-yl]-amide The title compound was prepared according to the procedure described in Example 101C, except for substituting Example 101B for Example 101A and substituting cyclohexane carbonyl chloride for acetyl chloride. ¹H NMR (500 MHz, CDCl$_3$) δ ppm 8.46 (d, J=1.83 Hz, 1H) 7.87 (d, J=8.85 Hz, 1H) 7.24 (dd, J=8.85, 2.14 Hz, 1H) 3.75-3.83 (m, 1H) 3.05-3.14 (m, 1H) 2.50-2.60 (m, 4H) 2.21-2.37 (m, 4H) 1.96-2.02 (m, 2H) 1.82-1.90 (m, 2H) 1.69-1.76 (m, 1H) 1.54-1.64 (m, 6H) 1.43-1.51 (m, 2H) 1.24-1.40 (m, 4H). MS: (M+H)$^+$=398.

Example 130

Trans-Furan-2-carboxylic acid[2-(3-Piperidin-1-yl-cyclobutyl)-benzothiazole-6-yl]-amide The title compound was prepared according to the procedure described in Example 101C, except for substituting Example 101B for Example 101A and substituting 2-furoyl chloride for acetyl chloride. ¹H NMR (500 MHz, CDCl$_3$) δ ppm 8.54 (d, J=2.14 Hz, 1H) 8.20 (s, 1H) 7.93 (d, J=8.85 Hz, 1H) 7.54 (s, 1H) 7.41 (dd, J=8.54, 2.14 Hz, 1H) 7.23-7.31 (m, 1H) 6.59 (dd, J=3.51, 1.68 Hz, 1H) 3.76-3.87 (m, 1H) 3.05-3.18 (m, 1H) 2.51-2.64 (m, 4H) 2.21-2.41 (m, 4H) 1.54-1.72 (m, 4H) 1.40-1.52 (m, 2H). MS: (M+H)$^+$=382.

Example 131

Trans-Morpholine-4-carboxylic acid-[2-(3-Piperidin-1-yl-cyclobutyl)-benzothiazole-6-yl]-amide The title compound was prepared according to the procedure described in Example 101C, except for substituting Example 101B for Example 101A and substituting 4-morpholine carbonyl chloride for acetyl chloride. ¹H NMR (400 MHz, CDCl$_3$) δ ppm 8.16 (s, 1H) 7.84 (s, 1H) 7.84 (s, 1H) 7.18 (d, J=8.59 Hz, 1H) 6.45 (s, 1H) 3.71-3.85 (m, 4H) 3.45-3.56 (m, 4H) 3.35-3.45 (m, 1H) 3.04-3.12 (m, 1H) 2.47-2.59 (m, 4H) 2.21-2.38 (m, 4H) 1.40-1.67 (m, 4H) 1.20-1.31 (m, 2H). MS: (M+H)$^+$=401.

Example 132

Trans-Pyrimidine-5-carboxylic acid-[2-(3-Piperidin-1-yl-cyclobutyl)-benzothiazole-6-yl]-amide The title compound was prepared according to the procedure described in Example 117, except for substituting Example 101B for Example 101A, and substituting 5-pyrimidine carboxylic acid for 2-pyrazine carboxylic acid. ¹H NMR (500 MHz, CDCl$_3$) δ ppm 9.39 (s, 1H) 9.25 (s, 2H) 8.50 (s, 1H) 8.05 (s, 1H) 7.96 (d, J=8.85 Hz, 1H) 7.43 (dd, J=8.85, 2.14 Hz, 1H) 3.77-3.88 (m, 1H) 3.05-3.16 (m, 1H) 2.57 (t, J=7.17 Hz, 4H) 2.19-2.42 (m, 4H) 1.55-1.65 (m, 4H) 1.39-1.54 (m, 2H). MS: (M+H)$^+$=394.

Example 133

Trans-Pyrazine-2-carboxylic acid-[2-(3-Piperidin-1-yl-cyclobutyl)-benzothiazole-6-yl]-amide The title compound was prepared according to the procedure described in Example 117, except for substituting Example 101B for Example 101A. $^1$H NMR (500 MHz, CDCl$_3$) δ ppm 9.82 (s, 1H) 9.54 (d, J=1.53 Hz, 1H) 8.84 (d, J=2.44 Hz, 1H) 8.66 (d, J=1.83 Hz, 1H) 8.59-8.64 (m, 1H) 7.97 (d, J=8.54 Hz, 1H) 7.54 (dd, J=8.85, 2.14 Hz, 1H) 3.77-3.88 (m, 1H) 3.05-3.18 (m, 1H) 2.51-2.62 (m, 4H) 2.19-2.41 (m, 4H) 1.55-1.66 (m, 4H) 1.41-1.52 (m, 2H). MS: (M+H)$^+$=394.

Example 134

Racemic-[2-(3-Piperidin-1-yl-cyclobutyl)-benzothiazole-6-yl]-pyrimidin-5-yl-amine The product of Example 101A (cis-2-(3-piperidin-1-yl-cyclobutyl)-benzothiazole-6-ylamine) (50 mg, 0.174 mmole), 5-bromopyrimidine (42 mg, 0.264 mmole), tris(dibenzylideneacetone)dipalladium (0) (6.5 mg, 0.007 mmole), racemic-2,2'-bis(diphenylphosphino)-1,1'-binaphthyl (BINAP, 8.7 mg, 0.014 mmole) and sodium tert-butoxide (23 mg, 0.242 mmole) were charged in a tube and sealed. The tube was placed on high vacuum for 2 hours and refilled with nitrogen. Toluene (2 mL) was added and the reaction vessel was placed in a microwave reactor and heated at 145° C. for 15 minutes. After cooling to room temperature, the mixture was diluted with water and extracted three times with with dichloromethane. The combined organic layers were concentrated and the crude product was purified by column chromatography (0.4% ammonium hydroxide and 4% methanol in dichloromethane). The product collected was a mixture of cis and trans isomers. $^1$H NMR (400 MHz, CDCl$_3$) δ ppm 8.79 (s, 1H) 8.50-8.56 (m, 2H) 7.89 (d, J=8.90 Hz, 1H) 7.58 (d, J=2.15 Hz, 1H) 7.18 (dd, J=8.59, 2.15 Hz, 1H) 5.83 (s, 1H) 3.48-3.63 (m, 1H) 2.73-2.85 (m, 1H) 2.59-2.71 (m, 2H) 2.23-2.39 (m, 6H) 1.54-1.66 (m, 4H) 1.41-1.51 (m, 2H). MS: (M+H)$^+$=366.

Example 135

Racemic-[2-(3-Piperidin-1-yl-cyclobutyl)-benzothiazole-6-yl]-pyrimidin-2-yl-amine The product of Example 44A (trans-6-bromo-2-(3-piperidin-1-ylcyclobutyl)-1,3-benzothiazole) (100 mg, 0.285 mmole), 2-aminopyrimidine (35 mg, 0.368 mmole), tris(dibenzylideneacetone)dipalladium (0) (10.4 mg, 0.011 mmole), racemic-2,2'-bis(diphenylphosphino)-1,1'-binaphthyl (BINAP, 14 mg, 0.022 mmole) and sodium tert-butoxide (38 mg, 0.400 mmole) were charged in a tube and sealed. The tube was placed on high vacuum for 2 hours and refilled with nitrogen. Toluene (2 mL) was added and the reaction vessel was placed in a microwave reactor and heated at 145° C. for 15 minutes. After cooling to room temperature, the mixture was diluted with water and extracted three times with dichloromethane. The combined organic layers were concentrated under reduced pressure and the crude product was purified by column chromatography (0.4% ammonium hydroxide and 4% methanol in dichloromethane). The product collected was a mixture of cis and trans isomers (98 mg). $^1$H NMR (400 MHz, CDCl$_3$) δ ppm 8.42-8.49 (m, 3H) 7.89 (d, 2H) 7.37-7.46 (m, 2H) 6.75 (t, J=4.76 Hz, 1H) 3.75-3.86 (m, 0.6H) 3.48-3.62 (m, 0.4H) 3.03-3.17 (m, 0.6H) 2.73-2.84 (m, 0.4H) 2.48-2.72 (m, 4H) 2.21-2.42 (m, 4H) 1.55-1.66 (m, 4H) 1.41-1.51 (m, 2H). MS: (M+H)$^+$=366.

Example 136

Racemic-(5-bromo-pyrimidin-2-yl)-[2-(3-Piperidin-1-yl-cyclobutyl)-benzothiazole-6-yl]-amine The title compound was prepared according to the procedure described in Example 135, except for substituting 2-amino-5-bromopyrimidine for 2-aminopyrimidine. $^1$H NMR (400 MHz, CDCl$_3$) δ ppm 8.45 (s, 2H) 8.39 (dd, J=5.83, 2.15 Hz, 1H) 7.89 (dd, J=11.81, 8.75 Hz, 1H) 7.33-7.43 (m, 2H) 7.21-7.26 (m, 1H) 3.76-3.85 (m, 0.4H) 3.49-3.61 (m, 0.6H) 3.04-3.16 (m, 0.4H) 2.72-2.85 (m, 0.6H) 2.50-2.71 (m, 4H) 2.22-2.41 (m, 4H) 1.54-1.67 (m, 4H) 1.41-1.50 (m, 2H).

Example 137

Racemic-(5-methyl-pyridin-2-yl)-[2-(3-Piperidin-1-yl-cyclobutyl)-benzothiazole-6-yl]-amine The title compound was prepared according to the procedure described in Example 135, except for substituting 2-amino-5-methylpyridine for 2-aminopyrimidine. $^1$H NMR (300 MHz, CDCl$_3$) δ ppm 8.06 (s, 1H) 7.98 (d, J=2.37 Hz, 1H) 7.85 (d, J=8.82 Hz, 1H) 7.35 (dd, J=8.31, 2.20 Hz, 1H) 7.22-7.28 (m, 1H) 6.79 (d, J=8.48 Hz, 1H) 6.46 (s, 1H) 3.76-3.89 (m, 0.3H) 3.48-3.61 (m, 0.7H) 3.06-3.22 (m, 0.3H) 2.74-2.87 (m, 0.7H) 2.53-2.72 (m, 4H) 2.28-2.44 (m, 4H) 2.25 (s, 3H) 1.53-1.71 (m, 4H) 1.39-1.52 (m, 2H). MS: (M+H)$^+$=379.

Example 138

Racemic-6-[2-(3-Piperidin-1-yl-cyclobutyl)-benzothiazole-6-ylamino]-nicotinonitrile The title compound was prepared according to the procedure described in Example 135, except for substituting 2-amino-5-cyanopyridine for 2-aminopyrimidine. $^1$H NMR (400 MHz, CDCl$_3$) δ ppm 8.49 (t, J=2.45 Hz, 1H) 7.90-8.04 (m, 2H) 7.67 (dd, J=8.75, 2.30 Hz, 1H) 7.30-7.39 (m, 1H) 6.99 (s, 1H) 6.77 (dd, J=8.44, 2.92 Hz, 1H) 3.75-3.87 (m, 0.3H) 3.50-3.66 (m, 0.7H) 3.04-3.17 (m, 0.3H) 2.75-2.85 (m, 0.7H) 2.51-2.73 (m, 4H) 2.22-2.40 (m, 4H) 1.61 (s, 4H) 1.40-1.51 (m, 2H). MS: (M+H)$^+$=390.

Example 139

2-{Trans-3-[(S)-2-methylpiperidin-1-yl]cyclobutyl}-1,3-benzothiazol-6-yl-azetidin-2-one

Example 139A

6-Bromo-2-{trans-3-[(S)-2-methylpiperidin-1-yl]cyclobutyl}-1,3-benzothiazole

The title compound was prepared according to the procedure described in Example 1E, substituting (S)-2-methylpiperidine for 2-(R)-methylpyrrolidine. $^1$H NMR (300 MHz, CDCl$_3$): δ=7.98 ppm (d, J=2.3 Hz, 1H), 7.83 (d, J=8.5 Hz, 1H), 7.56 (dd, J=8.5, 2.3 Hz, 1H), 3.75 (m, 1H), 3.53 (m, 1H), 2.50-2.85 (m, 6H), 2.19 (m, 1H), 1.65 (m, 4H), 1.41 (m, 2H), 1.06 (d, J=6.8 Hz, 3H). MS (ESI, M+H$^+$): 365.9.

Example 139B

2-{Trans-3-[(S)-2-methylpiperidin-1-yl]cyclobutyl}-1,3-benzothiazol-6-yl-azetidin-2-one To a microwave vial equipped with magnetic stir bar, Example 139A (50 mg, 0.14 mmol) was added, followed by azetidin-2-one (50 mg, 0.7 mmol), Pd$_2$(dba)$_3$ (3.5 mg, 0.004 mmol), Xantphos (6.1 mg, 0.011 mmol, Strem Chemicals, 7 Mulliken Way, Newburyport, Mass. 01950-4098) and CsCO$_3$ (65 mg, 0.2 mmol). The reaction vial was then sealed with an aluminum cap, and purged with N$_2$ for at least 10 times. Dioxane (2 mL) was then introduced via a syringe. The mixture was then sonicated, and then heated in a microwave oven at 200° C. for 20 minutes. The mixture was cooled down to 23° C., and filtered. Solvent was removed under reduced pressure, the residue purified via chromatography (SiO$_2$, ethyl acetate (0-80%)/hexanes) to give the titled compound. $^1$H NMR (300 MHz, CDCl$_3$): δ=7.97 ppm (d, J=2.0 Hz, 1H), 7.92 (d, J=8.5 Hz, 1H), 7.38 (dd, J=8.5, 2.0 Hz, 1H), 3.75 (m, 1H), 3.71 (t, J=4.7 Hz, 2H), 3.46 (m, 1H), 3.17 (t, J=4.7 Hz, 2H), 2.64 (m, 3H), 2.51 (m, 3H), 2.11 (m, 1H), 1.64 (m, 4H), 1.38 (m, 2H), 1.01 (d, J=6.5 Hz, 3H). MS (ESI, M+H$^+$): 356.1.

Example 140

2-{Trans-3-[(S)-2-methylpiperidin-1-yl]cyclobutyl}-1,3-benzothiazol-6-yl-pyrrolidin-2-one The title compound was prepared according to the procedure described in Example 139B, substituting pyrrolidin-2-one for azetidin-2-one. $^1$H NMR (300 MHz, CDCl$_3$): δ=8.29 ppm (d, J=2.3 Hz, 1H), 7.95 (d, J=9.1 Hz, 1H), 7.58 (dd, J=9.1, 2.3 Hz, 1H), 3.94 (t, J=4.8 Hz, 2H), 3.74 (m, 1H), 3.47 (m, 1H), 2.48-2.73 (m, 8H), 2.21 (m, 2H), 2.11 (m, 1H), 1.62 (m, 4H), 1.38 (m, 1H), 1.02 (d, J=6.5 Hz, 3H). MS (ESI, M+H$^+$): 370.1.

Example 141

2-{Trans-3-[(S)-2-methylpiperidin-1-yl]cyclobutyl}-1,3-benzothiazol-6-yl-piperidin-2-one The title compound was prepared according to the procedure described in Example 139B, substituting piperidin-2-one for azetidin-2-one. $^1$H NMR (300 MHz, CDCl$_3$): δ=7.98 ppm (d, J=8.5 Hz, 1H), 7.75 (d, J=2.0 Hz, 1H), 7.33 (dd, J=8.5, 2.0 Hz, 1H), 3.75 (m, 1H), 3.70 (t, J=6.1 Hz, 2H), 3.52 (m, 1H), 2.49-2.80 (m, 8H), 2.14 (m, 1H), 1.97 (m, 4H), 1.60 (m, 4H), 1.43 (m, 2H), 1.06 (m, 3H). MS (ESI, M+H$^+$): 384.1.

Example 142

2-{Trans-3-[(S)-2-methylpiperidin-1-yl]cyclobutyl}-1,3-benzothiazol-6-yl-homopyrrolidin-2-one The title compound was prepared according to the procedure described in Example 139B, substituting homopyrrolidin-2-one for azetidin-2-one. $^1$H NMR (300 MHz, CDCl$_3$): δ=7.96 ppm (d, J=8.4 Hz, 1H), 7.71 (d, J=2.7 Hz, 1H), 7.29 (dd, J=8.4, 2.7 Hz, 1H), 3.80 (m, 2H), 3.76 (m, 1H), 3.49 (m, 1H), 3.73 (m, 2H), 2.66 (m, 4H), 2.50 (m, 2H), 2.10 (m, 1H), 1.86 (m, 6H), 1.62 (m, 4H), 1.41 (m, 1H), 1.04 (m, 3H). MS (ESI, M+H$^+$): 398.2.

Example 143

2-{Trans-3-[(S)-2-methylpiperidin-1-yl]cyclobutyl}-1,3-benzothiazole-6-carboxamide

Example 143A

Methyl 2-{trans-3-[(S)-2-methylpiperidin-1-yl]cyclobutyl}-1,3-benzothiazole-6-carboxylate 6-bromo-2-{trans-3-[(S)-2-methylpiperidin-1-yl]cyclobutyl}-1,3-benzothiazole (Example 139A, 2.0 g, 5.5 mmol) was dissolved in methanol (60 mL), followed by catalyst PdCl$_2$(dppf)CH$_2$Cl$_2$ (225 mg, 0.3 mmol, also known as Palladium(II) chloride-1,1'-bis(diphenylphosphino)ferrocene, CAS #72287-264), and heated at 80° C. under CO pressure (60 psi) for 2 hours. The mixture was then cooled down to 23° C., and filtrated. Solvent was removed under reduced pressure and the residue was purified via chromatography (SiO$_2$, 10-80% ethyl acetate in hexanes) to give the titled compound. $^1$H NMR (300 MHz, CDCl$_3$): δ=8.58 ppm (d, J=1.7 Hz, 1H), 8.16 (dd, J=8.5, 1.7 Hz, 1H), 8.01 (d, J=8.5 Hz, 1H), 4.10 (m, 2H), 4.00 (m, 1H), 3.97 (s, 3H), 3.72 (m, 1H), 3.52 (m, 1H), 3.49 (d, J=4.1 Hz, 3H), 2.76 (m, 4H), 1.60 (m, 2H), 1.40 (m, 2H), 1.00 (m, 2H). MS (ESI, M+H$^+$): 345.1.

Example 143B

2-{Trans-3-[(S)-2-methylpiperidin-1-yl]cyclobutyl}-1,3-benzothiazole-6-carboxylic acid Methyl 2-{trans-3-[(S)-2-methylpiperidin-1-yl]cyclobutyl}-1,3-benzothiazole-6-carboxylate (Example 143A, 2.0 g, 5.8 mmol) was dissolved in methanol (600 mL), followed by H$_2$O (300 mg, 16.7 mmol) and sodium methoxide (1.4 g, 26 mmol) at 23° C. The reaction mixture was then allowed to stir at 23° C. for 1 day. Solvent and excess of water were removed. HCl (2N) was added to make the mixture slightly acidic (pH ~5-6). Excess of water was removed. The solid was triturated with CH$_2$Cl$_2$/MeOH, and filtrated. The solvents of the filtrate were removed under vacuum. The residue was treated with CH$_2$Cl$_2$ and filtrated again. Removal of the solvent gave the desired product as an off-white solid (2.13 g, 100%). $^1$H NMR (300 MHz, CD$_3$OD): δ=8.54 ppm (d, J=1.3 Hz, 1H), 8.11 (dd, J=8.9, 1.3 Hz, 1H), 7.91 (d, J=8.9 Hz, 1H), 4.00 (m, 1H), 3.80 (m, 1H), 2.70-3.10 (m, 7H), 2.00 (m, 2H), 1.80 (m, 2H), 1.65 (m, 2H), 1.41 (d, J=6.8 Hz, 3H). MS (ESI, M+H$^+$): 331.0.

Example 143C

2-{Trans-3-[(S)-2-methylpiperidin-1-yl]cyclobutyl}-1,3-benzothiazole-6-carboxamide 2-{trans-3-[(S)-2-methylpiperidin-1-yl]cyclobutyl}-1,3-benzothiazole-6-carboxylic acid (Example 143B, 20 mg, 0.062 mmol) was added to a solution of oxalyl chloride (17 mg, 0.13 mmol) in CH$_2$Cl$_2$ (1 mL) at 23° C., followed by 1 drop of catalytic amount of DMF. The reaction mixture was allowed to stir for 1 h. Solvent and excess of oxalyl chloride were removed under vacuum, the residue solid was re-dissolved in CH$_2$Cl$_2$ (0.5 mL). Excess of ammonia (2 mL, 1.2 mmol) in CH$_2$Cl$_2$ (2 mL) was then added to the reaction vial. The reaction mixture was then stirred overnight. Solvent was removed, and the crude product was purified via HPLC (C-18 column, 0.1% TFA in acetonitrile) to give 16 mg product as a TFA salt (65%). $^1$H NMR (500 MHz, CD$_3$OD): δ=8.51 ppm (m, 1H), 8.01 (m, 2H), 4.00 (m, 1H), 3.80 (m, 1H), 3.83 (m, 2H), 2.80-3.15 (m, 5H), 2.74 (m, 1H), 1.94 (m, 3H), 1.75 (m, 3H), 1.41 (m, 3H). MS (ESI, M+H$^+$): 330.0.

Example 144

N-Isopropyl-2-{trans-3-[(S)-2-methylpiperidin-1-yl]cyclobutyl}-1,3-benzothiazole-6-carboxamide The title compound was prepared according to the procedure described in Example 143C, substituting 2-isopropylamine for ammonia. $^1$H NMR (300 MHz, CD$_3$OD): δ=8.43 ppm (m, 1H), 7.94-8.03 (m, 2H), 4.23 (m, 1H), 3.96 (m, 2H), 3.02 (m, 1H), 2.93 (m, 3H), 2.86 (m, 2H), 1.94 (m, 3H), 1.75 (m, 3H), 1.40 (m, 3H), 1.30 (d, J=6.7 Hz, 6H). MS (ESI, M+H$^+$): 372.1.

Example 145

N-cyclopropyl-2-{trans-3-[(S)-2-methyl piperidin-1-yl]cyclobutyl}-1,3-benzothiazole-6-carboxamide The title compound was prepared according to the procedure described in Example 143C, substituting cyclopropylamine for ammonia. $^1$H NMR (300. MHz, CD$_3$OD): δ=8.43 ppm (m, 1H), 7.93-8.02 (m, 2H), 4.00 (m, 1H), 3.82 (m, 2H), 3.02 (m, 1H), 2.90 (m, 4H), 2.86 (m, 2H), 1.94 (m, 3H), 1.69 (m, 3H), 1.40 (m, 3H), 0.82 (m, 2H), 0.67 (m, 2H). MS (ESI, M+H$^+$): 370.1.

Example 146

N-phenyl-2-{trans-3-[(S)-2-methylpiperidin-1-yl]cyclobutyl}-1,3-benzothiazole-6-carboxamide The title compound was prepared according to the procedure described in Example 143C, substituting aniline for ammonia. $^1$H NMR (300 MHz, CD$_3$OD): δ=8.57 ppm (m, 1H), 8.04-8.10 (m, 2H), 7.71 (d, J=7.6 Hz, 2H), 7.37 (m, 2H), 7.16 (t, J=7.7 Hz, 1H), 4.00 (m, 1H), 3.82 (m, 2H), 3.07 (m, 1H), 2.96 (m, 3H), 2.87 (m, 2H), 1.94 (m, 3H), 1.75 (m, 3H), 1.41 (m, 3H). MS (ESI, M+H$^+$): 406.1.

Example 147

N-thiazol-2-yl-2-{trans-3-[(S)-2-methylpiperidin-1-yl]cyclobutyl}-1,3-benzothiazole-6-carboxamide The title compound was prepared according to the procedure described in Example 143C, substituting 2-aminothiazole for ammonia. $^1$H NMR (300 MHz, CD$_3$OD): δ=8.68 ppm (m, 1H), 8.17 (m, 1H), 8.09 (m, 1H), 7.53 (d, J=3.6 Hz, 1H), 7.19 (d, J=3.6 Hz, 1H), 4.00 (m, 1H), 3.85 (m, 2H), 3.10 (m, 1H), 2.95 (m, 3H), 2.76 (m, 2H), 1.94 (m, 3H), 1.73 (m, 3H), 1.41 (m, 3H). MS (ESI, M+H$^+$): 413.1.

Example 148

N-benzyl-2-{trans-3-[(S)-2-methylpiperidin-1-yl]cyclobutyl}-1,3-benzothiazole-6-carboxamide The title compound was prepared according to the procedure described in Example 143C, substituting 2-benzylamine for ammonia. $^1$H NMR (300 MHz, CD$_3$OD): δ=8.48 ppm (m, 1H), 8.00 (m, 2H), 7.38 (m, 2H), 7.33 (m, 2H), 7.25 (m, 1H), 4.61 (s, 2H), 4.00 (m, 1H), 3.82 (m, 2H), 3.04 (m, 1H), 2.93 (m, 3H), 2.73 (m, 2H), 1.94 (m, 3H), 1.73 (m, 3H), 1.40 (m, 3H). MS (ESI, M+H$^+$): 420.1.

Example 149

N-(2-phenethyl)-2-{trans-3-[(S)-2-methylpiperidin-1-yl]cyclobutyl}-1,3-benzothiazole-6-carboxamide The title compound was prepared according to the procedure described in Example 143C, substituting 2-phenethylamine for ammonia. $^1$H NMR (300 MHz, CD$_3$OD): δ=8.40 ppm (m, 1H), 8.00 (m, 1H), 7.91 (m, 1H), 7.27 (m, 3H), 7.20 (m, 2H), 4.00 (m, 1H), 3.82 (m, 2H), 3.63 (t, J=7.0 Hz, 2H), 3.04 (m, 1H), 2.94 (t, J=7.0 Hz, 2H), 2.83 (m, 3H), 2.75 (m, 2H), 1.94 (m, 3H), 1.73 (m, 3H), 1.40 (m, 3H). MS (ESI, M+H$^+$): 434.2.

Example 150

N,N-dimethyl-2-{trans-3-[(S)-2-methylpiperidin-1-yl]cyclobutyl}-1,3-benzothiazole-6-carboxamide The title compound was prepared according to the procedure described in Example 143C, substituting dimethylamine for ammonia. $^1$H NMR (300 MHz, CD$_3$OD): δ=8.08 ppm (m, 1H), 8.03 (m, 1H), 7.58 (m, 1H), 4.00 (m, 1H), 3.83 (m, 2H), 3.14 (s, 3H), 3.08 (m, 1H), 3.03 (s, 3H), 2.90 (m, 3H), 2.72 (m, 2H), 1.92 (m, 3H), 1.68 (m, 3H), 1.40 (m, 3H). MS (ESI, M+H$^+$): 358.1.

Example 151

(Pyrrolidin-1-yl)-2-{trans-3-[(S)-2-methylpiperidin-1-yl]cyclobutyl}-1,3-benzothiazole-6-methanone The title compound was prepared according to the procedure described in Example 143C, substituting pyrrolidine for ammonia. $^1$H NMR (300 MHz, CD$_3$OD): δ=8.17 ppm (m, 1H), 8.03 (m, 1H), 7.68 (m, 1H), 4.00 (m, 1H), 3.81 (m, 2H), 3.63 (t, J=6.7 Hz, 2H), 3.49 (t, J=6.7 Hz, 2H), 3.08 (m, 1H), 2.90 (m, 3H), 2.75 (m, 2H), 1.92 (m, 7H), 1.68 (m, 3H), 1.40 (m, 3H). MS (ESI, M+H$^+$): 384.1.

Example 152

2-[Trans-3-(piperidin-1-yl)cyclobutyl]-1,3-benzothiazol-6-yl-3-methyl-pyrrolidin-2-one

Example 152A

6-Bromo-2-[trans-3-(piperidin-1-yl)cyclobutyl]-1,3-benzothiazole

The title compound was prepared according to the procedure described in Example 1E, substituting piperidine for 2-(R)-methylpyrrolidine. $^1$H NMR (300 MHz, CDCl$_3$): δ=7.98 ppm (d, J=2.0 Hz, 1H), 7.83 (d, J=8.5 Hz, 1H), 7.55 (dd, J=8.5, 2.0 Hz, 1H), 3.80 (m, 1H), 3.09 (m, 1H), 2.56 (m, 4H), 2.30 (m, 4H), 1.61 (m, 4H), 1.47 (m, 2H). MS (ESI, M+H$^+$): 351.9.

Example 152B

2-[Trans-3-(piperidin-1-yl)cyclobutyl]-1,3-benzothiazol-6-yl-3-methyl-pyrrolidin-2-one To a microwave vial equipped with magnetic stir bar, 6-bromo-2-[trans-3-(piperidin-1-yl)cyclobutyl]-1,3-benzothiazole (3, 50 mg, 0.14 mmol) was added, Pd$_2$(dba)$_3$ (4.0 mg, 0.004 mmol), Xantphos (6.9 mg, 0.012 mmol) and CsCO₃ (68 mg, 0.2 mmol), followed by 3-methylpyrrolidin-2-one (50 mg, 0.5 mmol). The reaction vial was then sealed with an aluminum cap, and placed under inert atmosphere by purging with N₂. Dioxane (2 mL) was then introduced via a syringe. The reaction mixture was then subjected to sonication briefly to ensure mixing of the contents, and then heated in a commercial microwave oven at 150° C. for 60 min. The reaction mixture was cooled down to 23° C., and filtered to remove solids. The solvent was removed under vacuum, and from this, the residual mixture was purified by chromatography (SiO₂, ethyl acetate (0-80%)/hexanes) to give the title compound as a pure product (28 mg, 55%). ¹H NMR (300 MHz, CDCl₃): δ=8.33 ppm (d, J=2.1 Hz, 1H), 7.94 (d, J=9.2 Hz, 1H), 7.61 (dd, J=9.2, 2.1 Hz, 1H), 3.85 (m, 3H), 2.72 (m, 1H), 2.59 (m, 4H), 2.43 (m, 2H), 2.40 (m, 2H), 1.82 (m, 1H), 1.40-1.75 (m, 8H), 1.33 (d, J=7.1 Hz, 3H). MS (ESI, M+H⁺): 370.1.

Example 153

2-[Trans-3-(piperidin-1-yl)cyclobutyl]-1,3-benzothiazol-6-yl-oxazolidin-2-one

The title compound was prepared according to the procedure described in Example 152B, substituting oxazolidin-2-one for azetidin-2-one. ¹H NMR (300 MHz, CDCl₃): δ=8.14 ppm (d, J=2.4 Hz, 1H), 7.95 (d, J=9.1 Hz, 1H), 7.62 (dd, J=9.1, 2.4 Hz, 1H), 4.55 (m, 2H), 4.15 (m, 2H), 3.97 (m, 1H), 3.70 (m, 2H), 3.36 (m, 3H), 2.70 (m, 4H), 1.50-2.00 (m, 6H). MS (ESI, M+H⁺): 358.0.

Example 154

2-[Trans-3-(piperidin-1-yl)cyclobutyl]-1,3-benzothiazol-6-yl-3-methylimidazolidin-2-one The title compound was prepared according to the procedure described in Example 152B, substituting 3-methylimidazolidin-2-one for azetidin-2-one. ¹H NMR (300 MHz, CDCl₃): δ=8.12 ppm (d, J=2.4 Hz, 1H), 7.89 (d, J=8.9 Hz, 1H), 7.65 (dd, J=8.9, 2.4 Hz, 1H), 3.88 (m, 3H), 3.75 (m, 1H), 3.52 (m, 2H), 3.23 (m, 4H), 2.93 (s, 3H), 2.70 (m, 4H), 1.50-2.00 (m, 6H). MS (ESI, M+H⁺): 371.1.

Determination of Biological Activity

To determine the effectiveness of representative compounds of this invention as histamine-3 receptor ligands (H₃ receptor ligands), the following tests were conducted according to previously described methods (see European Journal of Pharmacology, 188:219-227 (1990); Journal of Pharmacology and Experimental Therapeutics, 275:598-604 (1995); Journal of Pharmacology and Experimental Therapeutics, 276:1009-1015 (1996); and Biochemical Pharmacology, 22:3099-3108 (1973)).

The rat H₃ receptor was cloned and expressed in cells, and competition binding assays carried out, according to methods previously described (see Esbenshade, et al. Journal of Pharmacology and Experimental Therapeutics, vol. 313:165-175, 2005; Esbenshade et al., Biochemical Pharmacology 68 (2004) 933-945; Krueger, et al. Journal of Pharmacology and Experimental Therapeutics, vol. 314:271-281, 2005. Membranes were prepared from C6 or HEK293 cells, expressing the rat histamine H₃ receptor, by homogenization on ice in TE buffer (50 mM Tris-HCl buffer, pH 7.4, containing 5 mM EDTA), 1 mM benzamidine, 2 μg/ml aprotinin, 1 μg/ml leupeptin, and 1 μg/ml pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer.

Membrane preparations were incubated with [³H]-N-α-methylhistamine (0.5-1.0 nM) in the presence or absence of increasing concentrations of ligands for H₃ receptor competition binding. The binding incubations were conducted in a final volume of 0.5 ml TE buffer at 25° C. and were terminated after 30 minutes. Thioperamide (30 μM) was used to define non-specific binding. All binding reactions were terminated by filtration under vacuum onto polyethylenimine (0.3%) presoaked Unifilters (Perkin Elmer Life Sciences) or Whatman GF/B filters followed by three brief washes with 2 ml of ice-cold TE buffer. Bound radiolabel was determined by liquid scintillation counting. For all of the radioligand competition binding assays, IC₅₀ values and Hill slopes were determined by Hill transformation of the data and pK$_i$ values were determined by the Cheng-Prusoff equation.

Generally, representative compounds of the invention demonstrated binding affinities in the above assay from about 0.01 nM to about 500 nM. Preferred compounds of the invention bound to histamine-3 receptors with binding affinities from about 0.01 nM to about 10 nM. More preferred compounds of the invention bound to histamine-3 receptors with binding affinities from about 0.01 nM to about 0.9 nM.

Compounds of the invention are histamine-3 receptor ligands that modulate function of the histamine-3 receptor by altering the activity of the receptor. These compounds may be inverse agonists that inhibit the basal activity of the receptor or they may be antagonists that completely block the action of receptor-activating agonists. These compounds may also be partial agonists that partially block or partially activate the histamine-3 receptor or they may be agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:
1. A compound of formula:

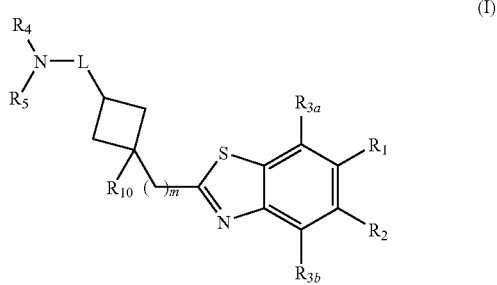

or a pharmaceutically acceptable salt thereof, wherein:
m is 0 or 1;
one of R₁ and R₂ is hydrogen, acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, haloalkoxy, haloalkyl, halogen, hydroxy, hydroxyalkyl, mercapto, nitro, alkylthio, —$NR_AR_B$, $(NR_AR_B)$carbonyl, —$SO_2N(R_{14a})(R_{14b})$, —$N(R_{14a})SO_2(R_{14b})$, a group of the formula —$L_2$—$R_6$, or a group of the formula —$L_{3a}$—$R_{6a}$—$L_{3b}$—$R_{6b}$;

the other of $R_1$ and $R_2$ is selected from the group consisting of hydrogen, cyano, halogen, alkyl, cycloalkyl, fluoroalkyl, alkoxy, alkoxyalkyl, fluoroalkoxy, alkylthio, —$SO_2N(R_{14a})(R_{14b})$, and —$N(R_{14a})SO_2(R_{14b})$;

$R_{3a}$ and $R_{3b}$ are each independently selected from the group consisting of hydrogen, cyano, halogen, alkyl, cycloalkyl, fluoroalkyl, alkoxy, alkoxyalkyl, fluoroalkoxy, alkylthio, —$SO_2N(R_{14a})(R_{14b})$, and —$N(R_{14a})SO_2(R_{14b})$;

$R_4$ and $R_5$ are each independently selected from the group consisting of alkyl, fluoroalkyl, hydroxyalkyl, alkoxyalkyl, and cycloalkyl; or $R_4$ and $R_5$ taken together with the nitrogen atom to which each is attached form a non-aromatic ring;

$R_6$ is aryl, heterocycle or heterocyclealkyl;
$R_{6a}$ is aryl or heterocycle;
$R_{6b}$ is aryl or heterocycle;
L is a bond or alkylene;
$L_2$ is a bond, —O—, alkylene, —C(=O)—, —S—, —$SO_2N(R_{14a})$—, $N(R_{14a})SO_2$—, —$C(O)N(R_{14a})$—, —$N(R_{14a})C(O)$—, or —$N(R_{15})$—;
$L_{3a}$ and $L_{3b}$ are each independently selected from the group consisting of a bond, —O—, alkylene, —C(=O)—, —S—, —$SO_2N(R_{14a})$—, —$N(R_{14a})SO_2$—, —C(O)N$(R_{14a})$—, $N(R_{14a})C(O)$—, and —$N(R_{15})$—;
$R_{10}$ is selected from the group consisting of hydrogen, cyano, fluoro, hydroxy, and alkyl;
$R_{14a}$ and $R_{14b}$ are each independently selected at each occurrence from the group consisting of hydrogen, alkyl, and cycloalkyl;
$R_{15}$ is selected from the group consisting of hydrogen, alkyl, acyl, alkoxycarbonyl, and $(R_{14a})(R_{14b})NC(O)$—; and
$R_A$ and $R_B$ are independently selected from hydrogen, alkyl, acyl, haloalkyl, alkoxycarbonyl, cycloalkyl, and formyl.

2. The compound of claim 1, wherein $R_1$ is —$L_2$—$R_6$, wherein $L_2$ is a bond and $R_6$ is as defined in claim 1.

3. The compound of claim 2, wherein $R_6$ is a heterocycle which may be unsubstituted, or alternatively may be optionally substituted with one or more substituents chosen from the list of acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, oxo, alkylthio, —$NR_AR_B$, $(NR_AR_B)$carbonyl, —$SO_2N(R_{14a})(R_{14b})$, and —$N(R_{14a})SO_2(R_{14b})$.

4. The compound of claim 3, wherein $R_6$ is selected from the group consisting of furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, pyrimidinonyl, indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, pyrrolopyrimidinyl, azepanyl, azetidinyl, aziridinyl, azocanyl, morpholinyl, piperazinyl, piperidinyl, pyrrolidinyl, pyrrolinyl, dihydrothiazolyl, dihydropyridinyl, thiomorpholinyl, dioxanyl, dithianyl, tetrahydrofuryl, dihydropyranyl, tetrahydropyranyl, and [1,3]dioxolanyl.

5. The compound of claim 4, wherein $R_6$ is selected from the group consisting of cyanophenyl, pyrazolyl, pyrimidinyl, pyrimidinonyl, pyridinyl, pyridazinonyl, and quinolinyl, wherein each ring is substituted with 0, 1, or 2 substituents selected from methoxy and methyl.

6. The compound of claim 1, wherein $R_{3a}$ and $R_{3b}$ are both hydrogen.

7. The compound of claim 1, wherein $R_4$ and $R_5$ taken together with the nitrogen atom to which each is attached form a non-aromatic ring, wherein the non-aromatic ring is a 4- to 9-membered non-aromatic ring.

8. The compound of claim 7, wherein the non-aromatic ring is a ring of the structure:

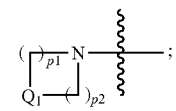
(a)

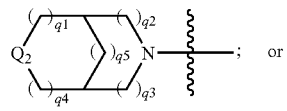
(b)

or

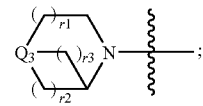
(c)

$Q_1$ is O, S, —$N(R_{20})$—, or C;
$Q_2$ is —$N(R_{20})$— or C;
$Q_3$ is N or C;
$R_{20}$ is selected from the group consisting of hydrogen, alkyl and alkylcarbonyl;
p1 and p2 are each independently 1, 2 or 3;
q1, q2, q3, q4, and q5 are each independently 0, 1, or 2; and
r1, r2 and r3 are each independently 1 or 2;
wherein each carbon atom in the ring is substituted with hydrogen, or with 0, 1, or 2 substituents independently selected at each occurrence from the group consisting of hydrogen, hydroxy, fluoro, alkyl, hydroxyalkyl, fluoroalkyl, cycloalkyl, cyano, fluoroalkoxy, alkoxyalkyl, alkoxy, fluoroalkoxy, haloalkyl, and $N(R_{21a})(R_{21b})$, wherein $R_{21a}$ and $R_{21b}$ are each independently selected from the group consisting of hydrogen, alkyl, and alkylcarbonyl.

9. The compound of claim 1, wherein $R_4$ and $R_5$ are taken together with the nitrogen atom to which each is attached to form azepanyl, azetidinyl, aziridinyl, azocanyl, morpholinyl, piperazinyl, piperidinyl, pyrrolidinyl, pyrrolinyl, and hexahydropyrrolo[3,4-b]pyrrolyl, wherein each group is substituted with 0, 1, or 2 substituents selected from alkyl, hydroxyalkyl, and fluoro.

10. The compound of claim 1, where m is 0, L is a bond, and $R_6$ is heterocycle.

11. The compound of claim 1, wherein the compound has the formula (II):

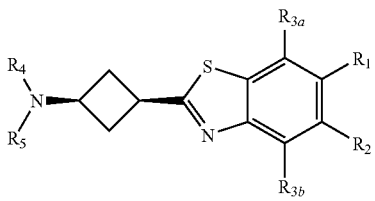

wherein $R_1$, $R_2$, $R_{3a}$, $R_{3b}$, $R_4$, and $R_5$ are as defined in claim 1.

12. The compound of claim 1, wherein the compound has the formula (III):

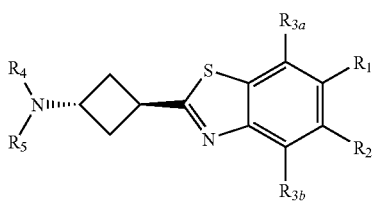

wherein $R_1$, $R_2$, $R_{3a}$, $R_{3b}$, $R_4$, and $R_5$ are as defined in claim 1.

13. The compound of claim 1, wherein one of $R_1$ and $R_2$ is $L_2R_6$, $L_2$ is a bond, and $R_6$ is a structure of formula:

(e)

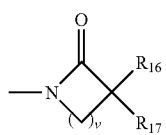

wherein $R_{16}$ and $R_{17}$ each are independently selected from hydrogen, alkyl, haloalkyl, cycloalkyl, alkoxyalkyl, aryl, and heteroaryl; or $R_{16}$ and $R_{17}$ taken together with the carbon atom to which each is attached form a 3- to 7-membered ring; v is 1, 2, 3, 4, 5, or 6.

14. The compound of claim 1, selected from the group consisting of:
Trans-2-{3-[(2R)-2-methylpyrrolidin-1-yl]cyclobutyl}-6-pyrimidin-5-yl-1,3-benzothiazole;
Trans-6-(2,6-dimethylpyridin-3-yl)-2-{3-[(2R)-2-methylpyrrolidin-1-yl]cyclobutyl}-1,3-benzothiazole;
Trans-6-(2,4-dimethoxypyrimidin-5-yl)-2-{3-[(2R)-2-methylpyrrolidin-1-yl]cyclobutyl}-1,3-benzothiazole;
Trans-6-(2-methoxypyrimidin-5-yl)-2-{3-[(2R)-2-methylpyrrolidin-1-yl]cyclobutyl}-1,3-benzothiazole;
Trans-2-{3-[(2R)-2-methylpyrrolidin-1-yl]cyclobutyl}-6-pyridin-4-yl-1,3-benzothiazole;
Trans-6-(6-methoxypyridin-3-yl)-2-{3-[(2R)-2-methylpyrrolidin-1-yl]cyclobutyl}-1,3-benzothiazole;
Trans-2-{3-[(2R)-2-methylpyrrolidin-1-yl]cyclobutyl}-6-pyridin-3-yl-1,3-benzothiazole;
Trans-3-(2-{3-[(2R)-2-methylpyrrolidin-1-yl]cyclobutyl}-1,3-benzothiazol-6-yl)quinoline;
Trans-6-(6-fluoropyridin-3-yl)-2-{3-[(2R)-2-methylpyrrolidin-1-yl]cyclobutyl}-1,3-benzothiazole;
Trans-4-(2-{3-[(2R)-2-methylpyrrolidin-1-yl]cyclobutyl}-1,3-benzothiazol-6-yl)benzonitrile;
Trans-2-{3-[(2S)-2-methylpyrrolidin-1-yl]cyclobutyl}-6-pyrimidin-5-yl-1,3-benzothiazole;
Trans-6-(2,4-dimethoxypyrimidin-5-yl)-2-{3-[(2S)-2-methylpyrrolidin-1-yl]cyclobutyl}-1,3-benzothiazole;
Trans-6-(2,6-dimethylpyridin-3-yl)-2-{3-[(2S)-2-methylpyrrolidin-1-yl]cyclobutyl}-1,3-benzothiazole;
Trans-6-(2-methoxypyrimidin-5-yl)-2-{3-[(2S)-2-methylpyrrolidin-1-yl]cyclobutyl}-1,3-benzothiazole;
Trans-6-(6-methoxypyridin-3-yl)-2-{3-[(2S)-2-methylpyrrolidin-1-yl]cyclobutyl}-1,3-benzothiazole;
Trans-3-(2-{3-[(2S)-2-methylpyrrolidin-1-yl]cyclobutyl}-1,3-benzothiazol-6-yl)quinoline;
Cis-2-{3-[(2R)-2-methylpyrrolidin-1-yl]cyclobutyl}-6-pyrimidin-5-yl-1,3-benzothiazole;
Cis-6-(2,6-dimethylpyridin-3-yl)-2-{3-[(2R)-2-methylpyrrolidin-1-yl]cyclobutyl}-1,3-benzothiazole;
Cis-2-{3-[(2S)-2-methylpyrrolidin-1-yl]cyclobutyl}-6-pyrimidin-5-yl-1,3-benzothiazole;
Cis-6-(2,4-dimethoxypyrimidin-5-yl)-2-{3-[(2S)-2-methylpyrrolidin-1-yl]cyclobutyl}-1,3-benzothiazole;
Cis-6-(2,6-dimethylpyridin-3-yl)-2-{3-[(2S)-2-methylpyrrolidin-1-yl]cyclobutyl}-1,3-benzothiazole;
Trans-2-(2-{3-[(2R)-2-methylpyrrolidin-1-yl]cyclobutyl}-1,3-benzothiazol-6-yl)pyridazin-3(2H)-one;
Trans-6-methyl-2-(2-{3-[(2R)-2-methylpyrrolidin-1-yl]cyclobutyl}-1,3-benzothiazol-6-yl)pyridazin-3(2H)-one;
Trans-5-methyl-1-(2-{3-[(2R)-2-methylpyrrolidin-1-yl]cyclobutyl}-1,3-benzothiazol-6-yl)pyridin-2(1H)-one;
Trans-3-methyl-1-(2-{3-[(2R)-2-methylpyrrolidin-1-yl]cyclobutyl}-1,3-benzothiazol-6-yl)pyridin-2(1H)-one;
Trans-2-(2-{3-[(2S)-2-methylpyrrolidin-1-yl]cyclobutyl}-1,3-benzothiazol-6-yl)pyridazin-3(2H)-one;
Trans-6-methyl-2-(2-{3-[(2S)-2-methylpyrrolidin-1-yl]cyclobutyl}-1,3-benzothiazol-6-yl)pyridazin-3(2H)-one;
Trans-5-methyl-1-(2-{3-[(2S)-2-methylpyrrolidin-1-yl]cyclobutyl}-1,3-benzothiazol-6-yl)pyridin-2(1H)-one;
Trans-3-methyl-1-(2-{3-[(2S)-2-methylpyrrolidin-1-yl]cyclobutyl}-1,3-benzothiazol-6-yl)pyridin-2(1H)-one;
Cis-6-pyrimidin-5-yl-2-(3-pyrrolidin-1-ylcyclobutyl)-1,3-benzothiazole;
Cis-6-(2-methoxypyrimidin-5-yl)-2-(3-pyrrolidin-1-ylcyclobutyl)-1,3-benzothiazole;
Cis-2-(3-piperidin-1-ylcyclobutyl)-6-pyrimidin-5-yl-1,3-benzothiazole
Cis-6-(2-methoxypyrimidin-5-yl)-2-(3-piperidin-1-ylcyclobutyl)-1,3-benzothiazole;
Cis-2-(3-azepan-1-ylcyclobutyl)-6-pyrimidin-5-yl-1,3-benzothiazole;
Cis-2-(3-morpholin-4-ylcyclobutyl)-6-pyrimidin-5-yl-1,3-benzothiazole;
Cis-{(2S)-1-[3-(6-pyrimidin-5-yl-1,3-benzothiazol-2-yl)cyclobutyl]pyrrolidin-2-yl}methanol;
Cis-((2S)-1-{3-[6-(2-methoxypyrimidin-5-yl)-1,3-benzothiazol-2-yl]cyclobutyl}pyrrolidin-2-yl)methanol;
Cis-2-{3-[(3aR,6aR)-hexahydropyrrolo[3,4-b]pyrrol-5(1H)-yl]cyclobutyl}-6-pyrimidin-5-yl-1,3-benzothiazole;
Cis-2-{3-[(3aR,6aR)-hexahydropyrrolo[3,4-b]pyrrol-5(1H)-yl]cyclobutyl}-6-(2-methoxypyrimidin-5-yl)-1,3-benzothiazole;
Cis-2-{3-[(2R)-2-methylpiperidin-1-yl]cyclobutyl}-6-pyrimidin-5-yl-1,3-benzothiazole;
Cis-N-isopropyl-N-methyl-N-[3-(6-pyrimidin-5-yl-1,3-benzothiazol-2-yl)cyclobutyl]amine;
Cis-{1-[3-(6-pyrimidin-5-yl-1,3-benzothiazol-2-yl)cyclobutyl]piperidin-4-yl}methanol;
Trans-{1-[3-(6-pyrimidin-5-yl-1,3-benzothiazol-2-yl)cyclobutyl]piperidin-4-yl}methanol;

Trans-2-(3-piperidin-1-ylcyclobutyl)-6-pyrimidin-5-yl-1,3-benzothiazole;
Trans-6-(2,6-dimethylpyridin-3-yl)-2-(3-piperidin-1-ylcyclobutyl)-1,3-benzothiazole;
Trans-6-(6-methoxypyridin-3-yl)-2-(3-piperidin-1-ylcyclobutyl)-1,3-benzothiazole;
Trans-6-(2-methoxypyrimidin-5-yl)-2-(3-piperidin-1-ylcyclobutyl)-1,3-benzothiazole;
Trans-2-[2-(3-piperidin-1-ylcyclobutyl)-1,3-benzothiazol-6-yl]pyridazin-3(2H)-one;
Cis-2-[2-(3-piperidin-1-ylcyclobutyl)-1,3-benzothiazol-6-yl]pyridazin-3(2H)-one;
Trans-6-methyl-2-[2-(3-piperidin-1-ylcyclobutyl)-1,3-benzothiazol-6-yl]pyridazin-3(2H)-one;
Trans-3-methyl-1-[2-(3-piperidin-1-ylcyclobutyl)-1,3-benzothiazol-6-yl]pyridin-2(1H)-one;
Trans-6-(1-methyl-1H-pyrazol-4-yl)-2-(3-piperidin-1-ylcyclobutyl)-1,3-benzothiazole;
Trans-N-isopropyl-N-methyl-N-[3-(6-pyrimidin-5-yl-1,3-benzothiazol-2-yl)cyclobutyl]amine;
Trans-N-isopropyl-N-{3-[6-(2-methoxypyrimidin-5-yl)-1,3-benzothiazol-2-yl]cyclobutyl}-N-methylamine;
Trans-N-isopropyl-N-{3-[6-6-methoxypyridin-3-yl)-1,3-benzothiazol-2-yl]cyclobutyl}-N-methylamine;
Trans-N-isopropyl-N-{3-[6-(2-methoxypyridin-3-yl)-1,3-benzothiazol-2-yl]cyclobutyl}-N-methylamine;
Trans-N-{3-[6-(2,6-dimethylpyridin-3-yl)-1,3-benzothiazol-2-yl]cyclobutyl}-N-isopropyl-N-methylamine;
Trans-2-(2-{3-[isopropyl(methyl)amino]cyclobutyl}-1,3-benzothiazol-6-yl)pyridazin-3(2H)-one;
Trans-2-(2-{3-[isopropyl(methyl)amino]cyclobutyl}-1,3-benzothiazol-6-yl)-6-methylpyridazin-3(2H)-one;
Trans-1-(2-{3-[isopropyl(methyl)amino]cyclobutyl}-1,3-benzothiazol-6-yl)-3-methylpyridin-2(1H)-one;
Trans-1-(2-{3-[isopropyl(methyl)amino]cyclobutyl}-1,3-benzothiazol-6-yl)-5-methylpyridin-2(1H)-one;
Trans-2-(3-azetidin-1-ylcyclobutyl)-6-pyrimidin-5-yl-1,3-benzothiazole;
Trans-6-pyrimidin-5-yl-2-(3-pyrrolidin-1-ylcyclobutyl)-1,3-benzothiazole;
Trans-6-(2,6-dimethylpyridin-3-yl)-2-(3-pyrrolidin-1-ylcyclobutyl)-1,3-benzothiazole;
Trans-6-(2-methoxypyrimidin-5-yl)-2-(3-pyrrolidin-1-ylcyclobutyl)-1,3-benzothiazole;
Trans-6-(2,4-dimethoxypyrimidin-5-yl)-2-(3-pyrrolidin-1-ylcyclobutyl)-1,3-benzothiazole;
Trans-6-(6-methoxypyridin-3-yl)-2-(3-pyrrolidin-1-ylcyclobutyl)-1,3-benzothiazole;
Trans-2-[2-(3-pyrrolidin-1-ylcyclobutyl)-1,3-benzothiazol-6-yl]pyridazin-3(2H)-one;
Trans-6-methyl-2-[2-(3-pyrrolidin-1-ylcyclobutyl)-1,3-benzothiazol-6-yl]pyridazin-3(2H)-one;
Trans-5-methyl-1-[2-(3-pyrrolidin-1-ylcyclobutyl)-1,3-benzothiazol-6-yl]pyridin-2(1H)-one;
Trans-3-methyl-1-[2-(3-pyrrolidin-1-ylcyclobutyl)-1,3-benzothiazol-6-yl]pyridin-2(1H)-one;
Trans-2-(3-azepan-1-ylcyclobutyl)-6-pyrimidin-5-yl-1,3-benzothiazole;
Trans-2-(3-morpholin-4-ylcyclobutyl)-6-pyrimidin-5-yl-1,3-benzothiazole;
Trans-2-{3-[(2S)-2-(fluoromethyl)pyrrolidin-1-yl]cyclobutyl}-6-pyrimidin-5-yl-1,3-benzothiazole;
Trans-{(2S)-1-[3-(6-pyrimidin-5-yl-1,3-benzothiazol-2-yl)cyclobutyl]pyrrolidin-2-yl}methanol;
Trans-((2S)-1-{3-[6-(2,6-dimethylpyridin-3-yl)-1,3-benzothiazol-2-yl]cyclobutyl}pyrrolidin-2-yl)methanol;
Trans-2-[3-(2-methylpiperidin-1-yl)cyclobutyl]-6-pyrimidin-5-yl-1,3-benzothiazole;
Trans-2-(3-hexahydropyrrolo[3,4-b]pyrrol-5(1H)-ylcyclobutyl)-6-pyrimidin-5-yl-1,3-benzothiazole;
Trans-2-[3-(4-fluoropiperidin-1-yl)cyclobutyl]-6-pyrimidin-5-yl-1,3-benzothiazole;
Trans-2-[3-(4-fluoropiperidin-1-yl)cyclobutyl]-6-(2-methoxypyrimidin-5-yl)-1,3-benzothiazole;
Trans-6-(2,6-dimethylpyridin-3-yl)-2-[3-(4-fluoropiperidin-1-yl)cyclobutyl]-1,3-benzothiazole;
Trans-(3R)-1-[3-(6-pyrimidin-5-yl-1,3-benzothiazol-2-yl)cyclobutyl]piperidin-3-ol;
Trans-N-ethyl-N-propyl-N-[3-(6-pyrimidin-5-yl-1,3-benzothiazol-2-yl)cyclobutyl]amine;
Trans-Diethyl-[3-(6-pyrimidin-5-yl-benzothiazol-2-yl)-cyclobutyl]-amine;
Trans-Diethyl-{3-[6-(2-methoxy-pyrimidin-5-yl)-benzothiazol-2-yl]-cyclobutyl}-amine;
Trans-{3-[6-(2-Methoxy-pyrimidin-5-yl)-benzothiazol-2-yl]-cyclobutyl}-methyl-propyl-amine;
Trans-{3-[6-(2,6-Dimethyl-pyridin-3-yl)-benzothiazol-2-yl]-cyclobutyl}-methyl-propyl-amine;
Trans-Methyl-{3-[6-(1-methyl-1H-pyrazol-4-yl)-benzothiazol-2-yl]-cyclobutyl}-propyl-amine;
Trans-2-(Ethyl-{3-[6-(2-methoxy-pyrimidin-5-yl)-benzothiazol-2-yl]-cyclobutyl}-amino)-ethanol;
Trans-2-({3-[6-(2,6-Dimethyl-pyridin-3-yl)-benzothiazol-2-yl]-cyclobutyl}-ethyl-amino)-ethanol;
6-Pyrimidin-5-yl-2-(3-pyrrolidin-1-ylmethyl-cyclobutyl)-benzothiazole;
Trans-5-(2,6-Dimethyl-pyridin-3-yl)-2-[3-(2-methyl-pyrrolidin-1-yl)-cyclobutyl]-benzothiazole;
Trans-5-(2,4-Dimethoxy-pyrimidin-5-yl)-2-[3-(2-methyl-pyrrolidin-1-yl)-cyclobutyl]-benzothiazole;
Trans-6-(1-Methyl-1H-pyrazol-4-yl)-2-[3-(2-methyl-pyrrolidin-1-yl)-cyclobutyl]-benzothiazole;
Trans-2-[3-(4-Fluoro-piperidin-1-yl)-cyclobutyl]-6-(1-methyl-1H-pyrazol-4-yl)-benzothiazole;
Trans-2-(3-azetidin-1-ylcyclobutyl)-6-(2-methoxypyrimidin-5-yl)-1,3-benzothiazole;
Trans-2-(3-azetidin-1-ylcyclobutyl)-6-(2,6-dimethylpyridin-3-yl)-1,3-benzothiazole;
Trans-2-(3-azetidin-1-ylcyclobutyl)-6-(1-methyl-1H-pyrazol-4-yl)-1,3-benzothiazole;
Trans-2-(3-azepan-1-ylcyclobutyl)-6-(2-methoxypyrimidin-5-yl)-1,3-benzothiazole;
Trans-2-(3-azepan-1-ylcyclobutyl)-6-(2,6-dimethylpyridin-3-yl)-1,3-benzothiazole;
Trans-2-(3-azepan-1-ylcyclobutyl)-6-(1-methyl-1H-pyrazol-4-yl)-1,3-benzothiazole;
Cis-N-[2-(3-Piperidin-1-yl-cyclobutyl)-benzothiazole-6-yl]-acetamide;
Cis-2-Chloro-N-[2-(3-Piperidin-1-yl-cyclobutyl)-benzothiazole-6-yl]-acetamide;
Cis-N-[2-(3-Piperidin-1-yl-cyclobutyl)-benzothiazole-6-yl]-propionamide;
Cis-N-[2-(3-Piperidin-1-yl-cyclobutyl)-benzothiazole-6-yl]-isobutyramide;
Cis-Cyclopropanecarboxylic acid[2-(3-Piperidin-1-yl-cyclobutyl)-benzothiazole-6-yl]-amide;
Cis-Cyclobutanecarboxylic acid[2-(3-Piperidin-1-yl-cyclobutyl)-benzothiazole-6-yl]-amide;
Cis-Cyclopentanecarboxylic acid[2-(3-Piperidin-1-yl-cyclobutyl)-benzothiazole-6-yl]-amide;
Cis-Cyclohexanecarboxylic acid[2-(3-Piperidin-1-yl-cyclobutyl)-benzothiazole-6-yl]-amide;

Cis-Furan-2-carboxylic acid[2-(3-Piperidin-1-yl-cyclobutyl)-benzothiazole-6-yl]-amide;
Cis-4-Cyano-N-[2-(3-Piperidin-1-yl-cyclobutyl)-benzothiazole-6-yl]-benzamide;
Cis-4-Cyano-N-[2-(3-Piperidin-1-yl-cyclobutyl)-benzothiazole-6-yl]-benzenesulfonamide;
Cis-Thiophene-2-sulfonic acid-[2-(3-Piperidin-1-yl-cyclobutyl)-benzothiazole-6-yl]-amide;
Cis-Thiophene-2-carboxylic acid-[2-(3-Piperidin-1-yl-cyclobutyl)-benzothiazole-6-yl]-amide;
Cis-Thiophene-2-carboxylic acid-[2-(3-Piperidin-1-yl-cyclobutyl)-benzothiazole-6-yl]-amide;
Cis-[2-(3-Piperidin-1-yl-cyclobutyl)-benzothiazole-6-yl]-carbamic acid isobutyl ester;
Cis-Morpholine-4-carboxylic acid-[2-(3-Piperidin-1-yl-cyclobutyl)-benzothiazole-6-yl]-amide;
Cis-Pyrazine-2-carboxylic acid-[2-(3-Piperidin-1-yl-cyclobutyl)-benzothiazole-6-yl]-amide;
Cis-N-[2-(3-Piperidin-1-yl-cyclobutyl)-benzothiazole-6-yl]-2-thiophen-3-yl-acetamide;
Cis-N-[2-(3-Piperidin-1-yl-cyclobutyl)-benzothiazole-6-yl]-3-thiophen-2-yl-propionamide;
Cis-3-Furan-2-yl-N-[2-(3-Piperidin-1-yl-cyclobutyl)-benzothiazole-6-yl]-propionamide;
Cis-Pyrimidine-5-carboxylic acid-[2-(3-Piperidin-1-yl-cyclobutyl)-benzothiazole-6-yl]-amide;
Trans-4-Cyano-N-[2-(3-Piperidin-1-yl-cyclobutyl)-benzothiazole-6-yl]-benzamide;
Trans-N-[2-(3-Piperidin-1-yl-cyclobutyl)-benzothiazole-6-yl]-propionamide;
Trans-N-[2-(3-Piperidin-1-yl-cyclobutyl)-benzothiazole-6-yl]-isobutyramide;
Trans-[2-(3-Piperidin-1-yl-cyclobutyl)-benzothiazole-6-yl]-carbamic acid isobutyl ester;
Trans-Cyclopropanecarboxylic acid[2-(3-Piperidin-1-yl-cyclobutyl)-benzothiazole-6-yl]-amide;
Trans-Cyclobutanecarboxylic acid[2-(3-Piperidin-1-yl-cyclobutyl)-benzothiazole-6-yl]-amide;
Trans-Cyclopentanecarboxylic acid[2-(3-Piperidin-1-yl-cyclobutyl)-benzothiazole-6-yl]-amide;
Trans-Cyclohexanecarboxylic acid[2-(3-Piperidin-1-yl-cyclobutyl)-benzothiazole-6-yl]-amide;
Trans-Furan-2-carboxylic acid[2-(3-Piperidin-1-yl-cyclobutyl)-benzothiazole-6-yl]-amide;
Trans-Morpholine-4-carboxylic acid-[2-(3-Piperidin-1-yl-cyclobutyl)-benzothiazole-6-yl]-amide;
Trans-Pyrimidine-5-carboxylic acid-[2-(3-Piperidin-1-yl-cyclobutyl)-benzothiazole-6-yl]-amide;
Trans-Pyrazine-2-carboxylic acid-[2-(3-Piperidin-1-yl-cyclobutyl)-benzothiazole-6-yl]-amide;
Racemic-[2-(3-Piperidin-1-yl-cyclobutyl)-benzothiazole-6-yl]-pyrimidin-5-yl-amine;
Racemic-[2-(3-Piperidin-1-yl-cyclobutyl)-benzothiazole-6-yl]-pyrimidin-2-yl-amine;
Racemic-(5-bromo-pyrimidin-2-yl)-[2-(3-Piperidin-1-yl-cyclobutyl)-benzothiazole-6-yl]-amine;
Racemic-(5-methyl-pyridin-2-yl)-[2-(3-Piperidin-1-yl-cyclobutyl)-benzothiazole-6-yl]-amine;
Racemic-6-[2-(3-Piperidin-1-yl-cyclobutyl)-benzothiazole-6-ylamino]-nicotinonitrile;
Racemic-6-[2-(3-Piperidin-1-yl-cyclobutyl)-benzothiazole-6-ylamino]-nicotinonitrile;
2-{Trans-3-[(S)-2-methylpiperidin-1-yl]cyclobutyl}-1,3-benzothiazol-6-yl-azetidin-2-one;
2-{Trans-3-[(S)-2-methylpiperidin-1-yl]cyclobutyl}-1,3-benzothiazol-6-yl-pyrrolidin-2-one;
2-{Trans-3-[(S)-2-methylpiperidin-1-yl]cyclobutyl}-1,3-benzothiazol-6-yl-piperidin-2-one;
2-{Trans-3-[(S)-2-methylpiperidin-1-yl]cyclobutyl}-1,3-benzothiazol-6-yl-homopyrrolidin-2-one;
2-{Trans-3-[(S)-2-methylpiperidin-1-yl]cyclobutyl}-1,3-benzothiazole-6-carboxamide;
N-Isopropyl-2-{trans-3-[(S)-2-methylpiperidin-1-yl]cyclobutyl}-1,3-benzothiazole-6-carboxamide;
N-cyclopropyl-2-{trans-3-[(S)-2-methylpiperidin-1-yl]cyclobutyl}-1,3-benzothiazole-6-carboxamide;
N-phenyl-2-{trans-3-[(S)-2-methylpiperidin-1-yl]cyclobutyl}-1,3-benzothiazole-6-carboxamide;
N-thiazol-2-yl-2-{trans-3-[(S)-2-methylpiperidin-1-yl]cyclobutyl}-1,3-benzothiazole-6-carboxamide;
N-benzyl-2-{trans-3-[(S)-2-methylpiperidin-1-yl]cyclobutyl}-1,3-benzothiazole-6-carboxamide;
N-(2-phenethyl)-2-{trans-3-[(S)-2-methylpiperidin-1-yl]cyclobutyl}-1,3-benzothiazole-6-carboxamide;
N,N-dimethyl-2-{trans-3-[(S)-2-methylpiperidin-1-yl]cyclobutyl}-1,3-benzothiazole-6-carboxamide;
(Pyrrolidin-1-yl)-2-{trans-3-[(S)-2-methylpiperidin-1-yl]cyclobutyl}-1,3-benzothiazole-6-methanone;
2-[Trans-3-(piperidin-1-yl)cyclobutyl]-1,3-benzothiazol-6-yl-3-methyl-pyrrolidin-2-one;
2-[Trans-3-(piperidin-1-yl)cyclobutyl]-1,3-benzothiazol-6-yl-oxazolidin-2-one;
2-[Trans-3-(piperidin-1-yl)cyclobutyl]-1,3-benzothiazol-6-yl-3-methylimidazolidin-2-one;
Trans-6-bromo-2-{3-[(2R)-2-methylpyrrolidin-1-yl]cyclobutyl}-1,3-benzothiazole;
Trans-6-bromo-2-{3-[(2S)-2-methylpyrrolidin-1-yl]cyclobutyl}-1,3-benzothiazole;
Cis 6-bromo-2-{3-[(2R)-2-methylpyrrolidin-1-yl]cyclobutyl}-1,3-benzothiazole;
Cis-6-bromo-2-(3-pyrrolidin-1-ylcyclobutyl)-1,3-benzothiazole;
Cis-6-bromo-2-(3-piperidin-1-ylcyclobutyl)-1,3-benzothiazole;
Cis-2-(3-azepan-1-ylcyclobutyl)-6-bromo-1,3-benzothiazole;
Cis-{(2S)-1-[3-(6-bromo-1,3-benzothiazol-2-yl)cyclobutyl]pyrrolidin-2-yl}methanol;
Cis-tert-butyl(3aR,6aR)-5-[3-(6-bromo-1,3-benzothiazol-2-yl)cyclobutyl]hexahydropyrrolo[3,4-b]pyrrole-1(2H)-carboxylate;
Cis-6-bromo-2-{3-[(2R)-2-methylpiperidin-1-yl]cyclobutyl}-1,3-benzothiazole;
Cis-N-[3-(6-bromo-1,3-benzothiazol-2-yl)cyclobutyl]-N-isopropyl-N-methylamine;
Cis-{1-[3-(6-bromo-1,3-benzothiazol-2-yl)cyclobutyl]piperidin-4-yl}methanol;
Trans-{1-[3-(6-bromo-1,3-benzothiazol-2-yl)cyclobutyl]piperidin-4-yl}methanol;
Trans-6-bromo-2-(3-piperidin-1-ylcyclobutyl)-1,3-benzothiazole;
Trans-N-[3-(6-bromo-1,3-benzothiazol-2-yl)cyclobutyl]-N-isopropyl-N-methylamine;
Trans-2-(3-azetidin-1-ylcyclobutyl)-6-bromo-1,3-benzothiazole;
Trans-6-bromo-2-(3-pyrrolidin-1-ylcyclobutyl)-1,3-benzothiazole;
Trans-2-(3-azepan-1-ylcyclobutyl)-6-bromo-1,3-benzothiazole;
Trans-6-bromo-2-(3-morpholin-4-ylcyclobutyl)-1,3-benzothiazole;
Trans-6-bromo-2-{3-[(2S)-2-(fluoromethyl)pyrrolidin-1-yl]cyclobutyl}-1,3-benzothiazol;

Trans-{(2S)-1-[3-(6-bromo-1,3-benzothiazol-2-yl)cyclobutyl]pyrrolidin-2-yl}methanol;

Trans-6-bromo-2-[3-(2-methylpiperidin-1-yl)cyclobutyl]-1,3-benzothiazole;

Trans-tert-butyl 5-[3-(6-bromo-1,3-benzothiazol-2-yl)cyclobutyl]hexahydropyrrolo[3,4-b]pyrrole-1(2H)-carboxylate;

Trans-6-bromo-2-[3-(4-fluoropiperidin-1-yl)cyclobutyl]-1,3-benzothiazole;

Trans-[3-(6-Bromo-benzothiazol-2-yl)-cyclobutyl]-diethyl-amine;

Trans-[3-(6-Bromo-benzothiazol-2-yl)-cyclobutyl]-methyl-propyl-amine;

Trans-2-{[3-(6-Bromo-benzothiazol-2-yl)-cyclobutyl]-ethyl-amino}-ethanol;

6-Bromo-2-(3-pyrrolidin-1-ylmethyl-cyclobutyl)-benzothiazole; and

Trans-5-Chloro-2-[3-(2-methyl-pyrrolidin-1-yl)-cyclobutyl]-benzothiazole.

15. The compound of claim 1, selected from the group consisting of:

Trans-2-(3-piperidin-1-ylcyclobutyl)-6-pyrimidin-5-yl-1,3-benzothiazole;

Trans-Diethyl-{3-[6-(2-methoxy-pyrimidin-5-yl)-benzothiazol-2-yl]-cyclobutyl}-amine; and Trans-2-(Ethyl-{3-[6-(2-methoxy-pyrimidin-5-yl)-benzothiazol-2-yl]-cyclobutyl}-amino)-ethanol;

Trans-2-[2-(3-piperidin-1-ylcyclobutyl)-1,3-benzothiazol-6-yl]pyridazin-3(2H)-one; and Cis-2-[2-(3-piperidin-1-ylcyclobutyl)-1,3-benzothiazol-6-yl]pyridazin-3(2H)-one.

16. A pharmaceutical composition comprising a therapeutically effective amount of a compound of claim 1 in combination with a pharmaceutically acceptable carrier.

17. A compound that is trans-2-[2-(3-piperidin-1-ylcyclobutyl)-1,3-benzothiazol-6-yl]pyridazin-3(2H)-one or a pharmaceutically acceptable salt thereof.

18. A compound that is cis-2-[2-(3-piperidin-1-ylcyclobutyl)-1,3-benzothiazol-6-yl]pyridazin-3(2H)-one or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,576,110 B2 | Page 1 of 1 |
| APPLICATION NO. | : 11/518132 | |
| DATED | : August 18, 2009 | |
| INVENTOR(S) | : Cowart et al. | |

It is certified that error appears in the above-identified patent and that said Letters Patent is hereby corrected as shown below:

Claims:

Claim 4 Column 105 Line 59 - After "triazinyl," delete "triazolyl,"

Claim 14 Column 108 Line 44 - Delete "benzothiazole" and insert -- benzothiazole; --

Claim 14 Column 111 Line 43 - Delete "Fu ran" and insert -- Furan --

Claim 14 Column 112 Line 33 - Delete "Cis 6" and insert -- Cis-6 --

Signed and Sealed this
Twelfth Day of June, 2012

David J. Kappos
*Director of the United States Patent and Trademark Office*